United States Patent [19]

Nakae et al.

[11] Patent Number: 5,795,890
[45] Date of Patent: Aug. 18, 1998

[54] SULFONAMIDE DERIVATIVES

[75] Inventors: Takahiko Nakae; Masashi Kato; Takehito Fujita; Kazuhito Kawabata; Hiroyuki Ohno, all of Osaka, Japan

[73] Assignee: ONO Pharmaceutical Co., Ltd., Osaka, Japan

[21] Appl. No.: 718,722

[22] Filed: Sep. 24, 1996

[30] Foreign Application Priority Data

Sep. 27, 1995 [JP] Japan ................... 7-272568
Feb. 8, 1996 [JP] Japan ................... 8-045663

[51] Int. Cl.⁶ .................. A61K 31/535; C07D 413/12
[52] U.S. Cl. ............... 514/235.5; 540/575; 540/611; 544/105; 544/141; 544/158; 544/159; 544/295; 544/336; 544/372; 544/373; 544/393; 546/19; 546/133; 546/208; 546/276.4; 546/335; 548/188; 548/201; 548/229; 548/314.7
[58] Field of Search .................. 544/141; 514/235.5

[56] References Cited

U.S. PATENT DOCUMENTS 5,214,191 5/1993 Kirschenheuter et al. .
5,240,956 8/1993 Kirschenheuter et al. .
5,314,910 5/1994 Kirschenheuter et al. .
5,336,681 8/1994 Imaki et al. .
5,403,850 4/1995 Imaki et al. .

FOREIGN PATENT DOCUMENTS 465802 10/1991 European Pat. Off. .

*Primary Examiner*—Robert W. Ramsuer
*Attorney, Agent, or Firm*—Watson Cole Stevens Davis, P.L.L.C.

[57] ABSTRACT

A sulfonamide derivatives of formula (I)

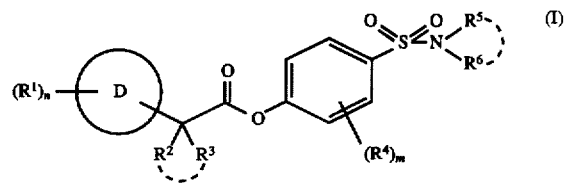

a non-toxic salts, an acid addition salts or a solvates thereof which has an inhibitory effect on elastase.

13 Claims, No Drawings

SULFONAMIDE DERIVATIVES

FIELD OF INVENTION

This invention relates to sulfonamide derivatives useful as pharmaceutical use. More particularly, this invention relates to:

(1) sulfonamide derivatives of the following formula:

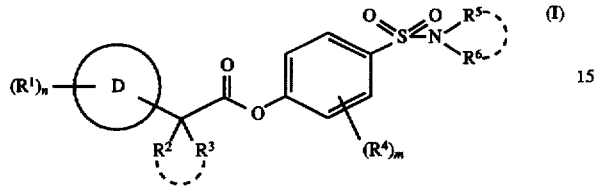

wherein all of the symbols are as hereinafter defined, and non-toxic salts, acid addition salts and solvates thereof, (2) processes for their preparation, and (3) pharmaceutical compositions containing them as active ingredient.

1. Background of the Invention

Lysosomal hydrolases of neutrophils have an important role in the defence reaction of organisms against tissue damage caused, for example, by microbes or inflammation.

Elastase and cathepsin G, which are neutral serine proteinases existed locally in azurophil granules play a part in the decomposition of connective tissue.

In particular, elastase degrades elastic connective tissue by cleaving the cross-linking of elastin which directly maintains the elasticity of e.g. lung tissue, by cleaving the hydrophobic part of protein [J. Cell. Biol., 40, 366 (1969)] and selectively degrading the cross-linking of collagen as well as elastin [J. Biochem., 84, 559 (1978)]. It also acts on tissue proteins such as proteoglycans [J. Clin. Invest., 57, 615 (1976)]. It will be seen therefore that, elastase plays an important role in the metabolism of connective tissue.

Elastase is inactivated by $\alpha_1$-proteinase inhibitor ($\alpha_1$-PI) which is a common inhibitor for serine proteinases in vivo and an imbalance of enzyme and inhibitor causes the destruction of tissue [Schweiz. Med. Wshr., 114, 895 (1984)].

The turnover of elastin in normal tissue is very slow [Endocrinology, 120, 92 (1978)], but pathological acceleration in degradation of elastin is found under various diseased conditions such as pulmonary emphysema [Am. Rev. Respir. Dis., 110, 254 (1974)], atherosclerosis [Lab. Invest., 22, 228 (1970)] and rheumatoid arthritis [in Neutral Proteases of Human Polymorphonuclear Leukocytes, Urban and Schwarzenberg, Baltimore—Munich (1978), page 390], which suggests a relationship between elastase and diseases [Infection Inflammation Immunity, 13, 13 (1983)].

2. Related Arts

In view of this background, many studies on the development of elastase inhibitors have been conducted recently, and various substances inhibiting elastase have been proposed and many patent applications have been filed.

For example, (1) it is disclosed in EP-A-0347168 that the compound of formula (A)

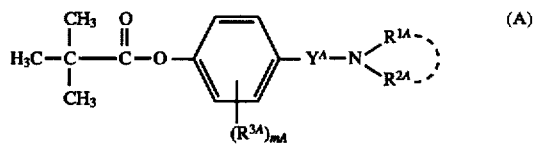

(wherein $Y^A$ is sulfonyl or carbonyl;

(i) $R^{1A}$ and $R^{2A}$, which may be the same or different, each represents, inter alia, hydrogen atom, C1–16 alkyl or a group of the formula

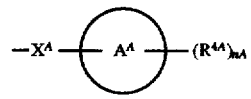

(wherein $X^A$ is bond, sulfonyl, C1–4 alkylene, C1–4 alkyl substituted by —COOH or benzyloxycarbonyl;

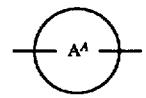

is carbocyclic ring or heterocyclic ring;

nA is 1–5; and $R^{4A}$ which may be the same or different, represents, inter alia, hydrogen atom, C1–8 alkyl, C1–14 alkoxy, C1–6 alkylthio, hydroxy, halogen atom, nitro, trihalomethyl, —$Z^{41A}$—$COOR^{43A}$, —$CONR^{41A}R^{42A}$, a group of the formula

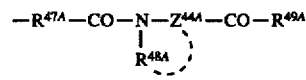

in which the group of formula

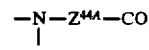

is an amino acid residue;

$R^{49A}$ is hydroxy, C1–4 alkoxy, amino, amino or carbamoyl substituted by one or two C1–4 alkyl, etc.) or (ii) $R^{1A}$ and $R^{2A}$ and the nitrogen atom bonded to $R^{1A}$ and $R^{2A}$ together represent a heterocyclic ring containing at least one nitrogen atom and substituted by —COOH or an unsubstituted heterocyclic ring containing at least one nitrogen atom;

$R^{3A}$ is hydrogen atom, hydroxy, C1–6 alkyl, etc.; and mA is 1–4) and non-toxic salts and acid addition salts thereof have an inhibitory activity on elastase;

(2) it is disclosed in EP-A-0465802 that the compound of formula (B)

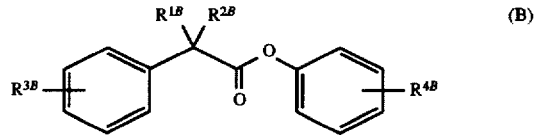

(wherein $R^{1B}$ and $R^{2B}$, which may be the same or different, each represent, hydrogen, C1–6 alkyl or C3–6 cycloalkyl, or $R^{1B}$ and $R^{2B}$ taken together represent —$(CH_2)_{nB}$— (in which nB is 1–6);

$R^{3B}$ is one to five of hydrogen, halogen, C1–12 haloalkyl, C1–12 alkyl, C1–12 alkoxy, C2–12 alkenyl, C3–12 cycloalkyl, mono or bicyclic aryl, —$Z^B R^{5B}$ (in which $Z^B$ is O, S, S(O) or SO$_2$; $R^{5B}$ is hydrogen, C1–18 alkyl, C3–12 cycloalkyl, or phenyl), —$NR^{6B}R^{7B}$ (in which $R^{6B}$ and $R^{7B}$, which may be the same or different, each represent, hydrogen, C1–12 alkyl, C3–6 cycloalkyl, phenyl, C1–12 alkoxy or —C(O)—$R^{3B}$, or $R^{6B}$ and $R^{7B}$ taken together represent —C(O)CH$_2$CH$_2$—C(O)—, —C(O)—C$_6$H$_4$—C(O)— or —(CH$_2$)$_{XB}$— (XB is 2, 3, 4, 5 or 6);), or morpholino, imizazolyl or piperazino, etc., bonded to phenyl ring on nitro atom; and $R^{4B}$ is one to five of hydrogen, halogen, nitro, —C(O)CH$_3$, S(O)$_{pB}R^{9B}$ (pB is 0, 1 or 2; $R^{9B}$ is hydroxy, —ONa, C1–12 alkyl optionally substituted, cycloalkyl optionally substituted))

and non-toxic pharmaceutically acceptable salts thereof have an inhibitory activity on elastase;

(3) it is disclosed in EP-A-0484949 that the compound of formula (C)

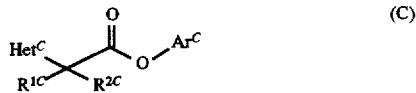
(C)

(wherein $R^{1C}$ and $R^{2C}$, which may be the same or different, each represent, hydrogen, C1–6 alkyl or C3–6 cycloalkyl, or $R^{1C}$ and $R^{2C}$ taken together represent —(CH$_2$)$_{nC}$— (in which nC is 1–6);

$Ar^C$ is optionally substituted phenyl; and $Het^C$ is heterocyclic ring containing at least one nitrogen atom, sulfur atom or oxygen atom)

have an inhibitory activity on elastase.

Few of the compounds known to have an inhibitory activity on elastase have been reported to show an inhibitory activity on elastase by oral administration. Most compounds could not be expected to show an effect by oral administration. In order to show activity by oral administration, pharmaceutical agents must be readily absorbed by the digestive organs and must maintain their activity until they are transported to an active site. Therefore, only those the compounds have good stability, absorbability and/or solubility in the digestive organs are expected to show sufficient activity by oral administration.

PURPOSE OF THE INVENTION

Energetic investigations have been carried out to find new compounds having inhibitory good activity on elastase and high safety. As a result, the present inventors have found that these aims may be accomplished by a sulfonamide derivatives of the formula (I). Further, we have found that the new compounds have good stability, absorbability and solubility and are active as elastase inhibitors by oral administration.

SUMMARY OF THE INVENTION

The present invention provides:

(1) a sulfonamide derivative of formula (I):

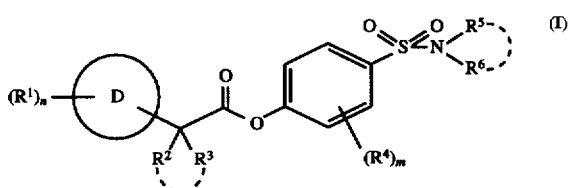
(I)

wherein $R^1$ is C1–8 alkyl, C1–8 alkoxy, hydroxy, keto, nitro, halogen atom, trihalomethyl, cyano, amidino, —COOR$^7$ (in which R$^7$ is hydrogen atom or C1–8 alkyl), or

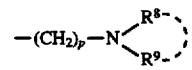

(in which p is an integer from 0 to 4, and $R^8$ and $R^9$ each, independently, is hydrogen atom, C1–4 alkyl, C2–5 acyl, —COOR$^{10}$ (in which R$^{10}$ is hydrogen atom or C1–8 alkyl), —CONR$^{11}$R$^{12}$ (in which R$^{11}$ and R$^{12}$ each, independently, is hydrogen atom or C1–4 alkyl),

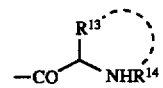

(in which

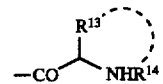

is an α-amino acid residue), or $R^8$ and $R^9$ taken together with the nitrogen atom to which they are attached represent an aliphatic heterocyclic ring which is unsubstituted or substituted by C1–4 alkyl or phenyl C1–4 alkyl);

n is an integer from 0 to 5;

is a carbocyclic ring or heterocyclic ring;

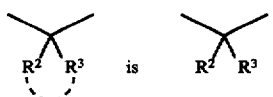

in which $R^2$ and $R^3$ each, independently, is hydrogen atom, C1–4 alkyl, C1–4 alkoxy, halogen atom, trihalomethyl or phenyl, or $R^2$ and $R^3$, taken together, represent C1–4 alkylidene, or

in which $R^2$ and $R^3$, taken together with the carbon atom to which they are attached represent C3–7 cycloalkyl;

$R^4$ is C1–4 alkyl or C1–4 alkoxy or two of $R^4$, attached to the benzene nucleus at ortho positions relative to each other, taken together, represent C3–5 alkylene;

m is an integer from 0 to 4; and

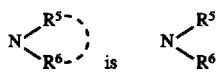

in which $R^5$ and $R^6$ each, independently, is
1) hydrogen atom,
2) hydroxy,
3) C1–8 alkyl,
4) C1–8 alkoxy
5) phenyl C1–4 alkoxy,
6) amidino,
7) —M—$R^{16}$ (in which M is single bond or C1–8 alkylene, and $R^{16}$ is
i) —$NR^{17}R^{18}$ (in which $R^{17}$ and $R^{18}$ each, independently, is hydrogen atom or C1–4 alkyl),
ii) —$CONR^{19}R^{20}$ (in which $R^{19}$ and $R^{20}$ each, independently, is hydrogen atom or C1–4 alkyl),
iii)

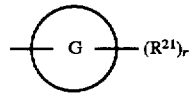

(in which

is a carbocyclic ring,
r is an integer from 0 to 5, and
$R^{21}$ is C1–4 alkyl, C1–4 alkoxy, nitro, amidino, —$COOR^{22}$ (in which $R^{22}$ is hydrogen atom, C1–8 alkyl, phenyl or phenyl C1–4 alkyl), —$SO_3H$, —$CONR^{23}$—E—$R^{24}$ (in which $R^{23}$ is hydrogen atom or C1–4 alkyl, E is 1–4 alkylene and $R^{24}$ is —$COOR^{25}$ (in which $R^{25}$ is hydrogen atom, C1–8 alkyl, phenyl or phenyl C1–4 alkyl) or tetrazole ring), tetrazole ring or morpholino ring),
iv) heterocyclic ring, unsubstituted or substituted by 1 to 4 substituents selected from C1–4 alkyl, C1–4 alkoxy, hydroxy, phenyl C1–4 alkyl, —$COOR^{26}$ (in which $R^{26}$ is hydrogen atom, C1–8 alkyl, phenyl or phenyl C1–4 alkyl), hydroxy C1–4 alkyl or C2–4 alkoxyalkyl),
8) C1–8 alkyl substituted by one or two of —$OR^{27}$ (in which $R^{27}$ is hydrogen atom, C1–4 alkyl, C2–4 alkoxyalkyl or C2–4 alkyl substituted by —$OR^{28}$ (in which $R^{28}$ is hydrogen atom or C2–4 alkoxyalkyl)),
9) —J—$COOR^{29}$ (in which $R^{29}$ is hydrogen atom, C1–8 alkyl, phenyl or phenyl C1–4 alkyl, and
J is a single bond, —$(CH_2)_s$— or

(in which s is an integer from 2 to 6, and $R^{30}$ and $R^{31}$ each, independently, is
i) hydrogen atom,
ii) C1–8 alkyl, iii) —$COOR^{32}$ (in which $R^{32}$ is hydrogen atom, C1–8 alkyl, phenyl or phenyl C1–4 alkyl),
iv) carbocyclic or heterocyclic ring, unsubstituted or substituted by one or more substituents selected from C1–4 alkyl, C1–4 alkoxyalkyl, amino, nitro, hydroxy, halogen atom, nitrile, guanidino and amidino, or
v) C1–8 alkyl substituted by one or more substituents selected from hydroxy, —$COOR^{33}$ (in which $R^{33}$ is hydrogen atom, C1–8 alkyl, phenyl or phenyl C1–4 alkyl), —$NR^{34}R^{35}$ (in which $R^{34}$ and $R^{35}$ each, independently, is hydrogen atom or C1–4 alkyl), carbocyclic or heterocyclic ring, unsubstituted or substituted by one or more substituents selected from C1–4 alkyl, C1–4 alkoxyalkyl, amino, nitro, hydroxy, halogen atom, nitrile, guanidino and amidino, with the proviso that a carbon atom of C1–8 alkyl may be replaced by a sulfur atom), or

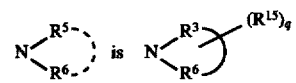

in which $R^5$ and $R^6$, taken together with the nitrogen atom to which they are attached represent a heterocyclic ring,
q is an integer from 0 to 4, and
$R^{15}$ is
1) hydroxy,
2) keto,
3) protected keto,
4) C1–4 alkyl,
5) C1–4 alkoxy,
6) phenyl,
7) phenoxy,
8) phenyl C1–4 alkyl,
9) phenyl C1–4 alkoxy,
10) nitro,
11) —$COOR^{36}$ (in which $R^{36}$ is hydrogen atom, C1–8 alkyl, C1–4 alkyl substituted by —$CONR^{37}R^{38}$ (in which $R^{37}$ and $R^{38}$ each, independently, is hydrogen atom or C1–4 alkyl), C1–4 alkyl substituted by —$NR^{39}R^{40}$ (in which $R^{39}$ and $R^{40}$ each, independently, is hydrogen atom or C1–4 alkyl), C1–4 alkyl substituted by —$OR^{41}$ (in which $R^{41}$ is C2–4 alkyl substituted by —$OR^{42}$ (in which $R^{42}$ is hydrogen atom or C2–4 alkoxyalkyl)) or C1–4 alkyl substituted by piperazino ring),
12) —$NR^{43}R^{44}$ (in which $R^{43}$ and $R^{44}$ each, independently, is hydrogen atom, C1–4 alkyl or C2–5 acyl),
13) —$CONR^{45}R^{46}$ (in which $R^{45}$ and $R^{46}$ each, independently, is hydrogen atom, hydroxy, C1–4 alkyl, phenyl C1–4 alkyloxy or C1–4 alkyl substituted by hydroxy or —$COOR^{47}$ (in which $R^{47}$ is hydrogen atom or C1–8 alkyl),),
14) C1–4 alkyl substituted by one or more substituents selected from hydroxy, —$COOR^{48}$ (in which $R^{48}$ is hydrogen atom or C1–8 alkyl), —$NR^{49}R^{50}$ (in which $R^{49}$ and $R^{50}$ each, independently, is hydrogen atom or C1–4 alkyl), —$OSO_3H$ or 5- or 6-membered heterocyclic ring containing one or two nitrogen atoms,
15) 5- or 6-membered heterocyclic ring containing one or two nitrogen atoms,
16) halogen atom, 17) —CHO, or 18) —NR$^{51}$—COOR$^{52}$ (in which R$^{51}$ and R$^{52}$ each, independently, is hydrogen atom or C1-8 alkyl); or a non-toxic salt, acid addition salt or solvate thereof, (2) processes for their preparation, and (3) pharmaceutical compositions containing them as active ingredient.

COMPARISON

The sulfonamide derivatives of the present invention are novel compared with compounds disclosed in prior arts.

To summarize, the compounds of formula (A) in described in EP-A-0347168 necessarily contain a pivaloyloxy group. In contrast, the compounds of the present invention have a ring D which may be substituted by various substituent R$^1$.

Thus the compounds of the present invention have a chemical structure quite different from that of the compounds of formula (A).

The compound of the formula (B) in described in EP-A-0465802 include compounds in which R$^{4B}$ represents S(O)$_{pB}$R$^{9B}$. R$^{9B}$ can represent hydroxy, —ONa, optionally substituted C1-12 alkyl or optionally substituted cycloalkyl, but can not represent amino group. Further, the compounds of formula (C) described in EP-A-0484949 include those in which a substituent of Ar$^C$ represents S(O)$_{pC}$R$^{9C}$. R$^{9C}$ can represents hydroxy, —ONa, optionally substituted C1-12 alkyl or optionally substituted cycloalkyl, but not represent amino group.

In contract, the compounds of the present invention have sulfonamide group which may be substituted by various substituents. Thus the compounds of the present invention have a chemical structure quite different from that of the compounds of formula (B) and (C).

Furthermore, related compounds show no activity by oral administration, but some compounds in the present invention have good stability, absorbability and solubility, and are, therefore, active as elastase inhibitors by oral administration.

DETAILED DESCRIPTION OF THE INVENTION

In the formula (I), C1-4 alkyl represented by R$^2$, R$^3$, R$^4$, R$^8$, R$^9$, R$^{11}$, R$^{12}$, R$^{15}$, R$^{17}$, R$^{18}$, R$^{19}$, R$^{20}$, R$^{21}$, R$^{23}$, R$^{27}$, R$^{34}$, R$^{35}$, R$^{36}$, R$^{37}$, R$^{38}$, R$^{39}$, R$^{40}$, R$^{43}$, R$^{44}$, R$^{45}$, R$^{46}$, R$^{49}$, R$^{50}$, and substituents of aliphatic heterocyclic ring, carbocyclic ring or heterocyclic ring means methyl, ethyl, propyl, butyl and isomers thereof.

In the formula (I), C1-8 alkyl represented by R$^1$, R$^5$, R$^6$, R$^7$, R$^{10}$, R$^{22}$, R$^{25}$, R$^{26}$, R$^{29}$, R$^{30}$, R$^{31}$, R$^{32}$, R$^{33}$, R$^{36}$, R$^{47}$, R$^{48}$, R$^{51}$ and R$^{52}$ means methyl, ethyl, propyl, butyl, pentyl, hexyl, heptyl, octyl and isomers thereof.

In the formula (I), C2-4 alkyl represented by R$^{27}$ and R$^{41}$ means ethyl, propyl, butyl and isomers thereof.

In the formula (I), C3-5 alkylene represented by two of R$^4$ attached at ortho position relative to each other means trimethylene, tetramethylene, pentamethylene and isomers thereof.

In the formula (I), C1-8 alkylene represented by M means methylene, ethylene, trimethylene, tetramethylene, pentamethylene, hexamethylene, heptamethylene, octamethylene and isomers thereof.

In the formula (I), C1-4 alkylene represented by E means methylene, ethylene, trimethylene, tetramethylene and isomers thereof.

In the formula (I), phenyl C1-4 alkyl or phenyl C1-4 alkoxy means C1-4 alkyl or C1-4 alkoxy substituted by a phenyl group.

In the formula (I), phenyl C1-4 alkyl represented by R$^{29}$, R$^{32}$, R$^{33}$, R$^{15}$ and substituent of aliphatic heterocyclic ring or heterocyclic ring means methyl, ethyl, propyl, butyl and isomers thereof, which are substituted by a phenyl group.

In the formula (I), phenyl C1-4 alkoxy represented by R$^5$, R$^6$, R$^{15}$, R$^{45}$ and R$^{46}$ means methoxy, ethoxy, propoxy, butoxy and isomers thereof, which are substituted by a phenyl group.

In the formula (I), C2-5 acyl represented by R$^8$, R$^9$, R$^{43}$ and R$^{44}$ means acetyl, propionyl, butyryl, valeryl and isomers thereof.

In the formula (I), C2-4 alkoxyalkyl represented by R$^{27}$, R$^{28}$, R$^{42}$ and substituent of heterocyclic ring means methoxymethyl, ethoxymethyl, propoxymethyl, methoxyethyl, ethoxyethyl, methoxypropyl and isomers thereof.

In the formula (I), C1-8 alkoxy represented by R$^1$, R$^5$ and R$^6$ means methoxy, ethoxy, propoxy, butoxy, pentyloxy, hexyloxy, heptyloxy, octyloxy and isomers thereof.

In the formula (I), C1-4 alkoxy represented by R$^2$, R$^3$, R$^4$, R$^{15}$, R$^{21}$ and substituents of carbocyclic ring or heterocyclic ring means methoxy, ethoxy, propoxy, butoxy and isomers thereof.

In the formula (I), halogen atom represented by R$^1$, R$^2$, R$^3$ and R$^{15}$ means fluorine, chlorine, bromine and iodine.

In the formula (I), the α-amino acid residue represented by

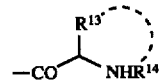

may be any α-amino acid residue. For example, it may be a residue of glycine, alanine, serine, threonine, cystine, valine, methionine, leucine, isoleucine, phenylalanine, tyrosine, tryptophan, aspartic acid, glutamic acid, arginine, glutamine, lysine, histidine or proline.

In the formula (I), C3-7 cycloalkyl represented by R$^2$ and R$^3$, taken together with the carbon atom to which they are attached means cyclopropyl, cyclobutyl, cyclopentyl, cyclohexyl and cycloheptyl.

In the formula (I), C1-4 alkylidene represented by R$^2$ and R$^3$, taken together, means methylidene, ethylidene, propylidene, butylidene and isomers thereof.

In the formula (I), aliphatic heterocyclic ring represented by R$^8$ and R$^9$, taken together with the nitrogen atom to which they are attached preferably means 5–15 membered mono- or bi-cyclic saturated heterocyclic ring or partly saturated heterocyclic ring containing one or two nitrogen atom or one nitrogen atom and one sulfur atom or oxygen atom. Example include pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, dihydrooxazole, tetrahydrooxazole, dihydroisooxazole, tetrahydroisooxazole, dihydrothiazole, tetrahydrothiazole, dihydroisothiazole, tetrahydroisothiazole, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole and perhydrobenzoimidazole rings.

In the formula (I), carbocyclic ring represented by

$R^{30}$ and $R^{31}$ preferably means 3–15 membered mono- or poly-cyclic aromatic hydrocarbon ring or aliphatic hydrocarbon ring. Examples include cyclopentadiene, benzene, pentalene, indene, naphthalene, azulene, cyclopropane, cyclobutane, cyclopentane, cyclopentene, cyclohexane, cyclohexene, cyclohexadiene, cycloheptane, dihydroindene, perhydroindene, dihydronaphthalene, tetranaphthalene, perhydronaphthalene, bicyclo[2.2.1]heptane, bicyclo[3.2.2]nonane and adamantane rings.

When the ring contains two free valencies, two substituents may be attached to the same carbon atom or to different carbon atoms.

In the formula (I), heterocyclic ring represented by

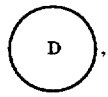

$R^{16}$, $R^{30}$ and $R^{31}$ preferably means 5–15 membered mono- or bi-cyclic aromatic heterocyclic ring, saturated heterocyclic ring or partly saturated heterocyclic ring containing one to four nitrogen atoms, one or two sulfur atoms, one or two oxygen atoms or one nitrogen atom and one sulfur atom or oxygen atom. Example include pyrrole, imidazole, pyrazole, pyridine, pyrazine, pyrimidine, pyridazine, azepine, diazepine, furan, pyran, oxepine, thiophene, thiaine (thiopyran), thiepine, oxazole, isooxazole, thiazole, isothiazole, oxazine, oxazepine, thiazine, thiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole, pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, hexahydrodiazepine, dihydrofuran, tetrahydrofuran, dihydropyran, tetrahydropyran, dihydrothiophene, tetrahydrothiophene, dihydrothiaine (dihydrothiopyran), tetrahydrothiaine (tetrahydrothiopyran), dihydrooxazole, tetrahydrooxazole, dihydroisooxazole, tetrahydroisooxazole, dihydrothiazole, tetrahydrothiazole, dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole, dihydrobenzoxazine, 1,3-dioxaindan, 1,4-benzodioxane, quinuclidine, triazole and tetrazole rings.

In the formula (I), heterocyclic ring represented by

that is, $R^5$ and $R^6$, taken together with the nitrogen atom to which they are attached preferably means 3–15 membered mono- or bi-cyclic aromatic heterocyclic ring, saturated heterocyclic ring or partly saturated heterocyclic ring containing one or two nitrogen atoms or one nitrogen atom and one sulfur atom or oxygen atom. Example include pyrrole, imidazole, pyrazole, pyridine, pyrazine, pyrimidine, pyridazine, azepine, diazepine, aziridine, azetidine, pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, hexahydrodiazepine, oxazole, isooxazole, thiazole, isothiazole, oxazine, oxazepine, thiazine, thiazepine, indole, isoindole, indazole, quinoline, isoquinoline, phthalazine, naphthyridine, quinoxaline, quinazoline, cinnoline, benzoxazole, benzothiazole, benzoimidazole, dihydrooxazole, tetrahydrooxazole, dihydroisooxazole, tetrahydroisooxazole, dihydrothiazole, tetrahydrothiazole, dihydroisothiazole, tetrahydroisothiazole, morpholine, thiomorpholine, indoline, isoindoline, perhydroindole, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole, 7-azabicyclo[3.2.1]octane and 3-azabicyclo[3.2.2]nonane rings.

In the formula (I), 5- or 6-membered heterocyclic ring containing one or two nitrogens atom represented by $R^{15}$ means, for example, pyrrole, imidazole, pyrazole, pyridine, pyrazine, pyrimidine, pyridazine, pyrroline, pyrrolidine, imidazoline, imidazolidine, pyrazoline, pyrazolidine, piperidine, piperazine, tetrahydropyrimidine ortetrahydropyridazine.

In the formula (I), examples of the ring represented by

to which a protected keto group is bonded, include 1,3-dioxolane and spiro ring derivatives of

One or two keto groups as substituent $R^{15}$ may be attached to the same or different sulfur atom. In this case, one group should be treated as one $R^{15}$.

m preferably represents 0, 1 or 2, more preferably 0 or 1.

$R^4$ preferably represents alkyl or alkoxy of 1–4 carbon atoms, for example methyl, ethyl, isopropyl, methoxy, ethoxy or isopropoxy. Methyl is especially preferred. When one or two substituents $R^4$ are present they preferably occupy one or both positions adjacent to the oxygen atom attached to the phenyl ring; compounds in which two substituents are present on the positions ortho and meta to the oxygen attached to the phenyl ring also constitute a feature of the invention; two such substituents may together form a five membered ring fused to the phenyl ring.

Compound in which m is 1 and $R^4$ represents methyl in the ortho position relative to the oxygen atom attached to the phenyl ring are especially preferred.

One of $R^2$ and $R^3$ preferably represents hydrogen, methyl, ethyl, or methoxy and the other represents methyl, ethyl, isopropyl, phenyl or trifluoromethyl or $R^2$ and $R^3$ together with the carbon atom to they are attached represent ethylidene or cycloalkyl of 3–6 carbon atoms.

D preferably represents phenyl, naphthyl (preferably 1- or 2-naphthyl), thiophenyl (preferably thiophen-2-yl), cyclohexyl, pyridinyl, (preferably pyridin-3-yl), thiazolyl (preferably thiazol-4-yl)imidazolinyl (preferably imidazolin-2-yl), benzimidazolyl (preferably benzimidazol-5-yl), 2H-1,4-benzoxazin-3-on-6-yl, or 1,3-benzodioxol-5-yl, or 1H-1-methyl-2-pyridon-3-yl. Phenyl is especially preferred.

n preferably represents 0, 1, 2 or 3, preferably 0 or 1. $R^1$ preferably represents alkyl of 1–4 carbon atoms, e.g. methyl; alkoxy of 1–4 carbon atoms, e.g., methoxy; amino; amino substituted by two alkyl groups each of 1–4 carbon atoms, for example dimethylamino; methyl substituted by carbamoyl; methyl substituted by alkanoyl of 2–5 carbon atoms for example by acetyl; nitro; hydroxy; cyano; carboxy; trihalomethyl, e.g., trifluoromethyl; amidino; amino substituted by alkoxycarbonyl; halogen, e.g., chlorine; pyrrolidinyl; piperidinyl; perhydroazepinyl; or morpholinyl or piperazinyl optionally substituted on the 4-position by benzyl.

Compounds in which D represents mono substituted phenyl constitute a feature of the invention; when D is substituted phenyl at least one substituent is preferably on the 4-position. Preferred 4-substituted phenyl groups are those in which the substituent is a 5-, 6- or 7-membered nitrogen-containing ring attached to phenyl via the nitrogen atom: pyrrolidin-1-yl is preferred.

In the grouping $NR^5R^6$, when $R^5$ and $R^6$, taken together with the nitrogen atom to which they are attached do not represent a heterocyclic ring, the grouping $NR^5R^6$ preferably represents hydrogen; methyl; ethyl; propyl; methoxy; benzyl; methoxyethoxyethyl; 1-hydroxyethyl; hydrogen is especially preferred, and the other represents phenyl; phenyl substituted by substituents, e.g., 2-((1-carboxymethyl)aminocarbonyl)phenyl, 4-nitrophenyl; heterocyclic ring, e.g., quinuclidine, piperidine, pyridine, imidazole, morpholine, tetrazole; C1–8 alkyl substituted by heterocyclic ring, e.g., piperazin-1-ylethyl, piperadin-1-ylethyl, morpholin-1-ylethyl, pyridin-2-ylethyl, pyrrol-2-ylethyl; morpholin-1-ylethyl is especially preferred.

In the grouping $NR^5R^6$, when $R^5$ and $R^6$, taken together with the nitrogen atom to which they are attached represent a heterocyclic ring, the ring preferably represents pyrrolidine; indole; indoline; perhydroindole; benzoimldazole; morpholine; piperidine; piperazine; 7-azabicyclo[3.2.1]octane; 3-azabicyclo[3.2.2]nonane, tetrahydrooxazole; tetrahydrothiazole; imidazole; hexahydrodiazepine; aziridine; azetidine; piperazine is especially preferred.

In the grouping $NR^5R^6$, when $R^5$ and $R^6$, taken together with the nitrogen atom to which they are attached represent a heterocyclic ring, $R^{15}$ preferably represents hydroxy; C1–4 alkyl substituted by a hydroxy, e.g., hydroxymethyl; C1–4 alkyl substituted by a heterocyclic ring, e.g., pyrrolidin-1-ylmethyl; benzyloxy; amino; methoxy; dimethylamino; acetylmino; methyl; nitro; halogen, e.g., fluorine; keto; carboxy; ester, e.g., ethoxycarbonyl, t-butoxycarbonyl, 2-aminoethoxycarbonyl, 2-(2-hydroxyethoxy) ethoxycarbonyl, 2-(piperazin-1-yl)ethoxycarbonyl; amide, e.g., carboxymethylaminocarbonyl; carboxy is especially preferred.

In the grouping $NR^5R^6$, when $R^5$ and $R^6$, taken together with the nitrogen atom to which they are attached represent a heterocyclic ring, q preferably represents 0, 1 or 2, more preferably 0 or 1.

Throughout the specification including claims, it may be easily understood by those skilled in the art, that all isomers are included in the present invention. For example, the alkyl, alkylene and alkenylene groups include straight-chain and also branched-chain ones. Double bond in alkenylene includes E, Z and EZ mixture. Accordingly, all isomers produced by the existence of asymmetric carbon atoms are included in the present invention when groups such as branched-chain alkyl are present.

The compounds of the formula (I), of the present invention may be converted into the corresponding non-toxic salts or acid addition salts by methods known per se.

Water-soluble salts are preferred. Suitable salts, for example, include salts of alkali metals (e.g., potassium or sodium), salts of alkaline earth metals (e.g., calcium or magnesium), ammonium salts, salts of pharmaceutically-acceptable organic amines (e.g., tetramethylammonium, triethylamine, methylamine, dimethylamine, cyclopentylamine, benzylamine, phenethylamine, piperidine, monoethanolamine, diethanolamine, tris (hydroxymethyl)amine, lysine, arginine or N-methyl-D-glucamine etc.).

Water-soluble acid addition salts are also preferred. Suitable acid addition salts, for example, include the salts with inorganic acids such as hydrochloric acid, hydrobromic acid, sulfuric acid, phosphoric acid and nitric acid, and the salts with organic acids such as acetic acid, trifluoroacetic acid, lactic acid, tartaric acid, oxalic acid, fumaric acid, maleic acid, benzenesulfonic acid, toluenesulfonic acid, isethionic acid, glucuronic acid and gluconic acid.

The compounds of the formula (I) or salts, of the present invention may be converted into the corresponding solvates by methods known per se.

Water-soluble solvates are preferred. Suitable solvates, for example, include the salts with water or with alcohol solvations such as ethanol.

Preferred compounds of the present invention are of the following formulae (I-A1), (I-A2), (I-B1) and (I-B2).

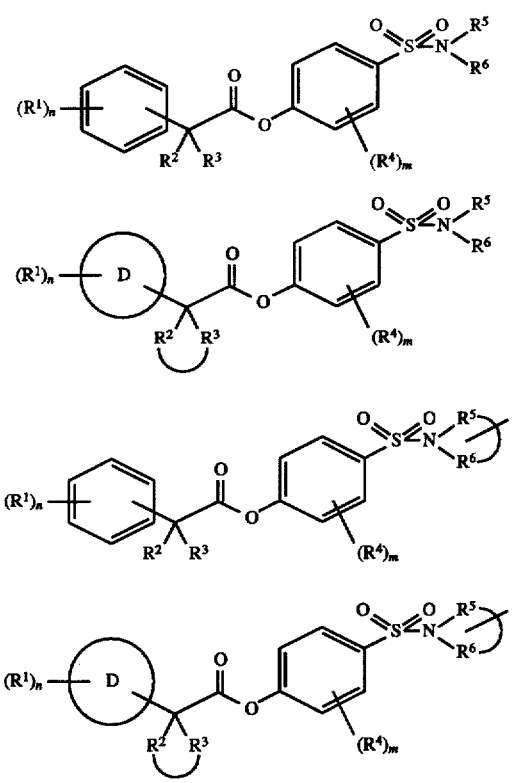
(wherein all symbols are as hereinbefore defined).
Representative compounds of the present invention are illustrated by the compounds in the following Tables 1–46 and the non-toxic salts and acid addition salts thereof.
In the Tables, Me is methyl, Et is ethyl, Pr is propyl, iPr is isopropyl and tBu is tert-butyl.

TABLE 1-continued
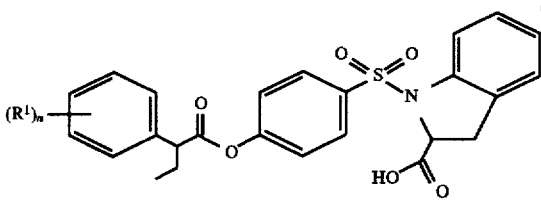
(I-1)
| No. | (R¹)ₙ— |
|---|---|
| 13 | 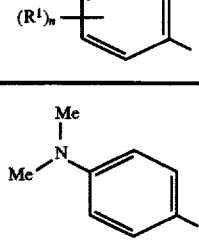 |
| 14 | 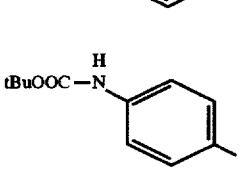 |
| 15 | 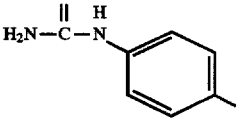 |
| 16 | 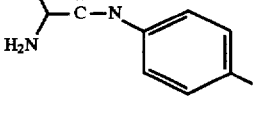 |
| 17 | 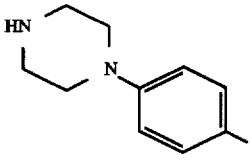 |
| 18 | 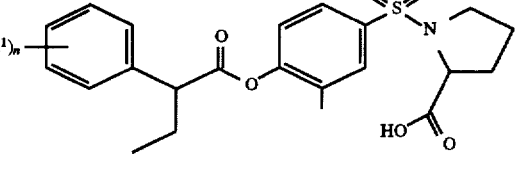 |
TABLE 2
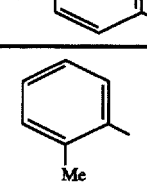
(I-2)
| No. | (R¹)ₙ— |
|---|---|
| 1 | 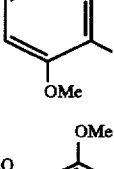 |
| 2 | 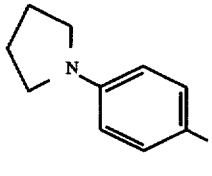 |
| 3 | 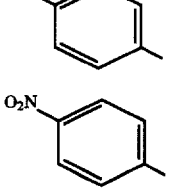 |
| 4 | 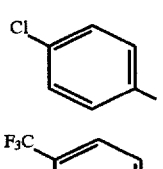 |
| 5 | 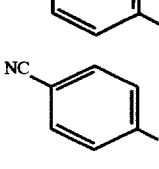 |
| 6 | 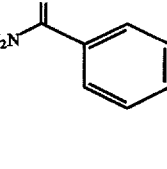 |
| 7 |  |
| 8 | |
| 9 | |
| 10 | |

TABLE 2-continued
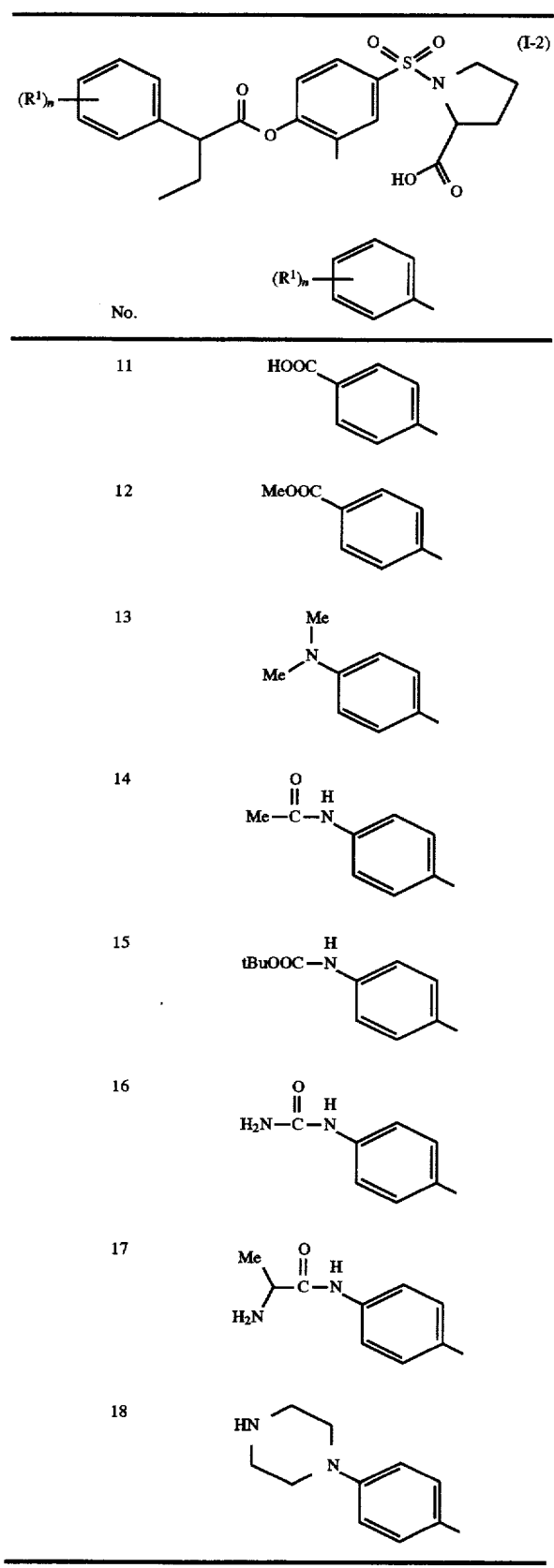
TABLE 3
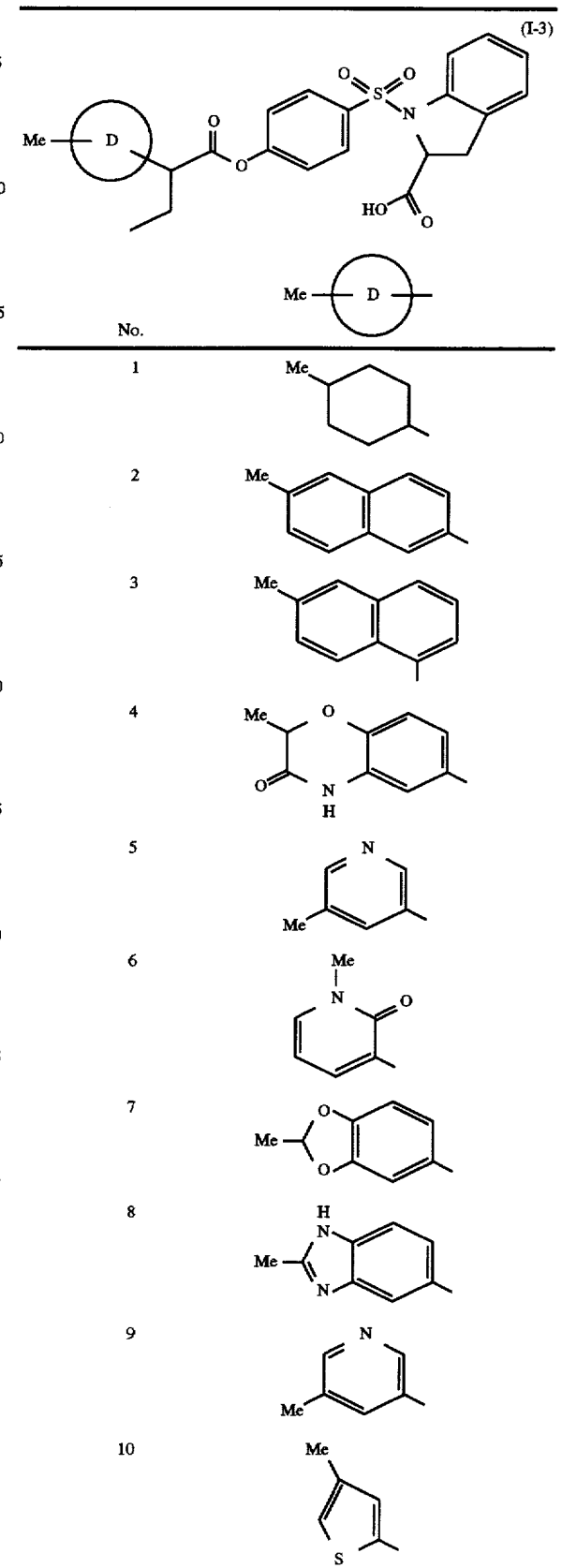

TABLE 4

(I-4)

TABLE 5

(I-5)

TABLE 5-continued
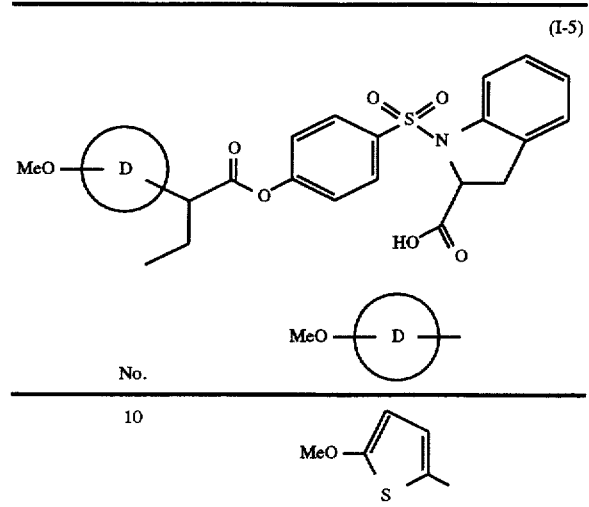
| No. | |
|---|---|
| 10 | 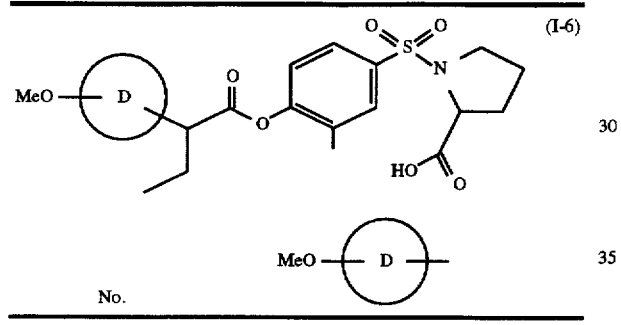 |
TABLE 6
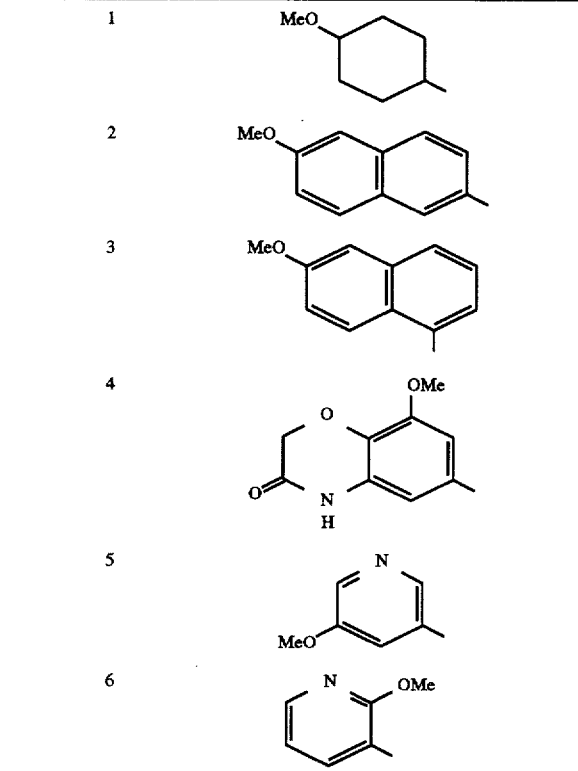
TABLE 6-continued
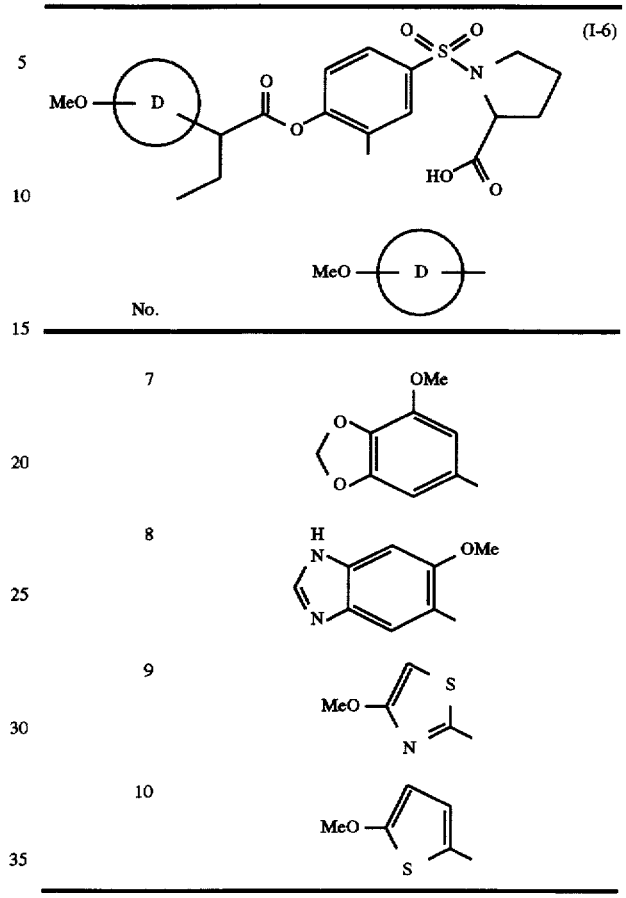
TABLE 7
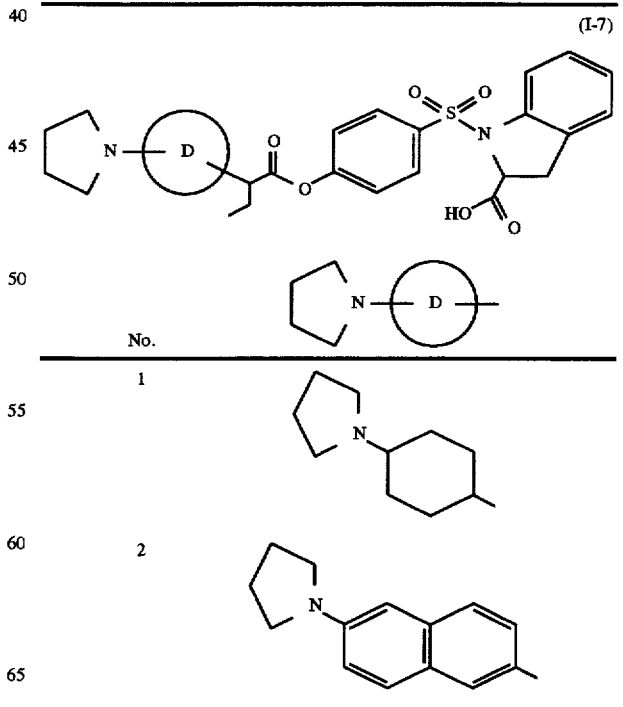

TABLE 7-continued (I-7)

[Structure shown with pyrrolidine-N-(D)-CH(Et)-C(O)O-C6H4-SO2-N(phenyl with CH2-CH(COOH)) group]

| No. | (D) group |
|-----|-----------|
| 3 | 6-pyrrolidinyl-naphthalene (methyl-substituted) |
| 4 | pyrrolidinyl-benzoxazinone (methyl-substituted) |
| 5 | 3-pyrrolidinyl-5-methylpyridine |
| 6 | 5-pyrrolidinyl-3-methyl-2(1H)-pyridinone |
| 7 | pyrrolidinyl-methylenedioxybenzene (methyl-substituted) |
| 8 | 2-pyrrolidinyl-5-methylbenzimidazole |
| 9 | pyrrolidinyl-methylthiazole |
| 10 | 2-pyrrolidinyl-5-methylthiophene |

TABLE 8

(I-8)

[Structure shown with pyrrolidine-N-(D)-CH(Et)-C(O)O-C6H3(CH3)-SO2-N-pyrrolidine-COOH group]

| No. | (D) group |
|-----|-----------|
| 1 | 4-methylcyclohexyl-pyrrolidine |
| 2 | 6-pyrrolidinyl-2-methylnaphthalene |
| 3 | 6-pyrrolidinyl-naphthalene (methyl-substituted) |
| 4 | pyrrolidinyl-benzoxazinone (methyl-substituted) |

TABLE 8-continued
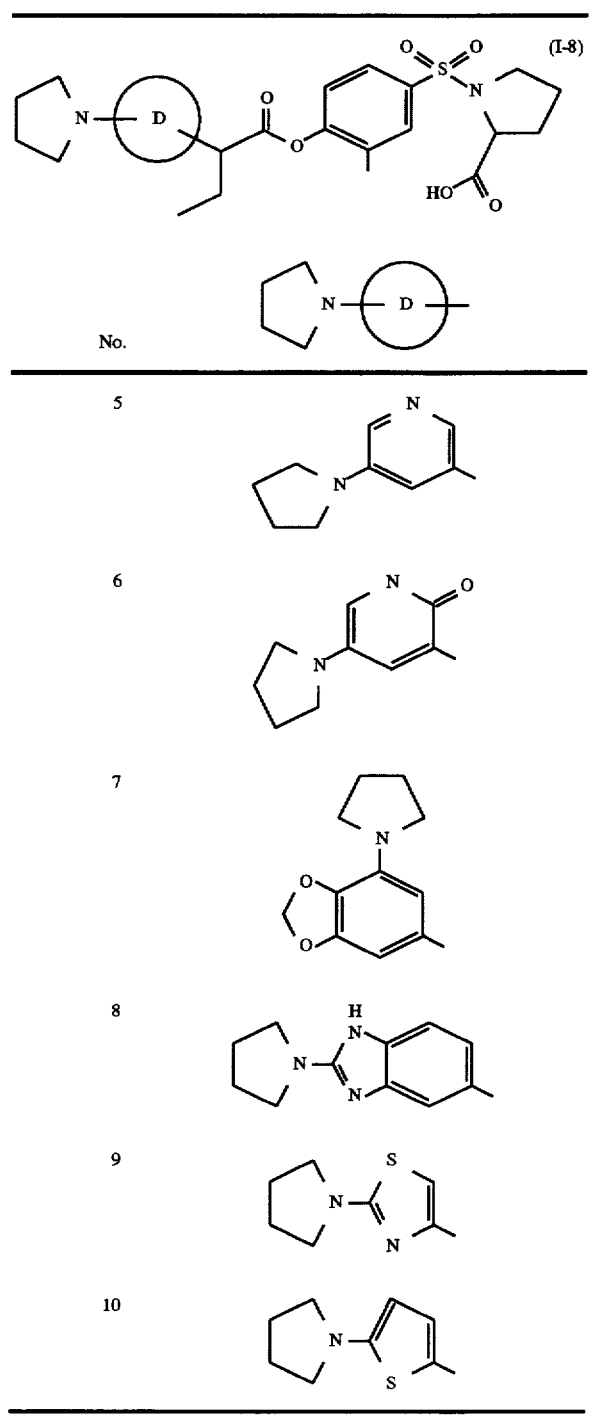
TABLE 9
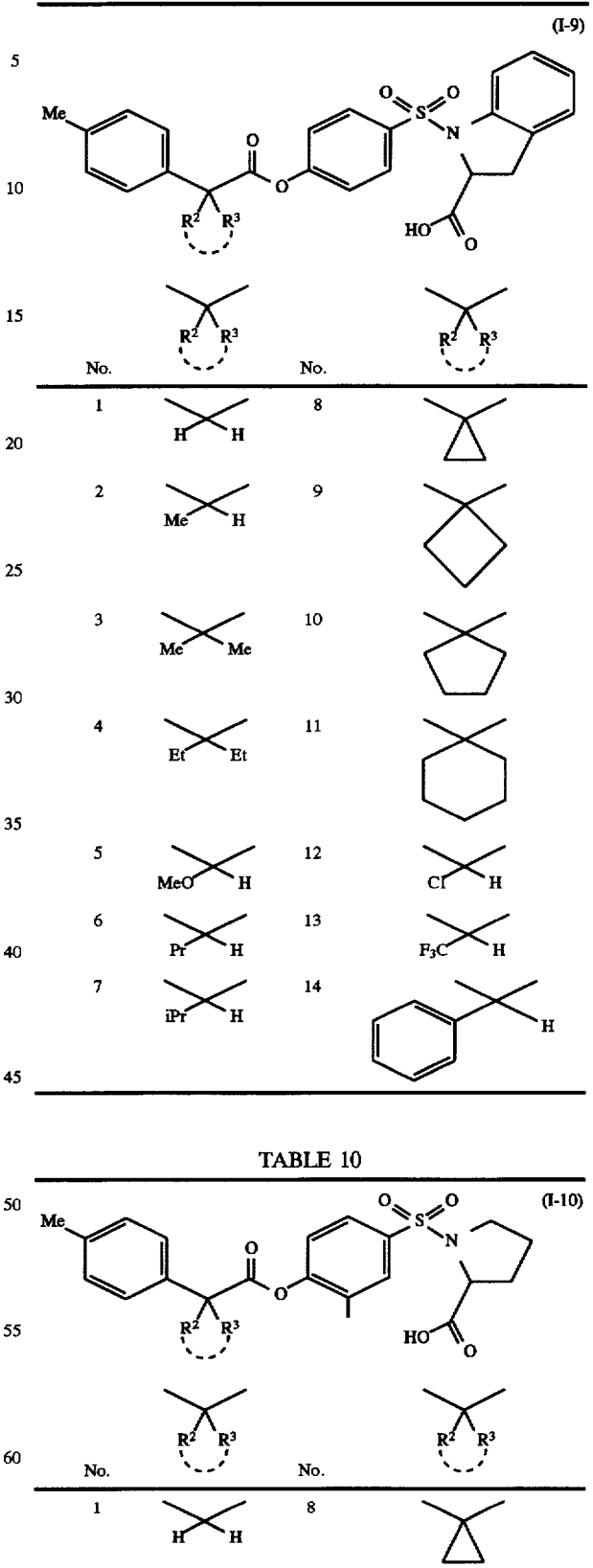
TABLE 10

TABLE 10-continued
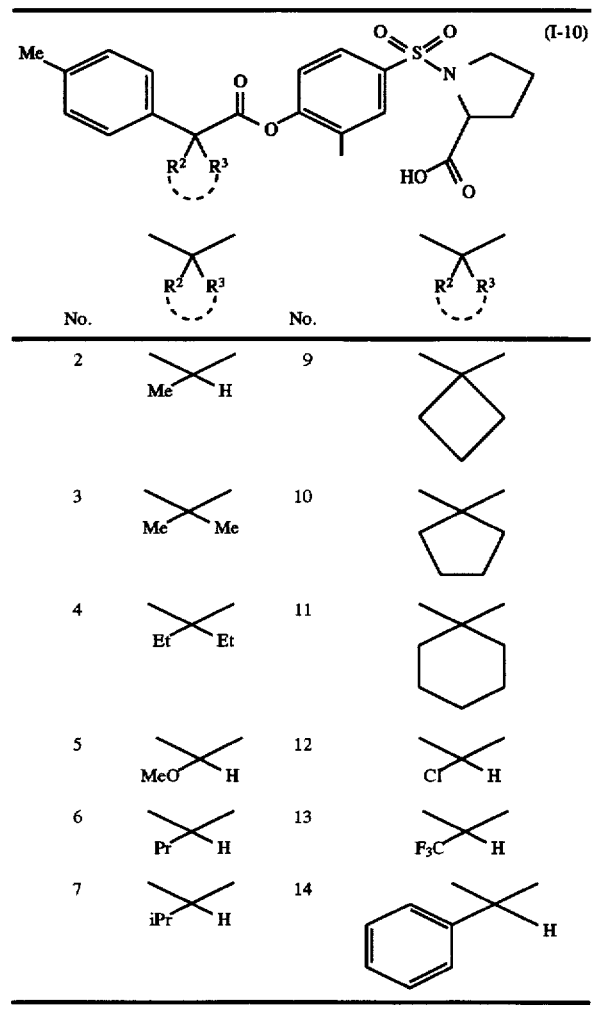
(I-10)
TABLE 11
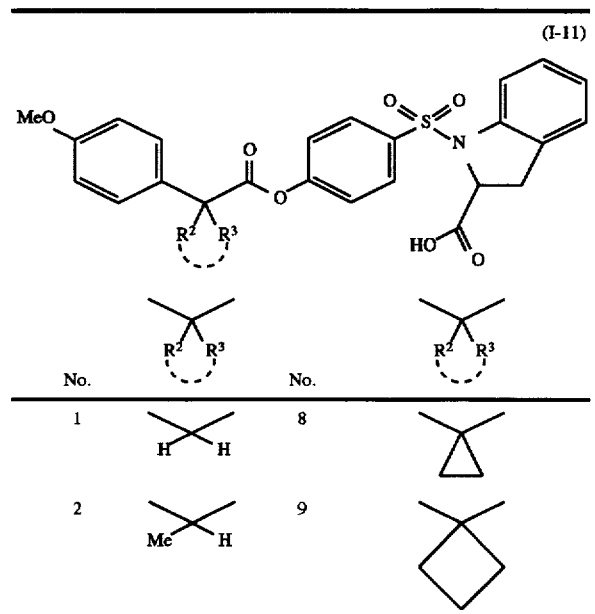
(I-11)
TABLE 11-continued
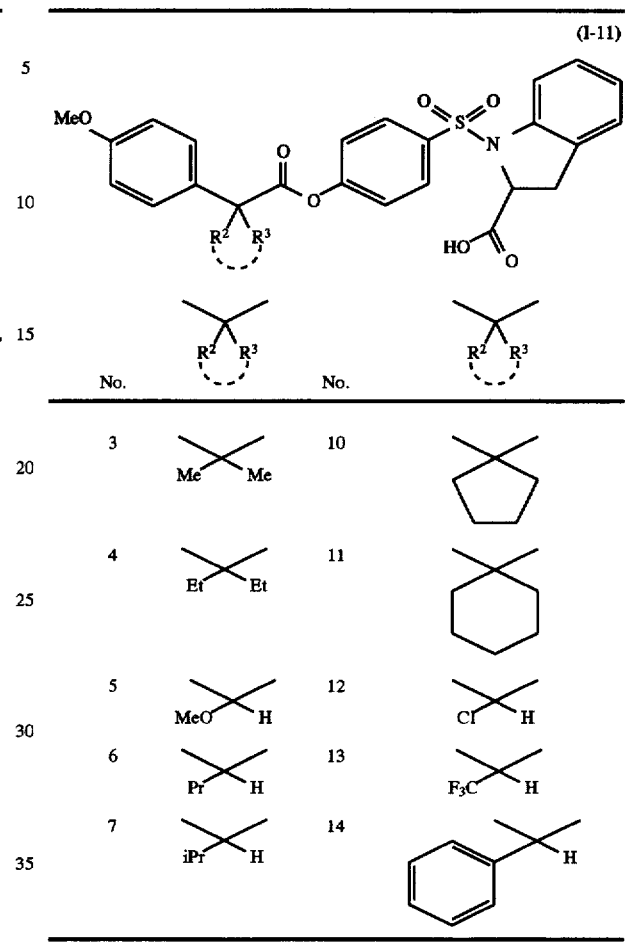
(I-11)
TABLE 12
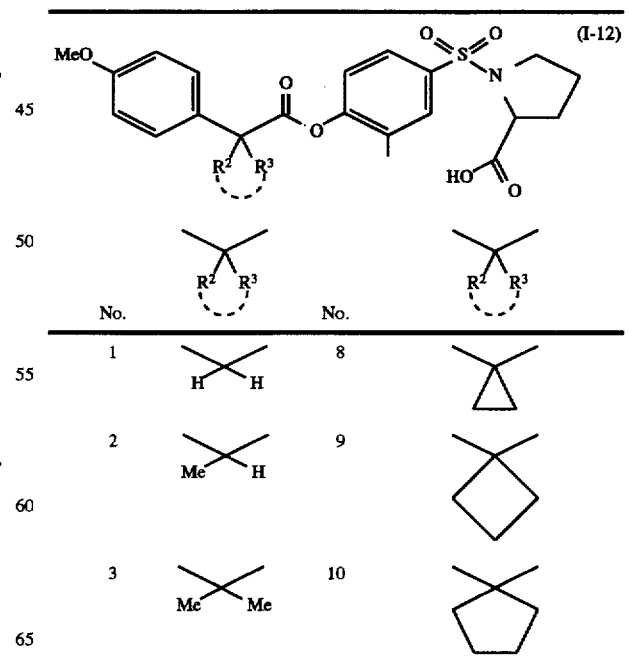
(I-12)

TABLE 12-continued
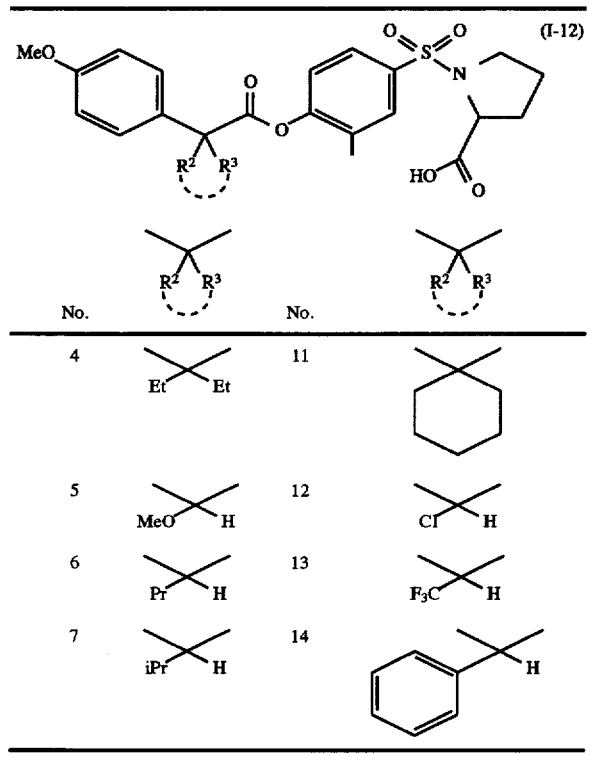
TABLE 13
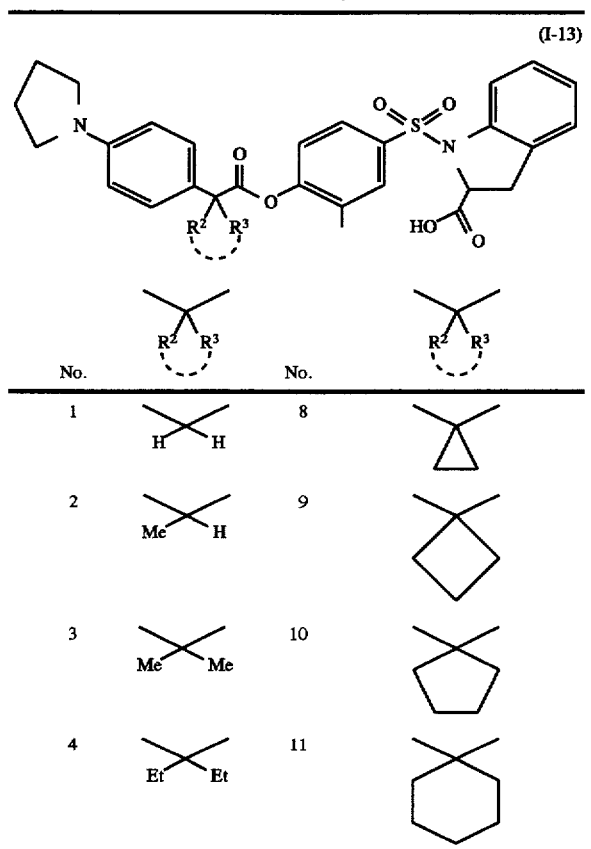
TABLE 13-continued
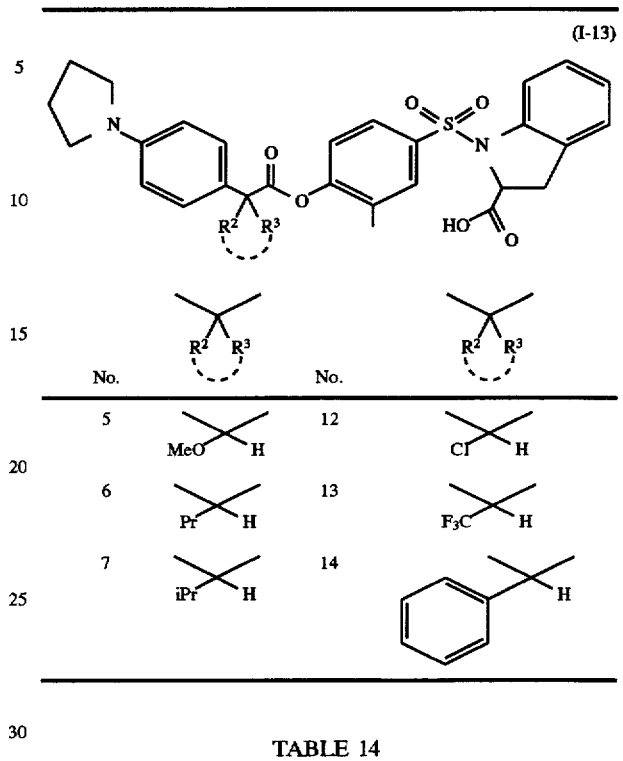
TABLE 14
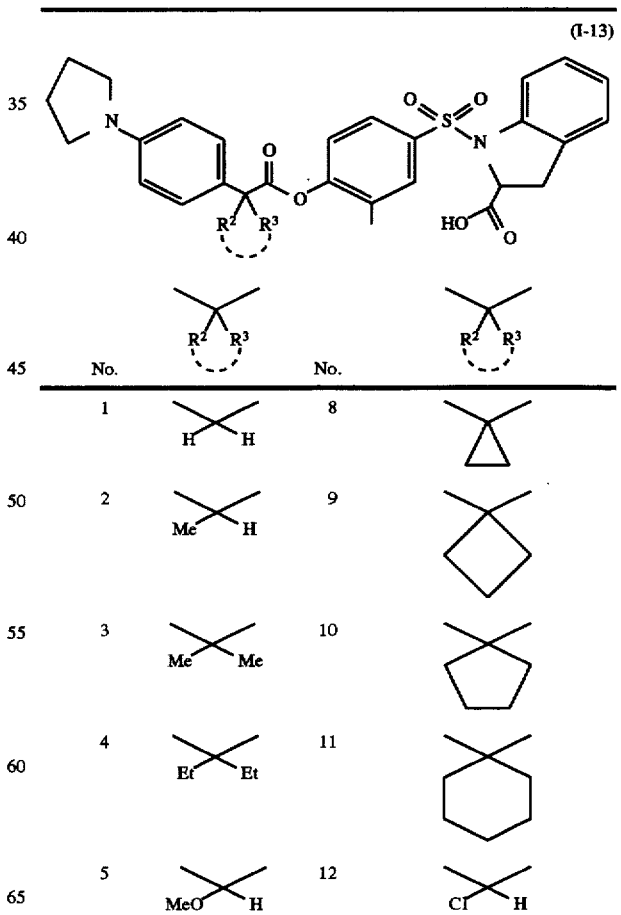

TABLE 14-continued
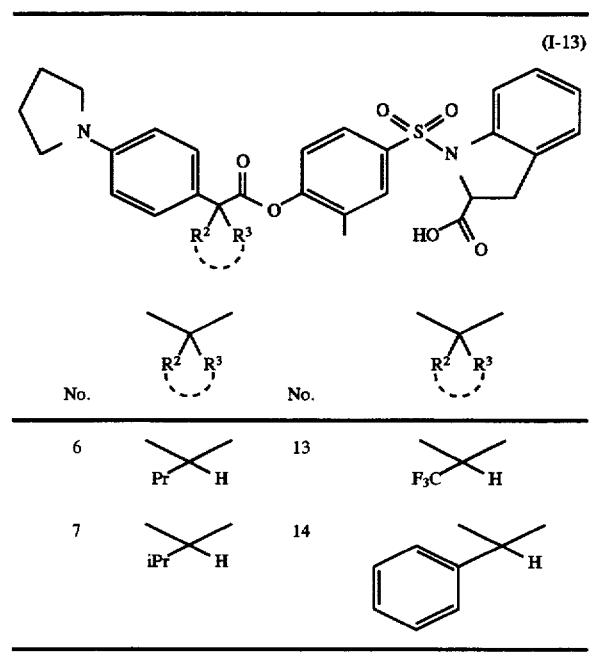
TABLE 15
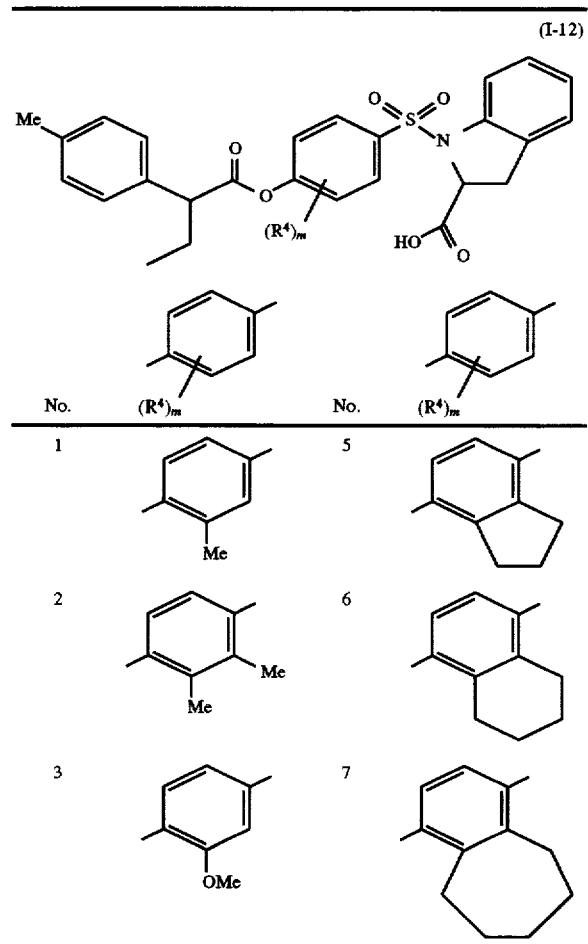
TABLE 15-continued
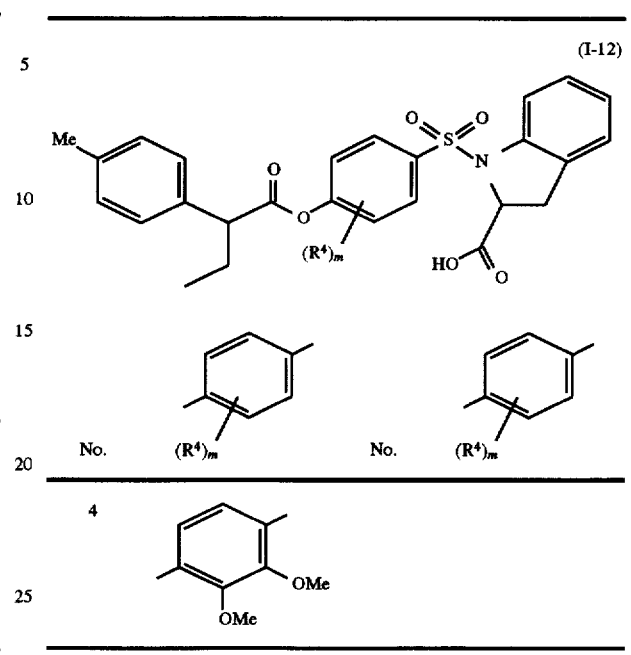
TABLE 16
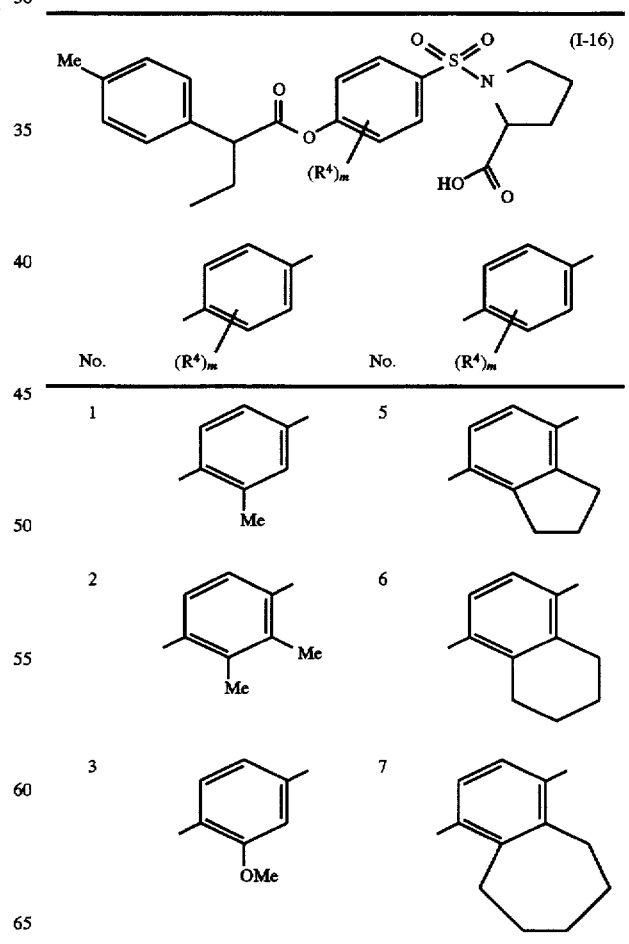

TABLE 16-continued
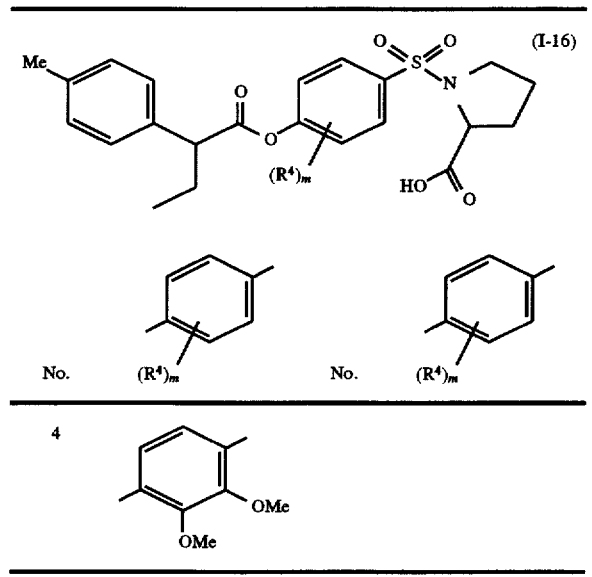
| No. | (R⁴)ₘ |
|---|---|
| 4 | (2,3-diOMe) |
TABLE 17
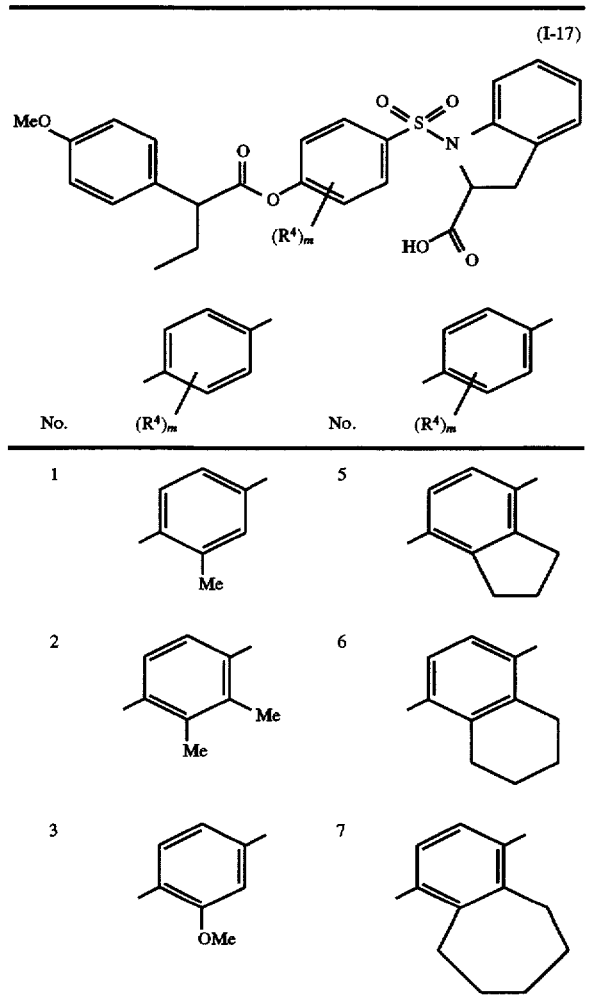
| No. | (R⁴)ₘ | No. | (R⁴)ₘ |
|---|---|---|---|
| 1 | Me | 5 | indane |
| 2 | 2,3-diMe | 6 | tetralin |
| 3 | OMe | 7 | benzocycloheptane |
TABLE 17-continued
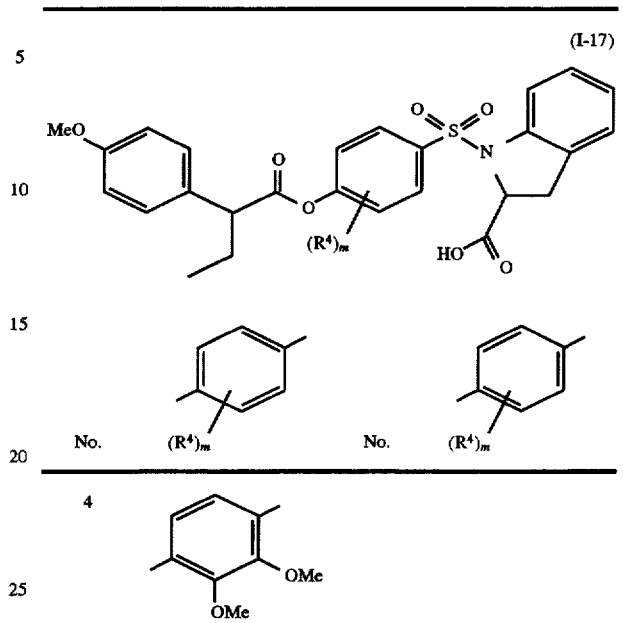
| No. | (R⁴)ₘ |
|---|---|
| 4 | (2,3-diOMe) |
TABLE 18
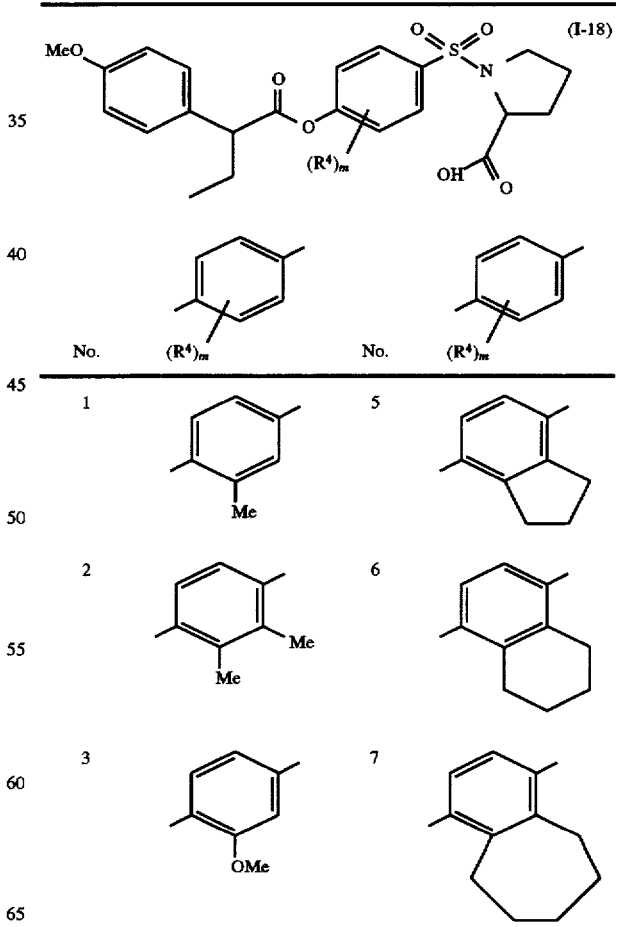
| No. | (R⁴)ₘ | No. | (R⁴)ₘ |
|---|---|---|---|
| 1 | Me | 5 | indane |
| 2 | 2,3-diMe | 6 | tetralin |
| 3 | OMe | 7 | benzocycloheptane |

TABLE 18-continued
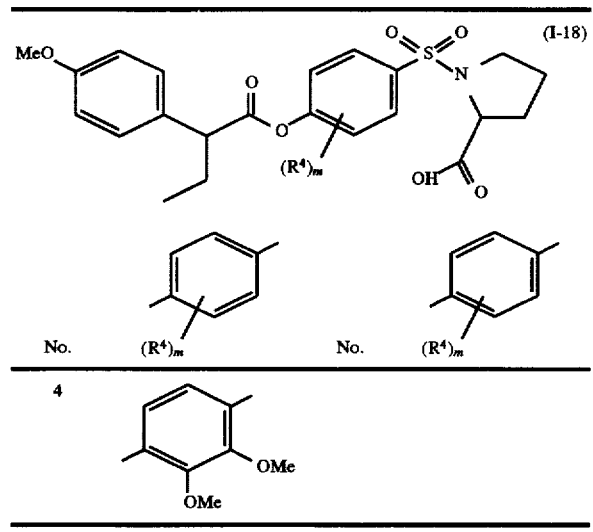
TABLE 19
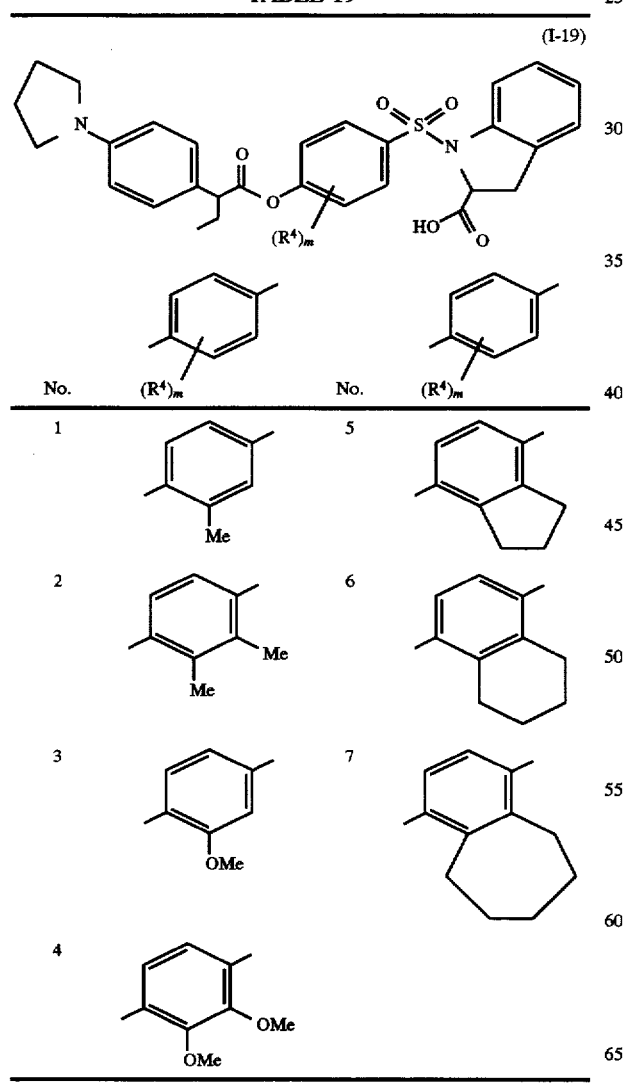
TABLE 20
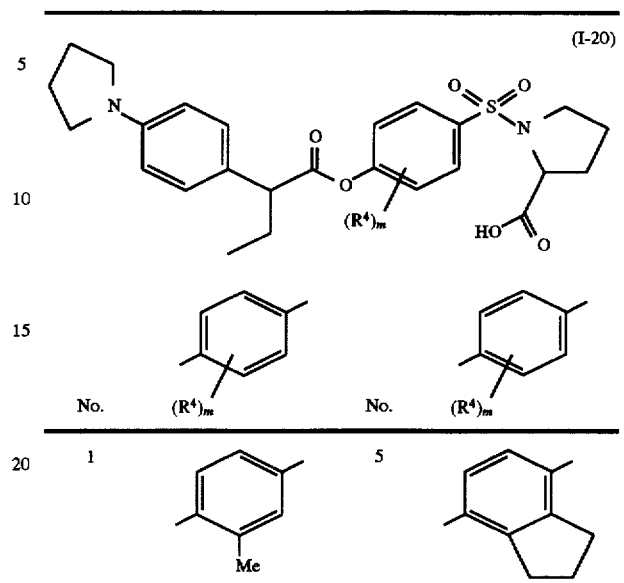
TABLE 21
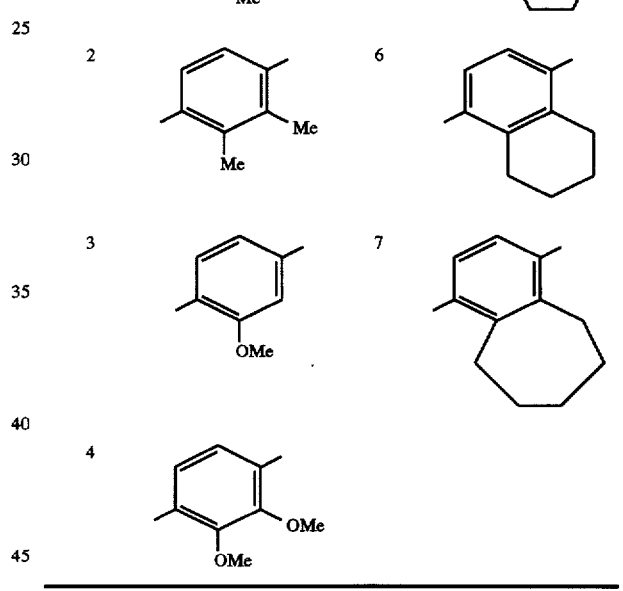
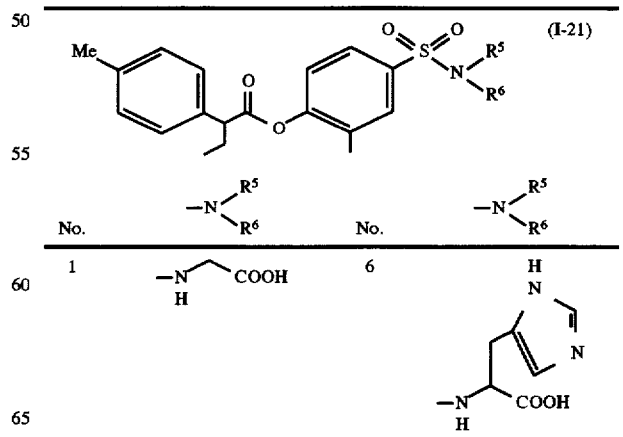

TABLE 21-continued
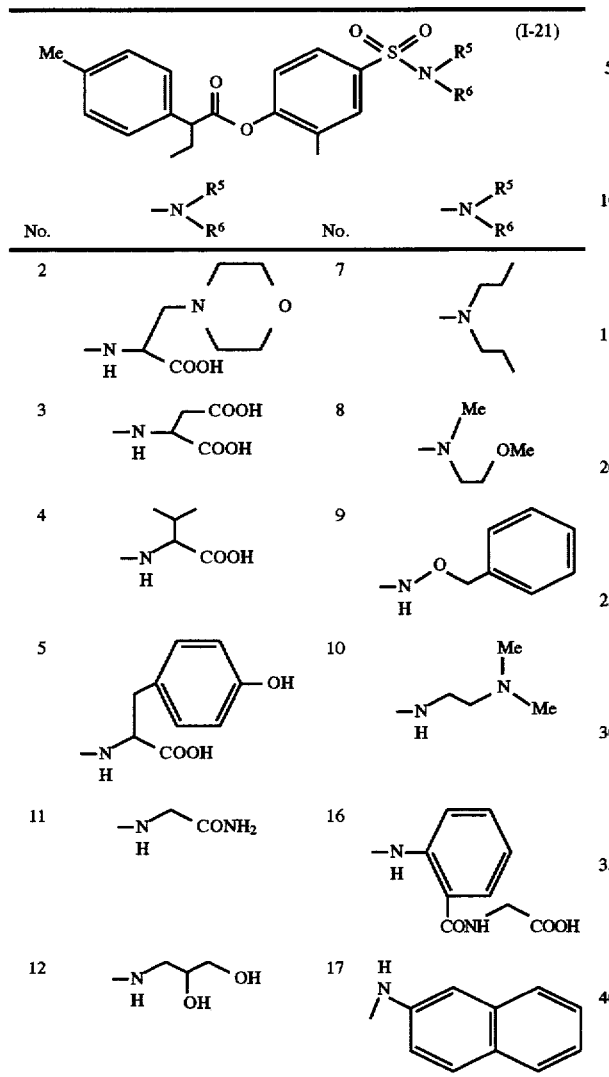
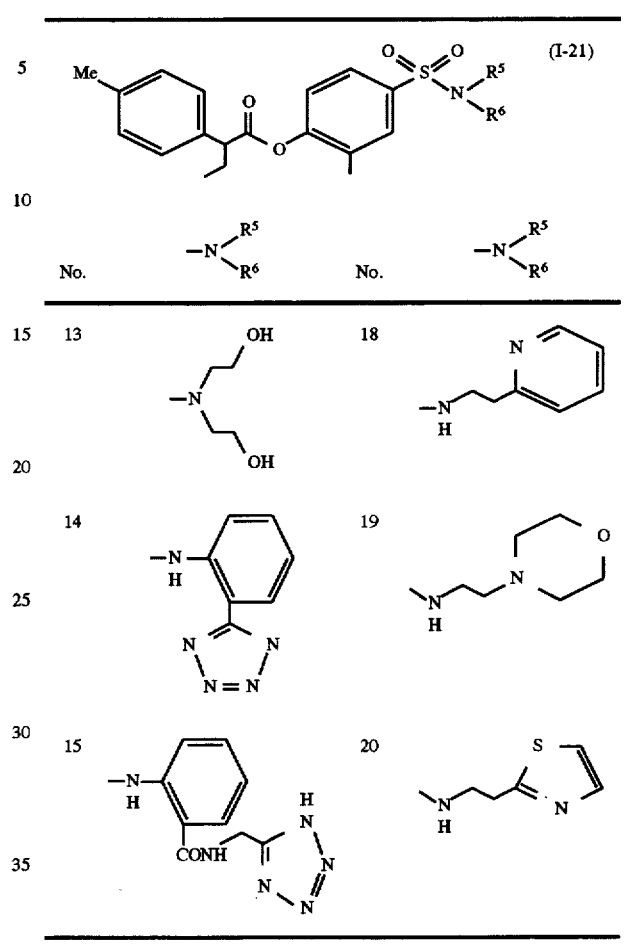
TABLE 22
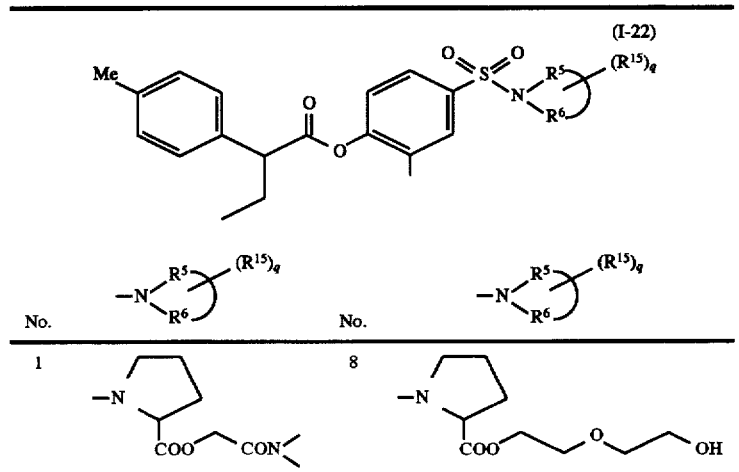

TABLE 22-continued (I-22) [Structure: Me-C6H4-CH(Et)-C(=O)-O-C6H3(Me)-S(=O)2-N(R5)(R6), with (R15)q ring]

| No. | -N(R5)(R6)(R15)q | No. | -N(R5)(R6)(R15)q |
|---|---|---|---|
| 2 | pyrrolidine-2-COO-CH2CH2-N(Me)2 | 9 | pyrrolidine-2-CONH-COOH |
| 3 | indoline-2-COO-CH2-CON(Me)2 | 10 | indoline-2-COO-CH2CH2-O-CH2CH2-OH |
| 4 | indoline-2-COO-CH2CH2-N(Me)2 | 11 | indoline-2-CONH-COOH |
| 5 | benzothiazoline | 12 | 4-hydroxy-pyrrolidine-2-COOH |
| 6 | piperazine-2-COOH (with NH) | 13 | azabicyclic lactam |
| 7 | pyrrole-2-COOH | 14 | morpholine |

TABLE 23
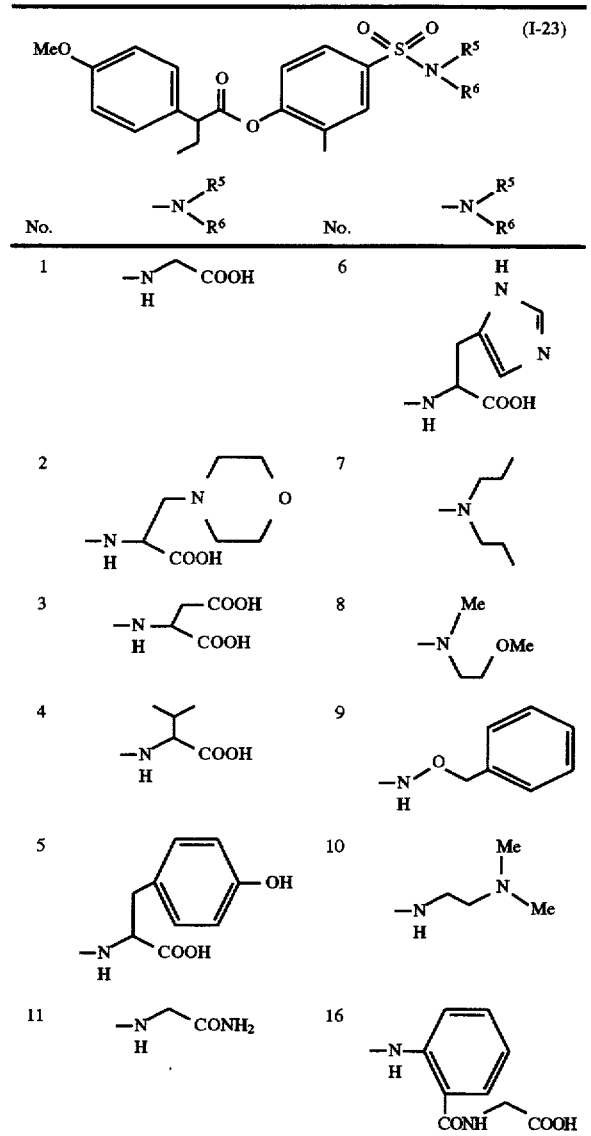
TABLE 23-continued
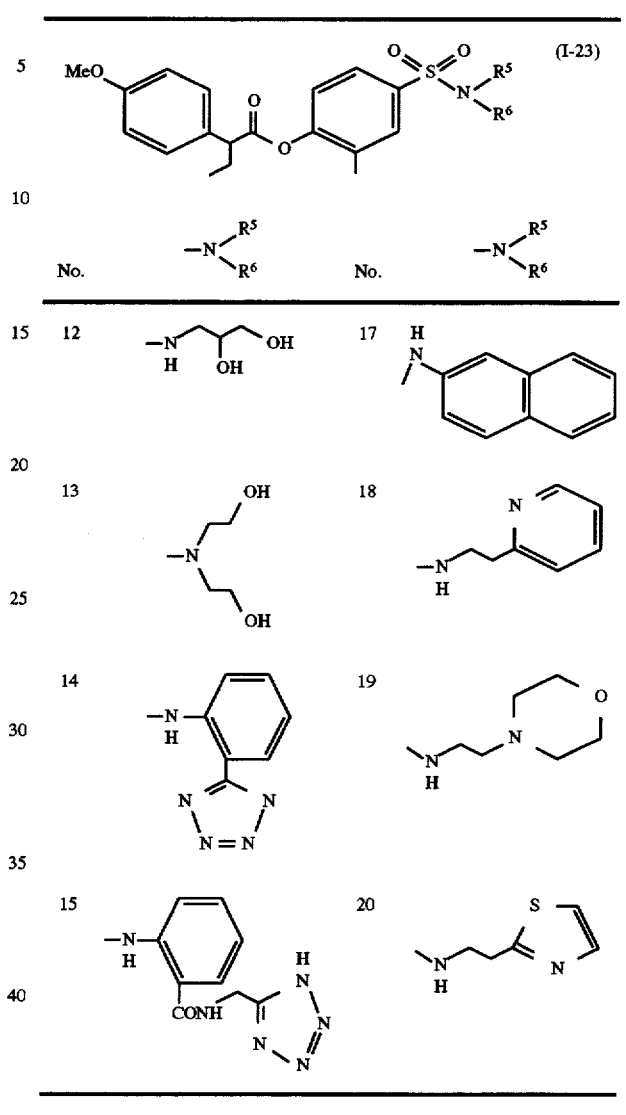

TABLE 24

(I-24)

[Structure: MeO-phenyl-CH(Et)-C(=O)-O-(methylphenyl)-SO₂-N(R⁵)(R⁶)-(R¹⁵)q]

| No. | -N(R⁵)(R⁶)(R¹⁵)q | No. | -N(R⁵)(R⁶)(R¹⁵)q |
|---|---|---|---|
| 1 | pyrrolidine-COO-CH₂-CON(CH₃)₂ | 8 | pyrrolidine-COO-CH₂CH₂-O-CH₂CH₂-OH |
| 2 | pyrrolidine-COO-CH₂CH₂-N(CH₃)₂ | 9 | pyrrolidine-CONH-CH₂-COOH |
| 3 | indoline-COO-CH₂-CON(CH₃)₂ | 10 | indoline-COO-CH₂CH₂-O-CH₂CH₂-OH |
| 4 | indoline-COO-CH₂CH₂-N(CH₃)₂ | 11 | indoline-CONH-CH₂-COOH |
| 5 | benzothiazoline | 12 | 4-hydroxy-pyrrolidine-2-COOH |
| 6 | piperazine-CH₂-COOH (with NH) | 13 | azabicyclic lactam |
| 7 | pyrrole-2-COOH | 14 | morpholine |

TABLE 25
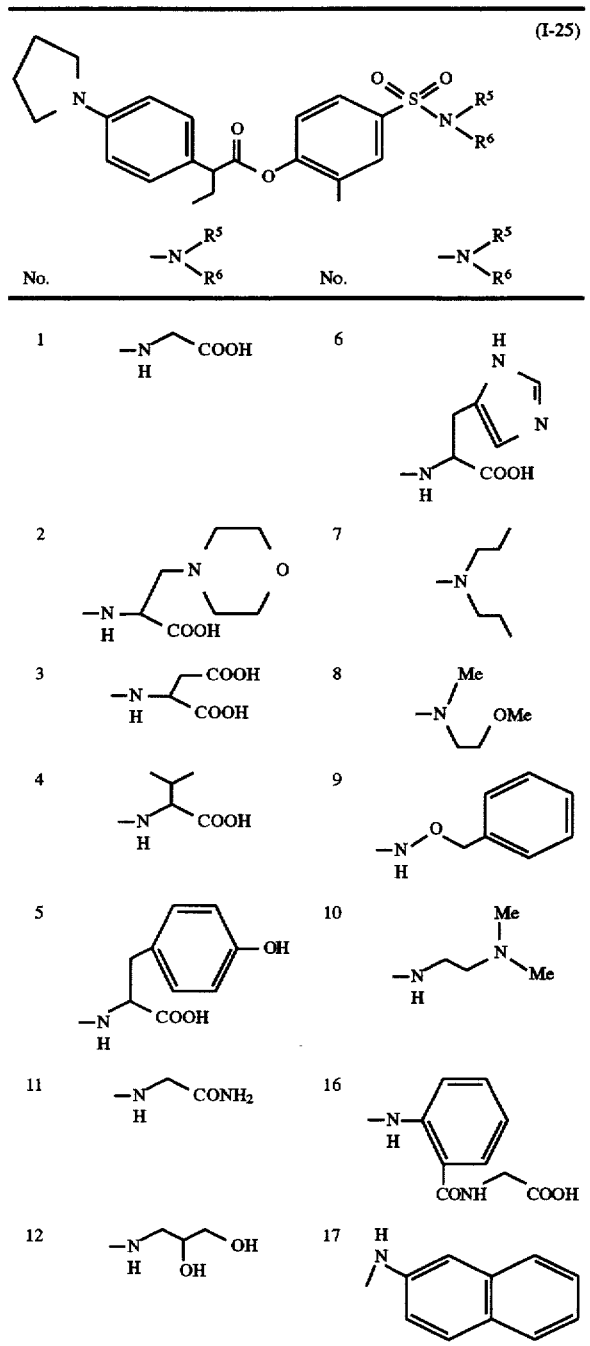
TABLE 25-continued
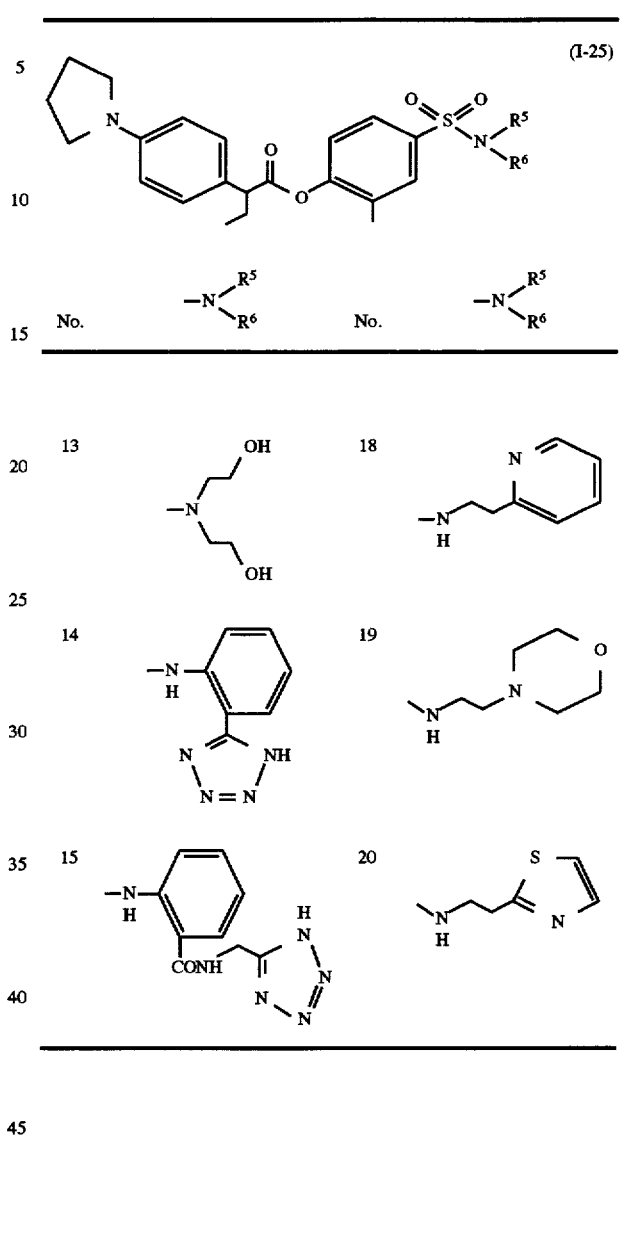

TABLE 26
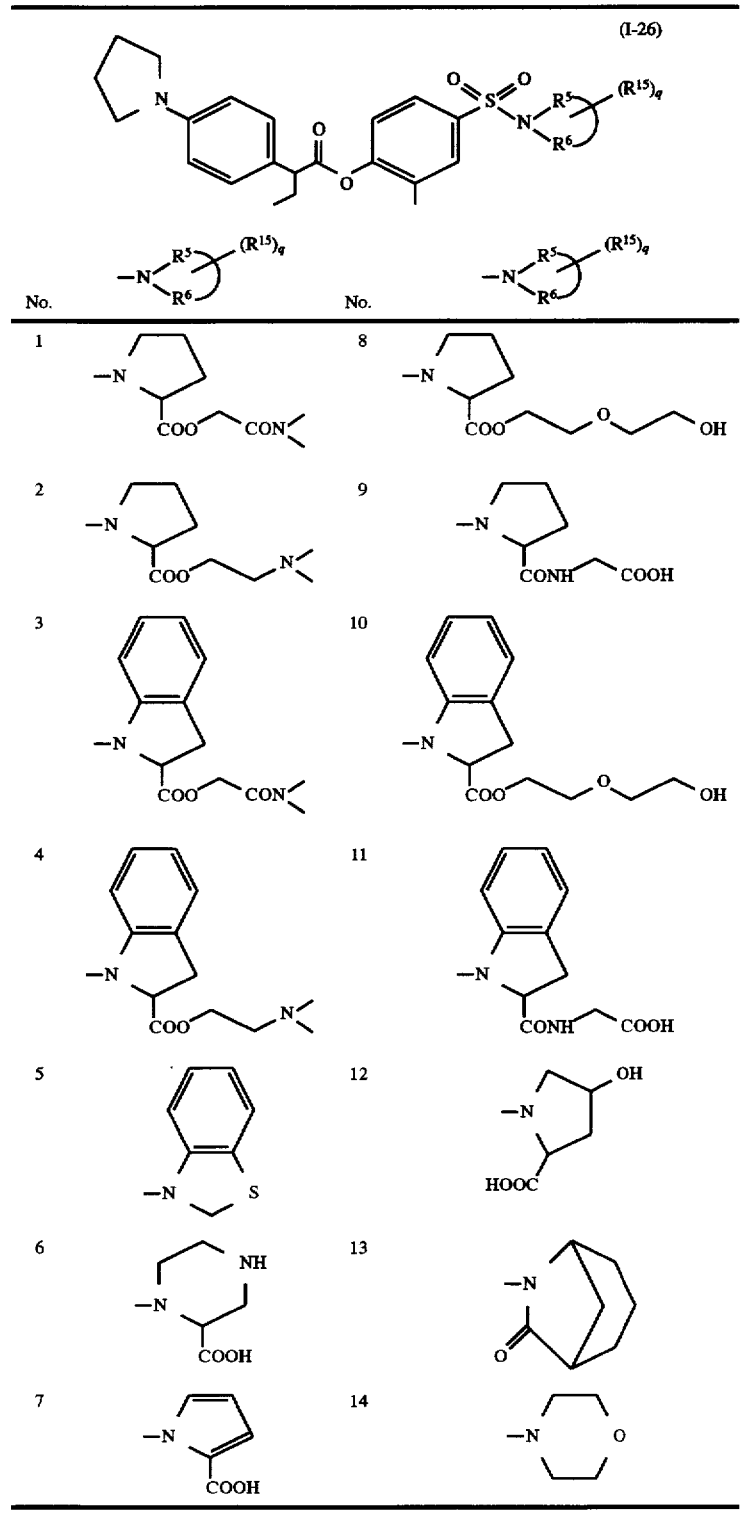

TABLE 27

(I-27)

Structure: (R¹)ₙ–phenyl–CH(Et)–C(=O)–O–[phenyl(2-Me)]–SO₂–NH–CH₂CH₂–N(morpholine)

(R¹)ₙ—phenyl—

| No. | (R¹)ₙ—phenyl— |
|---|---|
| 1 | 2-Me-phenyl |
| 2 | 2-OMe-phenyl |
| 3 | 3,4-di-OMe-phenyl (MeO, OMe) |
| 4 | 4-(pyrrolidin-1-yl)phenyl |
| 5 | 4-HO-phenyl |
| 6 | 4-O₂N-phenyl |
| 7 | 4-Cl-phenyl |
| 8 | 4-F₃C-phenyl |
| 9 | 4-NC-phenyl |
| 10 | 4-(H₂N–C(=NH)–)phenyl |
| 11 | 4-HOOC-phenyl |
| 12 | 4-MeOOC-phenyl |
| 13 | 4-(Me₂N)-phenyl |
| 14 | 4-(Me–C(=O)–NH–)phenyl |
| 15 | 4-(tBuOOC–NH–)phenyl |
| 16 | 4-(H₂N–C(=O)–NH–)phenyl |
| 17 | 4-(H₂N–CH(Me)–C(=O)–NH–)phenyl |
| 18 | 4-(4-piperazin-1-yl)phenyl (HN-piperazine) |

TABLE 28
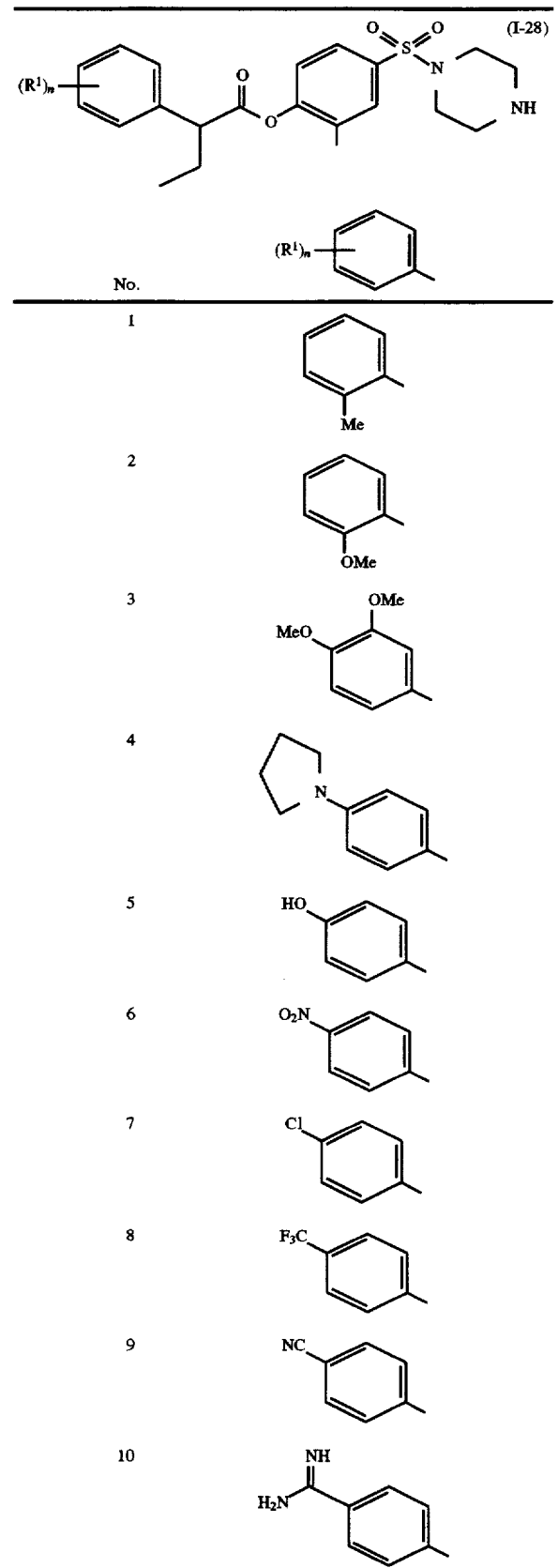
TABLE 28-continued
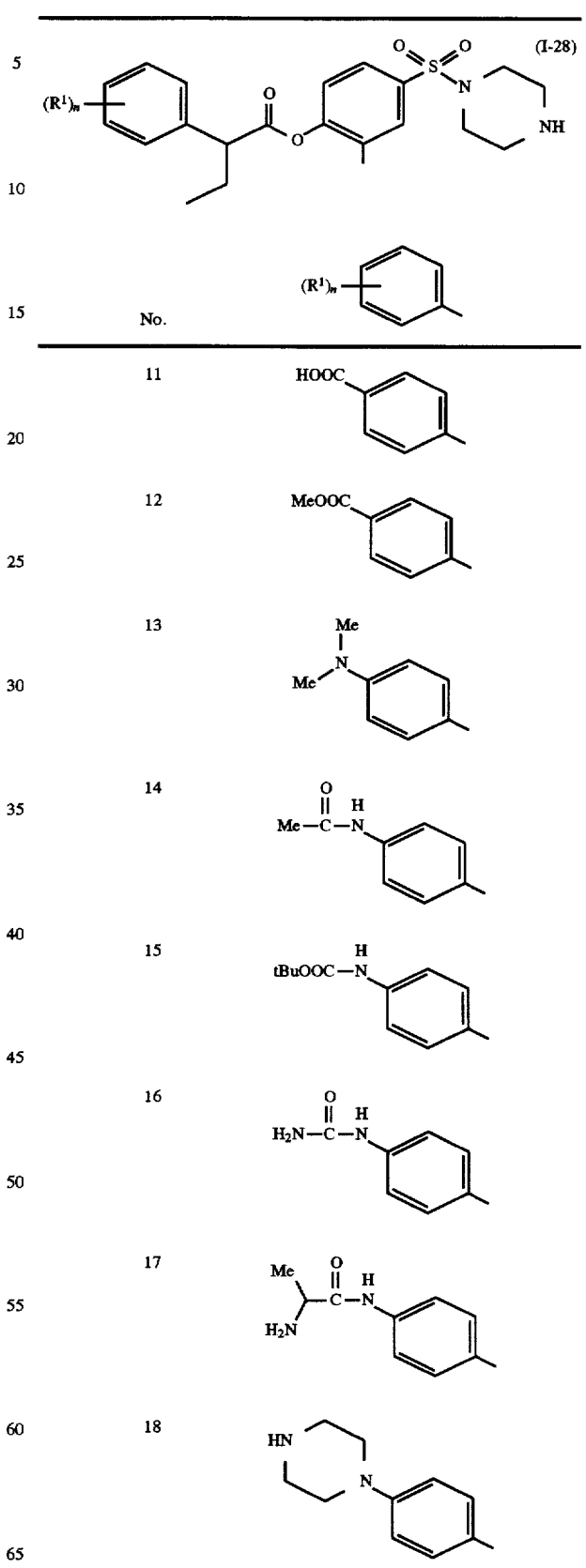

TABLE 29
(I-29)
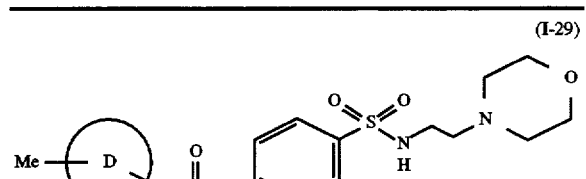
| No. | 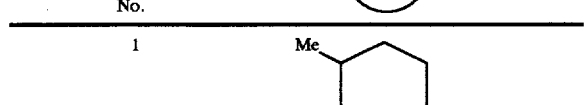 |
|---|---|
| 1 | 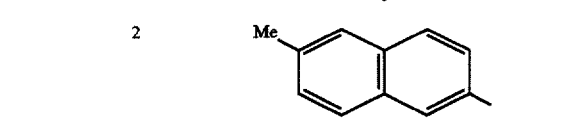 |
| 2 | 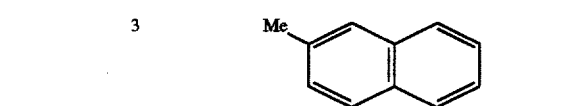 |
| 3 | 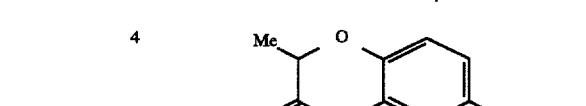 |
| 4 | 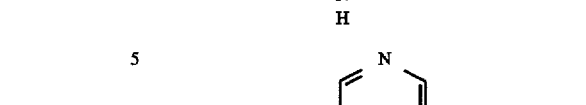 |
| 5 | 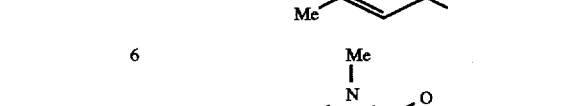 |
| 6 | 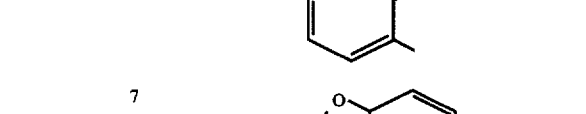 |
| 7 | 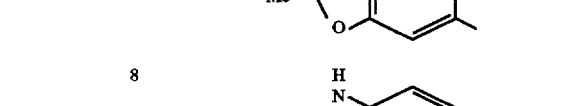 |
| 8 | 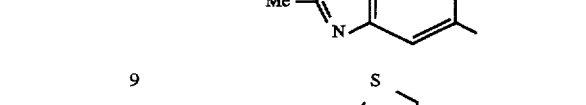 |
| 9 | 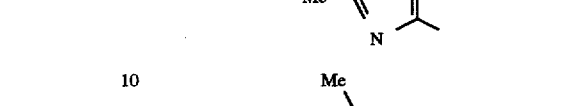 |
| 10 | 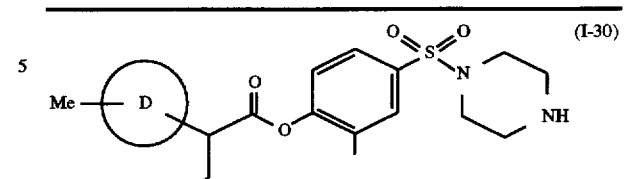 |
TABLE 30
(I-30)
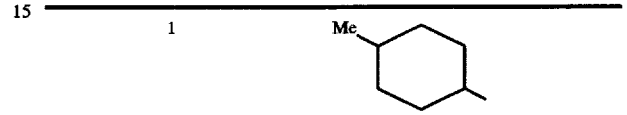
| No. | 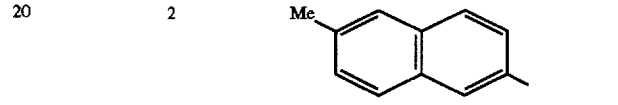 |
|---|---|
| 1 | 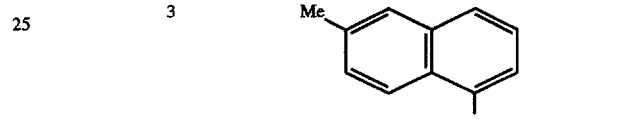 |
| 2 | 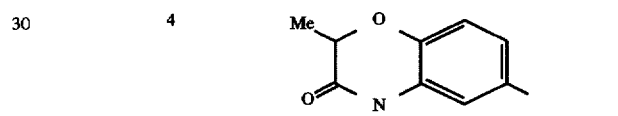 |
| 3 |  |
| 4 |  |
| 5 |  |
| 6 |  |
| 7 |  |
| 8 |  |

TABLE 31 (I-31)

[Structure: MeO-D-CH(Et)-C(=O)-O-C6H4-SO2-NH-CH2CH2-N(morpholine)]

MeO-D-

| No. | |
|---|---|
| 1 | 4-methoxycyclohexyl |
| 2 | 6-methoxynaphthalen-2-yl |
| 3 | 6-methoxynaphthalen-1-yl (with methyl) |
| 4 | 2-methoxy-4-methyl-6-(acetamido)phenyl |
| 5 | 3-methoxy-5-methylpyridinyl |
| 6 | 2-methoxy-3-methylpyridinyl |
| 7 | 4-methoxy-6-methyl-1,3-benzodioxole |
| 8 | 5-methoxy-6-methylbenzimidazole |
| 9 | 4-methoxy-2-methylthiazole |
| 10 | 5-methoxy-2-methylthiophene |

TABLE 32 (I-32)

[Structure: MeO-D-CH(Et)-C(=O)-O-C6H3(Me)-SO2-N(CH2CH2-piperazine-NH)]

MeO-D-

| No. | |
|---|---|
| 1 | 4-methoxycyclohexyl |
| 2 | 6-methoxynaphthalen-2-yl |
| 3 | 6-methoxynaphthalen-1-yl |
| 4 | 2-methoxy-4-methyl-6-(acetamido)phenyl |
| 5 | 3-methoxy-5-methylpyridinyl |
| 6 | 2-methoxy-3-methylpyridinyl |
| 7 | 4-methoxy-6-methyl-1,3-benzodioxole |
| 8 | 5-methoxy-6-methylbenzimidazole |
| 9 | 4-methoxy-2-methylthiazole |
| 10 | 5-methoxy-2-methylthiophene |

TABLE 33
(I-33)
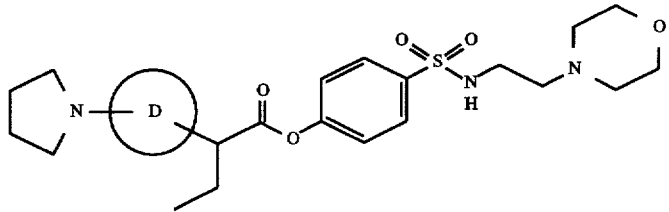
| No. | 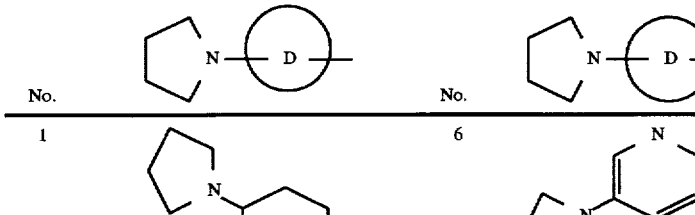 | No. | 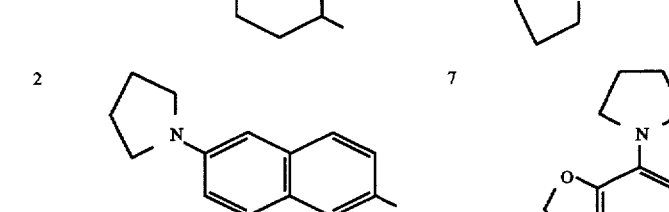 |
|---|---|---|---|
| 1 | 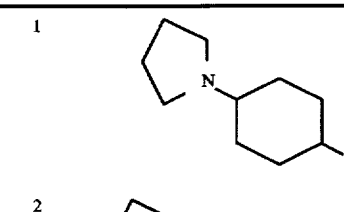 | 6 | 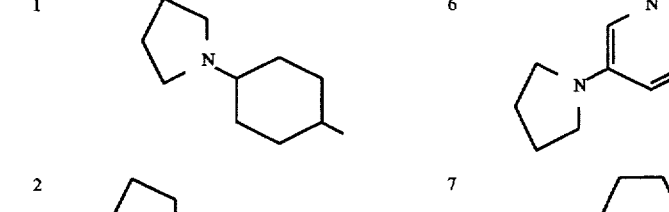 |
| 2 | 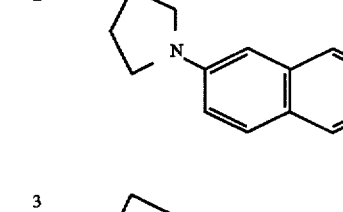 | 7 | 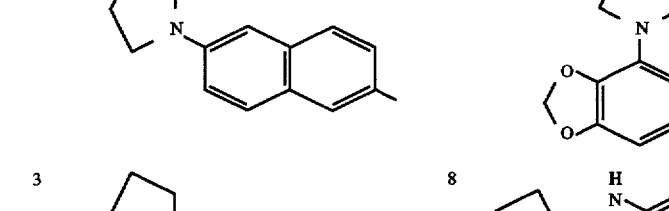 |
| 3 | 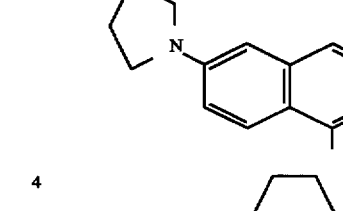 | 8 | 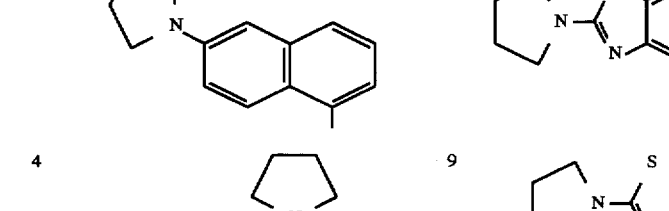 |
| 4 | 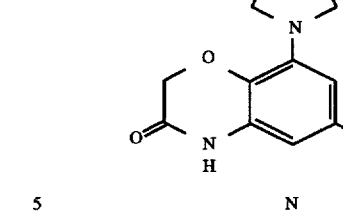 | 9 | 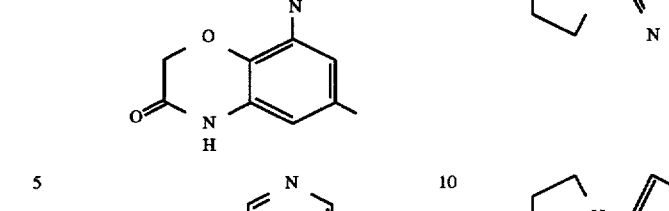 |
| 5 | 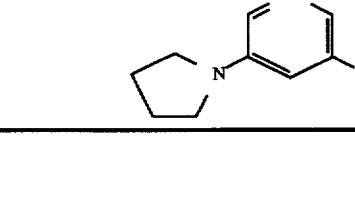 | 10 | 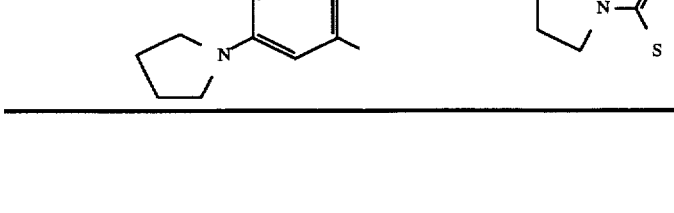 |

TABLE 34
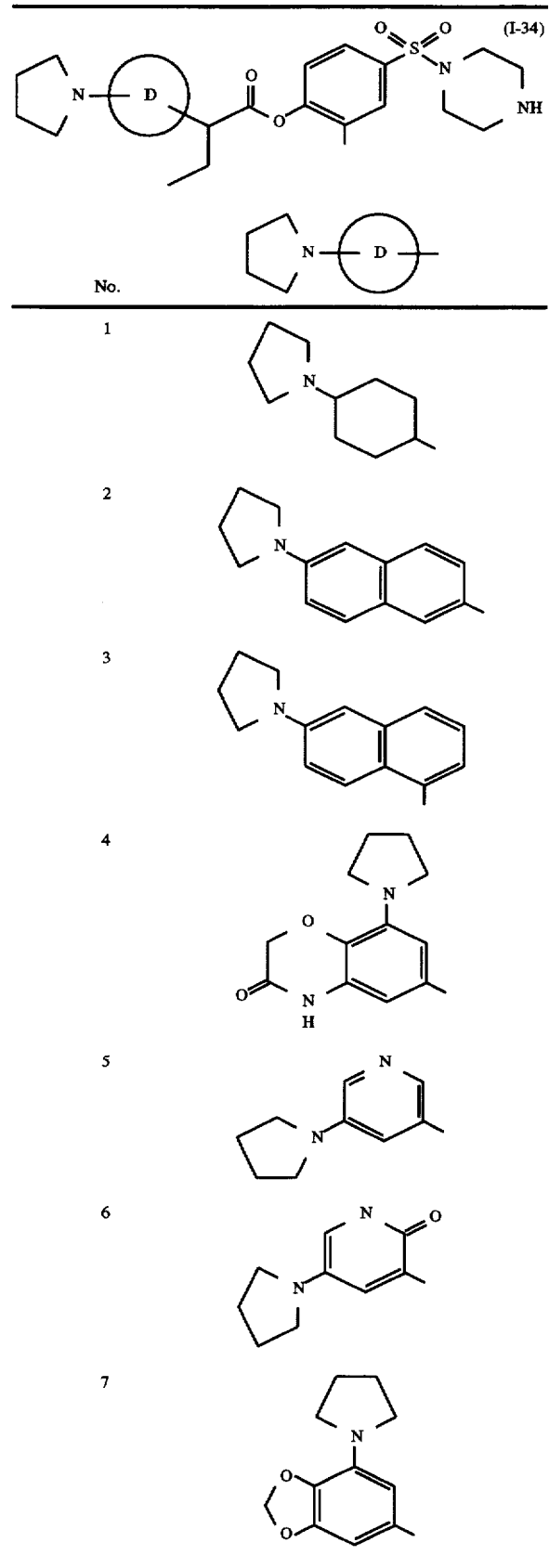
TABLE 34-continued
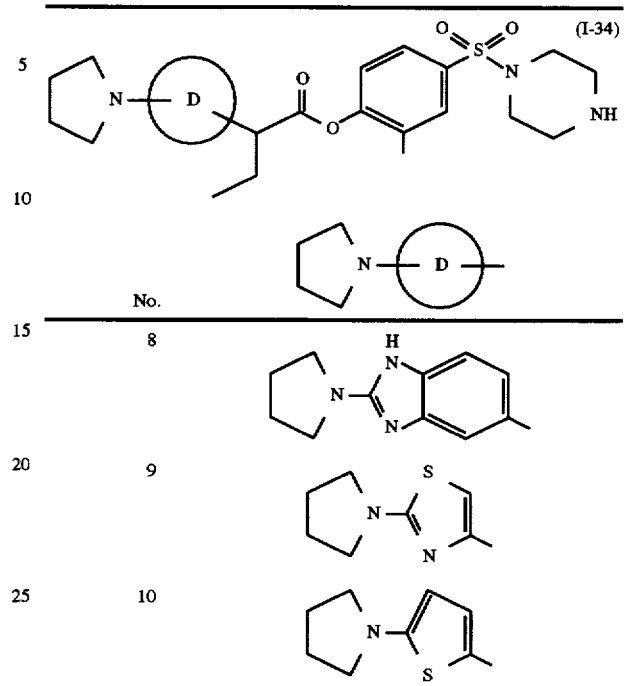
TABLE 35
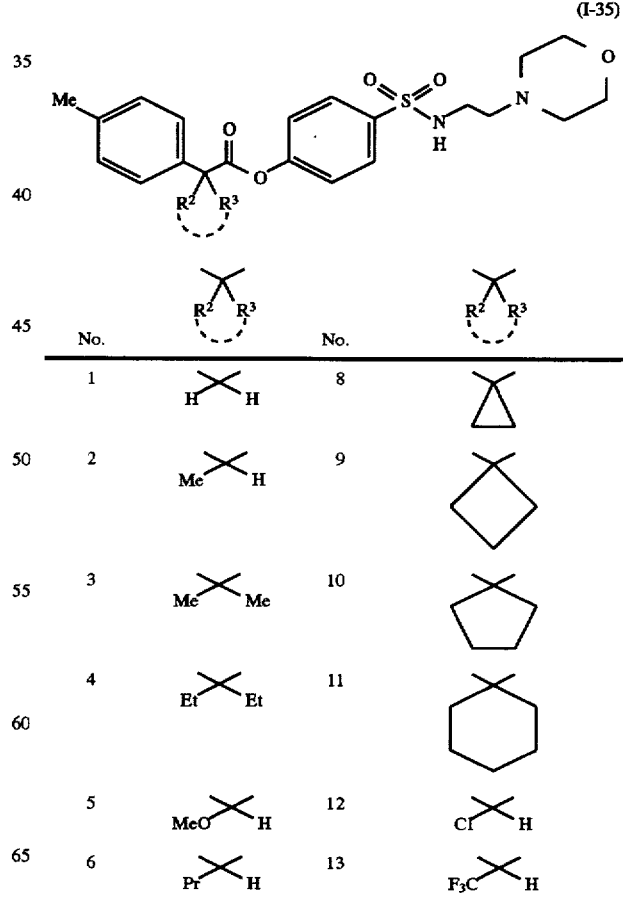

TABLE 35-continued
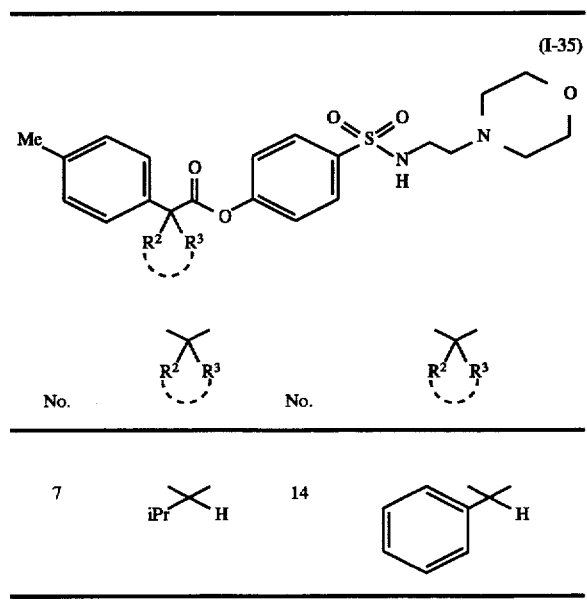
(I-35)
TABLE 36
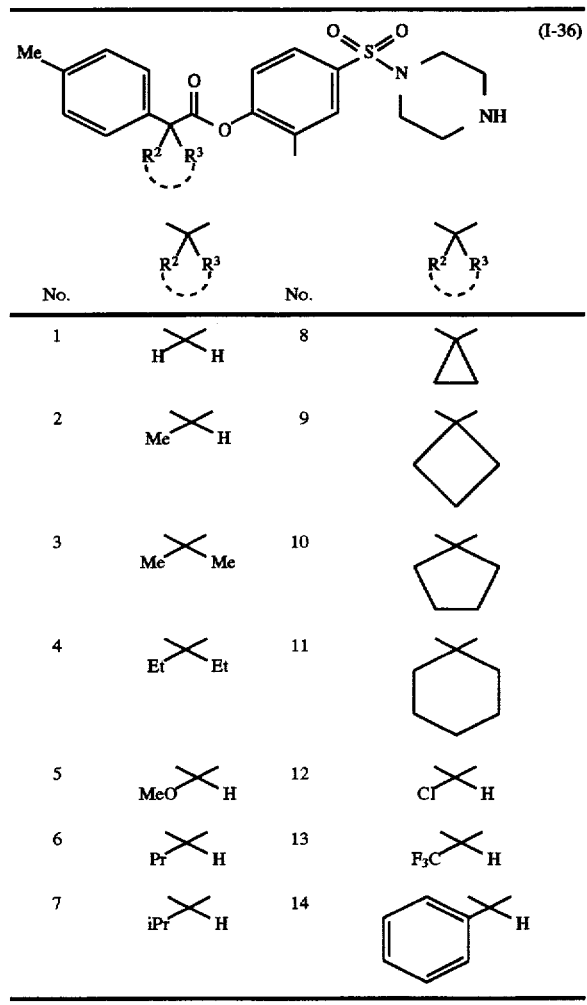
(I-36)
TABLE 37
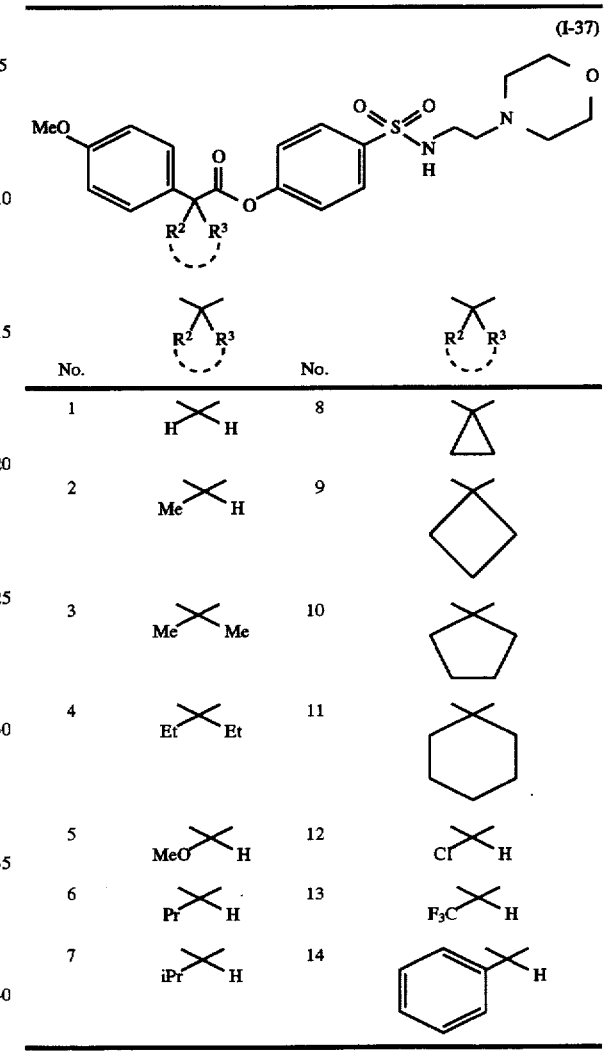
(I-37)
TABLE 38
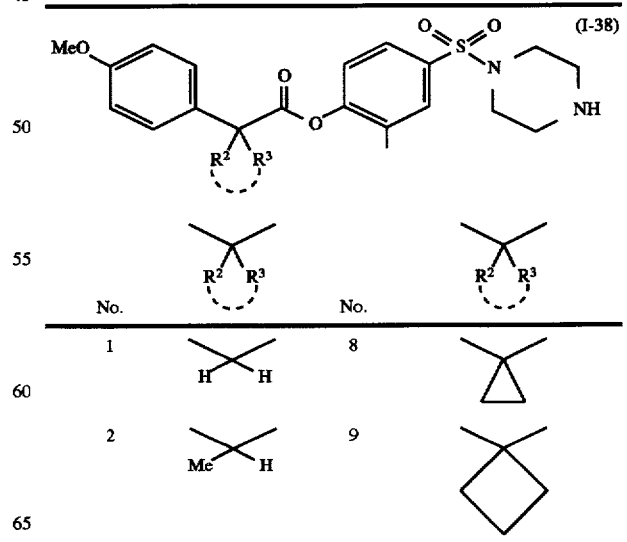
(I-38)

TABLE 38-continued
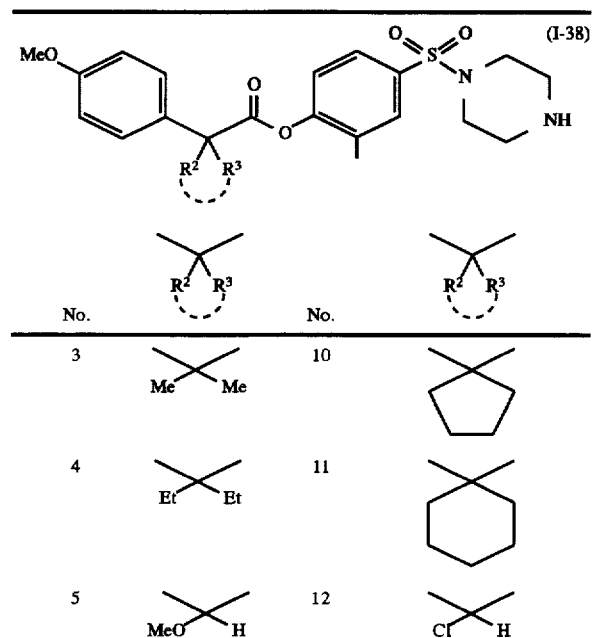
| No. | R²,R³ | No. | R²,R³ |
|---|---|---|---|
| 3 | Me, Me | 10 | cyclopentyl |
| 4 | Et, Et | 11 | cyclohexyl |
| 5 | MeO, H | 12 | Cl, H |
TABLE 38-continued
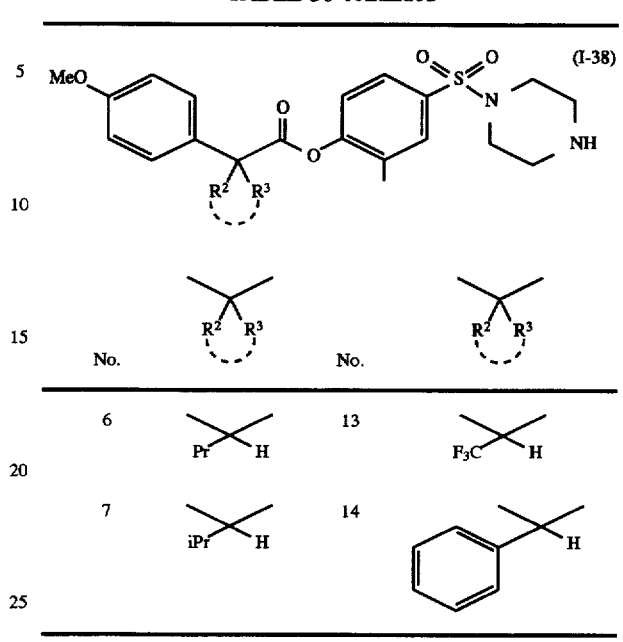
| No. | R²,R³ | No. | R²,R³ |
|---|---|---|---|
| 6 | Pr, H | 13 | F₃C, H |
| 7 | iPr, H | 14 | Ph, H |
TABLE 39
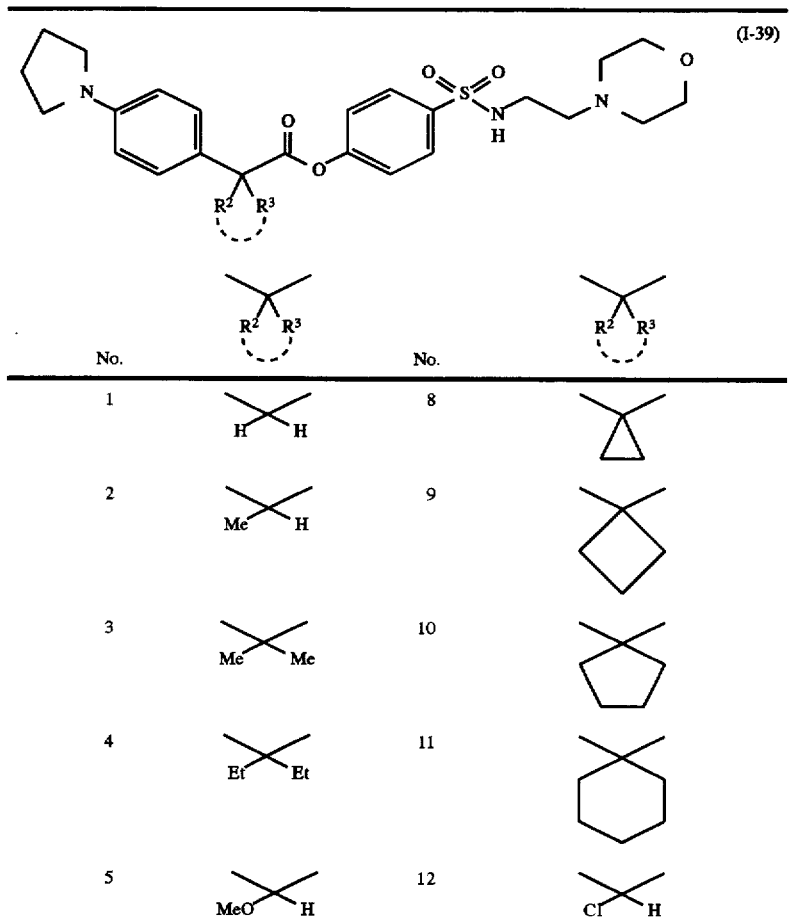
| No. | R²,R³ | No. | R²,R³ |
|---|---|---|---|
| 1 | H, H | 8 | cyclopropyl |
| 2 | Me, H | 9 | cyclobutyl |
| 3 | Me, Me | 10 | cyclopentyl |
| 4 | Et, Et | 11 | cyclohexyl |
| 5 | MeO, H | 12 | Cl, H |

TABLE 39-continued
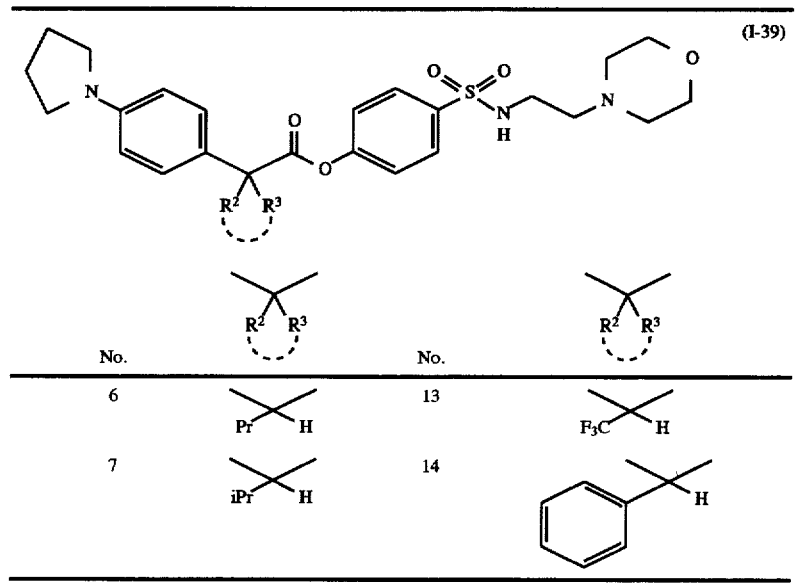
TABLE 40
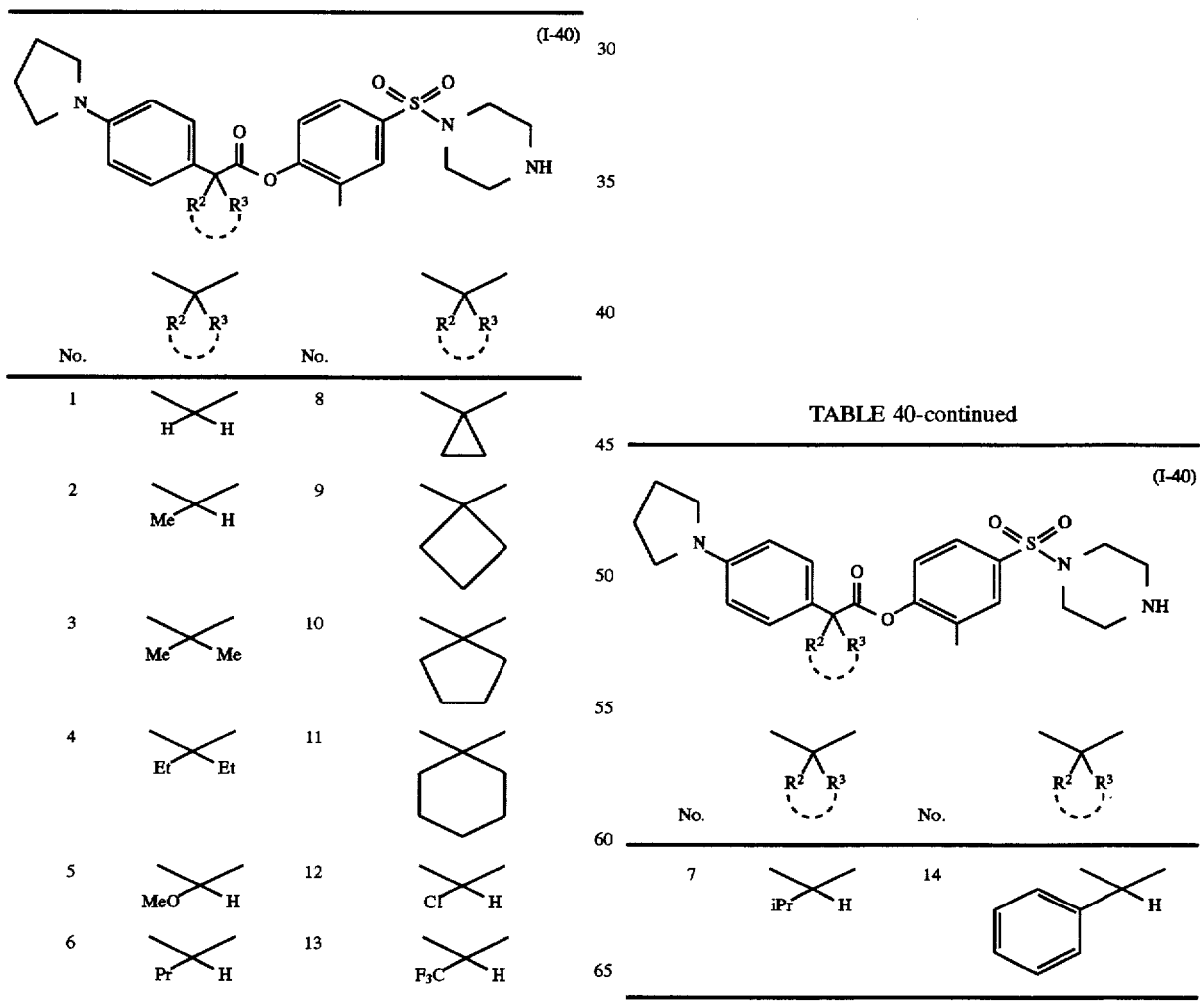

TABLE 41
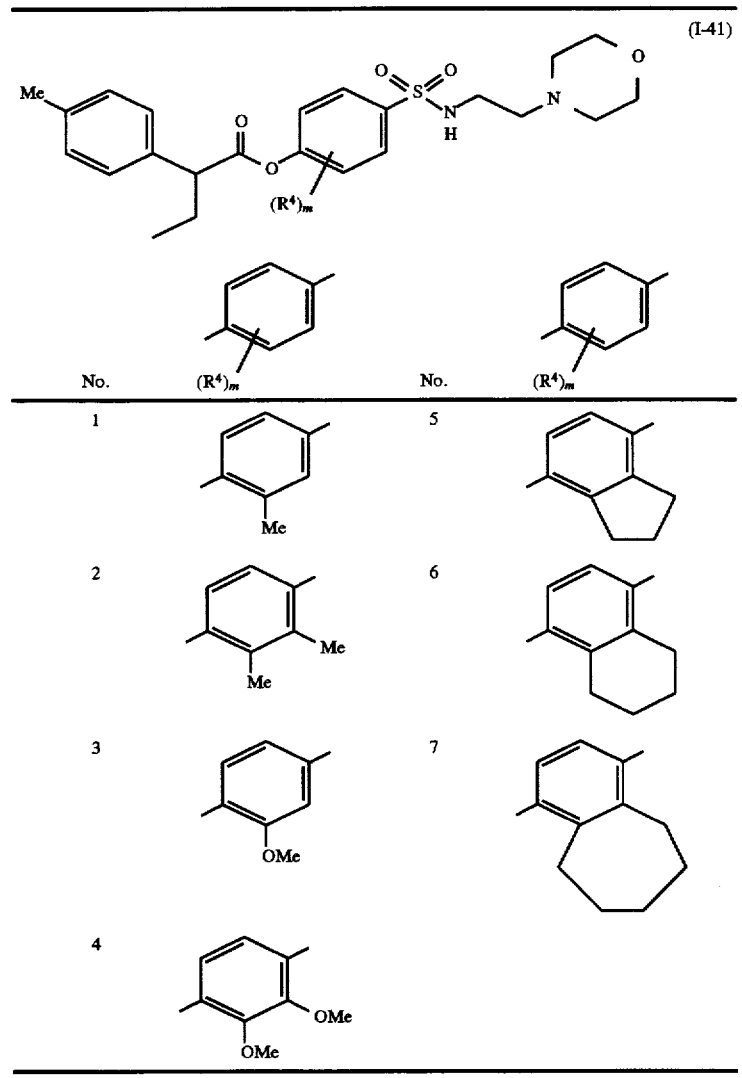

TABLE 42-continued
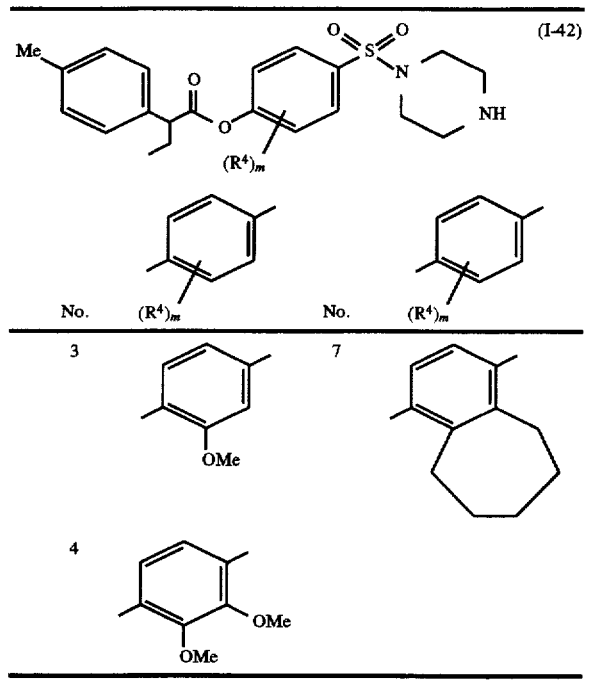
TABLE 43
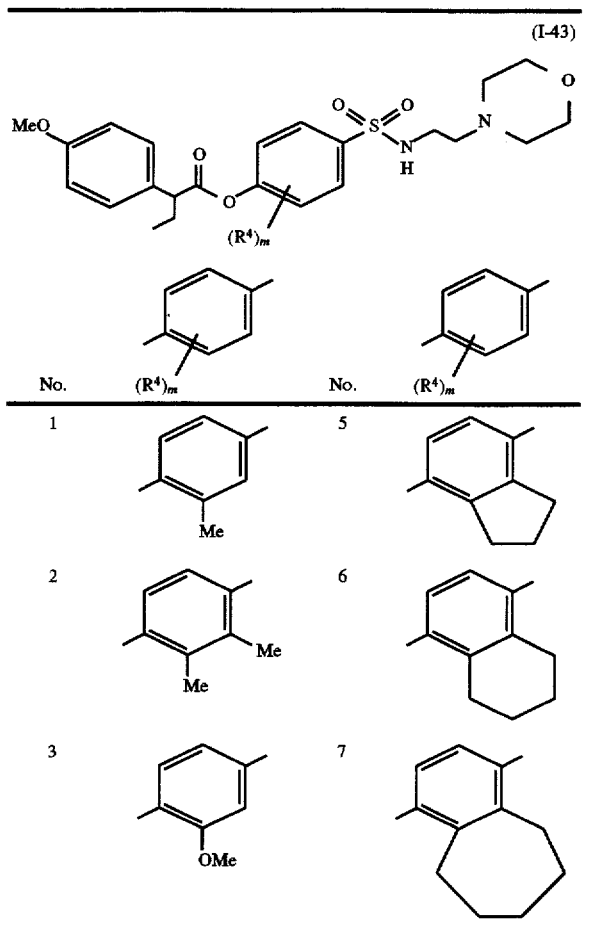
TABLE 43-continued
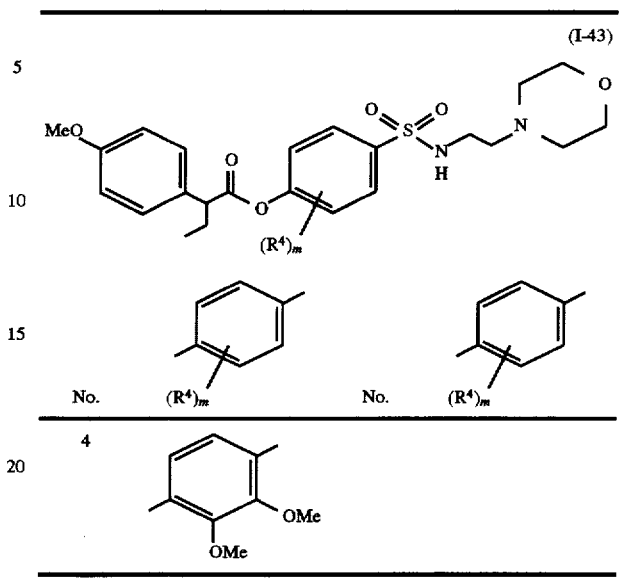
TABLE 44
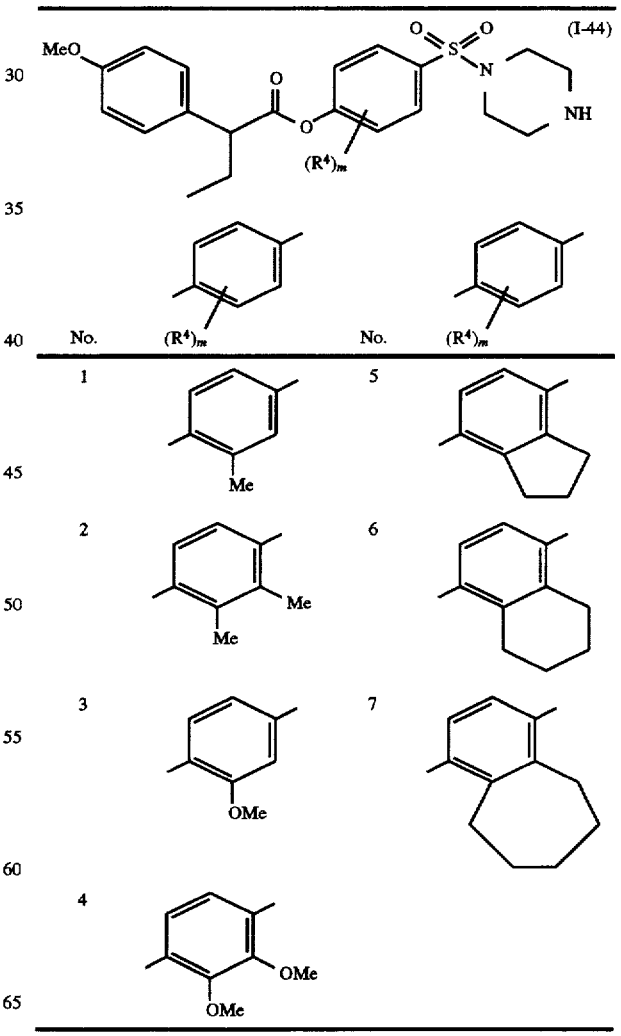

TABLE 45
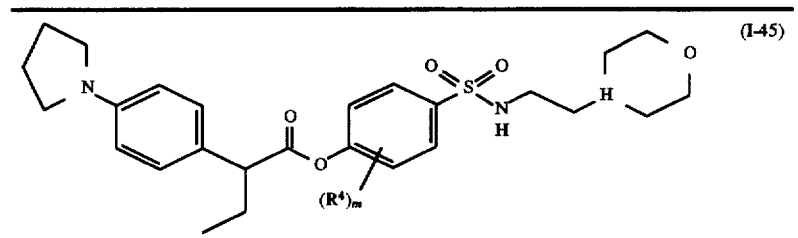
| No. | (R⁴)ₘ | No. | (R⁴)ₘ |
|---|---|---|---|
| 1 | 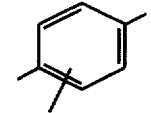 | 5 | 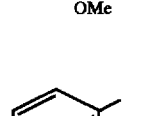 |
| 2 | 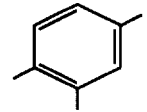 | 6 | 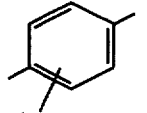 |
| 3 | 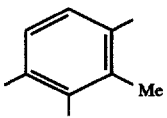 | 7 | 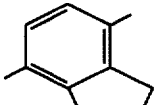 |
| 4 | 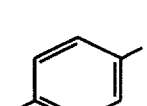 | | |
TABLE 46
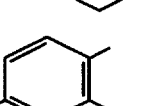
| No. | (R⁴)ₘ | No. | (R⁴)ₘ |
|---|---|---|---|
| 1 | 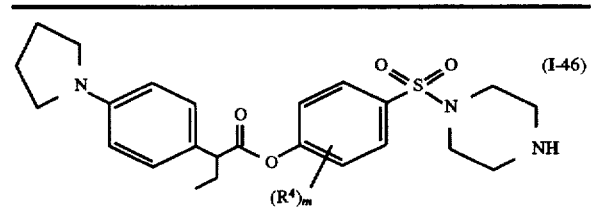 | 5 | 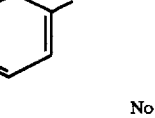 |
TABLE 46-continued
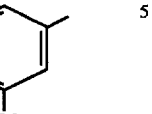
| No. | (R⁴)ₘ | No. | (R⁴)ₘ |
|---|---|---|---|

TABLE 46-continued

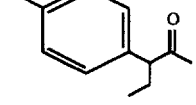

| No. | (R⁴)ₘ | No. | (R⁴)ₘ |
|---|---|---|---|
| 2 | 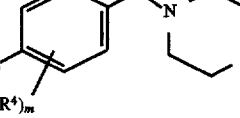 | 6 | 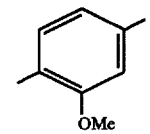 |
| 3 | 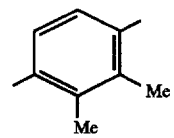 | 7 | 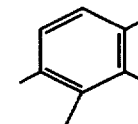 |
| 4 | 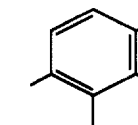 | | |

Processes for the Preparation

The compounds of formula (I), of the present invention, may be prepared by esterifying a compound of formula (II)

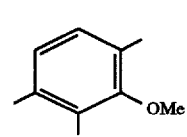 (II)

wherein $R^{1a}$ is C1–8 alkyl, C1–8 alkoxy, hydroxy, protected hydroxy, keto, nitro, halogen atom, trihalomethyl, cyano, amidino, —COOR⁷ᵃ (in which R⁷ᵃ is C1–8 alkyl or benzyl), or

(in which p is as hereinbefore defined, $R^{8a}$ and $R^{9a}$ each, independently, is hydrogen atom (with the proviso that, $R^{8a}$ and $R^{9a}$ do not represent hydrogen atom at the same time), t-butoxycarbonyl, benzyloxycarbonyl, C1–4 alkyl, C2–5 acyl, —COOR¹⁰ᵃ (in which R¹⁰ᵃ is C1–8 alkyl or benzyl), —CONR¹¹R¹² (in which R¹¹ and R¹² are as hereinbefore defined), or

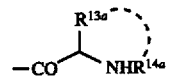

(in which

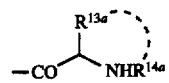

is a protected α-amino acid residue), or
R⁸ᵃ and R⁹ᵃ, taken together with the nitrogen atom to which they are attached represent an aliphatic heterocyclic ring which is unsubstituted or substituted by C1–4 alkyl or phenyl C1–4 alkyl, and the other symbols are as hereinbefore defined
with a compound of formula (III)

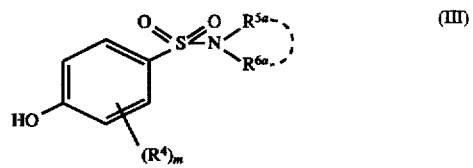 (III)

wherein

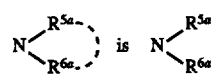

(in which $R^{5a}$ and $R^{6a}$ each, independently, is
1) hydrogen atom (with the proviso that, $R^{5a}$ and $R^{6a}$ do not represent hydrogen atom at the same time),
2) hydroxy,
3) hydroxy protected by a protecting group which is removable under acid conditions,
4) t-butoxycarbonyl,
5) benzyloxycarbonyl,
6) C1–8 alkyl,
7) C1–8 alkoxy,
8) phenyl C1–4 alkoxy,
9) amidino,
10) —M—R¹⁶ᵃ (in which M is as hereinbefore defined, and R¹⁶ᵃ is i) —NR¹⁷ᵃR¹⁸ᵃ (in which R¹⁷ᵃ and R¹⁸ᵃ each, independently, is hydrogen atom (with the proviso that, R¹⁷ᵃ and R¹⁸ᵃ do not represent hydrogen atom at the same time), t-butoxycarbonyl, benzyloxycarbonyl or C1–4 alkyl), ii) —CONR¹⁹R²⁰ (in which R¹⁹ and R²⁰ are as hereinbefore defined), iii)

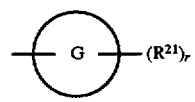

(in which all the symbols are as hereinbefore defined), iv) heterocyclic ring, unsubstituted or substituted by 1 to 4 substituents optionally selected from C1–4 alkyl, C1–4 alkoxy, hydroxy, phenyl C1–4 alkyl, —COOR²⁶ (in which R²⁶ is as hereinbefore defined), hydroxy C1–4 alkyl in which hydroxy is protected by a protecting group which is removable under acid conditions or C2–4 alkoxyalkyl), 11) C1–8 alkyl substituted by one or two of —OR$^{27a}$ (in which R$^{27a}$ is hydrogen atom, C1–4 alkyl, C2–4 alkoxyalkyl, t-butyldimethylsilyl, THP, benzyl, or C2–4 alkyl substituted by —OR$^{28a}$ (in which R$^{28a}$ is hydrogen atom, C2–4 alkoxyalkyl, t-butyidimethylsilyl, THP or benzyl)), 12) —J$^a$—COOR$^{29}$ (in which R$^{29}$ is as hereinbefore defined J$^a$ is single bond, —(CH$_2$)$_s$— or

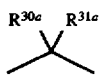

(in which s is as hereinbefore defined,

R$^{30a}$ and R$^{31a}$ each, independently, is i) hydrogen atom, ii) C1–8 alkyl, iii) —COOR$^{32}$ (in which R$^{32}$ is as hereinbefore defined), iv) carbocyclic or heterocyclic ring, unsubstituted or substituted by one or more substituents selected from C1–4 alkyl, C1–4 alkoxyalkyl, amino, nitro, hydroxy, protected hydroxy, halogen atom, nitrile, guanidino and amidino, or v) C1–8 alkyl substituted by one or more substituents selected from hydroxy, protected hydroxy, —COOR$^{33}$ (in which R$^{33}$ is as hereinbefore defined), —NR$^{34a}$R$^{35a}$ (in which R$^{34a}$ and R$^{35a}$ each, independently, is hydrogen atom (with the proviso that, R$^{34a}$ and R$^{35a}$ do not represent hydrogen atom at the same time), t-butoxycarbonyl, benzyloxycarbonyl or C1–4 alkyl), carbocyclic or heterocyclic ring, unsubstituted or substituted by one or more substituents selected from C1–4 alkyl, C1–4 alkoxyalkyl, protected amino, nitro, hydroxy, protected hydroxy, halogen atom, nitrile, guanidino and amidino, with the proviso that a carbon atom of C1–8 alkyl may be replaced by a sulfur atom), or

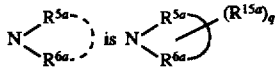

in which R$^{5a}$ and R$^{6a}$, taken together with the nitrogen atom to which they are attached represent a heterocyclic ring, q is as hereinbefore defined, R$^{15a}$ is 1) hydroxy,
2) hydroxy protected by a protecting group which is removable under acid conditions,
3) keto,
4) protected keto,
5) C1–4 alkyl,
6) C1–4 alkoxy,
7) phenyl,
8) phenoxy,
9) phenyl C1–4 alkyl,
10) phenyl C1–4 alkoxy,
11) nitro,
12) —COOR$^{36a}$ (in which R$^{36a}$ is hydrogen atom, C1–8 alkyl, C1–4 alkyl substituted by —CONR$^{37}$R$^{38}$ (in which R$^{37}$ and R$^{38}$ are as hereinbefore defined), C1–4 alkyl substituted by —NR$^{39a}$R$^{40a}$ (in which R$^{39a}$ and R$^{40a}$ each, independently, is hydrogen atom (with the proviso that, R$^{39a}$ and R$^{40a}$ do not represent hydrogen atom at the same time), t-butoxycarbonyl, benzyloxycarbonyl or C1–4 alkyl), C1–4 alkyl substituted by —OR$^{41a}$ (in which R$^{41a}$ is C2–4 alkyl substituted by —OR$^{42a}$ (in which R$^{42}$a is hydrogen atom, C2–4 alkoxyalkyl or benzyl),) or C1–4 alkyl substituted by protected piperazino ring), 13) —NR$^{43a}$R$^{44a}$ (in which R$^{43a}$ and R$^{44a}$ each, independently, is hydrogen atom (with the proviso that, R$^{43a}$ and R$^{44a}$ do not represent hydrogen atom at the same time) , t-butoxycarbonyl, benzyloxycarbonyl, C1–4 alkyl or C2–5 acyl), 14) —CONR$^{45a}$R$^{46a}$ (in which R$^{45a}$ and R$^{46a}$ each, independently, is hydrogen atom, C1–4 alkyl, hydroxy, hydroxy protected by a protecting group which is removable under acid conditions, phenyl C1–4 alkyloxy or C1–4 alkyl substituted by hydroxy, protected hydroxy or —COOR$^{47a}$ (in which R$^{47a}$ is hydrogen atom, C1–8 alkyl or benzyl),), 15) C1–4 alkyl substituted by one or more substituents selected from hydroxy, protected hydroxy, —COOR$^{48a}$ (in which R$^{48a}$ is hydrogen atom, C1–8 alkyl or benzyl), —NR$^{49a}$R$^{50a}$ (in which R$^{49a}$ and R$^{50a}$ each, independently, is hydrogen atom (with the proviso that, R$^{49a}$ and R$^{50a}$ do not represent hydrogen atom at the same time), t-butoxycarbonyl, benzyloxycarbonyl or C1–4 alkyl), or 5- or 6-membered heterocyclic ring containing one or two nitrogen atoms, 16) 5- or 6-membered heterocyclic ring containing one or two nitrogen atoms, 17) halogen atom, 18) —CHO protected by a protecting group which is removable under acid condition, or 19) —NR$^{51a}$—COOR$^{52a}$ (in which R$^{51a}$ and R$^{52a}$ each, independently, is hydrogen atom or C1–8 alkyl), and the other symbols are as hereinbefore defined, or may be prepared by esterifying a compound of formula (II) with a compound of formula (III) to obtain a compound having protected groups and then eliminating the protecting groups (e.g. hydrolysis of t-butylester, treatment with acid and/or hydrogenolysis), or may be prepared by esterifying a compound of formula (II) with a compound of formula (III), if necessary, eliminating the protecting groups to obtain a compound having R$^{15}$ represent C1–4 alkyl substituted by hydroxy and then subjecting to the sulfuric acid esterification.

Protected hydroxy means, for example, hydroxy protected by a protecting group which is removable under acid conditions (e.g., C2–4 alkoxyalkyl, t-butyidimethylsilyl, tetrahydropyran (THP), triphenylmethyl) or hydroxy protected by a protecting group which is removable by hydrogenation (e.g., benzyl).

Hydroxy protected by a protecting group which is removable under acid conditions means, for example, hydroxy group protected by C2–4 alkoxyalkyl, t-butyldimethylsilyl, tetrahydropyran (THP) or triphenylmethyl.

Protected amino acid, α-amino acid or piperazino ring means, for example, amino acid, α-amino acid or piperazino ring protected by t-butoxycarbonyl (Boc) or benzyloxycarbonyl (Cbz).

CHO protected by a protecting group which is removable under acid conditions means, for example, —CHO protected by acetal (e.g., dimethylacetal or diethylacetal) or ketal (e.g., ethylenedioxyketal or trimethylenedioxyketal).

The above esterification is known per se and can be carried out by methods for example:

(1) using an acid halide,
(2) using a mixed acid anhydride,
(3) using a condensing agent.

Each of these methods can be carried out, for example, as follows:

(1) the method using an acid halide may be carried out, for example, by reacting a carboxylic acid with an acid halide (e.g., oxalyl chloride or thionyl chloride) in an inert organic solvent (e.g., chloroform, methylene chloride, diethyl ether or tetrahydrofuran) or without a solvent at from −20° C. to the reflux temperature of the solvent, and then by reacting the acid halide obtained with a corresponding alcohol in the presence of a tertiary amine (e.g., pyridine, triethylamine, dimethylaniline or dimethylaminopyridine) in an inert organic solvent (e.g., chloroform, methylene chloride, diethyl ether or tetrahydrofuran), at a temperature of from 0° C. to 40° C., (2) the method using a mixed acid anhydride may be carried out, for example, by reacting a carboxylic acid and an acid halide (e.g., pivaloyl chloride, tosyl chloride or mesyl chloride) or an acid derivative (e.g., ethyl chloroformate or isobutyl chloroformate) in the presence of a tertiary amine (e.g., pyridine, triethylamine, dimethylaniline or dimethylaminopyridine) in an inert organic solvent (e.g., chloroform, methylene chloride, diethyl ether or tetrahydrofuran) or without a solvent at a temperature of from 0° C. to 40° C., and then by reacting the mixture of acid anhydride obtained with a corresponding alcohol in an inert organic solvent (e.g., chloroform, methylene chloride, diethyl ether or tetrahydrofuran), at a temperature of from 0° C. to 40° C., (3) the method using a condensing agent (e.g., 1,3-dicyclohexyl carbodiimide (DCC), 1-ethyl-3-[3-(dimethylamino)propyl]carbodiimide (EDC) or 2-chloro-1-methylpyridinium iodide) may be carried out, for example, by reacting a carboxylic acid with a corresponding alcohol using a condensing agent in the presence or absence of a tertiary amine (e.g., pyridine, triethylamine, dimethylaniline or dimethylaminopyridine) in an inert organic solvent (e.g., chloroform, methylene chloride, dimethyl formamide or diethyl ether) or without a solvent at a temperature of from 0° C. to 40° C.

The reactions (1), (2) and (3) hereinbefore described may be preferably carried out in an atmosphere of inert gas (e.g., argon or nitrogen) under anhydrous conditions.

The hydrolysis of t-butylester group or the reaction resulting from treatment with acid (e.g. elimination of C2–4 alkoxyalkyl, t-butoxycarbonyl or dimethylacetal) is known per se and may be carried out, for example, by using an organic acid (e.g., trifluoroacetic acid) or an inorganic acid (e.g., hydrochloric acid), or a mixture thereof, in an inert organic solvent (e.g., methylene chloride, chloroform, methanol, dioxane, ethyl acetate or anisole) at a temperature of from 0° C. to 90° C.

The hydrogenolysis is known per se, and may be carried out, for example, in an inert solvent [such as an ether (e.g., tetrahydrofuran, dioxane, diethoxyethane or diethyl ether), an alcohol (e.g., methanol or ethanol), benzene analogue (e.g., benzene or toluene), a ketone (e.g., acetone or methyl ethyl ketone), a nitrile (e.g., acetonitrile), an amide (e.g., dimethylformamide), water, ethyl acetate, acetic acid or a mixture of two or more of them, etc.], in the presence of a hydrogenation catalyst (e.g., palladium on activated carbon, palladium black, palladium, palladium hydroxide on carbon, platinum oxide, nickel or Raney nickel (registered trade mark)), in the presence of absence of an inorganic acid (e.g., hydrochloric acid, sulfuric acid, hypochlorous acid, boric acid or tetrafluoroboric acid) or an organic acid (e.g., acetic acid, p-toluenesulfonic acid, oxalic acid, trifluoroacetic acid or formic acid), at ordinary or elevated pressure under an atmosphere of hydrogen, at a temperature of from 0° C. to 200° C. When using an acid, its salt may be used at the same time.

The sulfuric acid esterification is known per se, and may be carried out, for example, by reacting sulfur trioxide pyridine complex in the presence of a tertiary amine (e.g., pyridine) at a temperature of from 0° C. to 40° C.

The compounds of the formulae (II) and (III) used as starting materials may be prepared by the methods of the following Scheme 1 or by methods known per se or are commercially available compounds. For example, 2-phenylbutanoic acid is commercially available. The compounds may also be prepared by the methods described in the Example of the present specification.

Scheme 1

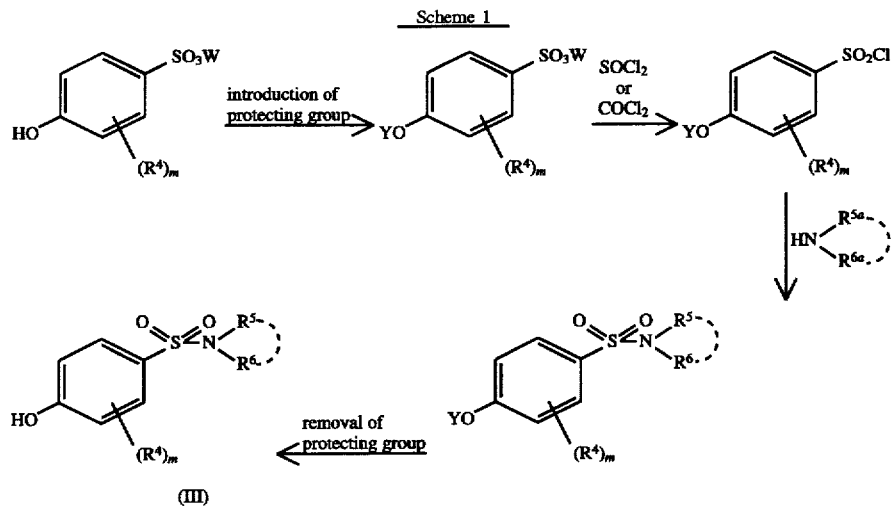

In Scheme 1 hereinbefore described

W is an alkali metal,

Y is benzyl, benzyloxycarbonyl or protecting group which may be removed under acid conditions (e.g., C2–4 alkoxyalkyl, t-butyldimethylsilyl, tetrahydropyran (THP) or triphenylmethyl), and the other symbols are as hereinbefore defined.

Effect

It has been confirmed that the compounds of the formula (I), of the present invention have inhibitory activities on elastase. For example, in laboratory tests the following results were obtained.

(1) Inhibitory effects on human polymorphonuclear elastase

A mixture with 0.5 ml of 0.2 mM HEPES buffer (pH 8.0), 0.2 ml of 2.5M NaCl, 0.1 ml of 1% polyethyleneglycol 6000, 0.13 ml of distilled water, test compound dissolved in 0.01 ml of dimethylsulfoxide (DMSO) and 0.05 ml of 0.8 Unit/ml human polymorphonuclearelastase (HSE) was preincubated at 37° C. for 20 min. 5 mM of Meo-Suc-Ala-Ala-Pro-Val-pNA (DMSO solution, 0.01 ml) was then added to the above mixture and was incubated at 37° C. for 5 min. The reaction was terminated by 0.1 ml of 50% acetic acid and the p-nitroanilide (pNA) released was measured spectrophotometrically at 405 nM. Percent inhibition of a compound was calculated by the following equation.

Inhibition (%)=1−{derlat $OD$(test-blank)/delta$OD$(control-blank)}× 100

Results are shown in Table 47.

TABLE 47

| Example No. | $IC_{50}$ (μM) |
| --- | --- |
| 1(16) | 0.017 |
| 1(40) | 0.019 |
| 1(56) | 0.014 |
| 1(78) | 0.0080 |
| 1(130) | 0.022 |
| 1(139) | 0.024 |
| 2 | 0.055 |
| 2(1) | 0.012 |
| 2(42) | 0.013 |
| 2(62) | 0.0068 |
| 2(69) | 0.011 |
| 2(77) | 0.018 |
| 2(111) | 0.0097 |
| 2(120) | 0.023 |
| 2(157) | 0.008 |
| 2(173) | 0.014 |
| 2(179) | 0.049 |
| 2(197) | 0.010 |
| 2(274) | 0.012 |
| 2(276) | 0.0093 |

(2) Inhibitory effects on human polymorphonuclear elastase-induced lung hemorrhage in hamster A test compound suspended in 0.5% Carboxymethylcellulose or 80% Polyethyleneglycol, 400 or 2% Tween 80 was administered orally to a group of 5 Syrian hamsters. At 60 min after the administration, 10 U/0.1 ml of HSE was injected intratracheally via surgically exposed trachea under pentobarbital anesthesia (60 mg/kg, i.p.) to induce lung injury. At 60 min after the injection, hamsters were bled to sacrifice and subjected to bronchoalveolar lavage with 2.5 ml of saline and recovered lavage solution (BALF). The recovered BALF (0.5 ml) was diluted by 4 times with 2% aqueous solution sodium carbonate and sonicated for 10 sec. The lavage fluid was further diluted by 2.5 times with 2% aqueous solution sodium carbonate and the amount of blood in BALF was calculated from absorbance at 414 nM using standard curve.

Results are shown in Table 48 and 49.

TABLE 48

| Example No. | inhibition at 500 mg/kg (%) |
| --- | --- |
| 1(68) | 51 |
| 1(90) | 65 |
| 2 | 81 |
| 2(42) | 67 |
| 2(69) | 83 |

TABLE 49

| Example No. | $ED_{50}$ |
| --- | --- |
| 1(139) | 192 mg/kg |
| 2(274) | 132 mg/kg |
| 2(276) | 73 mg/kg |

The above experiments show that compounds of the present invention possess inhibitory activity on elastase, even when administered orally.

Toxicity

The toxicity of the compounds of the present invention is very low. Therefore, the compounds of the present invention may be considered to be sufficiently safe and suitable for pharmaceutical use.

Application for Pharmaceuticals

The compounds of the formula (I), of the present invention, and non-toxic salts and acid addition salts thereof, possess inhibitory activity on elastase. Accordingly, they are useful for the treatment and/or prevention of diseases induced by an abnormal enhancement of the degradation of elastin, collagen fiber and/or proteoglycan, resulting from the action of elastase on a mammalian animal, especially a human (e.g., chronic obstructive pulmonary disease such as emphysema, rheumatoid arthritis, atherosclerosis, adult respiratory distress syndrome (ARDS), glomerular nephritis, myocardial infarction, idiopathic ulcerative colitis or gingivitis).

For the purpose above described, the compounds of the formula (I), of the present invention, or non-toxic salts or acid addition salts or solvates thereof may normally be administered systemically or locally, usually by oral or parenteral administration.

The doses to be administered are determined depending upon, for example, age, body weight, symptom, the desired therapeutic effect, the route of administration, and the duration of the treatment etc. In the human adult, the doses per person are generally from 1 mg to 1000 mg, by oral administration, up to several times per day, or from 0.1 mg to 100 mg, by parenteral administration up to several times per day, or by continuous administration for from 1 to 24 hrs. per day from vein.

As mentioned above, the doses to be used depend upon various conditions. Therefore, there are cases in which doses lower than or greater than the ranges specified above may be used.

The compounds of the present invention, may be administered in the from of, for example, solid compositions, liquid compositions or other compositions for oral administration, injections, liniments or suppositories for parenteral administration.

Solid compositions for oral administration include compressed tablets, pills, capsules, dispersible powders, and granules. Capsules include hard capsules and soft capsules.

In such compositions, one or more of the active compound(s) may be admixed with at least one inert diluent (such as lactose, mannitol, glucose, hydroxypropyl cellulose, microcrystalline cellulose, starch, polyvinylpyrrolidone or magnesium metasilicate aluminate). The compositions may also comprise, as is normal practice, additional substances other than inert diluents: e.g. lubricating agents (such as magnesium stearate), disintegrating agents (such as cellulose calcium glycolate), stabilizing agents (such as lactose, etc.), and agents to assist dissolution (such as glutamic acid or asparaginic acid).

The tablets or pills may, if desired, be coated with a film of gastric or enteric material (such as sugar, gelatin, hydroxypropyl cellulose or hydroxypropylmethyl cellulose phthalate etc.), or be coated with two or more films. And further, coating may include containment within capsules of absorbable materials such as gelatin.

Liquid compositions for oral administration include pharmaceutically-acceptable solutions, emulsions, suspensions, syrups and elixirs. In such compositions, one or more of the active compound(s) is or are contained in inert diluent(s) commonly used in the art (e.g., purified water or ethanol etc.). Besides inert diluents, such compositions may also comprise adjuvants (such as wetting agents or suspending agents), sweetening agents, flavouring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (such as sodium sulfate), isotonic buffer (such as sodium chloride, sodium citrate or citric acid). For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. In such compositions, one more of active compound(s) may be admixed with at least one of inert aqueous diluent(s) (e.g. distilled water for injection or physiological salt solution etc.) or inert non-aqueous diluent(s) (e.g., propylene glycol, polyethylene glycol, olive oil, ethanol or POLYSORBATE80 (registered trade mark)).

Injections may comprise additional ingredients other than inert diluents: e.g. preserving agents, wetting agents, emulsifying agents, dispersing agents, stabilizing agent (e.g., lactose), assisting agents such as agents to assist dissolution (e.g., glutamic acid or asparaginic acid).

They may be sterilized for example, by filtration through a bacteria-retaining filter, by incorporation of sterilizing agents in the compositions or by irradiation. They may also be manufactured in the form of sterile solid compositions, for example, by freeze-drying, which may be dissolved in sterile water or some other sterile diluent(s) for injection immediately before used.

Other compositions for parenteral administration include liquids for external use, and endermic liniments, ointment, suppositories and pessaries which comprise one or more of the active compound(s) and may be prepared by methods known per.

REFERENCE EXAMPLES AND EXAMPLES

The following reference examples and examples illustrate, but do not limit, the present invention.

The solvents in parentheses show the developing or eluting solvents and the ratios of the solvents used are by volume in chromatographic separations and TLC.

The NMR data show the solvents used in the measurements in parentheses.

Reference example 1

3-methyl-4-hydroxybenzenesulfonic acid.potassium salt

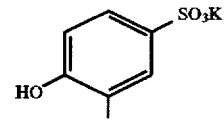

To stirring conc. sulfuric acid (26 ml) at 100° C. was slowly added o-cresol (50 ml), the mixture was stirred at 100° C. for 5 hours. After the reaction mixture was cooled at room temperature, to mixture was neutralized by slowly adding potassium hydroxide (27.5 g) in water (35 ml) solution. After to the mixture was added methanol (100 ml), the precipitate was filtered to give the title compound (56.5 g) having the following physical data.

TLC: Rf 0.18 (chloroform:methanol:water=6:4:1).

Reference example 2

3-methyl-4-(benzyloxycarbonyloxy)benzenesulfonic acid.potassium salt

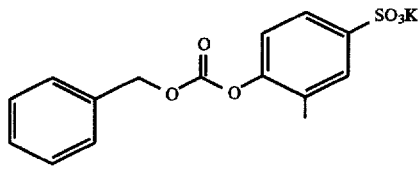

To a suspension of the compound prepared in reference example 1 (12.2 g) in tetrahydrofuran (THF) (100 ml) was added 2N aqueous solution of sodium hydroxide (28 ml) at room temperature, following added benzyloxycarbonyl chloride (8 ml) under cooling with ice. The reaction mixture was stirred for 30 min. The reaction mixture was concentrated under reduced pressure, and cooled with ice, and the precipitate was filtered to give the title compound (7.3 g) having the following physical data.

TLC: Rf 0.51 (chloroform:methanol:water=6:4:1).

Reference example 3

3-methyl-4-(benzyloxycarbonyloxy)benzenesulfonyl chloride

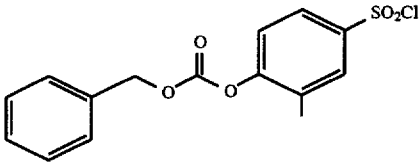

To a suspension of the compound prepared in reference example 2 (46.1 g) in dimethylformamide (DMF) (100 ml) was slowly added thionyl chloride (15 ml) under cooling with ice. The reaction mixture was stirred for 30 min at 5° C. To the reaction mixture was added ice water, and the precipitate was filtered to give the title compound (39.4 g) having the following physical data.

TLC: Rf 0.56 (chloroform:methanol:water=6:4:1).

Reference example 4

4-(2S-t-butyloxycarbonylpyrrolidin-1-ylsulfonyl)-2-methylphenol

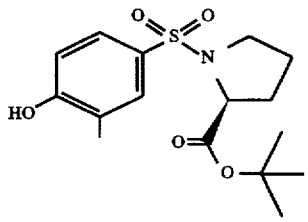

To a solution of L-proline.t-butylester (1.9 g) in pyridine (10 ml) was added the compound prepared in reference example 3 (3.7 g) under cooling with ice. The reaction mixture was stirred for 30 min. The mixture was quenched by adding 2N aqueous solution hydrochloric acid and extracted with ethyl acetate (200 ml). The organic layer was washed with a saturated aqueous solution of sodium hydrocarbonate and a saturated aqueous solution of sodium chloride, dried over anhydrous magnesium sulfate and concentrated. 10% Palladium on activated carbon (500 mg) was added to a solution of the residue (4.9 g) in methanol (200 ml) and the mixture was stirred for 2 h at room temperature under an atmosphere of hydrogen. The mixture was filtered through Celite (being on sale). The filtrate was concentrated to give the title compound (3.4 g) having the following physical data.

TLC: Rf 0.35 (hexane:ethyl acetate=1:1).

Reference example 5

2RS-(4-nitrophenyl)butanoic acid

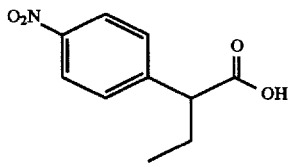

To a mixture solution of 2-phenylbutanoic acid (200 g) in acetic acid (200 ml) and conc. sulfuric acid (150 ml) was slowly added conc. nitric acid (150 ml) at 15° C. The reaction mixture was stirred for 10 min at same temperature. The reaction mixture was poured into ice water, and the precipitate was filtered. The residue was recrystallized from the mixture solution of hexane/ethyl acetate to give the title compound (103 g) having the following physical data.

TLC: Rf 0.50 (ethyl acetate).

Reference example 6

2RS-(4-aminophenyl)butanoic acid methylester

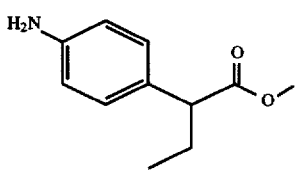

To a solution of the compound prepared in reference example 5 (15.7 g) in DMF (60 ml) was added potassium carbonate (12 g) under cooling with ice. To the mixture was added methyl iodide (5 ml) at same temperature. The reaction mixture was stirred for 2 h at room temperature. The mixture was quenched by adding 1N aqueous solution hydrochloric acid (200 ml) and extracted with the mixture of hexane/ethyl acetate (1:1, 200 ml). The organic layer was washed with water and a saturated aqueous solution of sodium chloride, dried over anhydrous magnesium sulfate and concentrated. 5% Palladium on activated carbon (1.3 g) was added to a solution of the residue in methanol (300 ml) and the mixture was stirred for 2 h at room temperature under an atmosphere of hydrogen. The mixture was filtered through Celite (being on sale). The filtrate was concentrated to give the tittle compound (14.2 g) having the following physical data.

TLC: Rf 0.47 (hexane:ethyl acetate=1:1).

Reference example 7

2RS-(4-(pyrrolidin-1-yl)phenyl)butanoic acid

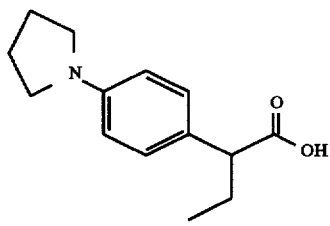

To a solution of the compound prepared in reference example 6 (14.2 g) in DMSO (75 ml) was added potassium carbonate (11 g) and 1,4-dibromobutane (9 ml). The reaction mixture was stirred for 1 h at 40° C. To the mixture was added sodium iodide (11.2 g). the reaction mixture was stirred for 3 h at 40° C. and stirred for 2 h at 60° C. The reaction mixture was quenched by adding water and extracted with the mixture of hexane/ethyl acetate (1:1, 1000 ml). The organic layer was washed with water and a saturated aqueous solution of sodium chloride, dried over anhydrous magnesium sulfate and concentrated. To a solution of the residue in methanol (80 ml) was added 5N aqueous solution of sodium hydroxide (20 ml) and the mixture was stirred for 5 h at room temperature. To the mixture was added aqueous solution hydrochloric acid until pH 8, and washed with ethyl acetate. The water layer was neutralized by adding aqueous solution hydrochloric acid, and extracted with ethyl acetate. The extract was washed with a saturated aqueous solution of sodium chloride, dried over anhydrous magnesium sulfate and concentrated. The residue was recrystallized from the mixture solution of hexane/ethyl acetate (3:1) to give the title compound (9.83 g) having the following physical data.

TLC: Rf 0.30 (hexane:ethyl acetate=1:1).

Example 1

4-(2S-t-butyloxycarbonylpyrrolidin-1-ylsulfonyl)-2-methylphenyl 2RS-(4-(pyrrolidin-1-yl)phenyl)butanoic acid ester

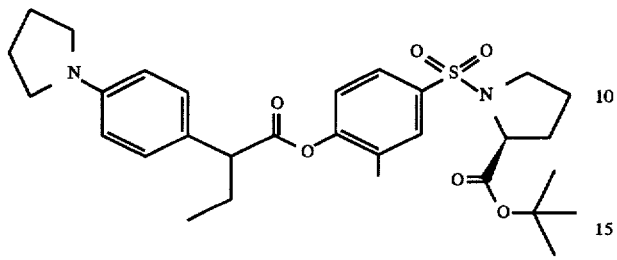

To a solution of the compound prepared in reference example 4 (748 mg), the compound prepared in reference example 7 (537 mg) and dimethylaminopyridine (64 mg) in dichloromethane (20 ml) was added 1-ethyl-3-(3-dimethylaminopropyl)-carbodiimide (482 mg) at room temperature. The reaction mixture was stirred for 2 h at room temperature. To the reaction mixture was added ethyl acetate, and washed with 1N aqueous solution hydrochloric acid (×2). The organic layer was dried over anhydrous magnesium sulfate and concentrated. The residue was purified by column chromatography on silica gel (hexane:ethyl acetate=5:1) to give the tittle compound (1.04 g) having the following physical data.

TLC: Rf 0.23 (hexane:ethyl acetate=5:1).

Example 1(1)–1(147)

By the same procedure as example 1 and by known method converted to corresponding salts or acid addition salts, the compounds having the following physical data were given by using corresponding phenol derivatives instead of the compound prepared in reference example 4 and by using corresponding carboxylic acid derivatives instead of the compound prepared in reference example 7.

Example 1(1)

4-(2S-hydroxymethylpyrrolidin-1-ylsulfonyl)phenyl 2RS-(4-(pyrrolidin-1-yl)phenyl)butanoic acid ester hydrochloride

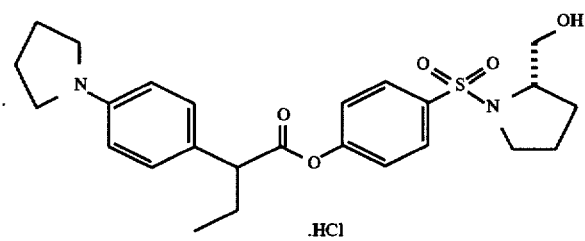

NMR (DMSO-d$_6$): δ7.85 (2H, d, J=9 Hz), 7.28 (2H, d, J=9 Hz), 7.28 (2H, d, J=9 Hz), 6.83 (2H, d, J=9 Hz), 3.75 (1H, t, J=7 Hz), 3.60–3.44 (2H, m), 3.40–3.20 (6H, m), 3.11–2.95 (1H, m), 2.21–1.90 (5H, m), 1.90–1.65 (3H, m), 1.55–1.30 (2H, m), 0.90 (3H, t, J=7 Hz);

TLC: Rf 0.48 (ethyl acetate:hexane=1:1).

Example 1(2)

4-(2-oxopyrrolidin-1-ylsulfonyl)phenyl 2RS-(4-(pyrrolidin-1-yl)phenyl)butanoic acid ester hydrochloride

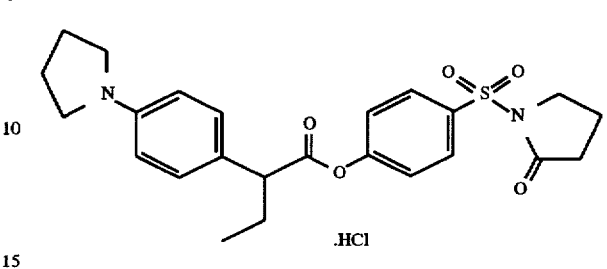

NMR (CDCl$_3$): δ8.05 (2H, d, J=8.8 Hz), 7.61 (2H, d, J=8.6 Hz), 7.47 (2H, d, J=8.6 Hz), 7.19 (2H, d, J=8.8 Hz), 3.89 (2H, t, J=7.2 Hz), 3.74 (1H, t, J=7.8 Hz), 3.85–3.45 (4H, brs), 2.44 (2H, t, J=7.8 Hz), 2.40–2.25 (4H, m), 2.35–1.75 (2H, m), 2.20–2.00 (2H, m), 0.99 (3H, t, J=7.4 Hz);

TLC: Rf 0.39 (ethyl acetate:hexane=1:1).

Example 1(3)

4-(pyrrolidin-1-ylsulfonyl)-2-methylphenyl 2RS-(4-(pyrrolidin-1-yl)phenyl)butanoic acid ester

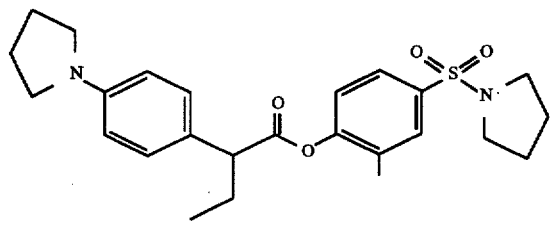

NMR (CDCl$_3$): δ7.68–7.57 (2H, m), 7.23 (2H, d, J=8 Hz), 7.06 (1H, d, J=8 Hz), 6.55 (2H, d, J=8 Hz), 3.61 (1H, t, J=7 Hz), 3.35–3.13 (8H, m), 2.30–1.65 (13H, m), 0.98 (3H, t, J=7 Hz);

TLC: Rf 0.49 (ethyl acetate:hexane=3:7).

Example 1(4)

4-(2S-(pyrrolidin-1-ylmethyl)pyrrolidin-1-ylsulfonyl)-2-methylphenyl 2RS-(4-(pyrrolidin-1-yl)phenyl)butanoic acid ester.2hydrochloride

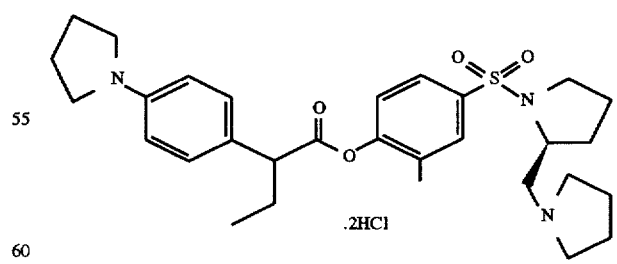

NMR (CD$_3$OD): 67 7.95–7.75 (2H, m), 7.65 (4H, s), 7.22 (1H, d, J=8.5 Hz), 4.26–3.90 (2H, m), 3.99 (1H, t, J=7.5 Hz), 3.90–3.70 (5H, m), 3.50–3.10 (6H, m), 2.40–2.25 (4H, m), 2.40–1.35 (10H, m), 2.07 (3H, s), 1.00 (3H, t, J=7.5 Hz);

TLC: Rf 0.43 (water:methanol:chloroform=1:10:90).

Example 1(5)

4-(pyrrolidin-1-ylsulfonyl)phenyl 2RS-phenylbutanoic acid ester

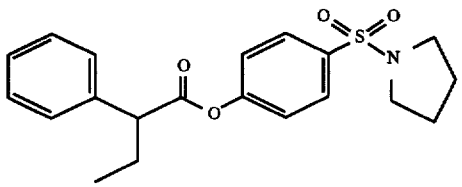

NMR (CDCl₃): δ7.85–7.74 (2H, m), 7.41–7.24 (5H, m), 7.23–7.10 (2H, m), 3.71 (1H, t, J=7 Hz), 3.30–3.15 (4H, m), 2.39–2.10 (1H, m), 2.03–1.80 (1H, m), 1.80–1.68 (4H, m), 0.99 (3H, t, J=7 Hz);

TLC: Rf 0.43 (hexane:ethyl acetate=2:1).

Example 1(6)

4-(indolin-1-ylsulfonyl)phenyl 2RS-(4-(pyrrolidin-1-yl)phenyl)butanoic acid ester.hydrochloride

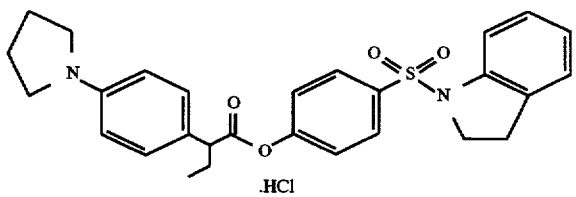

NMR (CDCl₃): δ7.78 (2H, d, J=8.8 Hz), 7.62 (1H, d, J=8.0 Hz), 7.50–7.34 (4H, m), 7.24–7.12 (1H, m), 7.08 (3H, d, J=8.8 Hz), 6.97 (1H, dt, J=1.0 and 7.2 Hz), 3.90 (2H, d, J=8.4 Hz), 3.68 (1H, t, J=7.6 Hz), 3.70–3.45 (4H, m), 2.89 (2H, t, J=8.4 Hz), 2.40–2.20 (4H, m), 2.30–2.05 and 2.00–1.75 (each 1H, m), 0.96 (3H, t, J=7.2 Hz);

TLC: Rf 0.47 (ethyl acetate:hexane=1:2).

Example 1(7)

4-(2-(ethoxycarbonyl)indolin-1-ylsulfonyl)2-methylphenyl 2RS-(4-(pyrrolidin-1-yl)phenyl)butanoic acid ester

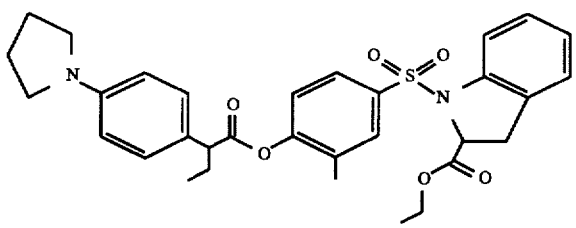

NMR (CDCl₃): δ7.7–7.5 (m, 3H), 7.2–6.9 (m, 6H), 6.8–6.4 (m, 2H), 4.71 (q, J=5.2 Hz, 1H), 4.23 (q, J=7.2 Hz, 2H), 3.57 (t, J=7.6 Hz, 1H), 3.4–3.0 (m, 6H), 2.4–1.8 (m, 9H), 1.29 (t, J=7.2 Hz, 3H), 1.0–0.9 (m, 3H);

TLC: Rf 0.63 (hexane:ethyl acetate=2:1).

Example 1(8)

4-(2-(ethoxycarbonyl)indolin-1-ylsulfonyl)phenyl 2RS-(4-(pyrrolidin-1-yl)phenyl)butanoic acid ester

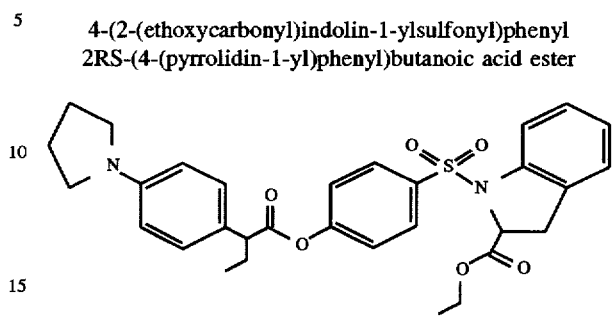

NMR (CDCl₃): δ7.77 (2H, d, J=8.5 Hz), 7.53 (1H, d, J=8.0 Hz), 7.24–6.93 (7H, m), 6.52 (2H, d, J=8.5 Hz), 4.71 (1H, dd, J=1 0.0, 5.5 Hz), 4.24 (2H, q, J=7.0 Hz), 3.54 (1H, t, J=8.0 Hz), 3.32–3.22 (4H, m), 3.22 (1H, dd, J=10.0, 16.0 Hz), 3.06 (1H, dd, J=16.0, 5.5 Hz), 2.05–1.90 (4H, m), 2.25–1.70 (2H, m), 1.29 (3H, t, J=7.0 Hz), 0.95 (3H, t, J=7.5 Hz);

TLC: Rf 0.57 (hexane:ethyl acetate=1:1).

Example 1(9)

4-(2RS-(N,N-dimethylaminocarbonylmethoxycarbonyl)indolin-1-ylsulfonyl)-2-methylphenyl 2RS-(4-(pyrrolidin-1-yl)phenyl)butanoic acid ester

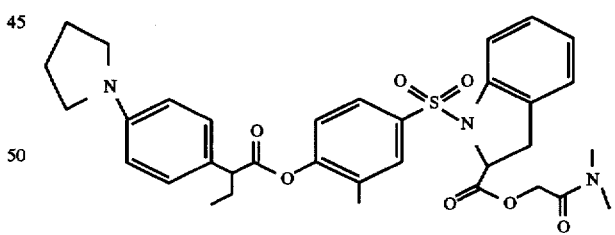

NMR (CDCl₃): δ7.7–7.5 (m, 3H), 7.2–6.9 (m, 6H), 6.54 (d, J=8.6 Hz, 2H), 4.85 (d, J=14.5 Hz, 1H), 4.82 (dd, J=1.0, 10.8 Hz, 1H), 4.70 (d, J=14.5 Hz, 1H), 3.58 (t, J=7.7 Hz, 1H), 3.65–3.50 (m, 1H), 3.45 (dd, J=1 0.8, 16.1 Hz, 1H), 3.4–3.2 (m, 4H), 2.96 (s, 3H), 2.94 (s, 3H), 2.3–1.8 (m, 6H), 1.97 (s, 3H), 0.96 (t, J=7.4 Hz, 3H);

TLC: Rf 0.52 (chloroform:ethyl acetate=1:1).

Example 1(10)

4-(2RS-(N-benzyloxycarbamoyl)indolin-1-ylsulfonyl)phenyl 2RS-(4-(pyrrolidin-1-yl)phenyl) butanoic acid ester

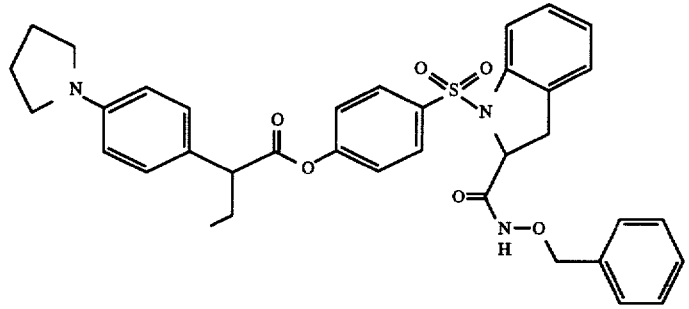

NMR (CDCl$_3$): δ 9.22 (1H, s), 7.60 (1H, d, J=8.0 Hz), 7.51 (2H, d, J=9.0 Hz), 7.29 (5H, s), 7.17–7.00 (8H, m), 6.52 (2H, d, J=9.0 Hz), 4.88 (2H, s), 4.60 (1H, dd, J=10.0 Hz, 1.5 Hz), 3.53 (1H, t, J=7.0 Hz), 3.26 (5H, t-like, J6.0 Hz), 2.74 (1H, dd, J=16.0 Hz, 10.0 Hz), 2.20–1.77 (2H, m), 2.03–1.98 (4H, m), 0.92 (3H, t, J=7.0 Hz);

TLC: Rf 0.44 (hexane:ethyl acetate=1:1).

Example 1(11)

4-(6-nitroindolin-1-ylsulfonyl)-2-methylphenyl 2RS-(4-(pyrrolidin-1-yl)phenyl)butanoic acid ester

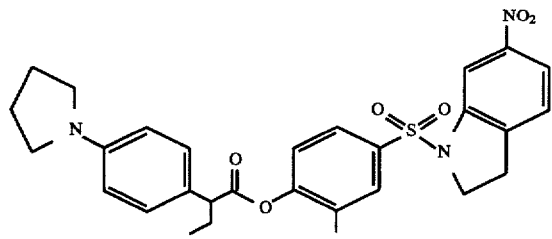

NMR (CDCl$_3$): δ 8.10 (dd, J=2.4, 8.8 Hz, 1H), 7.96 (s, 1H), 7.7–7.6 (m, 3H), 7.18 (d, J=8.4 Hz, 2H), 7.05 (d, J=8.0 Hz, 1H), 6.52 (d, J=8.4 Hz, 2H), 4.01 (t, J=8.6 Hz, 2H), 3.58 (t, J=7.8 Hz, 1H), 3.3–3.2 (m, 4H), 3.08 (t, J=8.6 Hz, 2H), 2.3–1.8 (m, 2H), 2.00 (s, 3H), 2.1–1.9 (m, 4H), 0.96 (t, J=7.4 Hz, 3H);

TLC: Rf 0.33 (hexane:ethyl acetate=3:1).

Example 1(12)

4-(6-aminoindolin-1-ylsulfonyl)-2-methylphenyl 2RS-(4-(pyrrolidin-1-yl)phenyl)butanoic acid ester

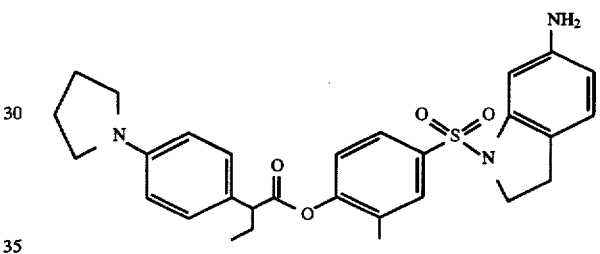

NMR (CDCl$_3$): δ 7.6–7.4 (m, 3H), 7.20 (d, J=8.7 Hz, 2H), 6.94 (d, J=8.4 Hz, 1H), 6.53 (d, J=8.7 Hz, 2H), 6.6–6.4 (m, 2H), 3.83 (t, J=8.2 Hz, 2H), 3.58 (t, J=7.7 Hz, 1H), 3.4–3.2 (m, 4H), 2.64 (t, J=8.2 Hz, 2H), 2.3–1.8 (m, 6H), 1.95 (s, 3H), 0.97 (t, J=7.4 Hz, 3H);

TLC: Rf 0.59 (hexane:ethyl acetate=1:1).

Example 1(13)

4-(7-nitroindolin-1-ylsulfonyl)-2-methylphenyl 2RS-(4-(pyrrolidin-1-yl)phenyl)butanoic acid ester

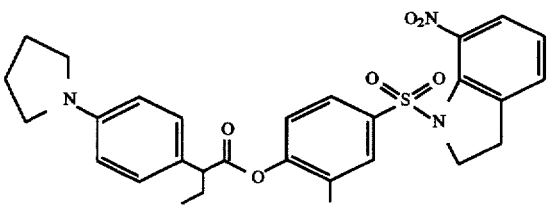

NMR (CDCl$_3$): δ 8.38 (d, J=2.2 Hz, 1H), 7.85 (dd, J=2.0, 8.4 Hz, 1H), 7.8–7.6 (m, 2H), 7.2–7.1 (m, 1H), 7.18 (d, J=8.6 Hz, 2H), 7.03 (d, J=8.2 Hz, 1H), 6.52 (d, J=8.6 Hz, 2H), 3.99 (t, J=8.6 Hz, 2H), 3.58 (t, J=7.6 Hz, 1H), 3.3–3.2 (m, 4H), 3.05 (t, J=8.6 Hz, 2H), 2.3–1.7 (m, 9H), 0.96 (t, J=7.4 Hz, 3H);

TLC: Rf 0.49 (hexane:ethyl acetate=1:1).

Example 1(14)

4-(7-aminoindolin-1-ylsulfonyl)-2-methylphenyl 2RS-(4-(pyrrolidin-1-yl)phenyl)butanoic acid ester

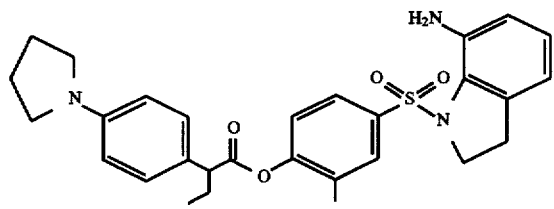

NMR (CDCl$_3$): δ 7.6–7.5 (m, 2H), 7.15 (d, J=8.6 Hz, 2H), 7.0–6.9 (m, 2H), 6.82 (d, J=8.0 Hz, 1H), 6.52 (d, J=8.6 Hz, 2H), 6.29 (dd, J=2.0, 8.0 Hz, 1H), 3.84 (t, J=8.0 Hz, 2H), 3.58 (t, J=7.6 Hz, 1H), 3.4–3.2 (m, 4H), 2.76 (t, J=7.6 Hz, 2H), 2.3–1.8 (m, 9H), 0.97 (t, J=7.4 Hz, 3H);

TLC: Rf 0.40 (hexane:ethyl acetate=2:1).

Example 1(15)

4-(benzimidazol-1-ylsulfonyl)-2-methylphenyl 2RS-(4-(pyrrolidin-1-yl)phenyl)butanoic acid ester

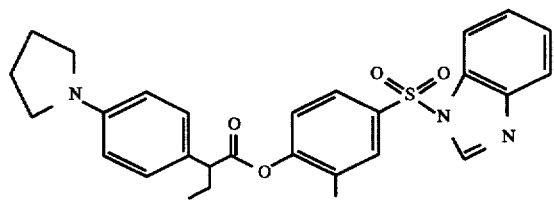

NMR (CDCl$_3$): δ 8.35 (1H, s), 7.79 (4H, m), 7.35 (2H, m), 7.17 (2H, d, J=8.8 Hz), 7.08 (1H, d, J=9.4 Hz), 6.52 (2H, d, J=8.8 Hz), 3.57 (1H, t, J=7.8 Hz), 3.26 (4H, m), 2.10 (1H, m), 2.00 (3H, s), 1.97 (4H, m), 1.88 (1H, m), 0.95 (3H, t, J=7.4 Hz);

TLC: Rf 0.49 (hexane:ethyl acetate=2:1).

Example 1(16)

4-(morpholin-4-ylsulfonyl)phenyl 2RS-(4-(pyrrolidin-1-yl)phenyl)butanoic acid ester

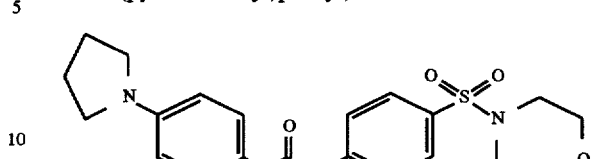

NMR (DMSO-d$_6$): δ 7.75 (2H, d, J=7 Hz), 7.27 (2H, d, J=7 Hz), 7.16 (2H, d, J=7 Hz), 6.52 (2H, d, J=7 Hz), 3.67 (1H, t, J=7 Hz), 3.61 (4H, t-like), 3.20 (4H, t-like), 2.83 (4H, t-like), 2.04 (1H, m), 1.94 (4H, t-like), 1.79 (1H, m), 0.88 (3H, t, J=7 Hz);

TLC: Rf 0.54 (hexane:ethyl acetate=1:1).

Example 1(17)

4-(6-aza-7-oxo-bicyclo[3.2.1]octan-6-ylsulfonyl) phenyl 2RS-(4-(pyrrolidin-1-yl)phenyl)butanoic acid ester.hydrochloride

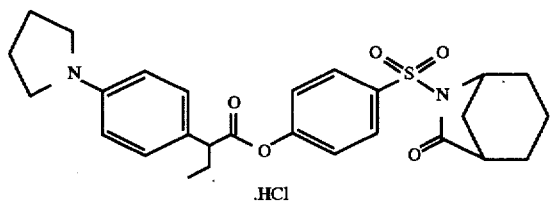

NMR (CDCl$_3$): δ 8.19 (2H, d, J=9 Hz), 7.38 (2H, d, J=9 Hz), 7.19 (4H, d, J=9 Hz), 4.65–4.55 (1H, m), 3.68 (1H, t, J=7 Hz), 3.61–3.37 (4H, m), 2.59–2.49 (1H, m), 2.35–1.46 (12H, m), 1.35–1.10 (2H, m), 0.99 (3H, t, J=7 Hz);

TLC: Rf 0.17 (ethyl acetate:hexane=1:3).

Example 1(18)

4-(4-benzylpiperazin-1-ylsulfonyl)phenyl 2RS-(4-(pyrrolidin-1-yl)phenyl)butanoic acid ester.2hydrochloride

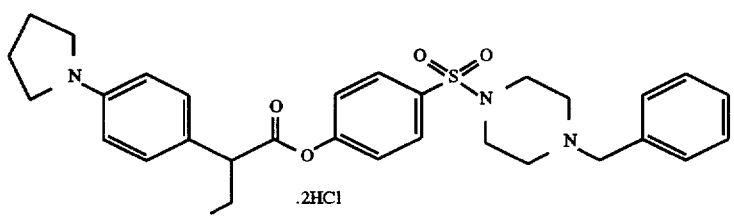

NMR (CD$_3$OD): δ 7.83 (2H, d, J=8.6 Hz), 7.75–7.40 (9H, m), 7.29 (2H, d, J=8.6 Hz), 4.35 (2H, s), 4.00–3.62 (7H, m), 3.60–3.40 (2H, m), 3.30–3.10 (2H, m), 2.98–2.72 (2H, m), 2.38–2.10 (5H, m), 2.04–1.80 (1H, m), 0.99 (3H, t, J=7.4 Hz);

TLC: Rf 0.40 (ethyl acetate:hexane=3:7).

Example 1(19)

4-(4-(2-hydroxyethyl)piperidin-1-ylsulfonyl)phenyl 2RS-(4-(pyrrolidin-1-yl)phenyl)butanoic acid ester

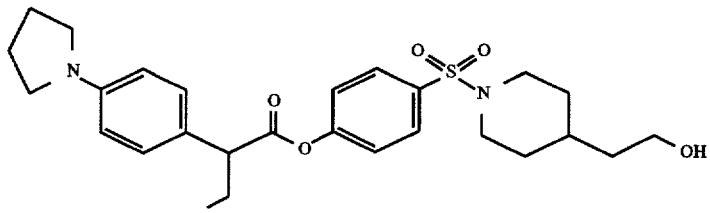

NMR (CDCl$_3$): δ 7.71 (2H, d, J=9.0 Hz), 7.72 (2H, d, J=8.7 Hz), 7.15 (2H, d, J=9.0 Hz), 6.55 (2H, d, J=8.7 Hz), 3.74 (2H, d, J=10.2 Hz), 3.63 (2H, t, J=6.0 Hz), 3.58 (1H, t, J=8.0 Hz), 3.36–3.22 (4H, m), 2.35–1.78 (8H, m), 1.72 (2H, d, J=10.0 Hz), 1.54–1.20 (5H, m), 0.98 (3H, t, J=7.4 Hz);

TLC: Rf 0.52 (chloroform:methanol=19:1).

Example 1(20)

4-(2RS-hydroxymethylpiperidin-1-ylsulfonyl)phenyl 2RS-(4-(pyrrolidin-1-yl)phenyl)butanoic acid ester.hydrochloride

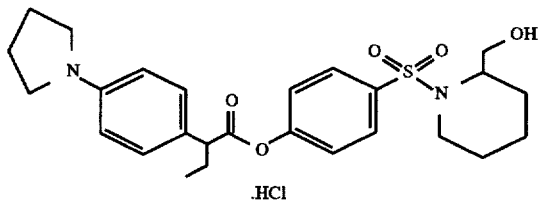

NMR (DMSO-d$_6$): δ 7.85 (2H, d, J=9 Hz), 7.27 (2H, d, J=9 Hz), 7.22 (2H, d, J=9 Hz), 6.83 (2H, d, J=9 Hz), 3.93–3.80 (1H, m), 3.75 (1H, t, J=7 Hz), 3.69–3.45 (2H, m), 3.45–3.20 (5H, m), 3.06–2.88 (1H, m), 2.21–1.80 (5H, m), 1.80–1.64 (2H, m), 1.55–1.30 (3H, m), 1.30–0.99 (2H, m), 0.90 (3H, t, J=7 Hz);

TLC: Rf 0.46 (ethyl acetate:hexane=1:1).

Example 1(21)

4-(4-(N,N-dimethylamino)piperidin-1-ylsulfonyl)phenyl 2RS-(4-(pyrrolidin-1-yl)phenyl)butanoic acid ester NMR (CDCl$_3$): δ 7.71 (2H, d, J=8.7 Hz), 7.20 (2H, d, J=8.8 Hz), 7.16 (2H, d, J=8.7 Hz), 6.54 (2H, d, J=8.8 Hz), 3.75 (2H, d, J=13.7 Hz), 3.58 (1H, t, J=7.7 Hz), 3.29 (4H, t, J=6.6 Hz), 2.36–1.53 (19H, m), 0.98 (3H, t, J=7.4 Hz);

TLC: Rf 0.25 (hexane:ethyl acetate=2:1).

Example 1(22)

4-(4-(pyrimidin-2-yl)piperazin-1-ylsulfonyl)phenyl 2RS-(4-(pyrrolidin-1-yl)phenyl)butanoic acid ester

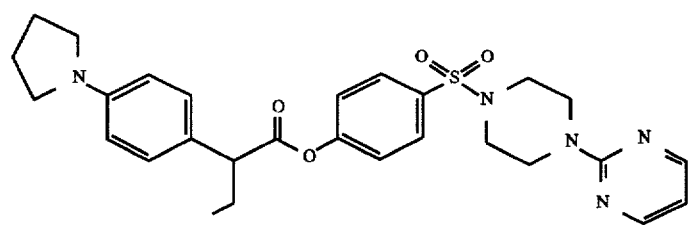

NMR (CDCl₃): δ 8.26 (2H, d, J=8.8 Hz), 7.72 (2H, d, J=8.7 Hz), 7.22–7.12 (4H, m), 6.56–6.47 (3H, m), 3.93 (4H, t, J=5.2 Hz), 3.57 (1H, t, J=7.7 Hz), 3.31–3.25 (4H, m), 3.04 (4H, t, J=5.1 Hz), 2.25–1.65 (6H, m), 0.97 (3H, t, J=7.3 Hz);

TLC: Rf 0.43 (hexane:ethyl acetate=1:1).

Example 1(23)

4-(1,4-dioxa-8-azaspiro[4.5]decan-8-ylsulfonyl)phenyl 2RS-(4-(pyrrolidin-1-yl)phenyl)butanoic acid ester

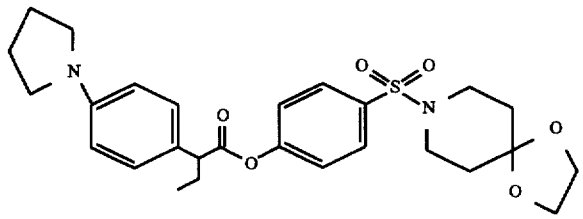

NMR (CDCl₃): δ 7.72 (2H, d, J=8.7 Hz), 7.24–7.15 (4H, m), 6.56 (2H, d, J=8.7 Hz), 3.89 (4H, s), 3.59 (1H, t, J=7.7 Hz), 3.29 (4H, t, J=6.6 Hz), 3.14 (4H, t, J=5.7 Hz), 2.30–1.61 (10H, m), 0.98 (3H, t, J=7.4 Hz);

TLC: Rf 0.48 (hexane:ethyl acetate=1:1).

Example 1(24)

4-(3-azabicyclo[3.2.2]nonan-3-ylsulfonyl)phenyl 2RS-(4-(pyrrolidin-1-yl)phenyl)butanoic acid ester.hydrochloride

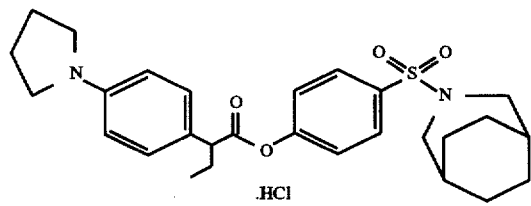

NMR (CDCl₃): δ 7.73 (2H, d, J=8.6 Hz), 7.53 (2H, d, J=8.6 Hz), 7.45 (2H, d, J=8.6 Hz), 7.15 (2H, d, J=8.8 Hz), 3.72 (1H, t, J=7.6 Hz), 3.75–3.50 (4H, m), 3.22 (4H, d, J=4.2 Hz), 2.40–2.20 (4H, m), 2.40–1.75 (2H, m), 2.10–2.00 (2H, m), 1.80–1.50 (8H, m), 0.99 (3H, t, J=7.4 Hz);

TLC: Rf 0.57 (ethyl acetate:hexane=1:3).

Example 1(25)

4-(1,3,3-trimethyl-6-azabicyclo[3.2.1]octan-6-ylsulfonyl)phenyl 2RS -(4-(pyrrolidin-1-yl)phenyl)butanoic acid ester.hydrochloride

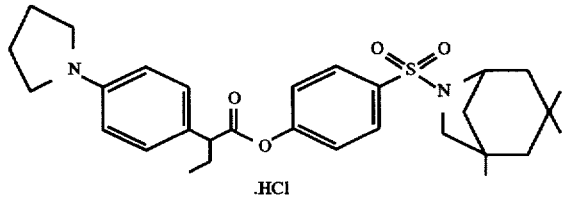

NMR (CDCl₃): δ 7.81 (2H, d, J=8.8 Hz), 7.40 (2H, d, J=8.4 Hz), 7.36–7.18 (2H, brs), 7.15 (2H, d, J=8.8 Hz), 4.08 (1H, t-like), 3.69 (1H, t, J=7.8 Hz), 3.64–3.38 (4H, m), 3.32 (1H, d, J=9.6 Hz), 2.76 (1H, dd, J=9.6 and 1.4 Hz), 2.36–2.08 (5H, m), 2.02–1.76 (2H, m), 1.52 (2H, d, J=14.4 Hz), 1.34 (2H, d, J=12.4 Hz), 1.22 (3H, s), 1.16–1.02 (1H, m), 0.99 (3H, t, J=7.4 Hz), 0.94 (3H, s), 0.92 (3H, s);

TLC: Rf 0.54 (ethyl acetate:hexane=1:3).

Example 1(26)

4-(2-oxopiperidin-1-ylsulfonyl)phenyl 2RS-(4-(pyrrolidin-1-yl)phenyl)butanoic acid ester.hydrochloride

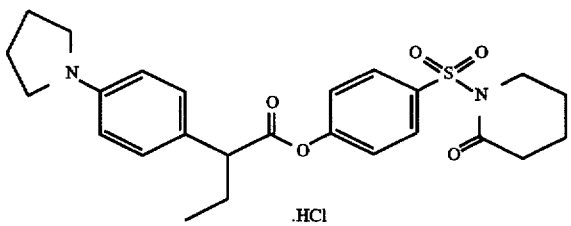

NMR (CDCl₃): δ 8.03 (2H, d, J=9.0 Hz), 7.65 (2H, d, J=8.6 Hz), 7.48 (2H, d, J=8.6 Hz), 7.17 (2H, d, J=9.0 Hz), 3.89 (2H, t, J=5.8 Hz), 3.74 (1H, t, J=7.8 Hz), 3.80–3.50 (4H, m), 2.42 (2H, t, J=6.6 Hz), 2.50–2.25 (4H, m), 2.40–1.70 (2H, m), 2.00–1.70 (4H, m), 0.99 (3H, t, J=7.4 Hz);

TLC: Rf 0.83 (acetic acid:methanol:chloroform=1:2:40).

Example 1(27)

4-(2-oxo-4S-benzyltetrahydroxazol-3-ylsulfonyl)phenyl 2RS-(4-(pyrrolidin-1-yl)phenyl)butanoic acid ester.hydrochloride

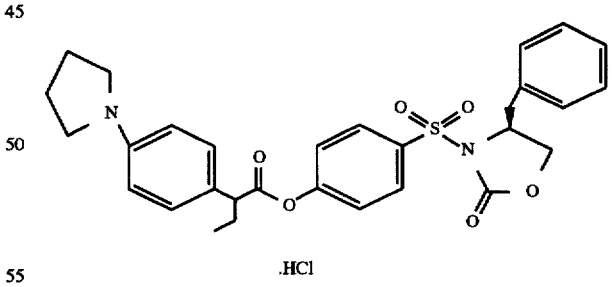

NMR (CDCl₃): δ 8.13 (2H, d, J=8.8 Hz), 7.64 (2H, d, J=8.8 Hz), 7.48 (2H, d, J=8.8 Hz), 7.23 (2H, d, J=8.8 Hz), 7.40–7.16 (5H, m), 4.75–4.58 (1H, m), 4.24–4.05 (2H, m), 3.76 (1H, t, J=7.6 Hz), 3.85–3.50 (4H, brs), 3.50 (1H, dd, J=13.2, 3.8 Hz),2.83 (1H, dd, J=13.2, 10.2 Hz), 2.44–2.26 (4H, m), 2.34–2.10 and 2.10–1.76 (each 1H, m), 0.99 (3H, t, J=7.4 Hz);

TLC: Rf 0.51 (ethyl acetate:hexane=1:2).

Example 1(28)

4-(2-oxo-4S-isopropylperhydroxazol-3-ylsulfonyl) phenyl 2RS-(4-(pyrrolidin-1-yl)phenyl)butanoic acid ester.hydrochloride

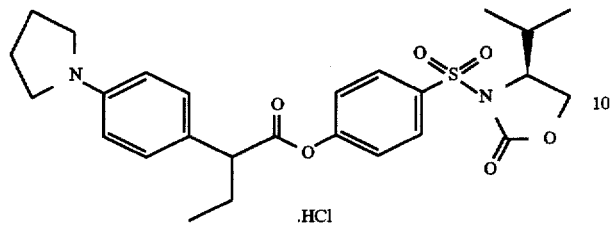

NMR (CDCl₃): δ 8.10 (2H, d, J=9.0 Hz), 7.63 (2H, d, J=8.6 Hz), 7.48 (2H, d, J=8.6 Hz), 7.22 (2H, d, J=9.0 Hz), 4.43 (1H, dt, J=8.2, 3.0 Hz), 4.29 (1H, t, J=8.8 Hz), 4.16 (1H, dd, J=8.8, 3.0 Hz), 3.75 (1H, t, J=7.6 Hz), 3.90–3.45 (4H, brs), 2.56–1.76 (7H, m), 0.99 (3H, t, J=7.2 Hz), 0.93 (3H, d, J=6.8 Hz), 0.75 (3H, d, J=6.8 Hz);

TLC: Rf 0.62 (ethyl acetate:hexane=1:1).

Example 1(29)

4-(2-oxo-4S-methyl-5S-phenylperhydroxazol-3-ylsulfonyl)phenyl 2RS-(4-(pyrrolidin-1-yl)phenyl)butanoic acid ester.hydrochloride

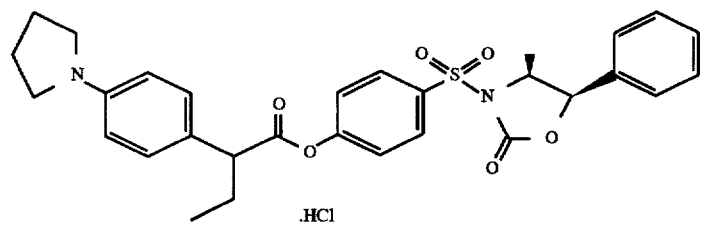

NMR (CDCl₃): δ 8.13 (2H, d, J=8.8 Hz), 7.72 (2H, d, J=8.8 Hz), 7.51 (2H, d, J=8.8 Hz), 7.46–7.34 (3H, m), 7.23 (2H, d, J=8.8 Hz), 7.30–7.20 (2H, m), 5.71 (1H, d, J=7.2 Hz), 4.78 (1H, dq, J=7.2 Hz), 3.77 (1H, t, J=7.2 Hz), 3.90–3.50 (4H, brs), 2.50–2.25 (4H, brs), 2.40–1.80 (2H, m), 1.00 (3H, t, J=7.2 Hz), 0.97 (3H, d, J=7.2 Hz);

TLC: Rf 0.66 (ethyl acetate:hexane=1:2).

Example 1(30)

4-(1RS-oxo-4S-methoxycarbonylperhydrothiazol-3-ylsulfonyl)phenyl 2RS-(4-(pyrrolidin-1-yl)phenyl) butanoic acid ester

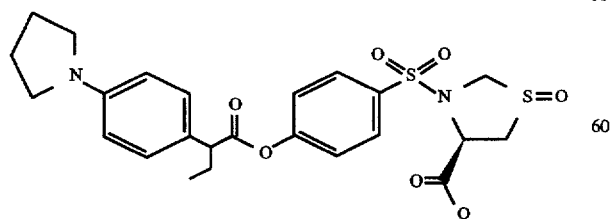

NMR (CDCl₃): δ 7.87 (2H, d, J=9.0 Hz), 7.21 (2H, d, J=9.0 Hz), 7.19 (2H, d, J=9.0 Hz), 6.55 (2H, d, J=9.0 Hz), 5.28–5.16 (2H, m), 4.09–4.01 (1H, m), 3.69–3.44 (5H, m), 3.33–3.26 (4H, m), 3.08–2.97 (1H, m), 2.24–1.80 (6H, m), 0.98 (3H, t, J=7.4 Hz);

TLC: Rf 0.50 (chloroform:methanol:acetic acid=40:2:1).

Example 1(31)

4-(morpholin-4-ylsulfonyl)-2-methylphenyl 2RS-(4-(pyrrolidin-1-yl)phenyl)butanoic acid ester

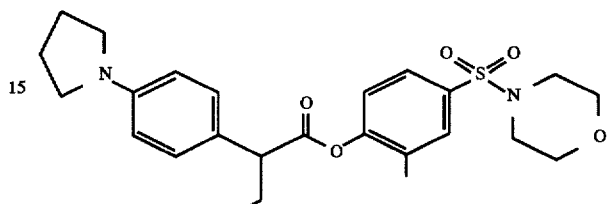

NMR (CDCl₃): δ 7.56–7.51 (2H, m), 7.26–7.21 (2H, m), 7.10 (1H, d, J=8 Hz), 6.55 (2H, d, J=8 Hz), 3.75–3.71 (4H, m), 3.62 (1H, t, J=8 Hz), 3.32–3.26 (4H, m), 3.01–2.96 (4H, m), 2.37–1.73 (2H, m), 2.06 (3H, s), 2.04–1.96 (4H, m), 1.00 (3H, t, J=8 Hz);

TLC: Rf 0.27 (hexane:ethyl acetate=3:1).

Example 1(32)

4-(imidazol-1-ylsulfonyl)-2-methylphenyl 2RS-(4-(pyrrolidin-1-yl)phenyl)butanoic acid ester

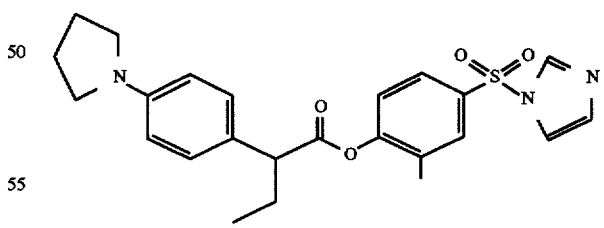

NMR (CDCl₃): δ 7.99 (1H, m), 7.75 (1H, s), 7.72 (1H, m), 7.27–7.08 (5H, m), 6.54 (2H, d, J=8.8 Hz), 3.60 (1H, t, J=7.6 Hz), 3.28 (4H, m), 2.14 (1H,m), 2.04 (3H, s), 2.01 (4H, m), 1.91 (1H, m), 0.97 (3H, t, J=7.4 Hz);

TLC: Rf 0.36 (hexane:ethyl acetate=2:1).

Example 1(33)

4-(piperazin-4-ylsulfonyl)-2-methylphenyl 2RS-(4-(pyrrolidin-1-yl)phenyl)butanoic acid ester.2hydrochloride

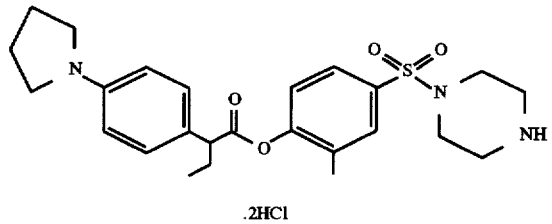

NMR (CD$_3$OD): δ 7.80–7.56 (6H, m), 7.18 (1H, d, J=8.2 Hz), 4.00 (1H, t, J=7.6 Hz), 3.90–3.72 (4H, m), 3.30 (8H, s-like), 2.43–2.15 (5H, m), 2.06 (3H, s), 2.15–1.84 (1H, m), 1.00 (3H, t, J=7.2 Hz);

TLC: Rf 0.53 (chloroform:methanol:acetic acid=15:2:1).

Example 1(34)

4-(morpholin-4-ylsulfonyl)phenyl 2RS-(4-nitrophenyl)butanoic acid ester

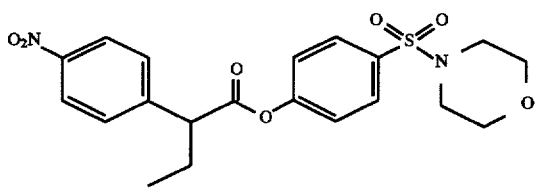

NMR (CDCl$_3$): δ 8.26 (2H, d, J=8 Hz), 7.77 (2H, d, J=8 Hz), 7.59 (2H, d, J=8 Hz), 7.20 (2H, d, J=8 Hz), 3.86 (1H, t, J=7 Hz), 3.80–3.68 (4H, m), 3.06–2.94 (4H, m), 2.30 (1H, ddq, J=14 Hz, 7 Hz, 7 Hz), 1.97 (1H, ddq, J=14 Hz, 7 Hz, 7 Hz), 1.03 (3H, t, J=7 Hz);

TLC: Rf 0.16 (hexane:ethyl acetate=7:3).

Example 1(35)

4-(morpholin-4-ylsulfonyl)phenyl 1-(4-nitrophenyl)cyclobutanecarboxylic acid ester

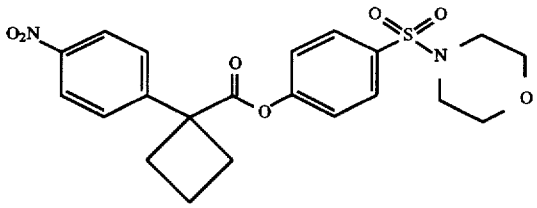

NMR (CDCl$_3$): δ 8.26 (2H, d, J=8 Hz), 7.77 (2H, d, J=8 Hz), 7.56 (2H, d, J=8 Hz), 7.16 (2H, d, J=8 Hz), 3.79–3.66 (4H, m), 3.15–2.91 (6H, m), 2.80–2.60 (2H, m), 2.39–1.91 (2H, m);

TLC: Rf 0.16 (hexane:ethyl acetate=7:3).

Example 1(36)

4-(6-aza-7-oxobicyclo[3.2.1]octan-6-ylsulfonyl)phenyl 2-(4-methoxyphenyl)-2-ethylbutanoic acid ester

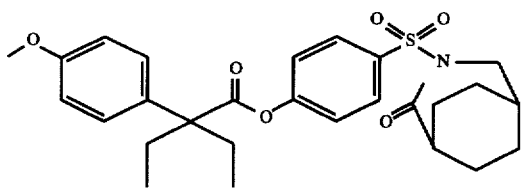

NMR (CDCl$_3$): δ 8.08 (2H, d, J=8.8 Hz), 7.27 (2H, d, J=8.8 Hz), 7.11 (2H, d, J=8.8 Hz), 6.91 (2H, d, J=8.8 Hz), 4.59 (1H, brt, J=4.8 Hz), 3.82 (3H, s), (1H, brs), 2.32–1.15 (12H, m), 0.84 (6H, t, J=7.4 Hz);

TLC: Rf 0.85 (acetic acid:methanol:chloroform=1:2:40).

Example 1(37)

4-(morpholin-4-ylsulfonyl)-2-methylphenyl 2RS-(4-methylphenyl)butanoic acid ester

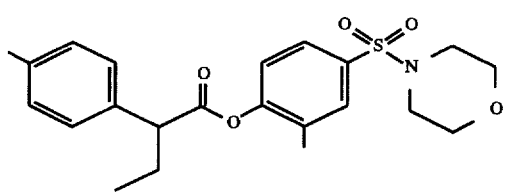

NMR (CDCl$_3$): δ 7.57–7.52 (2H, m), 7.30–7.08 (5H, m), 3.75–3.67 (5H, m), 3.01–2.96 (4H, m), 2.36 (3H, s), 2.32–2.13 and 2.03–1.82 (each1H, m), 2.02 (3H, s), 1.00 (3H, t, J=7 Hz);

TLC: Rf 0.30 (hexane:ethyl acetate=3:1).

Example 1(38)

4-(imidazol-1-ylsulfonyl)phenyl 2RS-phenylbutanoic acid ester

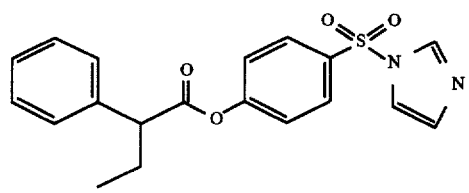

NMR (CDCl$_3$): δ 7.99 (1H, s), 7.97–7.86 (2H, m), 7.40–7.28 (5H, m), 7.28–7.25 (1H, m), 7.25–7.15 (2H, m), 7.13–7.05 (1H, m), 3.68 (I H, t, J=7 Hz), 2.34–2.05 (1H, m), 2.05–1.98 (1H, m), 0.96 (3H, t, J=7 Hz);

TLC: Rf 0.29 (hexane:ethyl acetate=6:4).

Example 1(39)

4-(morpholin-4-ylsulfonyl)phenyl 2RS-phenylbutanoic acid ester

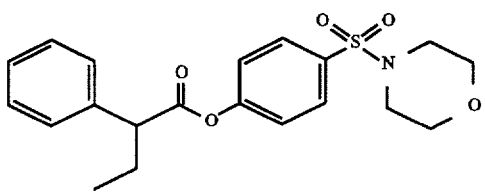

NMR (CDCl₃): δ 7.78–7.67 (2H, m), 7.43–7.24 (5H, m), 7.24–7.15 (2H, m), 3.78–3.65 (5H, m), 3.03–2.93 (4H, m), 2.36–2.11 (1H, m), 2.05–1.80 (1H, m), 0.99 (3H, t, J=7 Hz);

TLC: Rf 0.26 (hexane:ethyl acetate=2:1).

Example 1(40)

4-(N-1RS-(ethoxycarbonyl)-2-(morpholin-4-yl)ethylsulfamoyl)phenyl 2RS-(4-(pyrrolidin-1-yl)phenyl)butanoic acid ester

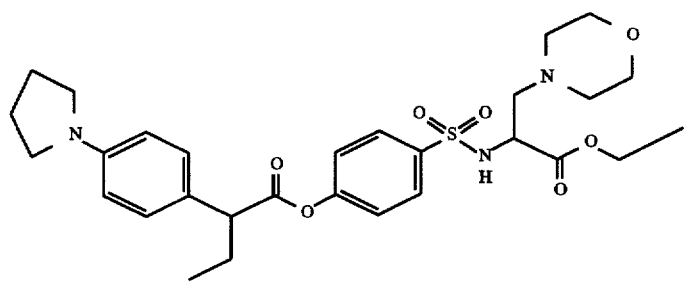

NMR (CDCl₃): δ 7.84 (2H, d, J=8.6 Hz), 7.20 (2H, d, J=8.6 Hz), 7.12 (2H, d, J=8.6 Hz), 6.55 (2H, d, J=8.6 Hz), 4.01 (3H, m), 3.57 (5H, m), 3.29 (4H, t, J=6.4 Hz), 2.63 (2H, m), 2.36 (4H, m), 2.14 (1H, m), 2.01 (4H, m), 1.89 (1H, m), 1.17 (3H, t, J=7.0 Hz), 0.97 (3H, t, J=7.4 Hz);

TLC: Rf 0.34 (hexane:ethyl acetate=1:1).

Example 1(41)

4-(N-1RS-(ethoxycarbonyl)-2-(morpholin-4-yl)ethylsulfamoyl)phenyl 2RS-(4-nitrophenyl)butanoic acid ester

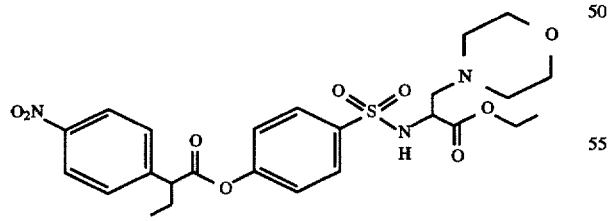

NMR (CDCl₃): δ 8.26 (2H, d, J=8.8 Hz), 7.89 (2H, d, J=8.6 Hz), 7.57 (2H, d, J=8.8 Hz), 7.13 (2H, d, J=8.6 Hz), 4.03 (2H, q, J=7.2 Hz), 3.96 (1H, t, J=7.0 Hz), 3.84 (1H, t, J=7.0 Hz), 3.58 (4H, m), 2.68 (1H, dd, J=13.1, 7.0 Hz), 2.61 (1H, dd, J=13.1, 7.0 Hz), 2.36 (4H, m), 2.82 (1H, m), 1.95 (1H, dq, J=13.6, 7.2 Hz), 1.17 (3H, t, J=7.2 Hz), 1.02 (3H, t, J=7.2 Hz);

TLC: Rf 0.45 (ethyl acetate).

Example 1(42)

4-(N-1RS-(ethoxycarbonyl)-2-(morpholin-4-yl)ethylsulfamoyl)phenyl 1-(4-nitrophenyl)cyclobutanecarboxylic acid ester

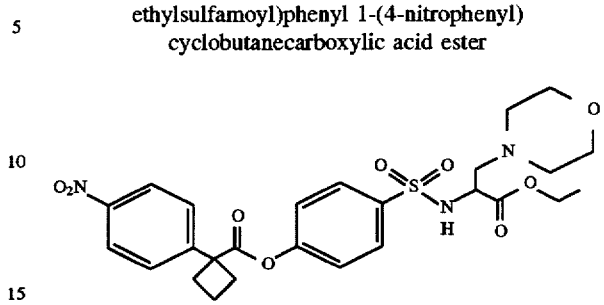

NMR (CDCl₃): δ 8.26 (2H, d, J=8.8 Hz), 7.86 (2H, d, J=8.8 Hz), 7.55 (2H, d, J=8.8 Hz), 7.09 (2H, d, J=8.8 Hz), 4.03 (2H, q, J=7.2 Hz), 3.95 (1H, t, J=6.2 Hz), 3.57 (4H, t, J=5.2 Hz), 3.05 (2H, m), 2.67 (2H, m), 2.66 (1H, dd, J=12.6, 6.2 Hz), 2.60 (1H, dd, J=12.6, 6.2 Hz), 2.35 (4H, t, J=5.2 Hz), 2.23 (1H, m), 2.04 (1H, m), 1.17 (3H, t, J=7.2 Hz);

TLC: Rf 0.40 (chloroform:methanol:water=9:1:0.1).

Example 1(43)

4-(N-1RS-(ethoxycarbonyl)-2-(morpholin-4-yl)ethylsulfamoyl)phenyl 2RS-phenyl-2-methoxyacetic acid ester

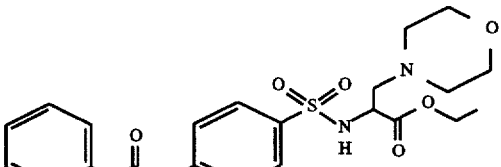

NMR (CDCl₃): δ 7.86 (2H, d, J=8.8 Hz), 7.52 (2H, m), 7.42 (3H, m), 7.12 (2H, d, J=8.8 Hz), 5.00 (1H, s), 4.01 (2H, q, J=7.0 Hz), 3.94 (1H, t, J=6.6 Hz), 3.57 (4H, t, J=5.2 Hz), 3.49 (3H, s), 2.66 (1H, dd, J=12.8, 6.6 Hz), 2.60 (1H, dd, J=12.8, 6.6 Hz), 2.34 (4H, t, J=5.2 Hz), 1.16 (3H, t, J=7.0 Hz);

TLC: Rf 0.26 (hexane:ethyl acetate=1:1).

Example 1(44)

4-(N-benzyloxycarbonylsulfamoyl)phenyl 2RS-(4-(pyrrolidin-1-yl)phenyl)butanoic acid ester.hydrochloride

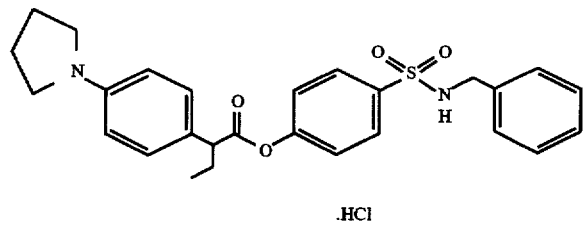

.HCl

NMR (CDCl$_3$): δ 8.3–8.0 (1H, brs), 8.00 (2H, d, J=8.8 Hz), 7.56 (2H, d-like), 7.46 (2H, d-like), 7.38–7.22 (5H, m), 7.15 (2H, d, J=8.8 Hz), 5.07 (2H, s), 3.74 (1H, t, J=7.8 Hz), 3.8–3.5 (4H, m), 2.4–2.2 (4H, m), 2.40–2.10 and 2.10–1.80 (each 1H, m), 1.00 (3H, t, J=7.2 Hz);

TLC: Rf 0.50 (acetic acid:ethyl acetate:hexane=1:8:16).

Example 1(45)

4-(N-1RS-phenyl-2RS-methylbutylsulfamoyl)phenyl 2RS-(4-(pyrrolidin-1-yl)phenyl)butanoic acid ester.hydrochloride

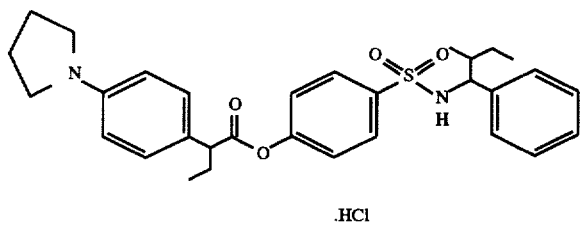

.HCl

NMR (CDCl$_3$): δ 7.80–7.57 (2H, m), 7.57–7.32 (4H, m), 7.12–6.93 (3H, m), 6.93–6.70 (4H, m), 5.38 (1H, m), 4.19–3.99 (1H, m), 3.90–3.30 (5H, m), 2.50–2.04 (5H, m), 1.96–1.40 (3H, m), 1.28–0.57 (10H, m);

TLC: Rf 0.24 (ethyl acetate:hexane=1:4).

Example 1(46)

4-sulfamoylphenyl 2RS-(4-(pyrrolidin-1-yl)phenyl)butanoic acid ester.hydrochloride

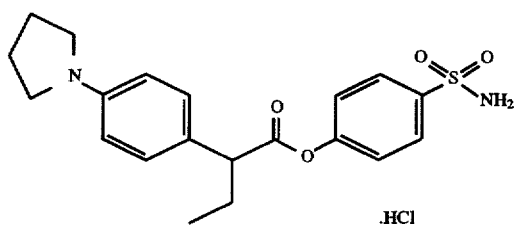

.HCl

NMR (CD3OD): δ 7.88 (2H, d, J=8.6 Hz), 7.18 (2H, d, J=8.8 Hz), 7.11 (2H, d, J=8.8 Hz), 6.57 (2H, d, J=8.6 Hz), 3.61 (1H, t, J=7.6 Hz), 3.34–3.19 (4H, m), 2.26–2.00 and 2.00–1.70 (each 1H, m), 2.07–1.96 (4H, m), 0.96 (3H, t, J=7.4 Hz);

TLC: Rf 0.22 (acetic acid:methanol:chloroform=1:2:40).

Example 1(47)

4-(N-2-methoxyethylsulfamoyl)phenyl 2RS-(4-(pyrrolidin-1-yl)phenyl)butanoic acid ester

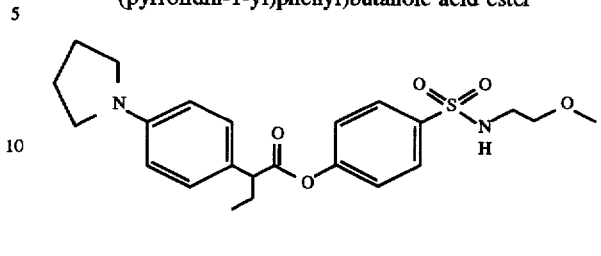

NMR (CDCl$_3$): δ 7.83 (2H, d, J=9.0 Hz), 7.22 (2H, d, J=8.6 Hz), 7.14 (2H, d, J=9.0 Hz), 6.56 (2H, d, J=8.6 Hz), 4.85 (1H, br), 3.59 (1H, t, J=7.7 Hz), 3.42–3.20 (9H, m), 3.11 (2H, m), 2.28–1.70 (6H, m), 0.98 (3H, t, J=7.6 Hz);

TLC: Rf 0.55 (hexane:ethyl acetate=2:3).

Example 1(48)

4-(N-2-methoxyethyl-N-benzylsulfamoyl)phenyl 2RS-(4-(pyrrolidin-1-yl)phenyl)butanoic acid ester

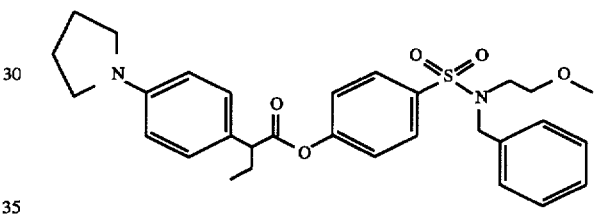

NMR (CDCl$_3$): δ 7.82 (2H, d, J=6.8 Hz), 7.29 (5H, s), 7.19 (2H, d, J=8.6 Hz), 7.13 (2H, d, J=6.8 Hz), 6.56 (2H, d, J=8.6 Hz), 4.40 (2H, s), 3.60(1H, t, J=7.4 Hz), 3.2–3.4 (8H, m), 3.10 (3H, s), 1.8–2.3 (6H, m), 0.99 (3H, t, J=7.3 Hz);

TLC: Rf 0.40 (hexane:ethyl acetate=3:1).

Example 1(49)

4-(N-t-butyloxysulfamoyl)phenyl 2RS-(4-(pyrrolidin-1-yl)phenyl)butanoic acid ester.hydrochloride

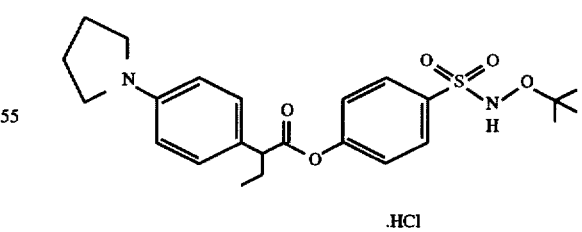

.HCl

NMR (CDCl$_3$): δ 7.88 (2H, d, J=8.8 Hz), 7.24–7.15 (4H, m), 6.56 (2H, d, J=8.2 Hz), 6.44 (1H, s), 3.59 (1H, t, J=7.2 Hz), 3.33–3.26 (4H, m), 2.45–1.80 (6H, m), 1.21 (9H, s), 0.98 (3H, t, J=7.2 Hz);

TLC: Rf 0.40 (hexane:ethyl acetate:acetic acid=5:2:0.1).

Example 1(50)

4-(N-4-hydroxybutylsulfamoyl)phenyl 2RS-(4-(pyrrolidin-1-yl)phenyl)butanoic acid ester

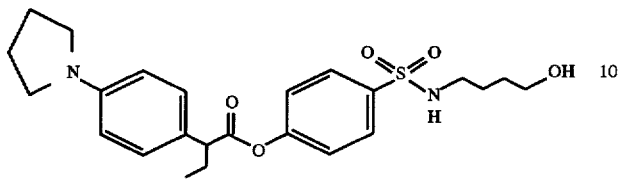

NMR (CDCl$_3$): δ 7.82 (2H, d, J=8.7 Hz), 7.22 (2H, d, J=8.6 Hz), 7.13 (2H, d, J=8.7 Hz), 6.56 (2H, d, J=8.6 Hz), 5.00 (1H, t, J=5.2 Hz), 3.70–3.48 (3H, m), 3.40–3.12 (4H, m), 3.06–2.86 (2H, m), 2.30–1.76 (6H, m), 1.78–1.62 (1H, brs), 1.60–1.40 (4H, m), 0.97 (3H, t, J=7.4 Hz);

TLC: Rf 0.48 (ethyl acetate).

Example 1(51)

4-(N-1RS-hydroxymethyl-2-methylpropylsulfamoyl)phenyl 2RS-(4-(pyrrolidin-1-yl)phenyl)butanoic acid ester

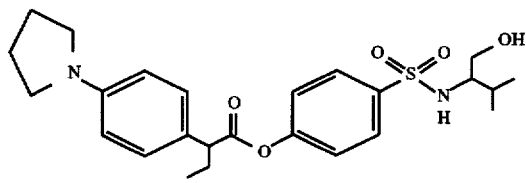

NMR (CDCl$_3$): δ 7.85 (2H, d, J=8.4 Hz), 7.21 (2H, d, J=8.6 Hz), 7.12 (2H, d, J=8.4 Hz), 6.55 (2H, d, J=8.6 Hz), 5.06 (1H, d, J=8.4 Hz), 3.58 (1H, t, J=5.8 Hz), 3.56–3.48 (2H, m), 3.36–3.22 (4H, m), 3.10–2.90 (1H, m), 2.23–1.65 (8H, m), 0.97 (3H, t, J=7.2 Hz), 0.78 (6H, d, J=6.8 Hz);

TLC: Rf 0.25 (ethyl acetate:hexane=2:3).

Example 1(52)

4-(N-2RS,3-dihydroxypropylsulfamoyl)phenyl 2RS-(4-(pyrrolidin-1-yl)phenyl)butanoic acid ester

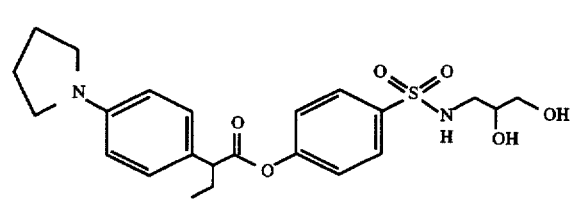

NMR (CDCl$_3$): δ 7.80 (2H, d, J=8.6 Hz), 7.20 (2H, d, J=8.8 Hz), 7.11 (2H, d, J=8.6 Hz), 6.54 (2H, d, J=8.8 Hz), 5.63 (1H, t, J=6.3 Hz), 3.80–3.64 (1H, m), 3.62–3.41 (3H, m), 3.35–3.20 (4H, m), 3.10–2.80 (3H, m), 2.30–1.70 (7H, m), 0.96 (3H, t, J=7.4 Hz);

TLC: Rf 0.28 (ethyl acetate:hexane=4:1).

Example 1(53)

4-(N-benzyloxysulfamoyl)phenyl 2RS-(4-(pyrrolidin-1-yl)phenyl)butanoic acid ester.hydrochloride

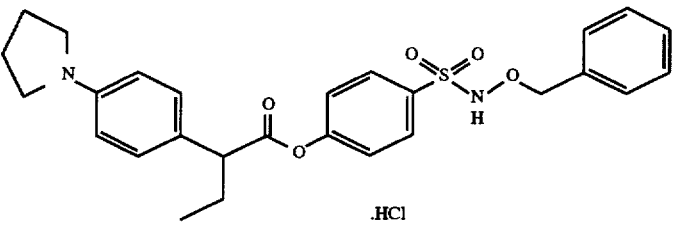

NMR (CDCl$_3$): δ 7.87 (2H, d, J=8.8 Hz), 7.32–7.12 (9H, m), 6.93 (1H, s), 6.54 (2H, d, J=8.8 Hz), 4.94 (2H, s), 3.57 (1H, t, J=7.8 Hz), 3.31–3.25 (4H, m), 2.25–1.80 (6H, m), 0.968 (3H, t, J=7.4 Hz);

TLC: Rf 0.55 (hexane:ethyl acetate:acetic acid=5:2:0.2).

Example 1(54)

4-(N-(N',N'-dimethylamino)sulfamoyl)phenyl 2RS-(4-(pyrrolidin-1-yl)phenyl)butanoic acid ester

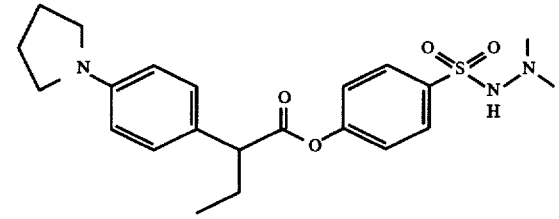

NMR (CDCl$_3$): δ 7.92 (2H, d, J=8.7 Hz), 7.23 (2H, d, J=8.7 Hz), 7.15 (2H, d, J=8.7 Hz), 6.55 (2H, d, J=8.7 Hz), 3.58 (1H, d, J=7.7 Hz), 3.29 (4H, t, J=6.6 Hz), 2.37 (6H, s), 2.25–1.75 (6H, m), 0.98 (3H, t, J=7.4 Hz);

TLC: Rf 0.45 (hexane:ethyl acetate=1:1).

Example 1(55)

4-(N-(N'-methylamino)sulfamoyl)phenyl 2RS-(4-(pyrrolidin-1-yl)phenyl)butanoic acid ester

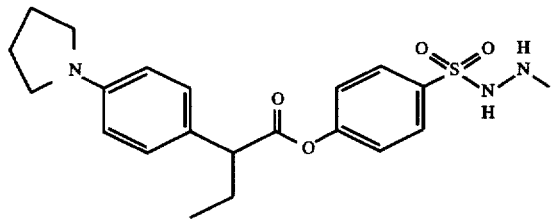

NMR (CDCl$_3$): δ 7.82 (2H, d, J=8.7 Hz), 7.23 (4H, m), 6.56 (2H, d, J=8.6 Hz), 3.60 (1H, m), 3.29 (4H, t, J=6.6 Hz), 2.85 (3H, s), 2.25–1.80 (6H, m), 0.99 (3H, t, J=7.4 Hz);

TLC: Rf 0.35 (hexane:ethyl acetate=1:1).

Example 1(56)

4-(N-(carbamoylmethyl)sulfamoyl)phenyl 2RS-(4-(pyrrolidin-1-yl)phenyl)butanoic acid ester

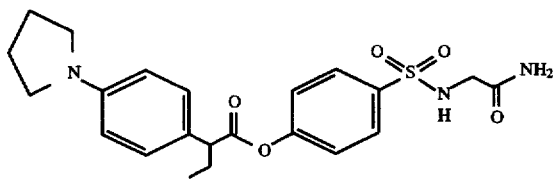

NMR (CDCl$_3$): δ 7.78 (2H, d, J=8.7 Hz), 7.20 (2H, d, J=8.6 Hz), 7.11 (2H, d, J=8.7 Hz), 6.54 (2H, d, J=8.6 Hz), 6.42–6.30 (1H, brs), 6.20–5.96 (2H, m), 3.58 (1H, t, J=7.8 Hz), 3.50 (2H, s), 3.38–3.18 (4H, m), 2.26–1.74 (6H, m), 0.96 (3H, t, J=7.3 Hz);

TLC: Rf 0.41 (chloroform:methanol=9:1).

Example 1(57)

4-(N-t-butylsulfamoyl)phenyl 2RS-(4-(pyrrolidin-1-yl)phenyl)butanoic acid ester.hydrochloride

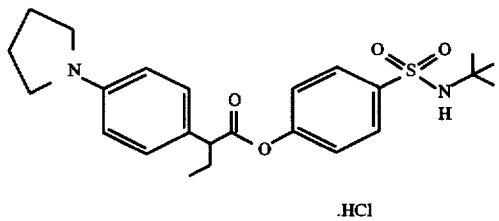

NMR (CDCl$_3$): δ 7.89 (2H, d, J=8.8 Hz), 7.63 (2H, d, J=8.6 Hz), 7.48 (2H, d, J=8.6 Hz), 7.12 (2H, d, J=8.8 Hz), 4.83 (1H, s), 3.74 (1H, t, J=7.6 Hz), 3.80–3.50 (4H, m), 2.40–2.25 (4H, m), 2.40–2.10 and 2.05–1.75 (each 1H, m), 1.22 (9H, s), 1.00 (3H, t, J=7.4 Hz);

TLC: Rf 0.55 (ethyl acetate:hexane=1:2).

Example 1(58)

4-(N-adamantan-1-ylsulfamoyl)phenyl 2RS-(4-(pyrrolidin-1-yl)phenyl)butanoic acid ester.hydrochloride

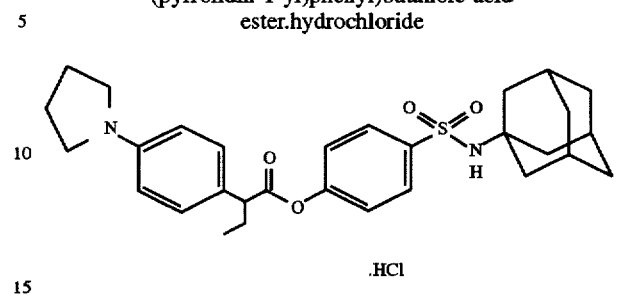

NMR (CDCl$_3$): δ 7.89 (2H, d, J=8.6 Hz), 7.60–7.45 (4H, m), 7.12 (2H, d, J=8.6 Hz), 4.64 (1H, brs, NH), 3.80–3.55 (5H, m), 2.40–1.48 (21H, m), 0.999 (3H, t, J=7.2 Hz);

TLC: Rf 0.44 (hexane:ethyl acetate:acetic acid=5:2:0.2).

Example 1(59)

4-guanidinosulfonyl-2-methylphenyl 2RS-(4-(pyrrolidin-1-yl)phenyl)butanoic acid ester.2hydrochloride

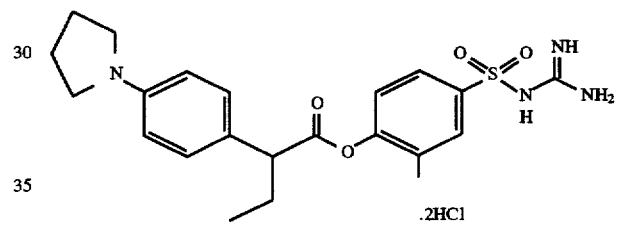

NMR (DMSO-d$_6$): δ 7.66–7.53 (2H, m), 7.28 (2H, d, J=8.0 Hz), 7.04 (1H, d, J=8.0 Hz), 7.10–6.50 (6H, m), 3.76 (1H, t, J=7.5 Hz), 3.50–3.20 (4H, m), 2.20–1.70 (2H, m), 2.10–1.90 (4H, m), 1.93 (3H, s), 0.91 (3H, t, J=7.5 Hz);

TLC: Rf 0.36 (water:methanol:chloroform=1:10:90).

Example 1(60)

4-(N-2RS,3-dihydroxypropylsulfamoyl)-2-methylphenyl 2RS-(4-(pyrrolidin-1-yl)phenyl)butanoic acid ester

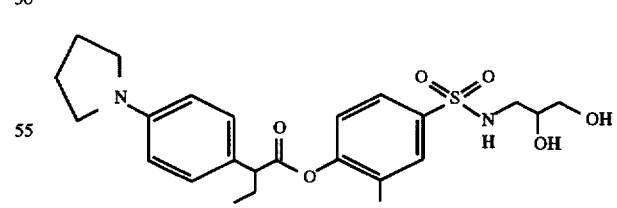

NMR (DMSO-d$_6$): δ 7.70–7.60 (2H, m), 7.47 (1H, t, J=6.0 Hz), 7.18 (2H, d, J=8.5 Hz), 7.13 (1H, d, J=8.5 Hz), 6.55 (2H, d, J=8.5 Hz), 3.70 (1H, t, J=7.5 Hz), 3.55–3.35 (6H, m), 2.94–2.78 (1H, m), 2.66–2.54 (1H, m), 2.25–1.60 (2H, m), 2.05–1.90 (4H, m), 1.96 (3H, s), 0.91 (3H, t, J=7.5 Hz);

TLC: Rf 0.29 (water:methanol:chloroform=1:10:90).

Example 1(61)

4-(N,N-bis(2-(methoxymethoxy)ethyl)sulfamoyl)-2-methylphenyl 2RS-(4-(pyrrolidin-1-yl)phenyl) butanoic acid ester

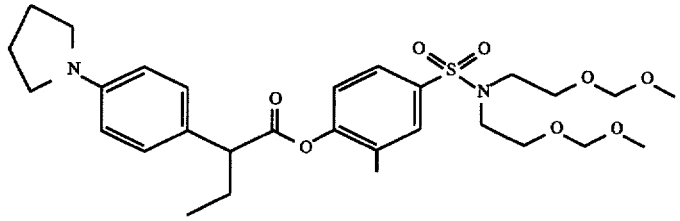

NMR (CDCl$_3$): δ 7.70–7.58 (2H, m), 7.22 (2H, d, J=9 Hz), 7.03 (1H, d, J=8 Hz), 6.55 (2H, d, J=9 Hz), 4.54 (4H, s), 3.67 (4H, t, J=6 Hz), 3.60 (1H, t, J=7 Hz), 3.43 (4H, t, J=6 Hz), 3.35–3.20 (1 OH, m), 2.30–1.75 (9H, m), 0.99 (3H, t, J=7 Hz);

TLC: Rf 0.27 (hexane:ethyl acetate=2:1).

Example 1(62)

4-(N, N-bis(2-(2-(methoxymethoxy)ethoxy)ethyl) sulfamoyl)-2-methylphenyl 2RS-(4-(pyrrolidin-1-yl) phenyl)butanoic acid ester

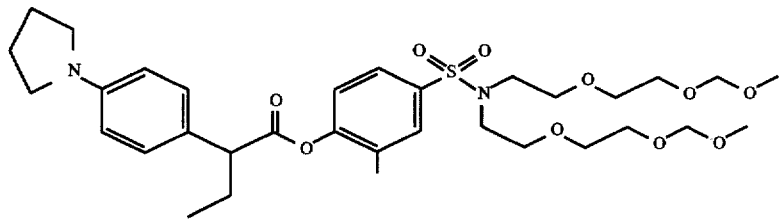

NMR (CDCl$_3$): δ 7.68–7.58 (2H, m), 7.22 (2H, d, J=9 Hz), 7.03 (1H, d, J=8 Hz), 6.55 (2H, d, J=9 Hz), 4.63 (4H, s), 3.70–3.50 (13H, m), 3.45–3.20 (8H, m), 3.35 (6H, s), 2.30–1.75 (9H, m), 0.99 (3H, t, J=7 Hz);

TLC: Rf 0.20 (hexane:ethyl acetate=1:1).

Example 1(63)

4-(N-methyl-N-methoxysulfamoyl)-2-methylphenyl 2RS-(4-(pyrrolidin-1-yl)phenyl)butanoic acid ester

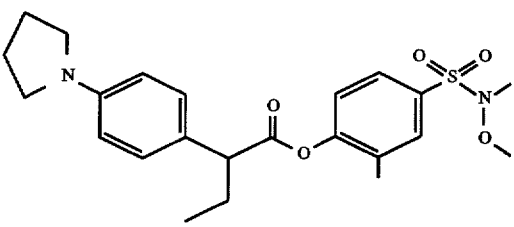

NMR (CDCl$_3$): δ 7.68 (1H, s), 7.66 (1H, d, J=8.4 Hz), 7.22 (2H, d, J=8.6 Hz), 7.11 (1H, d, J=8.4 Hz), 6.55 (2H, d, J=8.6 Hz), 3.78 (3H, s), 3.62 (1H, t, J=7.7 Hz), 3.28 (4H, t, J=6.6 Hz), 2.76 (3H, s), 2.3–2.1 (1H, m), 2.06 (3H, s), 2.1–1.9 (4H, m), 2.1–1.8 (1H, m), 0.99 (3H, t, J7.3 Hz);

TLC: Rf 0.36 (hexane:ethyl acetate=4:1).

Example 1(64)

4-(N-benzylsulfamoyl)-2-methylphenyl 2RS-(4-(pyrrolidin-1-yl)phenyl)butanoic acid ester

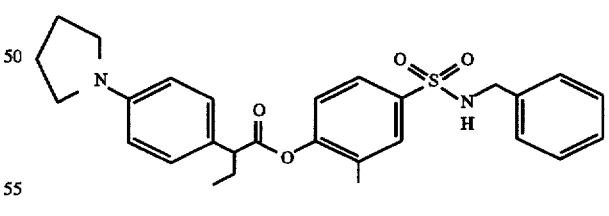

NMR (CDCl$_3$): δ 7.66–7.62 (2H, m), 7.29–7.15 (7H, m), 7.05 (1H, d, J=9.0 Hz), 6.55 (2H, d, J=8.6 Hz), 4.65 (1H, t, J=5.6 Hz), 4.11 (2H, d, J=5.6 Hz), 3.62 (1H, t, J=7.8 Hz), 3.33–3.26 (4H, m), 2.27–1.82 (6H, m), 2.00 (3H, s), 1.00 (3H, t, J=7.4 Hz);

TLC: Rf 0.86 (hexane:ethyl acetate=1:1).

Example 1(65)

4-(N-2-(N',N'-dimethylamino)ethylsulfamoyl)phenyl 2RS-(4-nitrophenyl)butanoic acid ester.hydrochloride

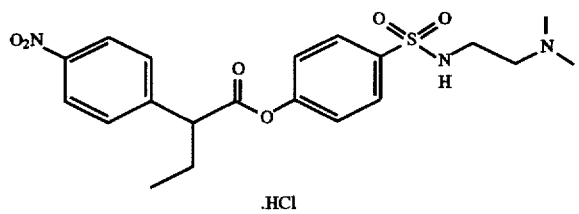

.HCl

NMR (CD₃OD): δ 8.27 (2H, d, J=8.5 Hz), 7.93 (2H, d, J=8.5 Hz), 7.68 (2H, d, J=8.5 Hz), 7.28 (2H, d, J=8.5 Hz), 4.04 (1H, t, J=7.6 Hz), 3.22 (4H, m), 2.93 (6H, s), 2.28 (1H, m), 1.97 (1H, m), 1.00 (3H, t, J=7.4 Hz);

TLC: Rf 0.39 (chloroform:methanol:water=9:1:0.1).

Example 1(66)

4-guanidinosulfonylphenyl 1-(4-nitrophenyl)cyclobutanecarboxylic acid ester

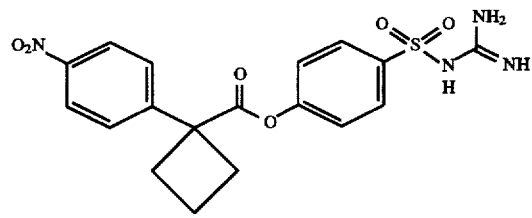

NMR (CDCl₃): δ 8.26 (2H, d, J=8.8 Hz), 7.85 (2H, d, J=8.8 Hz), 7.57 (2H, d, J=8.8 Hz), 7.04 (2H, d, J=8.8 Hz), 6.34 (1H, brs), 3.14–2.96 (2H, m), 2.77–2.59 (2H, m), 2.38–1.90 (2H, m);

TLC: Rf 0.56 (acetic acid:methanol:chloroform=1:5:25).

Example 1(67)

4-guanidinosulfonylphenyl 2RS-(4-nitrophenyl)butanoic acid ester

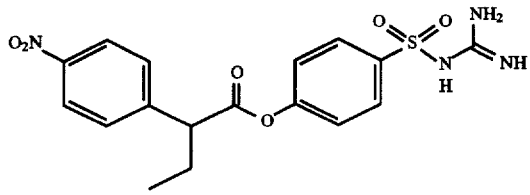

NMR (DMSO-d₆): δ 8.27 (2H, d, J=8.8 Hz), 7.78 (2H, d, J=8.8 Hz), 7.71 (2H, d, J=8.8 Hz), 7.19 (2H, d, J=8.8 Hz), 7.0–6.4 (4H, brs), 4.15 (1H, t, J=7.6 Hz), 2.30–2.05 and 2.05–1.75 (each 1H, m), 0.92 (3H, t, J=7.6 Hz);

TLC: Rf 0.09 (acetic acid:methanol:chloroform=1:2:40).

Example 1(68)

4-(N-2RS,3-dihydroxypropylsulfamoyl)-2-methylphenyl 2RS-(4-methylphenyl)butanoic acid ester

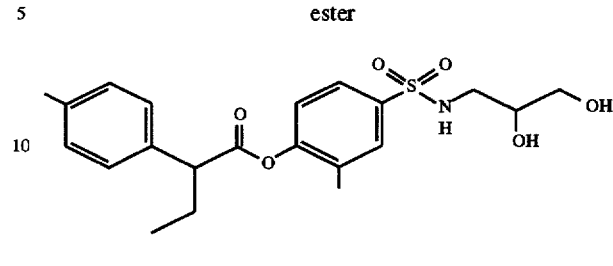

NMR (CDCl₃): δ 7.67–7.61 (2H, m), 7.27 (2H, d, J=8 Hz), 7.17 (2H, d, J=8 Hz), 7.04 (1H, d, J=8 Hz), 5.54 (1H, br), 3.80–3.46 (3H, m), 3.42 (1H, br), 3.70 (1H, t, J=8 Hz), 3.11–2.87 (2H, m), 2.83 (1H, br), 2.35 (3H, s), 2.32–2.11 and 2.03–1.79 (each 1H, m), 1.98 (3H, s), 0.99 (3H, t, J=8 Hz);

TLC: Rf 0.40 (chloroform:methanol:water=9:1:0.1).

Example 1(69)

4-(N-2-methoxyethylsulfamoyl)phenyl 2-(4-methoxyphenyl)-2-ethylbutanoic acid ester

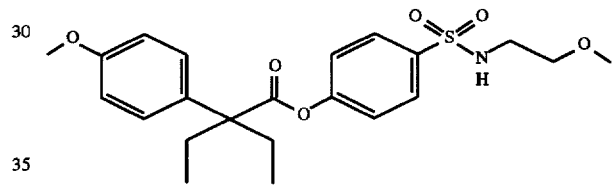

NMR (CDCl₃): δ 7.83 (2H, d, J=8.8 Hz), 7.27 (2H, d, J=8.8 Hz), 7.08 (2H, d, J=9.2 Hz), 6.90 (2H, d, J=8.8 Hz), 4.92 (1H, t, J=6.5 Hz), 3.82 (3H, s), 3.38 (2H, t, J=5.4 Hz), 3.25 (3H, s), 3.11 (2H, t, J=6.0 Hz), 2.28–2.04 (4H, m), 0.846 (6H, t, J=7.4 Hz);

TLC:Rf0.16 (hexane:ethyl acetate=2:1).

Example 1(70)

4-(N-2-(N',N'-dimethylamino)ethylsulfamoyl)phenyl 2-(4-methoxyphenyl)-2-ethylbutanoic acid ester.acetate

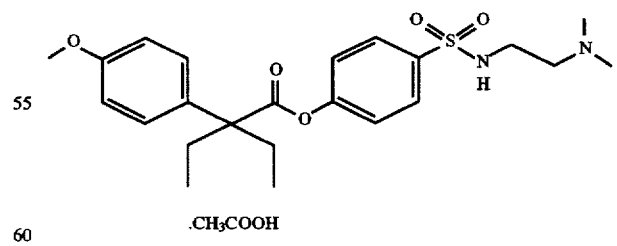

.CH₃COOH

NMR (CDCl₃): δ 7.85 (2H, d, J=8.6 Hz), 7.28 (2H, d, J=8.8 Hz), 7.09 (2H, d, J=8.6 Hz), 6.92 (2H, d, J=8.8 Hz), 3.83 (3H, s), 2.53–2.47 (4H, m), 2.24 (6H, s), 2.24–2.11 (4H, m), 0.847 (6H, t, J=7.4 Hz);

TLC: Rf 0.26 (chloroform:methanol:water=25:5:1).

Example 1(71)

4-(guanidinosulfonyl)-2-methylphenyl 2RS-(4-methoxyphenyl)butanoic acid ester.hydrochloride

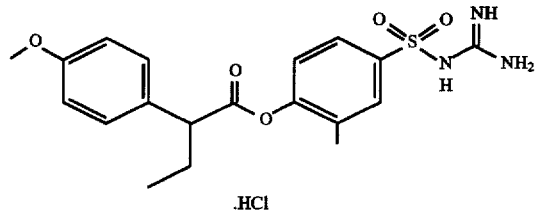

NMR (DMSO-d$_6$): δ 7.62 (1H, s), 7.60 (1H, d, J=8.0 Hz), 7.30 (2H, d, J=8.5 Hz), 6.96 (1H, d, J=8.0 Hz), 6.90 (2H, d, J=8.5 Hz), 6.6–6.1 (4H, brs), 3.80 (1H, t, J=7.5 Hz), 2.3–2.0 and 2.0–1.7 (each 1H, m), 1.65 (3H, s), 0.98 (3H, t, J=7.5 Hz);

TLC: Rf 0.60 (water:methanol:chloroform=1:10:40).

Example 1(72)

4-(N,N-diethylsulfamoyl)phenyl 2RS-phenylbutanoic acid ester

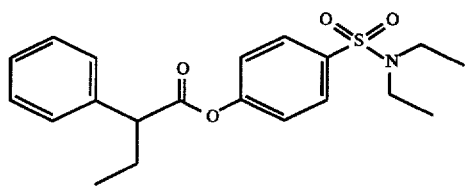

NMR (CDCl$_3$): δ 7.83–7.73 (2H, m), 7.40–7.23 (5H, m), 7.16–7.07 (2H, m), 3.69 (1H, t, J=7 Hz), 3.20 (4H, q, J=7 Hz), 2.35–1.75 (2H, m), 1.11 (6H, t, J=7 Hz), 0.98 (3H, t, J=7 Hz);

TLC: Rf 0.39 (hexane:ethyl acetate=7:3).

Example 1(73)

4-(N-benzylsulfamoyl)phenyl 2RS-phenylbutanoic acid ester

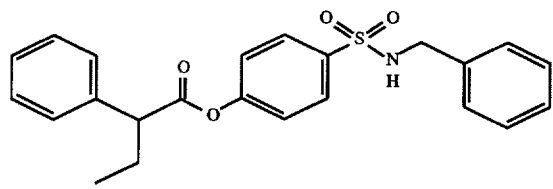

NMR (CDCl$_3$): δ 7.89–7.79 (2H, m), 7.42–7.08 (12H, m), 4.61 (1H, t, J=7 Hz), 4.13 (2H, d, J=7 Hz), 3.70 (1H, t, J=7 Hz), 2.36–2.11 (1H, m), 2.05–1.80 (1H, m), 0.99 (3H, t, J=7 Hz);

TLC: Rf 0.41 (hexane:ethyl acetate=2:1).

Example 1(74)

4-(N-methyl-N-benzylsulfamoyl)phenyl 2RS-phenylbutanoic acid ester

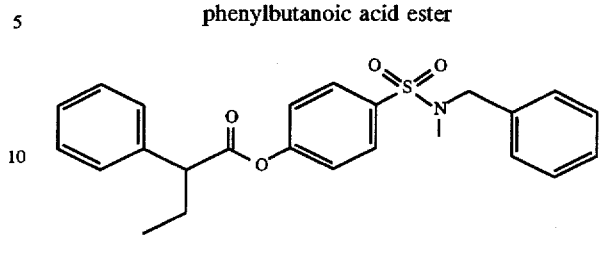

NMR (CDCl$_3$): δ 7.86–7.76 (2H, m), 7.43–7.14 (12H, m), 4.11 (2H, s), 3.73 (1H, t, J=7 Hz), 2.59 (3H, s), 2.38–2.13 (1H, m), 2.06–1.81 (1H, m), 1.01 (3H, t, J=7 Hz);

TLC: Rf 0.57 (hexane:ethyl acetate=2:1).

Example 1(75)

4-(N-2-phenylethylsulfamoyl)phenyl 2RS-phenylbutanoic acid ester

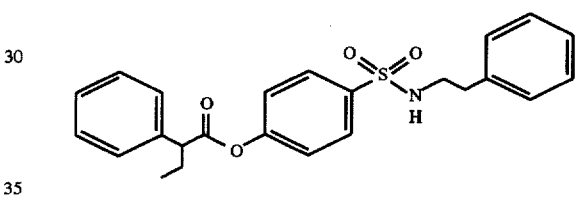

NMR (CDCl$_3$): δ 7.81–7.71 (2H, m), 7.43–7.03 (12H, m), 4.40 (1H, t, J=7 Hz), 3.71 (1H, t, J=7 Hz), 3.21 (2H, q, J=7 Hz), 2.76 (2H, t, J=7 Hz), 2.24 (1H, ddq, J=14 Hz, 7 Hz, 7 Hz), 1.93 (1H, ddq, J=14 Hz, 7 Hz, 7 Hz), 1.00 (3H, t, J=7 Hz);

TLC: Rf 0.46 (hexane:ethyl acetate=3:2).

Example 1(76)

4-(N-methyl-N-2-phenylethylsulfamoyl)phenyl 2RS-phenylbutanoic acid ester

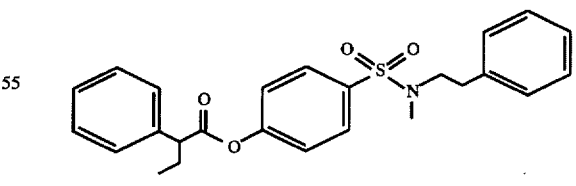

NMR (CDCl$_3$): δ 7.77–7.68 (2H, m), 7.41–7.08 (12H, m), 3.71 (1H, t, J=7 Hz), 3.33–3.18 (2H, m), 2.92–2.79 (2H, m), 2.73 (3H, s), 2.24 (1H, ddq, J=14 Hz, 7 Hz, 7 Hz), 1.92 (1H, ddq, J=14 Hz, 7 Hz, 7 Hz), 0.99 (3H, t, J=7 Hz);

TLC: Rf 0.32 (hexane:ethyl acetate=3:2).

Example 1(77)

4-(N-1RS-(4-methylphenyl)butylsulfamoyl)phenyl 2RS-phenylbutanoic acid ester

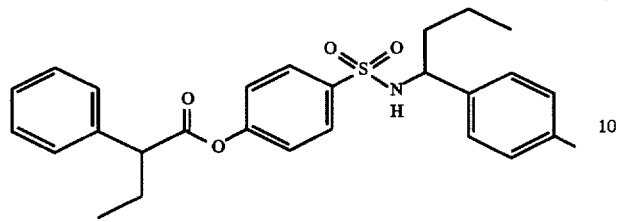

NMR (CDCl₃): δ 7.55 (2H, d, J=8 Hz), 7.41–7.23 (5H, m), 6.98–6.78 (6H, m), 4.81 (1H, d, J=7 Hz), 4.23 (1H, q, J=7 Hz), 3.68 (1H, t, J=7 Hz), 2.35–2.08 (1H, m), 2.20 (3H, s), 1.91 (1H, ddq, J=14 Hz, 7 Hz, 7 Hz), 1.79–1.52 (2H, m), 1.38–1.06 (2H, m), 0.99 (3H, t, J=7 Hz), 0.83 (3H, t, J=7 Hz);

TLC: Rf 0.15 (hexane:ethyl acetate=4:1).

Example 1(78)

4-(N-2-(pyridin-2-yl)ethylsulfamoyl)phenyl 2RS-(4-(pyrrolidin-1-yl)phenyl)butanoic acid ester.2hydrochloride

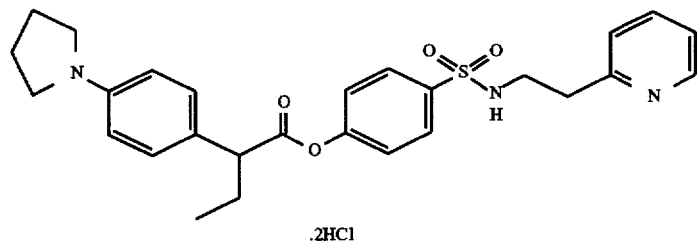

NMR (DMSO-d₆): δ 8.79 (1H, d, J=5.0 Hz), 8.50 (1H, t, J=7.4 Hz), 8.04 (1H, m), 7.90 (2H, m), 7.79 (2H, d, J=8.6 Hz), 7.28 (2H, m), 7.21 (2H, d, J=8.4 Hz), 6.90 (2H, m), 3.76 (1H, t, J=7.0 Hz), 3.34 (4H, brs), 3.23 (4H, brs), 2.01 (5H, m), 1.80 (1H, m), 0.91 (3H, t, J=7.0 Hz);

TLC: Rf 0.48 (chloroform:methanol:water=9:1:0.1).

Example 1(79)

4-(N-2-(piperidin-1-yl)ethylsulfamoyl)phenyl 2RS-(4-(pyrrolidin-1-yl)phenyl)butanoic acid ester.2hydrochloride

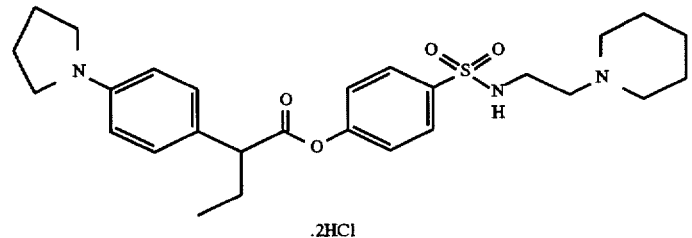

NMR (CD₃OD): δ 7.92 (2H, d, J=8.8 Hz), 7.71 (2H, d, J=8.8 Hz), 7.63 (2H, d, J=8.8 Hz), 7.26 (2H, d, J=8.8 Hz), 3.95 (1H, t, J=7.2 Hz), 3.81 (4H, m), 3.55 (2H, brd, J=12.0 Hz), 3.24 (4H, brs), 2.98 (2H, brt, J=12.0 Hz), 2.32 (4H, m), 1.89 (7H, m), 1.55 (1H, m), 0.99 (3H, t, J=7.2 Hz);

TLC: Rf 0.39 (chloroform:methanol:water=9:1:0.1).

Example 1(80)

4-(N-(tetrazol-5-yl)sulfamoyl)phenyl 2RS-(4-(pyrrolidin-1-yl)phenyl)butanoic acid ester

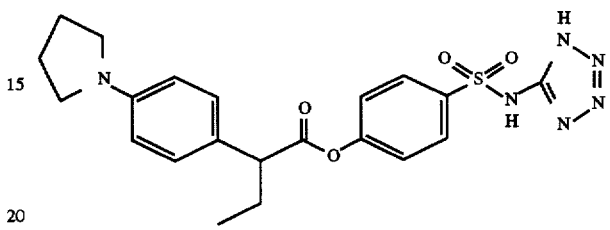

NMR (CD₃OD): δ 7.89 (2H, d, J=8.6 Hz), 7.15 (2H, d, J=8.6 Hz), 7.02 (2H, d, J=8.6 Hz), 6.55 (2H, d, J=8.6 Hz), 3.58 (1H, t, J=7.8 Hz), 3.35–3.15 (4H, m), 2.20–1.95 and 1.95–1.70 (each 1H, m), 2.05–1.95 (4H, m), 0.93 (3H, t, J=7.2 Hz);

TLC: Rf 0.46 (acetic acid:methanol:chloroform=1:5:25).

Example 1(81)

4-(N-(morpholin-4-yl)sulfamoyl)phenyl 2RS-(4-(pyrrolidin-1-yl)phenyl)butanoic acid ester.hydrochloride

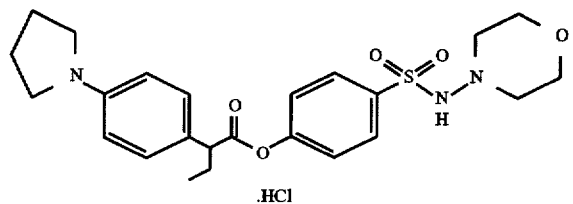

NMR (CDCl$_3$): δ 7.97 (2H, d, J=8.6 Hz), 7.61 (2H, d-like), 7.48 (2H, d-like), 7.16 (2H, d, J=8.6 Hz), 5.99 (1H, s), 3.74 (1H, t, J=7.8 Hz), 3.76–3.63 (4H, m), 3.65–3.54 (4H, m), 2.70–2.58 (4H, m), 2.42–2.29 (4H, m), 2.37–2.10 and 2.04–1.77 (each 1H, m), 1.00 (3H, t, J=7.2 Hz);

TLC: Rf 0.45 (methanol:chloroform=1:20).

Example 1(82)

4-(N-(pyrrolidin-3-yl)sulfamoyl)phenyl 2RS-(4-(pyrrolidin-1-yl)phenyl)butanoic acid ester.2hydrochloride

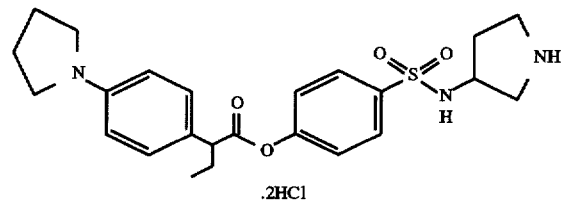

NMR (CDCl$_3$): δ 7.7–7.5 (4H, m), 7.42 (2H, d, J=8.6 Hz), 6.96 and 6.92 (2H, d, J=8.6 Hz), 4.35–4.13 (1H, m), 3.5–2.9 (10H, m), 2.40–2.25 (4H, m), 2.20–1.55 (4H, m), 0.94 (3H, t, J=7.2 Hz);

TLC: Rf 0.35 (methanol:chloroform=1:10).

Example 1(83)

4-(N-(1-benzylpiperidin-4-yl)sulfamoyl)phenyl 2RS-(4-(pyrrolidin-1-yl)phenyl)butanoic acid ester

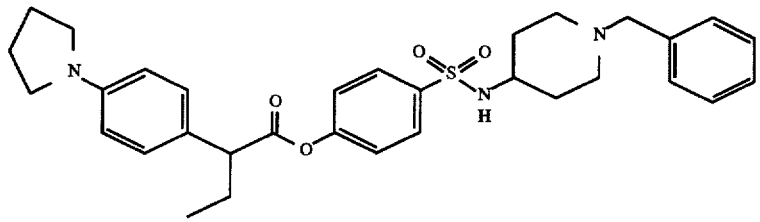

NMR (CDCl$_3$): δ 7.82 (2H, d, J=9.0 Hz), 7.36–7.08 (5H, m), 7.21 (2H, d, J=9.0 Hz), 7.13 (2H, d, J=8.8 Hz), 6.55 (2H, d, J=8.8 Hz), 4.50 (1H, d, J=5.7 Hz), 3.58 (1H, t, J=5.0 Hz), 3.43 (2H, s), 3.36–3.21 (4H, m), 3.21–3.02 (1H, m), 2.78–2.61 (2H, m), 2.28–1.65 (10H, m), 1.56–1.34 (1H, m), 0.97 (3H, t, J=7.2 Hz);

TLC: Rf 0.60 (ethyl acetate:hexane=9:1).

Example 1(84)

4-(N-(pyridin-2-yl)sulfamoyl)phenyl 2RS-(4-(pyrrolidin-1-yl)phenyl)butanoic acid ester.2hydrochloride

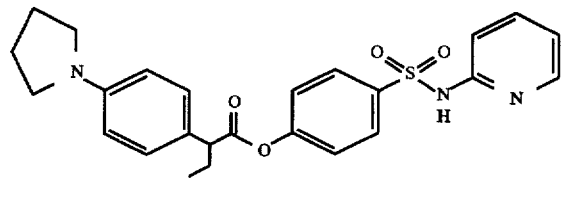

NMR (CDCl$_3$): δ 8.26 (1H, d, J=6.0 Hz), 7.96 (2H, d, J=8.6 Hz), 7.83 (1H, t, J=8.6 Hz), 7.72 (2H, d, J=8.6 Hz), 7.55 (1H, d, J=8.6 Hz), 7.48 (2H, d, J=8.6 Hz), 7.12 (2H, d, J=8.6 Hz), 6.95 (1H, t, J=6.0 Hz), 3.74 (1H, t, J=7.6 Hz), 3.80–3.60 (4H, m), 2.44–2.24 (4H, m), 2.32–2.02 and 2.02–1.72 (each 1H, m), 0.97 (3H, t, J=7.2 Hz);

TLC: Rf 0.51 (ethyl acetate:hexane=2:1).

Example 1(85)

4-(N-2-(morpholin-4-yl)ethylsulfamoyl)phenyl 2RS-(4-(pyrrolidin-1-yl)phenyl)butanoic acid ester

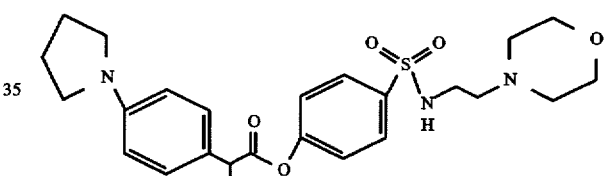

NMR (CDCl$_3$): δ 7.83 (2H, d, J=8.9 Hz), 7.21 (2H, d, J=8.7 Hz), 7.13 (2H, d, J=8.9 Hz), 6.55 (2H, d, J=8.7 Hz), 6.23–5.06 (1H, brs), 3.64–3.52 (5H, m), 3.36–3.20 (4H, m), 2.98 (2H, t, J=6.0 Hz), 2.38 (2H, t, J=6.0 Hz), 2.30–2.20 (4H, m), 2.20–1.70 (6H, m), 0.97 (3H, t, J=7.2 Hz);

TLC: Rf 0.24 (ethyl acetate:hexane=7:3).

Example 1(86)

4-(N-(pyrazin-2-yl)sulfamoyl)phenyl 2RS-(4-(pyrrolidin-1-yl)phenyl)butanoic acid ester.3hydrochloride

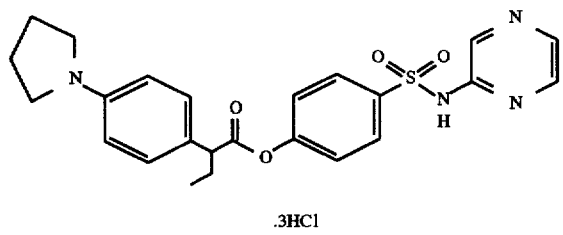

NMR (CDCl$_3$): δ 8.46 (1H, s), 8.17 (2H, s), 8.01 (2H, d, J=8.2 Hz), 7.7–7.4 (4H, m), 7.14 (2H, d, J=8.2 Hz), 3.9–3.5 (5H, m), 2.5–2.2 (4H, m), 2.4–2.1 and 2.1–1.8 (each 1H, m), 0.98 (3H, t, J=7.2 Hz);

TLC: Rf 0.18 (hexane:ethyl acetate=1:1).

Example 1(87)

4-(N-(imidazol-2-yl)sulfamoyl)phenyl 2RS-(4-(pyrrolidin-1-yl)phenyl)butanoic acid ester

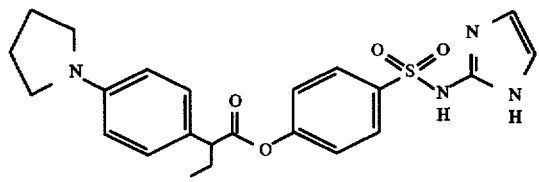

NMR (CDCl$_3$): δ 7.90 (2H, d, J=8.8 Hz), 7.19 (4H, d, J=8.8 Hz), 6.81 (1H, d, J=2.0 Hz), 6.54 (1H, d, J=2.0 Hz), 6.54 (2H, d, J=8.8 Hz), 3.57 (1H, t, J=7.8 Hz), 3.28 (4H, t-like), 2.30–2.00 and 2.00–1.70 (each 1H, m), 2.00 (4H, t-like), 0.96 (3H, t, J=7.4 Hz);

TLC: Rf 0.67 (methanol:chloroform=1:10).

Example 1(88)

4-(N-(quinuclidin-3RS-yl)sulfamoyl)phenyl 2RS-(4-(pyrrolidin-1-yl)phenyl)butanoic acid ester

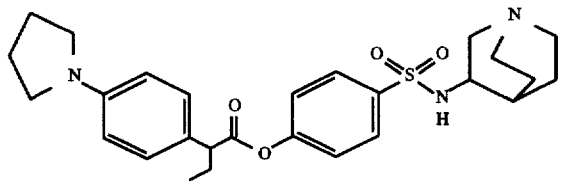

NMR (CDCl$_3$): δ 7.88 (2H, d, J=8.8 Hz), 7.21 (2H, d, J=8.8 Hz), 7.11 (2H, d, J=8.8 Hz), 6.55 (2H, d, J=8.8 Hz), 3.58 (1H, t, J=7.6 Hz), 3.60–3.47 (1H, m), 3.35–3.20 (4H, m), 3.30–2.80 (6H, m), 2.10–1.95 (4H, m), 2.30–1.40 (7H, m), 0.98 (3H, t, J=7.2 Hz);

TLC: Rf 0.43 (acetic acid:methanol:chloroform=1:5:25).

Example 1(89)

4-(N-(2,2,6,6-tetramethylpiperidin-4-yl)sulfamoyl)phenyl 2RS-(4-(pyrrolidin-1-yl)phenyl)butanoic acid ester

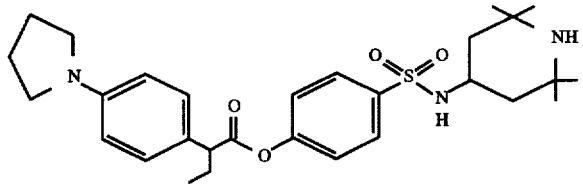

NMR (CDCl$_3$+CD$_3$OD): δ 7.85 (2H, d, J=8.8 Hz), 7.22 (2H, d, J=8.6 Hz), 7.14 (2H, d, J=8.8 Hz), 6.57 (2H, d, J=8.6 Hz), 3.59 (1H, t, J=7.8 Hz), 3.60–3.42 (1H, m), 3.35–3.20 (4H, m), 2.30–1.75 (2H, m), 2.06–1.96 (4H, m), 1.63 (2H, dd, J=13.2 and 3.8 Hz), 1.33–1.08 (2H, m), 1.19 (12H, s), 0.98 (3H, t, J=7.3 Hz);

TLC: Rf 0.55 (chloroform:methanol:acetic acid=25:5:1).

Example 1(90)

4-(N-(quinuclidin-3RS-yl)sulfamoyl)-2-methylphenyl 2RS-(4-(pyrrolidin-1-yl)phenyl)butanoic acid ester

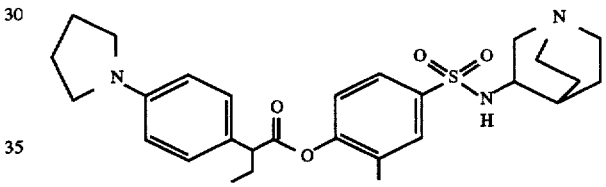

NMR (CDCl$_3$): δ 7.69 (1H, d, J=2 Hz), 7.66 (1H, dd, J=8 and 2 Hz), 7.30–7.13 (2H, m), 7.06 (1H, d, J=8 Hz), 6.55 (2H, d, J=9 Hz), 3.62 (1H, t, J=8 Hz), 3.38–3.23 (5H, m), 3.23–3.05 (1H, m), 2.90–2.48 (5H, m), 2.32–2.08 (1H, m), 2.04 (3H, s), 2.08–1.03 (10H, m), 0.99 (3H, t, J=7 Hz);

TLC: Rf 0.43 (chloroform:methanol:water=8:2:0.2).

Example 1(91)

4-(N-2-(morpholin-4-yl)ethylsulfamoyl)-2-methylphenyl 2RS-(4-(pyrrolidin-1-yl)phenyl)butanoic acid ester.2hydrochloride

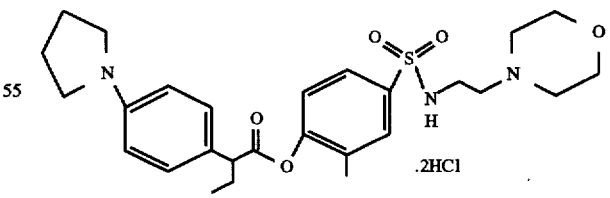

NMR (DMSO-d$_6$): δ 11.3–11.1 (1H, brs), 8.18 (1H, brs), 7.75 (1H, s), 7.70 (1H, d, J=8.0 Hz), 7.27 (2H, d, J=8.6 Hz), 7.18 (2H, d, J=9.2 Hz), 4.0–3.7 (5H, m), 3.4–3.0 (12H, m), 2.2–2.0 (1H, m), 2.1–1.9 (4H, brs), 2.0–1.7 (1H, m), 1.98 (3H, s), 0.91 (3H, t, J=7.3 Hz);

TLC: Rf 0.50 (chloroform:methanol=9:1).

Example 1(92)

4-(N-2-(piperazin-4-yl)ethylsulfamoyl)-2-methylphenyl 2RS-(4-(pyrrolidin-1-yl)phenyl)butanoic acid ester.3hydrochloride

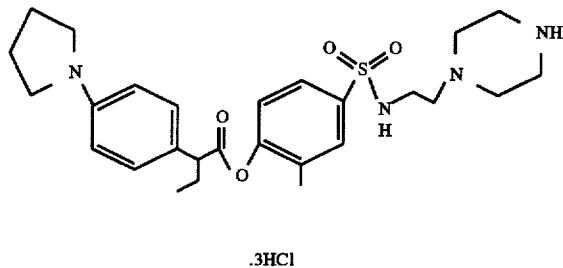

.3HCl

NMR (DMSO-d$_6$): δ 9.6–9.2 (2H, br), 7.71 (1H, s), 7.67 (1H, d, J=8.0 Hz), 7.18 (2H, d, J=8.4 Hz), 7.14 (1H, d, J=8.0 Hz), 6.53 (2H, d, J=8.4 Hz), 3.69 (1H, t, J=7.3 Hz), 3.7–2.6 (16H, br), 2.2–2.0 (1H, m), 2.0–1.9 (4H, brs), 1.96 (3H, s), 1.9–1.7 (1H, m), 0.90 (3H, t, J=7.1 Hz);

TLC: Rf 0.46 (chloroform:methanol:acetic acid=25:5:1).

Example 1(93)

4-(N-(piperidin-4-yl)sulfamoyl)-2-methylphenyl 2RS-(4-(pyrrolidin-1-yl)phenyl)butanoic acid ester.2hydrochloride

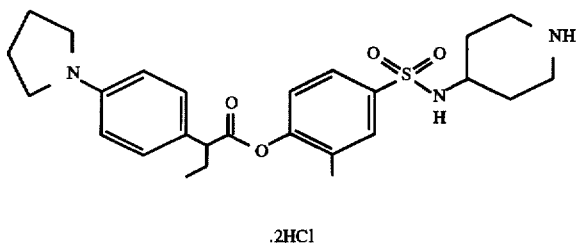

.2HCl

NMR (DMSO-d$_6$): δ 9.1–8.7 (1H, br), 8.00 (1H, d, J=7.2 Hz), 7.71 (1H, s), 7.68 (1H, d, J=8.4 Hz), 7.26 (2H, d, J=8.4 Hz), 7.15 (1H, d, J=8.4 Hz), 6.79 (2H, d, J=8.4 Hz), 3.76 (1H, t, J=7.8 Hz), 3.4–3.2 (4H, brs), 3.2–3.0 (3H, br), 3.0–2.7 (2H, br), 2.2–1.9 (1H, m), 1.99 (4H, brs), 1.97 (3H, s), 1.9–1.5 (5H, m), 0.91 (3H, t, J=7.3 Hz);

TLC: Rf 0.46 (chloroform:methanol:acetic acid=25:5:1).

Example 1(94)

4-(N-2-(morpholin-4-yl)ethylsulfamoyl)phenyl 2RS-(4-nitrophenyl)butanoic acid ester.hydrochloride

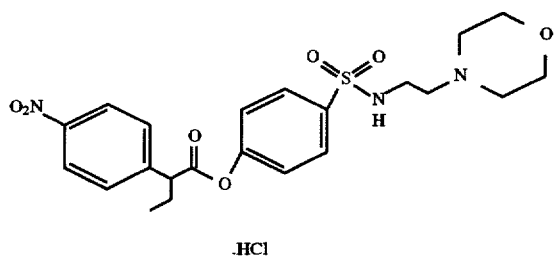

.HCl

NMR (CD$_3$OD): δ 8.27 (2H, d, J=8.6 Hz), 7.92 (2H, d, J=9.0 Hz), 7.67 (2H, d, J=8.6 Hz), 7.27 (2H, d, J=9.0 Hz), 4.03 (1H, t, J=7.6 Hz), 3.90 (2H, m), 3.50 (2H, m), 3.28 (8H, m), 2.28 (1H, m), 1.99 (1H, m), 1.00 (3H, t, J=7.4 Hz);

TLC: Rf 0.61 (chloroform:methanol:water=9:1:0.1).

Example 1(95)

4-(N-2-(pyridin-2-yl)ethylsulfamoyl)phenyl 1-(4-nitrophenyl)cyclobutanecarboxylic acid ester.hydrochloride

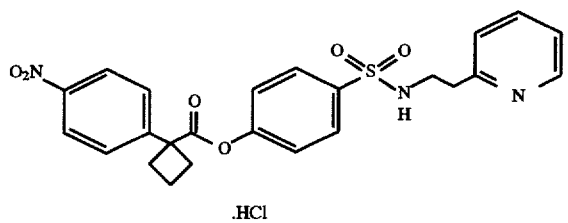

.HCl

NMR (CD$_3$OD): δ 8.72 (1H, d, J=8.0 Hz), 8.53 (1H, t, J=8.0 Hz), 8.28 (2H, d, J=8.6 Hz), 7.96 (1H, d, J=8.0 Hz), 7.93 (1H, d, J=8.0 Hz), 7.79 (2H, d, J=8.6 Hz), 7.66 (2H, d, J=8.6 Hz), 7.17 (2H, d, J=8.6 Hz), 3.30 (4H, m), 3.06 (2H, m), 2.72 (2H, m), 2.23 (1H, m), 2.04 (1H, m);

TLC: Rf 0.54 (chloroform:methanol:water=9:1:0.1).

Example 1(96)

4-(N-2-(piperidin-1-yl)ethylsulfamoyl)phenyl 1-(4-nitrophenyl)cyclobutanecarboxylic acid ester.hydrochloride

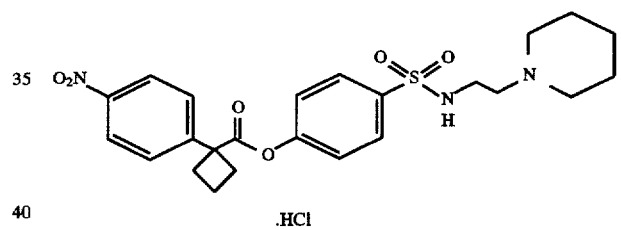

.HCl

NMR (CD$_3$OD): δ 8.26 (2H, d, J=8.4 Hz), 7.90 (2H, d, J=8.4 Hz), 7.66 (2H, d, J=8.4 Hz), 7.23 (2H, d, J=8.4 Hz), 3.50 (2H, m), 3.30 (4H, m), 3.06 (4H, m), 2.73 (2H, m), 2.22 (1H, m), 1.99 (1H, m), 1.87 (6H, m);

TLC: Rf 0.45 (chloroform:methanol:water=9:1:0.1).

Example 1(97)

4-(N-2-(1-methylpyrrol-2-yl)ethylsulfamoyl)phenyl 1-(4-nitrophenyl)cyclobutanecarboxylic acid ester

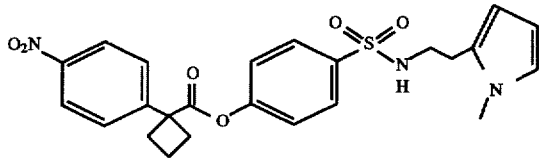

NMR (CDCl$_3$): δ 8.26 (2H, d, J=9.0 Hz), 7.78 (2H, d, J=9.0 Hz), 7.56 (2H, d, J=9.0 Hz), 7.09 (2H, d, J=9.0 Hz), 6.52 (1H, dd, J=2.0, 2.4 Hz), 6.01 (1H, dd, J=2.4, 2.6 Hz), 5.80 (1H, m), 4.64 (1H, t, J=6.6 Hz), 3.42 (3H, s), 3.16 (2H, q, J=6.6 Hz), 3.05 (2H, m), 2.74 (2H, t, J=6.6 Hz), 2.66 (2H, m), 2.25 (1H, m), 2.03 (1H, m);

TLC: Rf 0.26 (hexane:ethyl acetate=2:1).

Example 1(98)

4-(N-(tetrazol-5-ylmethyl)sulfamoyl)phenyl 2RS-(4-nitrophenyl)butanoic acid ester

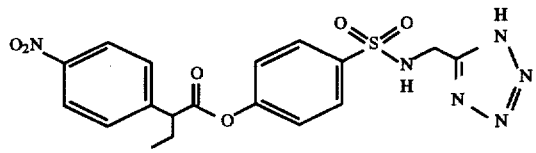

NMR (DMSO-d$_6$): δ 8.54 (1H, t, J=5.8 Hz), 8.28 (2H, d, J=8.8 Hz), 7.85 (2H, d, J=8.8 Hz), 7.73 (2H, d, J=8.8 Hz), 7.32 (2H, d, J=8.8 Hz), 4.30 (2H, d, J=5.8 Hz), 4.17 (1H, t, J=7.6 Hz), 2.35–2.05 and 2.03–1.75 (each 1H, m), 0.92 (3H, t, J=7.2 Hz);

TLC: Rf 0.45 (acetic acid:methanol:chloroform=1:5:25).

Example 1(99)

4-(N-(tetrazol-5-ylmethyl)sulfamoyl)phenyl 1-(4-nitrophenyl)cyclobutanecarboxylic acid ester

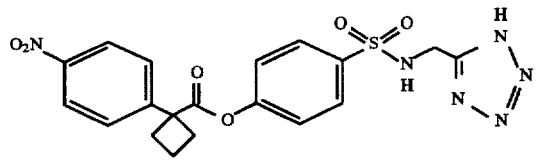

NMR (CD$_3$OD): δ 8.28 (2H, d, J=8.8 Hz), 7.85 (2H, d, J=8.8 Hz), 7.67 (2H, d, J=8.8 Hz), 7.19 (2H, d, J=8.8 Hz), 4.37 (2H, s), 3.16–2.96 (2H, m), 2.82–2.62 (2H, q-like), 2.37–2.12 and 2.12–1.90 (each 1H, m);

TLC: Rf 0.11 (acetic acid:methanol:chloroform=1:2:40).

Example 1(100)

4-(N-(tetrazol-5-yl)sulfamoyl)phenyl 1-(4-nitrophenyl)cyclobutanecarboxylic acid ester

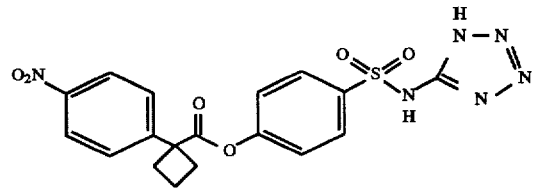

NMR (DMSO-d$_6$): δ 8.26 (2H, d, J=8.8 Hz), 7.84 (2H, d, J=8.8 Hz), 7.69 (2H, d, J=8.8 Hz), 7.12 (2H, d, J=8.8 Hz), 3.08–2.88 (2H, m), 2.74–2.54 (2H, q-like), 2.24–2.04 and 2.04–1.84 (each 1H, m);

TLC: Rf 0.29 (acetic acid:methanol:chloroform=1:5:25).

Example 1(101)

4-(N-(tetrazol-5-yl)sulfamoyl)phenyl 2RS-(4-nitrophenyl)butanoic acid ester

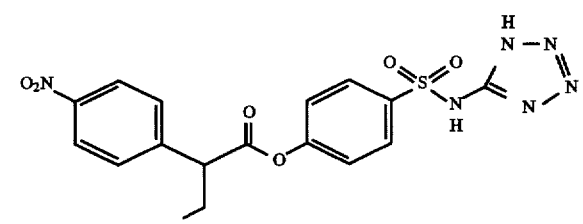

NMR (DMSO-d$_6$): δ 13.88 (1H, brs), 8.26 (2H, d, J=8.8 Hz), 7.82 (2H, d, J=8.8 Hz), 7.70 (2H, d, J=8.8 Hz), 7.06 (2H, d, J=8.8 Hz), 4.12 (1H, t, J=7.4 Hz), 2.30–2.00 and 2.00–1.70 (each 1H, m), 0.91 (3H, t, J=7.2 Hz);

TLC: Rf 0.26 (acetic acid:methanol:chloroform=1:2:40).

Example 1(102)

4-(N-(quinuclidin-3RS-yl)sulfamoyl)-2-methylphenyl 2RS-(4-methylphenyl)butanoic acid ester

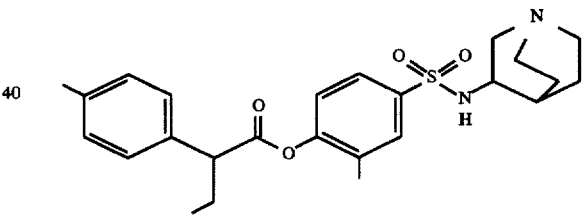

NMR (CDCl$_3$): δ 7.70 (1H, d, J=2 Hz), 7.67 (1H, dd, J=8 and 2 Hz), 7.27 (2H, d, J=8 Hz), 7.18 (2H, d, J=8 Hz), 7.06 (1H, d, J=8 Hz), 3.70 (1H, t, J=8 Hz), 3.38–3.23 (1H, m), 3.23–3.05 (1H, m), 2.90–2.49 (5H, m), 2.36 (3H, s), 2.35–2.11 (1H, m), 2.00 (3H, s), 2.05–1.22 (6H, m), 1.00 (3H, t, J=7 Hz);

TLC: Rf 0.40 (chloroform:methanol:water=8:2:0.2).

Example 1(103)

4-(N-2R-methoxy-3R-hydroxy-4S-hydroxy-5R-hydroxyperhydropyran-6R-ylmethylsulfamoyl)-2-methylphenyl 2RS-(4-(pyrrolidin-1-yl)phenyl) butanoic acid ester

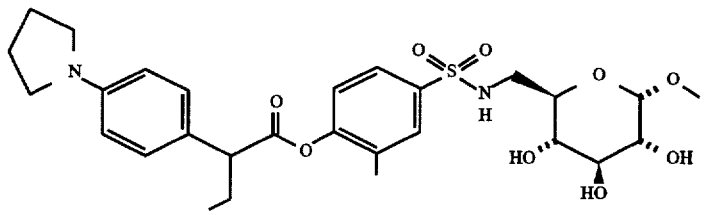

NMR (CDCl₃+6 drops of CD₃OD): δ 7.68–7.63 (m, 2H), 7.22 (d, J=8.8 Hz, 2H), 7.05 (d, J=8.1 Hz, 1H), 6.55 (d, J=8.8 Hz, 2H), 4.63 (d, J=3.7 Hz, 1H), 3.70–3.50 (m, 3H), 3.50–3.10 (m, 11H), 2.30–1.80 (m, 9H), 0.99 (t, J=7.4 Hz, 3H);

TLC: Rf 0.41 (chloroform:methanol=8:1).

Example 1(104)

4-(N-phenylsulfamoyl)phenyl 2RS-phenylbutanoic acid ester

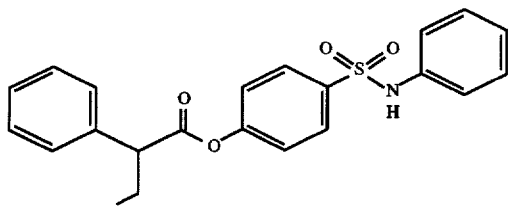

NMR (CDCl₃): δ 7.73 (2H, dd, J=2 Hz, 8 Hz), 7.40–7.16 (7H, m), 7.16–7.00 (5H, m), 6.76 (1H, s), 3.67 (1H, t, J=7 Hz), 2.20 (1H, m), 1.89 (1H, m), 0.96 (3H, t, J=7 Hz);

TLC: Rf 0.57 (hexane:ethyl acetate=1:1).

Example 1(105)

4-(N-4-nitrophenylsulfamoyl)phenyl 2RS-phenylbutanoic acid ester

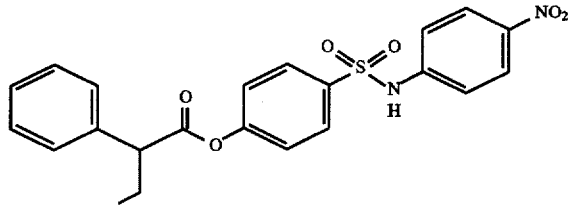

NMR (CDCl₃): δ 8.10 and 7.85 (each 2H, dd, J=2 Hz, 8 Hz), 7.75 (1H, brs), 7.35 (5H, m), 7.20 and 7.14 (each 2H, dd, J=2 Hz, J=8 Hz), 3.69 (1H, t, J=7 Hz), 2.20 and 1.90 (each 1H, m), 0.96 (3H, t, J=7 Hz);

TLC: Rf 0.59 (hexane:ethyl acetate=1:1).

Example 1(106)

4-(N-phenylsulfamoyl)phenyl 2RS-(4-aminophenyl) butanoic acid ester

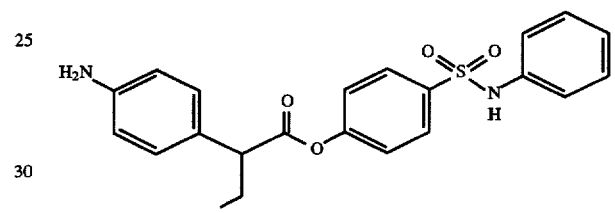

NMR (DMSO-d₆): δ 7.72 (2H, d, J=8 Hz), 7.42–6.91 (9H, m), 6.80–6.54 (3H, m), 3.56 (1H, t, J=7 Hz), 2.23–1.64 (2H, m), 0.92 (3H, t, J=7 Hz);

TLC: Rf 0.39 (hexane:ethyl acetate=1:1).

Example 1(107)

4-(N-(2-(tetrazol-5-yl)phenyl)sulfamoyl)phenyl 2RS-(4-(pyrrolidin-1-yl)phenyl)butanoic acid ester

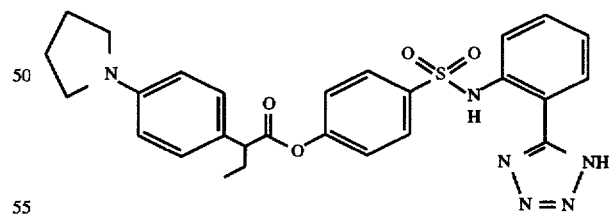

NMR (CDCl₃): δ 7.76 (1H, d, J=7.8 Hz), 7.59 (1H, d, J=7.8 Hz), 7.48 (1H, t-like), 7.35 (2H, d, J=8.8 Hz), 7.26 (1H, t-like), 7.17 (2H, d, J=8.4 Hz), 6.77 (2H, d, J=8.6 Hz), 6.55 (2H, d, J=8.4 Hz), 3.57 (1H, t, J=7.2 Hz), 3.31–3.24 (4H, t-like), 2.25–1.75 (2H, m), 2.05–1.95 (4H, m), 0.97 (3H, t, J=7.2 Hz);

TLC: Rf 0.33 (acetic acid:methanol:chloroform= 1:20:200).

Example 1(108)

4-(N-4-(morpholin-4-yl)phenylsulfamoyl)phenyl 2RS-(4-(pyrrolidin-1-yl)phenyl)butanoic acid ester.2hydrochloride

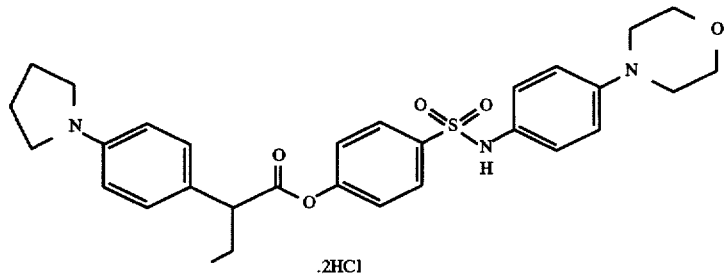

.2HCl

NMR (CD₃OD): δ 7.83 (2H, d, J=8.8 Hz), 7.60 (4H, s), 7.55 (2H, d, J=9.0 Hz), 7.29 (2H, d, J=9.0 Hz), 7.16 (2H, d, J=8.8 Hz), 4.05 (4H, t-like), 3.89 (1H, t, J=7.4 Hz), 3.84–3.68 (4H, m), 3.58 (4H, t-like), 2.35–2.23 (4H, m), 2.30–2.09 and 2.04–1.78 (each 1H, m), 0.96 (3H, t, J=7.2 Hz);

TLC: Rf 0.52 (methanol:chloroform=1:20).

Example 1(109)

2-(N-(4-(2RS-(4-(pyrrolidin-1-yl)phenyl)butylyloxy)-3-methylphenyl sulfonyl)amino)phenylsulfonic acid sodium salt

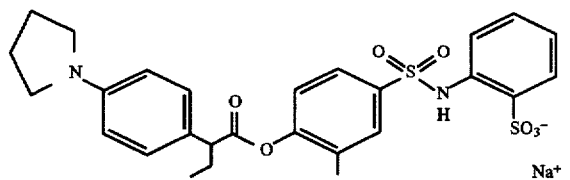

NMR (DMSO-d₆): δ 10.6 (1H, s), 7.81 (1H, d, J=2 Hz), 7.71 (1H, dd, J=9.2 Hz), 7.57 (1H, dd, J=8.2 Hz), 7.37 (1H, dd, J=8.1 Hz), 7.22 (1H, td, J=8.1 Hz), 7.16 (2H, d, J=9 Hz), 7.06 (1H, d, J=9 Hz), 6.97 (1H, td, J=8.1 Hz), 6.57 (2H, d, J=9 Hz), 3.67 (1H, t, J=7 Hz), 3.30–3.15 (4H, m), 2.18–1.90 (5H, m), 1.88 (3H, s), 1.87–1.65 (1H, m), 0.86 (3H, t, J=7 Hz);

TLC: Rf 0.19 (chloroform:methanol:acetic acid=25:5:1).

Example 1(110)

4-(N-3,5-dimethoxyphenylsulfamoyl)-2-methylphenyl 2RS-(4-(pyrrolidin-1-yl)phenyl) butanoic acid ester

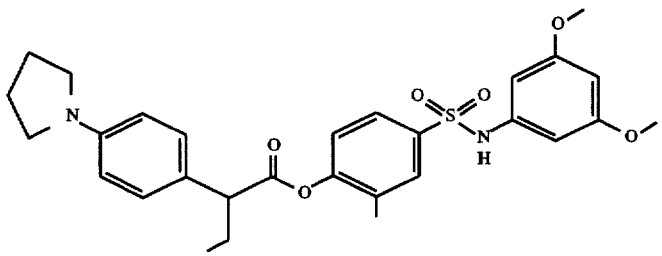

NMR (CDCl₃): δ 7.62–7.55 (2H, m), 7.18 (2H, d, J=8.4 Hz), 6.98 (1H, d, J=8.2 Hz), 6.69 (1H, s), 6.52 (2H, d, J=8.4 Hz), 6.21–6.16 (3H, m), 3.69 (6H, s), 3.57 (1H, t, J=7.6 Hz), 3.31–3.24 (4H, m), 2.25–1.80 (9H, m), 0.97 (3H, t, J=7.4 Hz);

TLC: Rf 0.83 (hexane:ethyl acetate=1:1).

Example 1(111)

4-(N-phenylsulfamoyl)-2-methylphenyl 2RS-(4-(pyrrolidin-1-yl)phenyl)butanoic acid ester

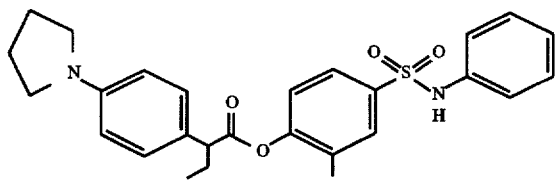

NMR (CDCl₃): δ 7.56–7.49 (2H, m), 7.26–6.94 (8H, m), 6.68 (1H, brs), 6.52 (2H, d, J=8.4 Hz), 3.57 (1H, t, J=7.8 Hz), 3.31–3.24 (4H, m), 2.27–1.75 (6H, m), 1.95 (3H, s), 0.97 (3H, t, J=7.4 Hz);

TLC: Rf 0.83 (hexane:ethyl acetate=3:1).

Example 1(112)

4-(N-2-(N'-(tetrazol-5-ylmethyl)carbamoyl)benzen-1-ylsulfamoyl)phenyl 2RS-(4-nitrophenyl)butanoic acid ester

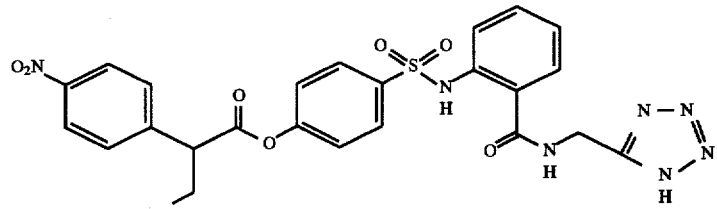

NMR (DMSO-d₆): δ 9.60–9.48 (1H, m), 8.25 (2H, d, J=8 Hz), 7.88–7.63 (5H, m), 7.55–7.45 (2H, m), 7.30–7.09 (3H, m), 4.79–4.65 (2H, m), 4.13 (1H, t, J=7 Hz), 2.31–2.04 (1H, m), 2.04–1.78 (1H, m), 0.88 (3H, t, J=7 Hz);

TLC: Rf 0.28 (acetic acid:methanol:chloroform=1:2:30).

Example 1(113)

4-(N-2-(N'-(tetrazol-5-ylmethyl)carbamoyl)benzen-1-ylsulfamoyl)phenyl 1-(4-nitrophenyl)cyclobutanecarboxylic acid ester

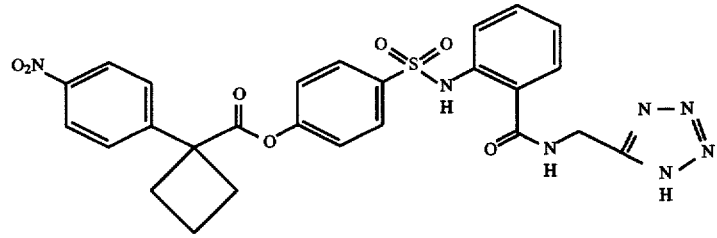

NMR (DMSO-d₆): δ 9.60–9.48 (1H, m), 8.33–8.20 (2H, m), 7.85–7.62 (5H, m), 7.55–7.40 (2H, m), 7.30–7.10 (3H, m), 4.78–4.65 (2H, m), 3.06–2.85 (2H, m), 2.75–2.55 (2H, m), 2.26–2.03 (1H, m), 2.03–1.80 (1H, m);

TLC: Rf 0.39 (acetic acid:methanol:chloroform=1:2:20).

Example 1(114)

4-(N-(4-amidinophenyl)sulfamoyl)phenyl 2RS-(4-nitrophenyl)butanoic acid ester.acetate

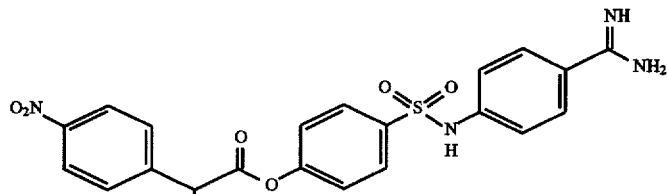

NMR (DMSO-d$_6$): δ 9.40–9.10 (2H, m), 8.75–8.55 (2H, m), 8.24 (2H, d, J=8 Hz), 7.78–7.61 (4H, m), 7.44 (2H, d, J=8 Hz), 7.05 (2H, d, J=8 Hz), 6.83 (2H, d, J=8 Hz), 4.09 (1H, t, J=7 Hz), 2.23–2.00 (1H, m), 1.95–1.65 (4H, m), 0.88 (3H, t, J=7 Hz);

TLC: Rf 0.52 (acetic acid:methanol:chloroform=1:2:10).

Example 1(115)

4-(N-(4-amidinophenyl)sulfamoyl)phenyl 1-(4-nitrophenyl)cyclobutanecarboxylic acid ester.acetate

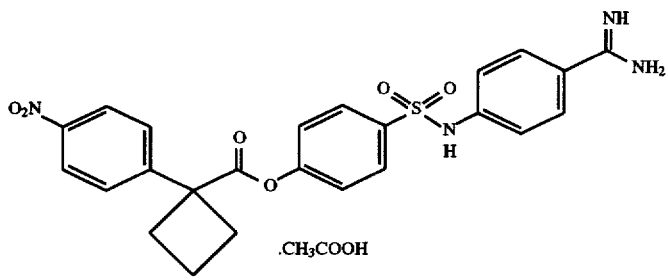

NMR (CD$_3$OD): δ 8.26 (2H, d, J=8 Hz), 7.87 (2H, d, J=8 Hz), 7.63 (4H, d, J=8 Hz), 7.23 (2H, d, J=8 Hz), 7.12 (2H, d, J=8 Hz), 3.10–2.94 (2H, m), 2.78–2.60 (2H, m), 2.35–1.95 (5H, m);

TLC: Rf 0.40 (acetic acid:methanol:chloroform=1:2:15).

Example 1(116)

4-(N-2-(tetrazol-5-yl)phenylsulfamoyl)phenyl 1-(4-nitrophenyl)cyclobutanecarboxylic acid ester NMR (CD$_3$OD): δ 8.22 (2H, d, J=8.8 Hz), 7.86–7.18 (8H, m), 6.96 (2H, d, J=8.8 Hz), 3.08–2.88 (2H, m), 2.65 (2H, q-like), 2.28–2.08 (2H, m), 2.08–1.88 (2H, m);

TLC: Rf 0.43 (acetic acid:methanol:chloroform=1:3:30).

Example 1(117)

4-(N-4-(morpholin-4-yl)phenylsulfamoyl)phenyl 1-(4-nitrophenyl)cyclobutanecarboxylic acid ester.hydrochloride

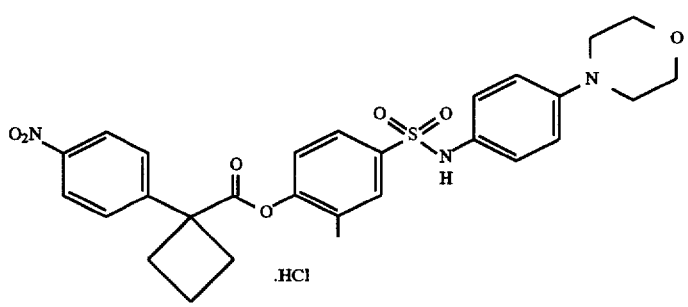

NMR (CD₃OD): δ 8.25 (2H, d, J=8.8 Hz), 7.82 (2H, d, J=8.8 Hz), 7.61 (2H, d, J=8.8 Hz), 7.54 (2H, d, J=8.8 Hz), 7.28 (2H, d, J=8.8 Hz), 7.12 (2H, d, J=8.8 Hz), 4.08 (4H, t, J=4.8 Hz), 3.57 (4H, t, J=4.8 Hz), 3.02 (2H, m), 2.70 (2H, m), 2.21 (1H, m), 2.03 (1H, m);

TLC: Rf 0.35 (hexane:ethyl acetate=1:1).

Example 1(118)
4-(N-2-(tetrazol-5-yl)phenylsulfamoyl)phenyl 2RS-(4-nitrophenyl)butanoic acid ester

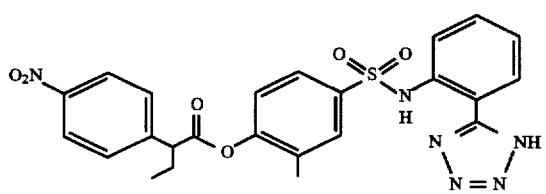

NMR (CD₃OD): δ 8.22 (2H, m), 7.93 (1H, d, J=7.8 Hz), 7.68 (1H, d, J=7.8 Hz), 7.64–7.60 (2H, t-like),7.60–7.56 (2H, m), 7.33 (1H, t, J=7.8 Hz), 7.16 (1H, t, J=7.8 Hz), 7.00–6.92 (2H, m), 3.92 (1H, t, J=8.0 Hz), 2.30–2.05 and 2.05–1.75 (each 1H, m), 0.93 (3H, t, J=7.2 Hz);
TLC: Rf 0.27 (acetic acid:methanol:chloroform= 1:20:200).

Example 1(119)
4-(N-2-(N'-carboxymethylcarbamoyl) phenylsulfamoyl)phenyl 2RS-(4-(N-t-butyloxycarbonylamino)phenyl)butanoic acid ester

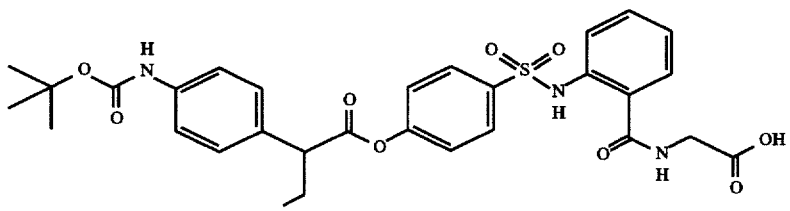

NMR (DMSO-d₆): δ 10.77 (1H, brs), 9.34 (1H, t-like), 7.82 (1H, d, J=7 Hz), 7.79 (2H, d, J=8 Hz), 7.44 (2H, d, J=8 Hz), 7.28–7.04 (7H, m), 6.78–6.70 (1H, m), 3.86 (2H, d-like), 3.72 (1H, t, J=7 Hz), 2.11–1.90 and 1.81–1.67 (each 1H, m), 1.47 (9H, s), 0.87 (3H, t, J=7 Hz);
TLC: Rf 0.21 (chloroform:methanol:water=8:2:0.2).

Example 1(120)
4-(3,5-dimethoxybenzylaminosulfonyl)-2-methylphenyl 2RS-(4-(pyrrolidin-1-yl)phenyl) butanoic acid ester

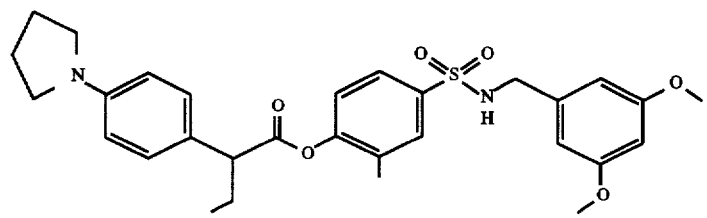

NMR (CDCl₃): δ7.67–7.62 (2H, m), 7.22 (2H, d, J=8.6 Hz), 7.05 (1H, d, J=9.4 Hz), 6.54 (2H, d, J=8.6 Hz), 6.32 (3H, s), 4.64 (1H, t, J=6.0 Hz), 4.05 (2H, d, J=6.0 Hz), 3.72 (6H, s), 3.61 (1H, t, J=7.6 Hz), 3.33–3.26 (4H, m), 2.27–1.81 (6H, m), 2.02 (3H, s), 0.99 (3H, t, J=7.2 Hz);

TLC: Rf 0.86 (hexane:ethyl acetate=1:1).

Example 1(121)

4-((4-t-butoxycarbonylaminopiperidin-1-yl)sulfonyl)
-2-methylphenyl 2RS-(4-(pyrrolidin-1-yl)phenyl)
butanoic acid ester

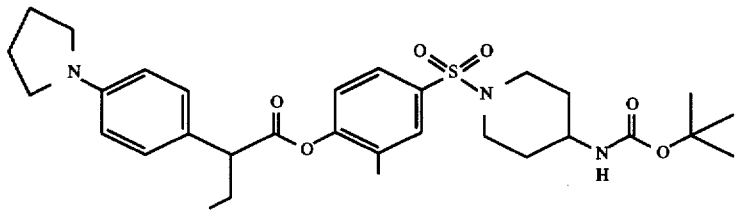

NMR (CDCl$_3$): δ7.55 (1H, s), 7.53 (1H, d, J=8.4 Hz), 7.23 (2H, d, J=8.6 Hz), 7.08 (1H, d, J=8.4 Hz), 6.55 (2H, d, J=8.6 Hz), 4.40 (1H, brs), 3.7–3.6 (2H, br), 3.62 (1H, t, J=7.7 Hz), 3.5–3.2 (1H, br), 3.28 (4H, br), 2.6–2.4 (2H, m), 2.3–2.1 (1H, m), 2.04 (3H, s), 2.00 (4H, brs), 2.1–1.8 (1H, m), 1.6–1.4 (4H, m), 1.41 (9H, s), 0.99 (3H, t, J=7.3 Hz);

TLC: Rf 0.81 (hexane:ethyl acetate=1:1).

Example 1(122)

4-(N-methoxy-N-benzylaminosulfonyl)-2-
methylphenyl 2RS-(4-(pyrrolidin-1-yl)phenyl)
butanoic acid ester

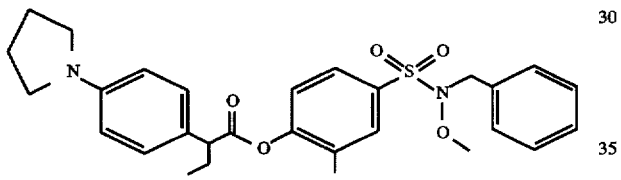

NMR (CDCl$_3$): δ7.74 (1H, s), 7.72 (1H, d, J=9.0 Hz), 7.32 (5H, s), 7.24 (2H, d, J=8.8 Hz), 7.14 (1H, d, J=9.0 Hz), 6.56 (2H, d, J=8.8 Hz), 3.98 (2H, s), 3.64 (1H, t, J=7.7 Hz), 3.43 (3H, s), 3.29 (4H, brs), 2.3–2.1 (1H, m), 2.08 (3H, s), 2.00 (4H, brs), 2.1–1.8 (1H, m), 1.00 (3H, t, J=7.4 Hz);

TLC: Rf 0.79 (hexane:ethyl acetate=2:1).

Example 1(123)

4-(N-benzyloxy-N-methylaminosulfonyl)-2-
methylphenyl 2RS-(4-(pyrrolidin-1-yl)phenyl)
butanoic acid ester.hydrochloride

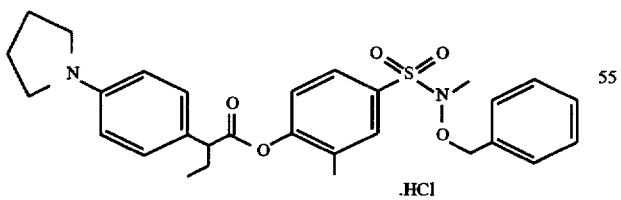

NMR (CDCl$_3$): δ7.71 (1H, s), 7.68 (1H, d, J=8.2 Hz), 7.5–7.2 (9H, brs), 7.09 (1H, d, J=8.2 Hz), 5.00 (2H, s), 3.73 (1H, t, J=7.5 Hz), 3.7–3.4 (4H, m), 2.65 (3H, s), 2.4–2.1 (5H, m), 2.03 (3H, s), 2.1–1.8 (1H, m), 0.99 (3H, t, J=7.2 Hz);

TLC: Rf 0.66 (hexane:ethyl acetate=2:1).

Example 1(124)

4-(2-(N,N-dimethylamino)ethylaminosulfonyl)-2-
methylphenyl 2RS-(4-(pyrrolidin-1-yl)phenyl)
butanoic acid ester

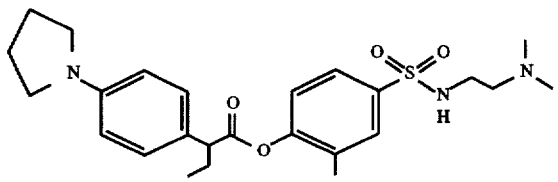

NMR (CDCl$_3$): δ 7.69–7.63 (2H, m), 7.22 (2H, d, J=8.6 Hz), 7.05 (1H, d, J=8.4 Hz), 6.55 (2H, d, J=8.6 Hz), 3.61 (1H, t, J=8.2 Hz), 3.32–3.25 (4H, m), 2.95 (2H, t, J=5.8 Hz), 2.30 (2H, t, J=5.8 Hz), 2.27–1.65 (15H, m), 0.99 (3H, t, J=7.2 Hz);

TLC: Rf 0.72 (chloroform:methanol:water=8:2:0.2).

Example 1(125)

4-(2-(piperidin-1-yl)ethylaminosulfonyl)-2-methylphenyl 2RS-(4-(pyrrolidin-1-yl)phenyl) butanoic acid ester

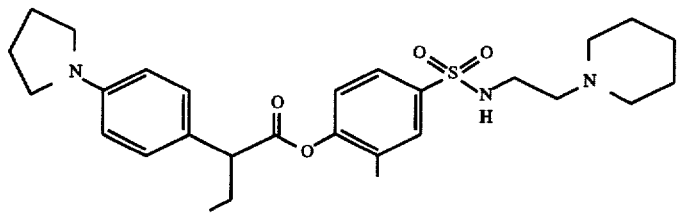

NMR (CDCl₃): δ7.7–7.4 (m, 2H), 7.23 (d, J=8.7 Hz, 2H), 7.05 (d, J=8.4 Hz, 1H), 6.56 (d, J=8.7 Hz, 2H), 3.61 (t, J=7.4 Hz, 1H), 3.4–3.2 (m, 4H), (m, 4H), 3.1–2.9 (m, 2H), 2.5–2.4 (m, 2H), 2.4–2.3 (m, 4H), 2.3–1.8 (m, 2H), 2.1–1.9 (m, 4H), 2.03 (s, 3H), 1.6–1.3 (m, 6H), 0.99 (t, J=7.4 Hz, 3H);

TLC: Rf 0.55 (chloroform:methanol=7:1).

Example 1(126)

4-(3-(morpholin-4-yl)propylaminosulfonyl)-2-methylphenyl 2RS-(4-(pyrrolidin-1-yl)phenyl) butanoic acid ester.2hydrochloride

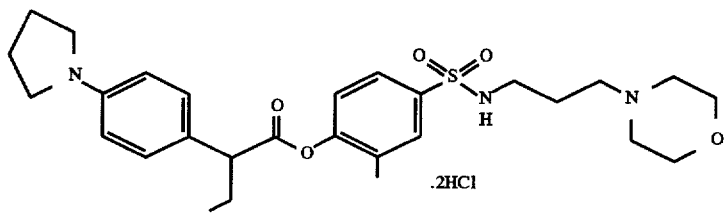

NMR (CDCl₃): δ7.8–7.4 (m, 5H), 7.3–7.0 (m, 3H), 4.3–3.4 (m, 11H), 3.2–2.8 (m, 6H), 2.4–1.8 (m, 11H), 0.99 (t, J=7.2 Hz, 3H);

TLC: Rf 0.56 (chloroform:methanol=9:1).

Example 1(127)

4-(indolin-1-ylsulfonyl)-2-methylphenyl 2RS-(4-(pyrrolidin-1-yl)phenyl)butanoic acid ester

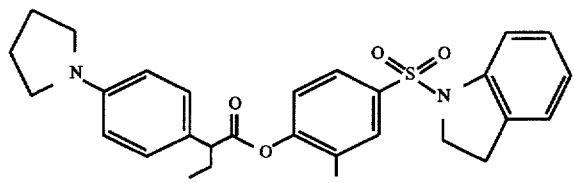

NMR (CDCl₃): δ7.66–7.51 (3H, m), 7.24–6.88 (6H, m), 6.53 (2H, d, J=8.8 Hz), 3.88 (2H, t, J=8.4 Hz), 3.58 (1H, t, J=7.8 Hz), 3.27 (4H, m), 2.89 (2H, t, J=8.4 Hz), 2.29–1.72 (9H, m), 0.96 (3H, t, J=7.2 Hz);

TLC: Rf 0.80 (hexane:ethyl acetate=1:1).

Example 1(128)

4-((2-oxo-4R-isopropylperhydroxazol-3-yl)sulfonyl)-2-methylphenyl 2RS-(4-(pyrrolidin-1-yl)phenyl) butanoic acid ester

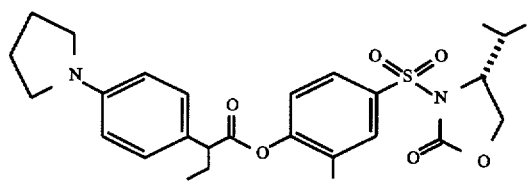

NMR (CDCl₃): δ7.93 (1H, s), 7.86 (1H, d, J=8.6 Hz), 7.22 (2H, d, J=8.4 Hz), 7.11 (1H, d, J=8.6 Hz), 6.55 (2H, d, J=8.4 Hz), 4.43–4.33 (1H, m), 4.26 (1H, t, J=8.6 Hz), 4.15 (1H, dd, J=8.6, 3.2 Hz), 3.61 (1H, t, J=7.7 Hz), 3.40–3.20 (4H, m), 2.55–2.33 (1H, m), 2.33–1.70 (9H, m), 0.99 (3H, t, J=7.4 Hz), 0.91 (3H, d, J=6.9 Hz), 0.76 (3H, d, J=6.9 Hz);

TLC: Rf 0.43 (hexane:ethyl acetate=7:3).

Example 1(129)

4-(N-2-(morpholin-4-yl)ethyl-N-methoxyaminosulfonyl)-2-methylphenyl 2RS-(4-(pyrrolidin-1-yl)phenyl)butanoic acid ester.2 hydrochloride

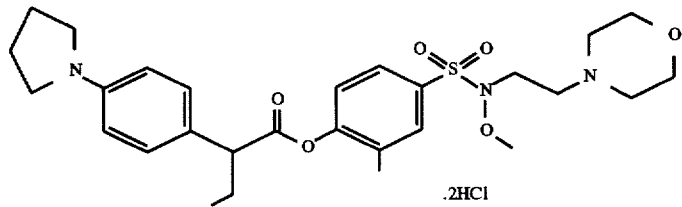

NMR (DMSO-d$_6$): δ7.85–7.65 (2H, m), 7.27 (3H, d, J=8.0 Hz), 6.95–6.70 (2H, brd), 4.05–3.70 (5H, m), 3.85 (3H, s), 3.50–2.95 (12H, m), 2.30–1.65 (6H, m), 2.02 (3H, s), 0.92 (3H, t, J=7.5 Hz);

TLC: Rf 0.52 (hexane:ethyl acetate=2:1).

Example 1(130)

4-(5-nitroindolin-1-ylsulfonyl)-2-methylphenyl 2S-(4-(pyrrolidin-1-yl)phenyl)butanoic acid ester

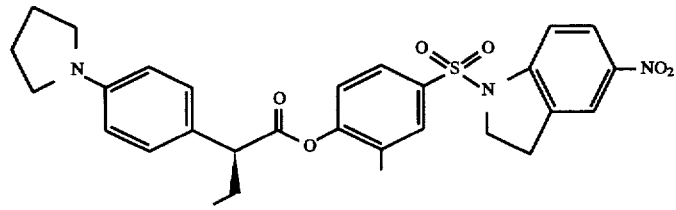

NMR (CDCl$_3$): δ8.10 (1H, d, J=9.0 Hz), 7.95 (1H, s), 7.72–7.56 (3H, m), 7.18 (2H, d, J=8.0 Hz), 7.05 (1H, d, J=8.0 Hz), 6.52 (2H, d, J=8.0 Hz), 4.01 (2H, t, J=8.5 Hz), 3.58 (1H, t, J=7.5 Hz), 3.35–3.18 (4H, m), 3.08 (2H, t, J=8.5 Hz), 2.30–1.70 (6H, m), 2.00 (3H, s), 0.96 (3H, t, J=7.5 Hz);

TLC: Rf 0.60 (hexane:ethyl acetate=2:1).

Example 1(131)

4-(morpholin-4-ylaminosulfonyl)-2-methylphenyl 2RS-(4-(pyrrolidin-1-yl)phenyl)butanoic acid ester.2hydrochloride

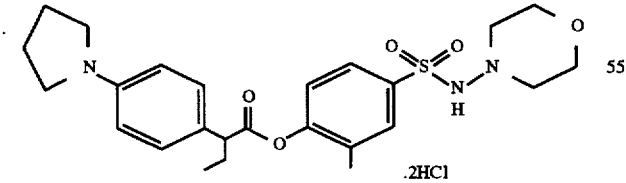

NMR (CD$_3$OD): δ7.84–7.70 (2H, m), 7.64 (4H, s-like), 7.13 (1H, d, J=8.2 Hz), 3.97 (1H, t, J=7.4 Hz), 3.87–3.66 (4H, m), 3.54 (4H, t, J=4.4 Hz), 2.55 (4H, t, J=4.4 Hz), 2.43–2.14 (5H, m), 2.14–1.80 (4H, m), 1.00 (3H, t, J=7.4 Hz);

TLC: Rf 0.51 (hexane:ethyl acetate=1:1).

Example 1(132)

4-(6-fluoroindolin-1-ylsulfonyl)-2-methylphenyl 2RS-(4-(pyrrolidin-1-yl)phenyl)butanoic acid ester.hydrochloride NMR (CD$_3$OD:CDCl$_3$=1:1): δ7.75–7.40 (6H, m), 7.29 (1H, dd, J=10.0 and 2.0 Hz), 7.15–7.01 (2H, m), 6.69 (1H, td, J=8.6 and 2.0 Hz), 3.94 (2H, t, J=8.4 Hz), 3.87 (1H, t, J=7.6 Hz), 3.79–3.63 (4H, m), 2.89 (2H, t, J=8.4 Hz), 2.40–2.12 (5H, m), 2.08–1.79 (4H, m), 0.99 (3H, t, J=7.4 Hz);

TLC: Rf 0.29 (hexane:ethyl acetate=3:1).

Example 1(133)

4-(5-(N,N-dimethylamino)indolin-1-ylsulfonyl)-2-methylphenyl 2RS-(4-(pyrrolidin-1-yl)phenyl)butanoic acid ester.2hydrochloride

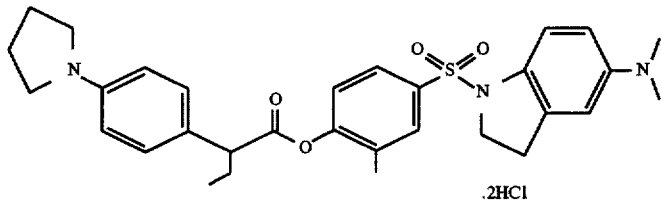

NMR (CD$_3$OD): δ7.78–7.64 (3H, m), 7.60 (4H, s-like), 7.52–7.42 (2H, m), 7.11 (1H, d, J=8.4 Hz), 4.01 (2H, t, J=8.5 Hz), 3.93 (1H, t, J=8.4 Hz), 3.87–3.70 (4H, m), 3.23 (6H, s), 3.06 (2H, t, J=8.5 Hz), 2.40–2.10 (5H, m), 2.10–1.80 (4H, m), 0.97 (3H, t, J=7.2 Hz);

TLC: Rf 0.24 (hexane:ethyl acetate=3:1).

Example 1(134)

4-(4-methylpiperazin-1-ylsulfonyl)-2-methylphenyl 2RS-(4-(pyrrolidin-1-yl)phenyl)butanoic acid ester.2hydrochloride

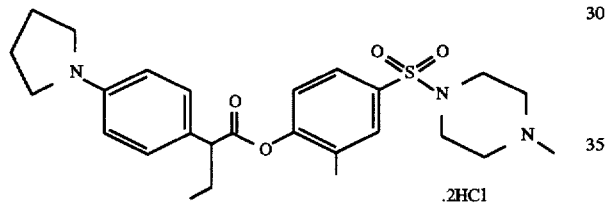

NMR (CD$_3$OD): δ7.75–7.59 (6H, m), 7.23 (1H, d, J=8.2 Hz), 4.06–3.84 (3H, m), 3.84–3.68 (4H, m), 3.64–3.49 (2H, m), 3.32–3.11 (2H, m), 2.89 (3H, s), 2.84–2.64 (2H, m), 2.44–2.14 (5H, m), 2.13–1.82 (4H, m), 1.00 (3H, t, J=7.2 Hz);

TLC: Rf 0.36 (ethyl acetate).

Example 1(135)

4-(5-nitroindolin-1-ylsulfonyl)-2-methylphenyl 2R-(4-(pyrrolidin-1-yl)phenyl)butanoic acid ester

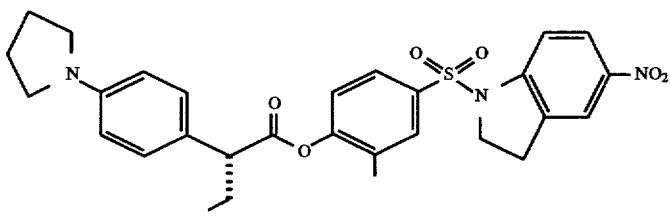

NMR (CDCl$_3$): δ8.10 (1H, dd, J=9.0,2.2 Hz), 7.95 (1H, d, J=2.2 Hz), 7.66 (1H, d, J=9.0 HZ), 7.66 (1H, s), 7.63 (1H, d, J=8.2 Hz), 7.18 (2H, d, J=8.8 Hz), 7.05 (1H, d, J=8.2 Hz), 6.53 (2H, d, J=8.8 Hz), 4.01 (2H, t, J=8.5 Hz), 3.58 (1H, t, J=7.7 Hz), 3.3–3.2 (4H, brs), 3.08 (2H, t, J=8.5 Hz), 2.3–2.0 (1H, m), 2.1–1.9 (4H, brs), 2.00 (3H, s), 2.0–1.8 (1H, m), 0.96 (3H, t, J=7.3 Hz);

TLC: Rf 0.60 (hexane:ethyl acetate=2:1).

Example 1(136)
4-(2-(morpholin-4-yl)ethylaminosulfonyl)-2-ethylphenyl 2S-(4-(pyrrolidin-1-yl)phenyl)butanoic acid ester.2hydrochloride

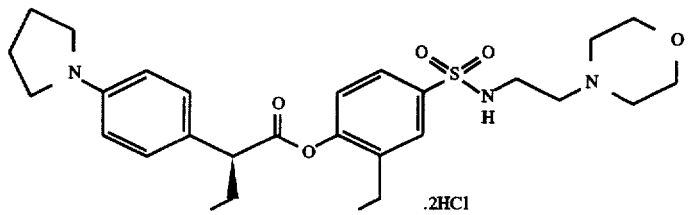

NMR (CD$_3$OD): δ7.83–7.58 (6H, m), 7.18 (1H, d, J=8.0 Hz), 4.12–3.70 (9H, m), 3.53 (2H, d, J=12.0 Hz), 3.38–3.08 (6H, m), 2.45–1.80 (8H, m), 1.00 (6H, t, J=7.5 Hz);

TLC: Rf 0.41 (hexane:ethyl acetate=1:4).

Example 1(137)

4-(2-(morpholin-4-yl)ethylaminosulfonyl)-2-ethylphenyl 2R-(4-(pyrrolidin-1-yl)phenyl)butanoic acid ester.2hydrochloride

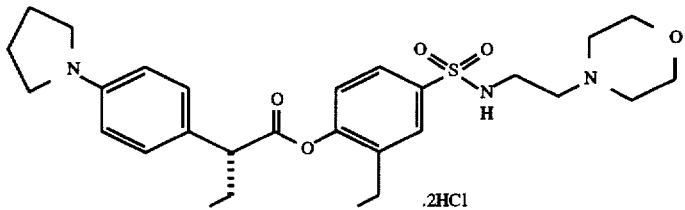

NMR (CD$_3$OD): δ7.83–7.58 (6H, m), 7.19 (1H, d, J=8.0 Hz), 4.12–3.70 (9H, m), 3.53 (2H, d, J=12.0 Hz), 3.40–3.08 (6H, m), 2.50–1.80 (8H, m), 0.99 (6H, t, J=7.5 Hz);

TLC: Rf 0.41 (hexane:ethyl acetate=1:4).

Example 1(138)

4-(2-(morpholin-4-yl)ethylaminosulfonyl)-2-methylphenyl 2R-(4-(pyrrolidin-1-yl)phenyl)butanoic acid ester.2hydrochloride

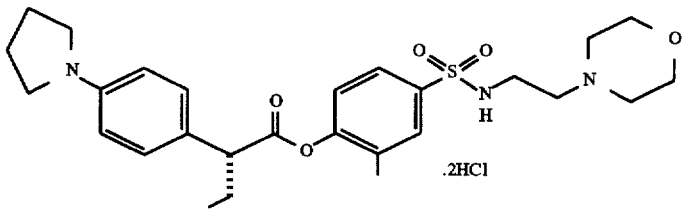

NMR (DMSO-d$_6$): δ11.0–10.8 (1H, brs), 7.75 (1H, s), 7.70 (1H, d, J=8.6 Hz), 7.22 (2H, d, J=8.4 Hz), 7.18 (1H, d, J=8.6 Hz), 6.64 (2H, d, J=8.4 Hz), 4.0–3.7 (5H, m), 3.4–3.0 (12H, m), 2.2–2.0 (1H, m), 2.1–1.9 (4H, brs), 2.0–1.7 (1H, m), 1.97 (3H, s), 0.91 (3H, t, J=7.3 Hz);

TLC: Rf 0.50 (chloroform:methanol=9:1).

Example 1(139)

4-(2-(morpholin-4-yl)ethylaminosulfonyl)-2-methylphenyl 2S-(4-(pyrrolidin-1-yl)phenyl) butanoic acid ester.2hydrochloride

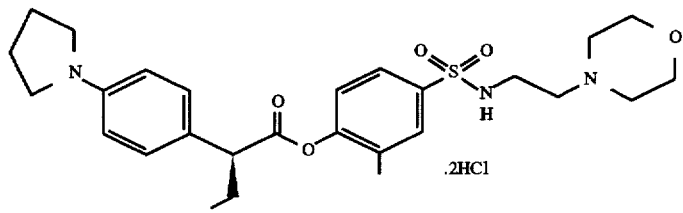

NMR (DMSO-$d_6$): δ11.4–11.2 (1H, brs), 7.76 (1H, s), 7.70 (1H, d, J=8.6 Hz), 7.30 (2H, d, J=8.4 Hz), 7.18 (1H, d, J=8.6 Hz), 6.87 (2H, d, J=8.4 Hz), 4.0–3.7 (5H, m), 3.5–3.3 (6H, m), 3.3–3.0 (6H, m), 2.2–2.0 (1H, m), 2.1–1.9 (4H, brs), 2.0–1.7 (1H, m), 1.98 (3H, s), 0.91 (3H, t, J=7.2 Hz);

TLC: Rf 0.50 (chloroform:methanol=9:1).

Example 1(140)

4-(4-methyl-1,4-perhydrodiazepin-1-ylsulfonyl)-2-methylphenyl 2RS-(4-(pyrrolidin-1-yl)phenyl) butanoic acid ester.2hydrochloride

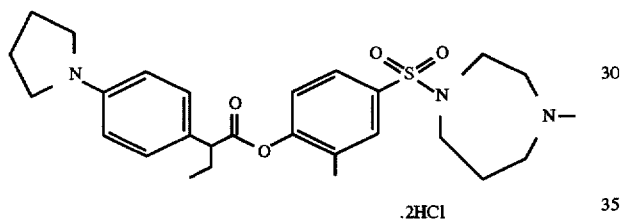

NMR (DMSO-$d_6$): δ7.72 (1H, d, J=2 Hz), 7.66 (1H, dd, J=2 and 8 Hz), 7.25 (2H, d, J=8 Hz), 7.19 (1H, d, J=8 Hz), 6.76 (2H, d-like), 3.76 (1H, J=7 Hz), 3.75–3.01 (12H, m), 2.76 and 2.74 (total 3H, each s), 2.21–1.66 (8H, m), 1.99 (3H, s), 0.91 (3H, t, J=7 Hz);

TLC: Rf 0.52 (chloroform:methanol:water=9:1:0.1).

Example 1(141)

4-(2RS-ethoxycarbonylindolin-1-ylsulfonyl)-2-methylphenyl 2S-(4-(pyrrolidin-1-yl)phenyl) butanoic acid ester

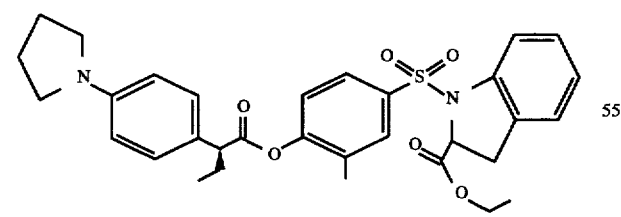

NMR (CDCl$_3$): δ7.62–7.51 (3H, m), 7.23–7.15 (3H, m), 7.07–6.95 (3H, m), 6.52 (2H, d, J=9 Hz), 4.75–4.67 (1H, m), 4.24 (2H, q, J=7 Hz), 3.57 (1H, t, J=7 Hz), 3.31–3.24 (4H, m), 3.21–3.00 (2H, m), 2.23–1.75 (2H, m), 2.04–1.99 (4H, m), 1.96 (3H, s), 1.29 (3H, t, J=7 Hz), 0.96 (3H, t, J=7 Hz);

TLC: Rf 0.29 (hexane:ethyl acetate=3:1).

Example 1(142)

4-(quinuclidin-3RS-ylaminosulfonyl)-2-methylphenyl 2S-(4-(pyrrolidin-1-yl)phenyl) butanoic acid ester.2hydrochloride

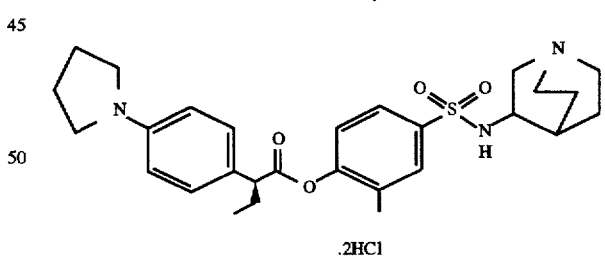

NMR (DMSO-$d_6$): δ8.35 (1H, d, J=7 Hz), 7.74–7.64 (2H, m), 7.26 (2H, d, J=8 Hz), 7.17 (1H, d, J=8 Hz), 6.82–6.70 (2H, br), 3.75 (1H, t, J=7 Hz), 3.61–3.43 (1H, br), 3.40–3.22 (5H, m), 3.18–2.94 (5H, m), 2.90–2.79 (1H, m), 2.17–1.60 (13H, m), 0.91 (3H, t, J=7 Hz);

TLC: Rf 0.35 (chloroform:methanol:water=8:2:0.2).

Example 1(143)

4-(2-(morpholin-4-yl)ethylaminosulfonyl)-2-methylphenyl 2RS-(4-(pyrrolidin-1-yl)phenyl) butanoic acid ester.2methanesulfonic acid salt

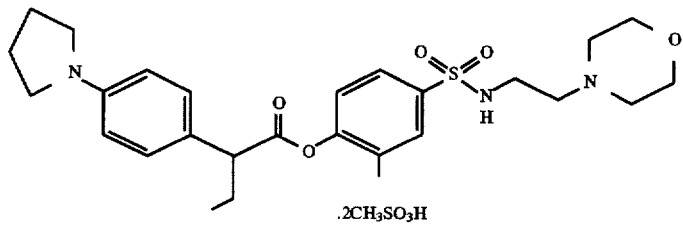

NMR (CD$_3$OD): δ7.80–7.70 (2H, m), 7.67 (4H, s), 7.17 (1H, d, J=8.0 Hz), 4.10–3.70 (9H, m), 3.54 (2H, d, J=12.0 Hz), 3.40–3.10 (6H, m), 2.70 (6H, s), 2.40–1.80 (6H, m), 2.05 (3H, s), 1.00 (3H, t, J=7.5 Hz);

TLC: Rf 0.31 (chloroform:methanol:acetic acid=40:2:1).

Example 1(144)

4-(3,5-dimethoxyphenylaminosulfonyl)-2-methylphenyl 2RS-(4-(pyrrolidin-1-yl)phenyl) butanoic acid ester.methanesulfonic acid salt

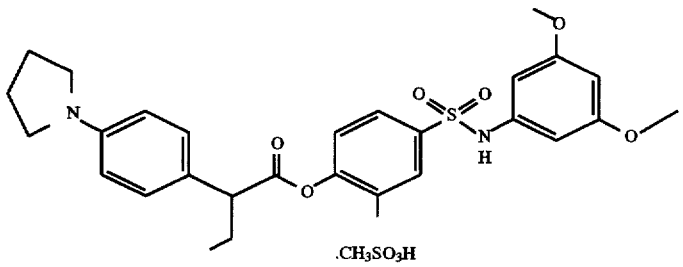

NMR (CD$_3$OD): δ7.70–7.50 (6H, m), 7.05 (1H, d, J=8.5 Hz), 6.24 (2H, d, J=2.0 Hz), 6.16 (1H, t, J=2.0 Hz), 3.94 (1H, t, J=7.5 Hz), 3.77 (4H, t-like), 3.67 (6H, s), 2.70 (3H, s), 2.40–1.80 (6H, m), 1.96 (3H, s), 0.98 (3H, t, J=7.5 Hz);

TLC: RF 0.73 (hexane:ethyl acetate=1:1).

Example 1(145)

4-(5-nitroindolin-1-ylsulfonyl)-2-methylphenyl 2RS-(4-(pyrrolidin-1-yl)phenyl)butanoic acid ester.hydrochloride

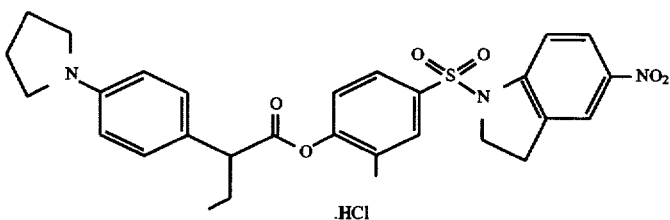

NMR (CDCl$_3$): δ8.11 (1H, dd, J=2.0, 9.0 Hz), 7.96 (1H, d, J=2.0 Hz), 7.72–7.60 (3H, m), 7.55 (2H, d, J=8.0 Hz), 7.44 (2H, d, J=8.0 Hz), 7.06 (1H, d, J=8.0 Hz), 4.03 (2H, t, J=8.5 Hz), 3.75 (1H, t, J=7.5 Hz), 3.85–3.40 (4H, m), 3.10 (2H, t, J=8.5 Hz), 2.45–2.20 (4H, m), 2.40–1.75 (2H, m), 2.02 (3H, s), 0.98 (3H, t, J=7.5 Hz);

TLC: Rf 0.60 (hexane:ethyl acetate=2:1).

Example 1(146)

4-(5-nitroindolin-1-ylsulfonyl)-2-methylphenyl 2RS-(4-(pyrrolidin-1-yl)phenyl)butanoic acid ester.methanesulfonic acid salt

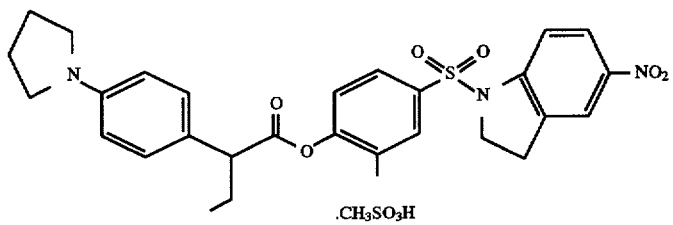

NMR (CDCl$_3$): δ8.11 (1H, dd, J=2.5, 9.0 Hz), 7.97 (1H, d, J=2.5 Hz), 7.74–7.62 (3H, m), 7.57 (2H, d, J=8.5 Hz), 7.49 (2H, d, J=8.5 Hz), 7.07 (1H, d, J=8.0 Hz), 4.03 (2H, t, J=8.5 Hz), 3.77 (1H, t, J=7.5 Hz), 4.10–3.30 (4H, m), 3.11 (2H, t, J=8.5 Hz), 2.85 (3H, s), 2.50–2.20 (4H, m), 2.40–2.10 and 2.10–1.80 (each 1H, m), 2.04 (3H, s), 0.99 (3H, t, J=7.5 Hz);

TLC: Rf 0.60 (hexane:ethyl acetate=2:1).

Example 1(147)

4-(indolin-1-ylsulfonyl)-2-methylphenyl 2RS-(4-(pyrrolidin-1-yl)phenyl)butanoic acid ester.hydrochloride

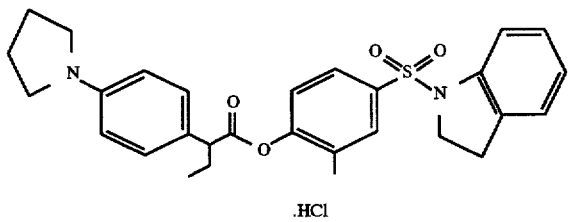

NMR (CDCl$_3$): δ7.65–7.53 (3H, m), 7.32 (2H, d, J=8.4 Hz), 7.24–6.90 (6H, m), 3.89 (2H, t, J=8.5 Hz), 3.66 (1H, t, J=8.2 Hz), 3.45 (4H, brs), 2.89 (2H, t, J=8.5 Hz), 2.34–2.04 (5H, m), 1.97 (3H, s), 2.04–1.73 (1H, m), 0.97 (3H, t, J=7.2 Hz);

TLC: Rf 0.42 (hexane:ethyl acetate=3:1).

Example 2

4-(2S-carboxypyrrolidin-1-ylsulfonyl)-2-methylphenyl 2RS-(4-(pyrrolidin-1-yl)phenyl) butanoic acid ester.hydrochloride

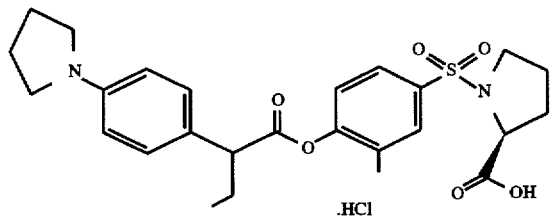

To a mixture solution of the compound prepared in example 1 (1.04 g) in dichloromethane(5 ml) and anisole (5 ml) were slowly added trifluoroacetic acid (5 ml) at 0° C. The reaction mixture was stirred for 6 h at room temperature. The reaction mixture was concentrated, and the residue was purified by column chromatography on silica gel (chloroform:methanol=20:1) to give N-{4-[2RS-(4-(1-pyrrolidinyl)phenyl)butylyloxy]-3-methylphenyl sulfonyl}-L-proline. The obtained above compound was converted to hydrochloride salt by the following method. To a solution of N-{4-[2RS-(4-(1-pyrrolidinyl)phenyl)butylyloxy]-3-methylphenyl sulfonyl}-L-proline in dioxane (5 ml) was added 4N hydrochloric acid in dioxane solution (1 ml) at 0° C. The reaction mixture was stirred for 5 min, and reaction mixture was concentrated to give the title compound (1 g) having the following physical data.

NMR (CDCl$_3$): δ 7.70 (1H, s), 7.67 (1H, d, J=8.0 Hz), 7.59 (2H, d, J=8.5 Hz), 7.49 (2H, d, J=8.5 Hz), 7.07 (1H, d, J=8.0 Hz), 4.26 (1H, dd, J=3.5, 7.0 Hz), 3.78 (1H, t, J=7.5 Hz), 3.75–3.60 (4H, m), 3.52–3.40 (1H, m), 3.33–3.14 (1H, m), 2.40–2.25 (4H, m), 2.40–1.65 (6H, m), 2.04 (3H, s), 1.00 (3H, t, J=7.5 Hz);

TLC: Rf 0.39 (acetic acid:methanol:chloroform=1:2:40).

Example 2(1)–2(286)

By the same procedure as example 1 and example 2 and by known method converted to corresponding salts or acid addition salts, the compounds having the following physical data were given by using corresponding phenol derivatives instead of the compound prepared in reference example 4 and by using corresponding carboxylic acid derivatives instead of the compound prepared in reference example 7.

Example 2(1)

4-(2S-carboxypyrrolidin-1-ylsulfonyl)phenyl 2RS-(4-(pyrrolidin-1-yl)phenyl)butanoic acid ester.hydrochloride

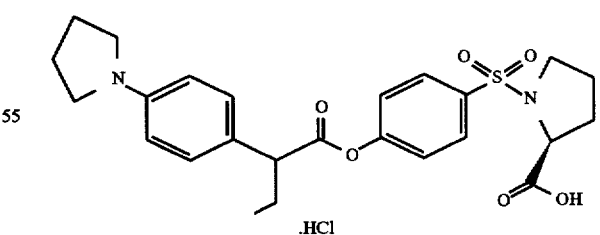

NMR (DMSO-d$_6$): δ7.86 (2H, d, J=8 Hz), 7.24 (4H, d, J=8 Hz), 6.78 (2H, d, J=8 Hz), 4.15–4.05 (1H, m), 3.73 (1H, t, J=7 Hz), 3.40–3.05 (6H, m), 2.20–1.45 (10H, m), 0.89 (3H, t, J=7 Hz);

TLC: Rf 0.26 (acetic acid:methanol:chloroform=1:2:60).

Example 2(2)

4-(2R-carboxypyrrolidin-1-ylsulfonyl)phenyl 2RS-(4-(pyrrolidin-1-yl)phenyl)butanoic acid ester.hydrochloride

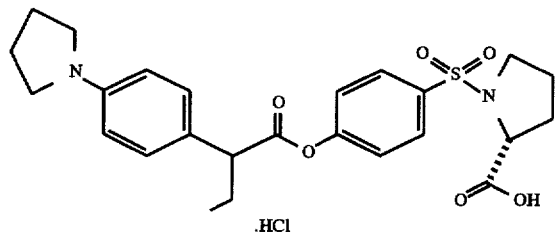

NMR (DMSO-d$_6$): δ7.86 (2H, d, J=8.8 Hz), 7.25 (4H, d, J=8.8 Hz), 6.78 (2H, d, J=8.8 Hz), 4.16–4.05 (1H, m), 3.74 (1H, t, J=7.2 Hz), 3.44–3.06 (2H, m), 3.36–3.24 (4H, m), 2.22–1.46 (10H, m), 0.90 (3H, t, J=7.2 Hz);

TLC: Rf 0.39 (acetic acid:methanol:chloroform=1:2:40).

Example 2(3)

4-(2S-carboxy-4R-hydroxypyrrolidin-1-ylsulfonyl) phenyl 2RS-(4-(pyrrolidin-1-yl)phenyl)butanoic acid ester.hydrochloride

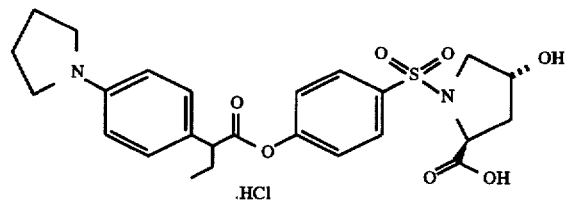

NMR (DMSO-d$_6$): δ 7.83 (2H, d, J=9 Hz), 7.31–7.18 (4H, m), 6.85–6.68 (2H, m), 4.25–4.14 (1H, m), 4.04 (1H, t, J=7 Hz), 3.73 (1H, t, J=7 Hz), 3.50–3.38 (5H, m), 3.18–3.05 (1H, m), 2.20–1.65 (8H, m), 0.90 (3H, t, J=7 Hz);

TLC: Rf 0.27 (chloroform:methanol:acetic acid=20:2:1).

Example 2(4)

4-(2S-carboxy-4R-benzyloxypyrrolidin-1-ylsulfonyl) phenyl 2RS-(4-(pyrrolidin-1-yl)phenyl)butanoic acid ester.hydrochloride

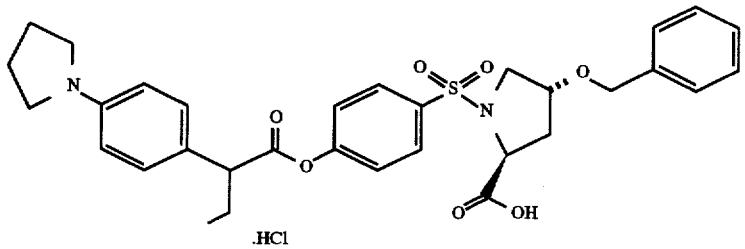

NMR (CDCl$_3$): δ 7.84 (2H, d, J=9 Hz), 7.62 (2H, d, J=9 Hz), 7.47 (2H, d, J=9 Hz), 7.34–7.19 (3H, m), 7.17–7.00 (4H, m), 4.30 (1H, t, J=8 Hz), 4.23 (2H, s), 4.15–4.03 (1H, m), 3.86–3.42 (7H, m), 2.47–2.05 (7H, m), 2.05–1.74 (1H, m), 0.97 (3H, t, J=7 Hz);

TLC: Rf 0.35 (chloroform:methanol:acetic acid=40:2:1).

Example 2(5)

4-(2S-carboxy-4S-aminopyrrolidin-1-ylsulfonyl) phenyl 2RS-(4-(pyrrolidin-1-yl)phenyl)butanoic acid ester.2hydrochloride

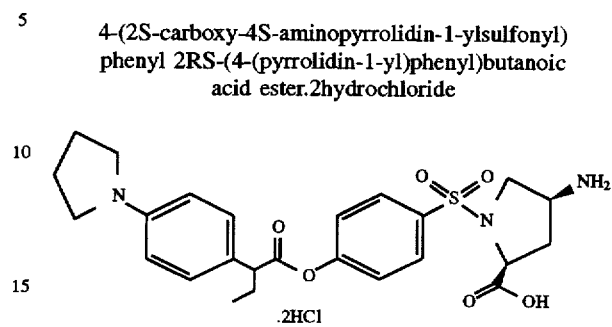

NMR (DMSO-d$_6$): δ 8.55–8.20 (2H, brs), 7.89 (2H, d, J=9 Hz), 7.29 (2H, d, J=9 Hz), 7.25 (2H, d, J=9 Hz), 6.73 (2H, d, J=9 Hz), 5.80–4.40 (1H, m), 4.18 (1H, t, J=7 Hz), 3.74 (1H, t, J=7 Hz), 3.64–3.10 (7H, m), 2.67–2.40 (1H, m), 2.20–1.65 (7H, m), 0.90 (3H, t, J=7 Hz);

TLC: Rf 0.49 (ethyl acetate:acetic acid:water=6:2:1).

Example 2(6)

4-(2S-carboxy-4R-aminopyrrolidin-1-ylsulfonyl) phenyl 2RS-(4-(pyrrolidin-1-yl)phenyl)butanoic acid ester.2hydrochloride

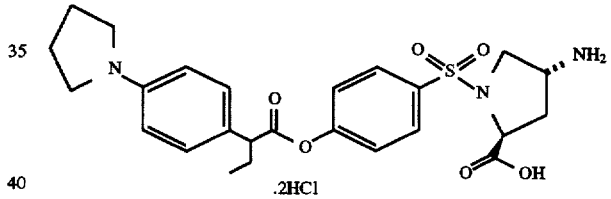

NMR (DMSO-d$_6$): δ 8.60–8.30 (2H, brs), 7.88 (2H, d, J=9 Hz), 7.28 (2H, d, J=9 Hz), 7.23 (2H, d, J=9 Hz), 6.72 (2H, d, J=9 Hz), 5.40–4.20 (1H, m), 4.40 (1H, dd, J=9 Hz, 4 Hz), 3.90–3.50 (2H, m), 3.50–3.10 (6H, m), 2.33–1.60 (8H, m), 0.90 (3H, t, J=7 Hz);

TLC: Rf 0.42 (ethyl acetate:acetic acid:water=6:2:1).

Example 2(7)

4-(2S-(N-carboxymethylcarbamoyl)pyrrolidin-1-ylsulfonyl)phenyl 2RS-(4-(pyrrolidin-1-yl)phenyl)butanoic acid ester

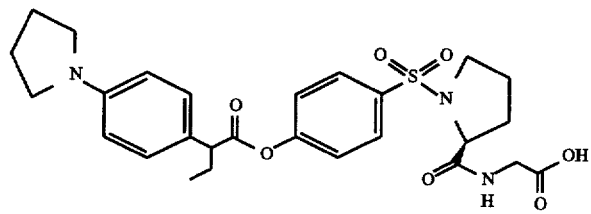

NMR (CDCl$_3$+CD$_3$OD): δ7.84 (2H, d, J=8.8 Hz), 7.28–7.18 (4H, m), 6.72 (2H, d, J=8.8 Hz), 4.09–3.85 (3H, m), 3.71–3.53 (2H, m), 3.41–3.31 (4H, m), 3.20–3.08 (1H, m), 2.26–1.59 (10H, m), 0.99 (3H, t, J=7.4 Hz);

TLC: Rf 0.24 (chloroform:methanol:acetic acid=40:2:1).

Example 2(8)

4-(2S-(2-aminoethoxycarbonyl)pyrrolidin-1-ylsulfonyl)-2-methylphenyl 2RS-(4-(pyrrolidin-1-yl)phenyl)butanoic acid ester.2hydrochloride

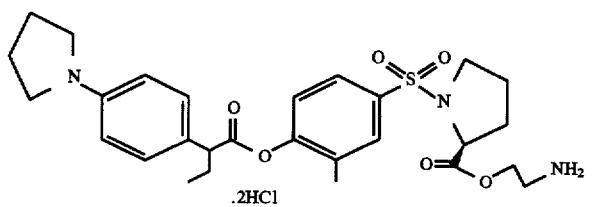

NMR (DMSO-d$_6$): δ 8.21 (2H, brs), 7.75 (1H, s), 7.69 (1H, d, J=8.2 Hz), 7.22 (3H, m), 6.70 (2H, d, J=8.8 Hz), 4.26 (3H, m), 3.50–3.36 (2H, m), 3.31 (4H, m), 3.20 (1H, m), 3.08 (2H, m), 2.12 (1H, m), 2.00 (3H, s), 1.96 (4H, m), 1.87 (4H, m), 1.66 (1H, m), 0.92 (3H, t, J=7.2 Hz);

TLC: Rf 0.31 (chloroform:methanol:acetic acid=12:1:1).

Example 2(9)

4-(2S-(2-(2-hydroxyethoxy)ethoxycarbonyl)pyrrolidin-1-ylsulfonyl)-2-methylphenyl 2RS-(4-(pyrrolidin-1-yl)phenyl)butanoic acid ester.hydrochloride

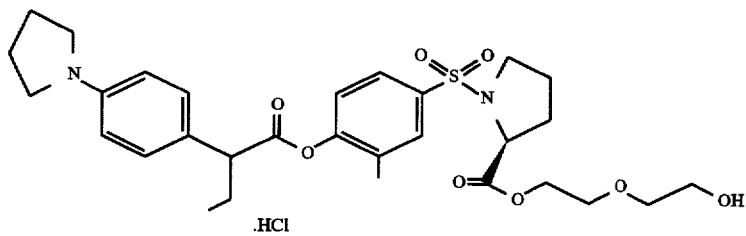

NMR (CDCl$_3$): δ 7.69 (1H, s), 7.67 (2H, d, J=8.4 Hz), 7.23 (2H, d, J=8.4 Hz), 7.07 (1H, d, J=8.2 Hz), 6.56 (2H, d, J=8.4 Hz), 4.29 (3H, m), 3.75–3.58 (7H, m), 3.50 (1H, m), 3.29 (4H, m), 3.22 (1H, m), 2.16 (1H, m), 2.04 (3H, s), 2.01 (4H, m), 1.98–1.64 (5H, m), 0.99 (3H, t, J=7.2 Hz);

TLC: Rf 0.62 (chloroform:methanol=9:1).

Example 2(10)

4-(2S-hydroxymethylpyrrolidin-1-ylsulfonyl)-2-methylphenyl 2RS-(4-(pyrrolidin-1-yl)phenyl)butanoic acid ester

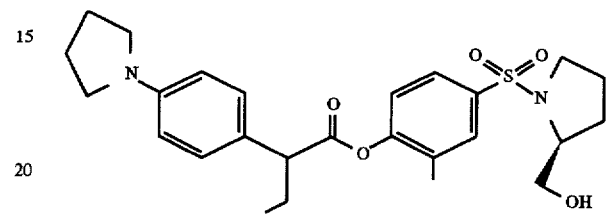

NMR (CDCl$_3$): δ 7.70–7.58 (2H, m), 7.22 (2H, d, J=8.5 Hz), 7.09 (1H, d, J=8.0 Hz), 6.55 (2H, d, J=8.5 Hz), 3.80–3.52 (3H, m), 3.62 (1H, t, J=7.5 Hz), 3.52–3.35 (1H, m), 3.35–3.12 (5H, m), 2.90–2.55 (1H, brs), 2.35–1.70 (2H, m), 2.05 (3H, s), 2.05–1.95 (4H, m), 1.80–1.30 (4H, m), 0.99 (3H, t, J=7.5 Hz);

TLC: Rf 0.36 (hexane:ethyl acetate=1:1).

Example 2(11)

4-(2S-(2-(piperazin-4-yl)ethyl)oxycarbonylpyrrolidin-1-ylsulfonyl)-2-methylphenyl 2RS-(4-(pyrrolidin-1-yl)phenyl)butanoic acid ester.2hydrochloride

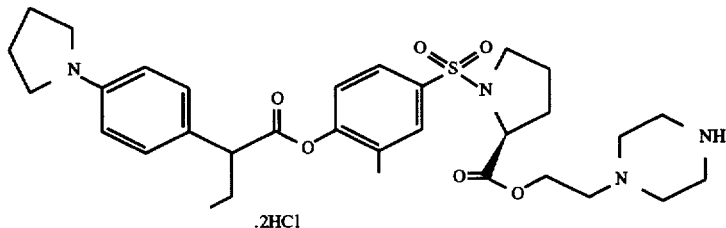

NMR (CD₃OD): δ 7.82–7.63 (6H, m), 7.00 (1H, d, J=8.2 Hz), 4.62 (2H, m), 4.41 (1H, m), 4.00 (1H, t, J=7.6 Hz), 3.81–3.66 (8H, m), 3.57 (1H, m), 3.21 (1H, m), 2.33 (7H, m), 2.07 (3H, s), 2.03–1.89 (5H, m), 1.69 (1H, m), 1.00 (3H, t, J=7.4 Hz);

TLC: Rf 0.48 (chloroform:methanol:water=40:10:1).

Example 2(12)

4-(2S-carboxypyrrolidin-1-ylsulfonyl)phenyl 2-(2-methoxyphenyl)-2-ethylbutanoic acid ester

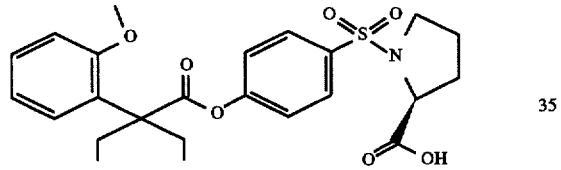

NMR (DMSO-d₆): δ 7.89 (2H, d, J=9 Hz), 7.34–7.16 (4H, m), 7.06–6.95 (2H, m), 4.03 (1H, dd, J=2 and 8 Hz), 3.82 (3H, s), 3.36–3.23 and 3.20–3.09 (each 1H, m), 2.23–1.91 (4H, m), 1.87–1.47 (4H, m), 0.72 (6H, t, J=7 Hz);

TLC: Rf 0.19 (chloroform:methanol:water=9:1:0.1).

Example 2(13)

4-(2S-carboxypyrrolidin-1-ylsulfonyl)-2-methylphenyl 2RS-(2-methoxyphenyl)butanoic acid ester

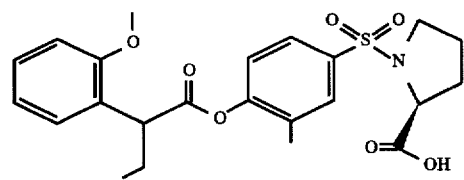

NMR (CDCl₃): δ 7.69 (1H, s), 7.68 (1H, d, J=9.0 Hz), 7.35–7.22 (2H, m), 7.10 (1H, d, J=9.0 Hz), 6.98 (1H, d, J=7.6 Hz), 6.92 (1H, d, J=7.8 Hz), 4.28–4.16 (1H, m), 4.15 (1H, t, J=7.6 Hz), 3.85 (3H, s), 3.60–3.43 (1H, m), 3.26–3.07 (1H, m), 2.35–1.56 (4H, m), 2.04 (3H, s), 0.98 (3H, t, J=7.6 Hz);

TLC: Rf 0.54 (chloroform:methanol:water=8:2:0.2).

Example 2(14)

4-(2S-carboxypyrrolidin-1-ylsulfonyl)-2-methylphenyl 2RS-(4-methoxyphenyl)butanoic acid ester

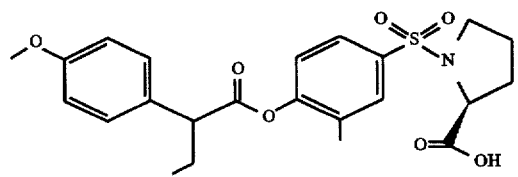

NMR (DMSO-d₆): δ 7.74 (1H, s), 7.69 (1H, d, J=8.2 Hz), 7.33 (2H, d, J=8.8 Hz), 7.17 (1H, d, J=8.2 Hz), 6.95 (2H, d, J=8.8 Hz), 4.11 (1H, m), 4.14 (1H, m), 3.76 (3H, s), 3.30 (1H, m), 3.17 (1H, m), 2.10 (1H, m), 1.96 (3H, s), 1.82 (4H, m), 1.56 (1H, m), 0.91 (3H, t, J=7.2 Hz);

TLC: Rf 0.58 (chloroform:methanol:acetic acid=12:1:1).

Example 2(15)

4-(2S-(2-(piperazin-1-yl)ethyl)
oxycarbonylpyrrolidin-1-ylsulfonyl)-2-methylphenyl
2RS-(4-methoxyphenyl)butanoic acid
ester.2hydrochloride

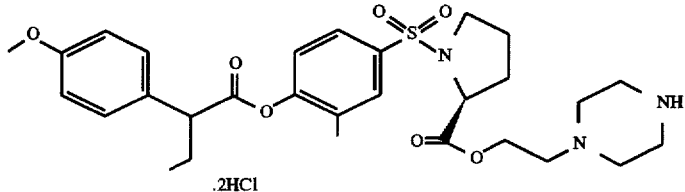

NMR (CD$_3$OD): δ 7.77 (1H, s), 7.75 (1H, d, J=7.4 Hz), 7.32 (2H, d, J=8.6 Hz), 7.16 (1H, d, J=7.4 Hz), 6.93 (2H, d, J=8.6 Hz), 4.62 (2H, brs), 4.5–4.3 (1H, br), 3.8–3.4 (12H, br), 3.79 (3H, s), 3.3–3.1 (1H, br), 2.3–1.8 (6H, br), 2.00 (3H, s), 0.98 (3H, t, J=7.3 Hz);

TLC: Rf 0.16 (chloroform:methanol:acetic acid=40:2:1).

Example 2(16)

4-(2S-(2-(2-hydroxyethoxy)ethoxycarbonyl)
pyrrolidin-1-ylsulfonyl)-2-methylphenyl 2RS-(4-
methoxyphenyl)butanoic acid ester

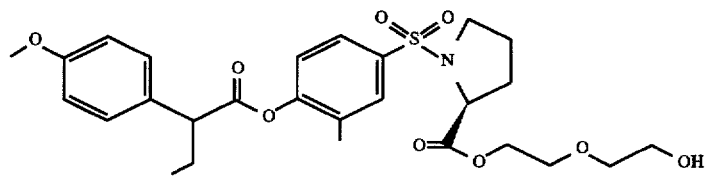

NMR (CDCl$_3$): δ 7.70 (1H, s), 7.68 (1H, d, J=8.8 Hz), 7.31 (2H, d, J=8.4 Hz), 7.01 (1H, d, J=8.8 Hz), 6.90 (2H, d, J=8.4 Hz), 4.3–4.2 (3H, m), 3.82 (3H, s), 3.8–3.7 (6H, m), 3.7–3.5 (2H, m), 3.3–3.2 (1H, m), 2.4–2.1 (2H, m), 2.00 (3H, s), 2.1–1.7 (4H, m), 0.99 (3H, t, J=7.3 Hz);

TLC: Rf 0.24 (hexane:ethyl acetate=1:2).

Example 2(17)

4-(2S-(2-aminoethyl)oxycarbonylpyrrolidin-1-
ylsulfonyl)-2-methylphenyl 2RS-(4-methoxyphenyl)
butanoic acid ester.hydrochloride

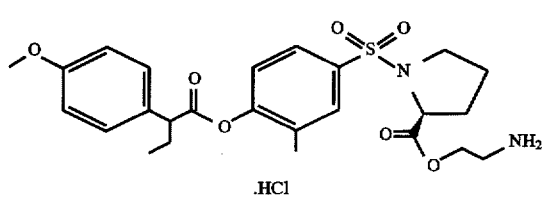

NMR (CDCl$_3$): δ 8.40 (2H, brs), 7.73 (1H, s), 7.70 (1H, d, J=9.2 Hz), 7.30 (2H, d, J=8.6 Hz), 7.08 (1H, d, J=9.2 Hz), 6.89 (2H, d, J=8.6 Hz), 4.6–4.3 (3H, br), 3.80 (3H, s), 3.67 (1H, t, J=7.6 Hz), 3.6–3.3 (3H, br), 3.2–3.1 (1H, br), 2.4–1.8 (6H, br), 2.00 (3H, s), 0.98 (3H, t, J=7.3 Hz);

TLC: Rf 0.23 (chloroform:methanol=9:1).

Example 2(18)

4-(2S-carboxypyrrolidin-1-ylsulfonyl)-2-
methylphenyl 2RS-(4-methylphenyl)butanoic acid
ester

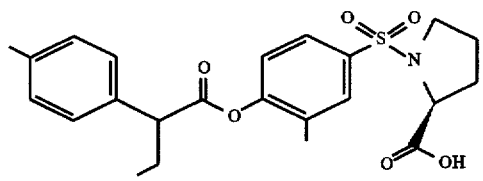

NMR (CDCl$_3$): δ 7.69 (1H, s), 7.66 (1H, d, J=9.0 Hz), 7.25 (2H, d, J=8.0 Hz), 7.15 (2H, d, J=8.0 Hz), 7.05 (1H, d, J=9.0 Hz), 4.20 (1H, m), 3.67 (1H, t, J=8.0 Hz), 3.60–3.40 (1H, m), 3.20–3.00 (1H, m), 2.34 (3H, s), 2.30–1.50 (6H, m), 1.96 (3H, s), 0.97 (3H, t, J=7.5 Hz);

TLC: Rf 0.39 (acetic acid:methanol:chloroform=1:2:40).

Example 2(19)

4-(2S-hydroxymethylpyrrolidin-1-ylsulfonyl)-2-methylphenyl 2RS-(4-methylphenyl)butanoic acid ester

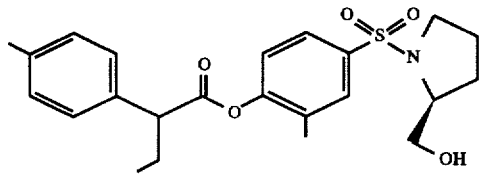

NMR (CDCl₃): δ 7.67 (1H, s), 7.65 (1H, d, J=8.0 Hz), 7.28 (2H, d, J=8.0 Hz), 7.18 (2H, d, J=8.0 Hz), 7.09 (1H, d, J=8.0 Hz), 3.70 (1H, t, J=7.5 Hz), 3.74–3.54 (3H, m), 3.54–3.38 (1H, m), 3.30–3.14 (1H, m), 2.71 (1H, t-like), 2.36 (3H, s), 2.40–1.80 (2H, m), 2.02 (3H, s), 1.90–1.60 (3H, m), 1.60–1.40 (1H, m), 1.00 (3H, t, J=7.5 Hz);

TLC: Rf 0.23 (ethyl acetate:hexane=1:2).

Example 2(20)

4-(2S-(2-aminoethyl)oxycarbonylpyrrolidin-1-ylsulfonyl)-2-methylphenyl 2RS-(4-methylphenyl)butanoic acid ester.hydrochloride

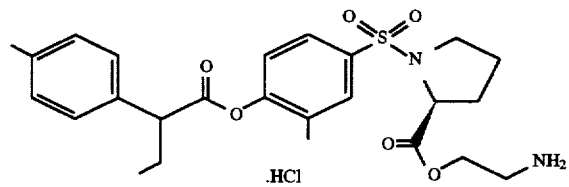

NMR (DMSO-d₆): δ 8.22 (3H, brs), 7.75 (1H, d, J=1.8 Hz), 7.70 (1H, dd, J=8.4 and 1.8 Hz), 7.30 (2H, d, J=8.0 Hz), 7.20 (3H, d, J=8.0 Hz), 4.33–4.15 (1H, m), 4.26 (2H, t, J=5.0 Hz), 3.85 (1H, t, J=7.6 Hz), 3.49–3.01 (2H, m), 3.09 (2H, t, J=5.6 Hz), 2.32 (3H, s), 2.25–1.50 (6H, m), 1.98 (3H, s), 0.92 (3H, t, J=7.2 Hz);

TLC: Rf 0.56 (chloroform:methanol:acetic acid=15:2:1).

Example 2(21)

4-(2S-(2-(piperazin-4-yl)ethyl)oxycarbonylpyrrolidin-1-ylsulfonyl)-2-methylphenyl 2RS-(4-methylphenyl)butanoic acid ester.2hydrochloride

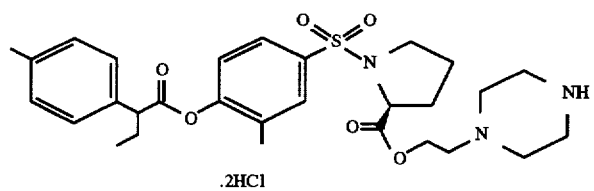

NMR (CD₃OD): δ 7.78 (1H, s), 7.75 (1H, dd, J=8.6 and 1.2 Hz), 7.29 (2H, d, J=8.0 Hz), 7.24–7.12 (3H, m), 4.66–4.54 (2H, m), 4.45–4.32 (1H, m), 3.85–3.60 (11H, m), 3.60–3.38 (1H, m), 3.26–3.15 (1H, m), 2.34 (3H, s), 2.30–1.55 (6H, m), 1.99 (3H, s), 0.98 (3H, t, J=7.2 Hz);

TLC: Rf 0.45 (chloroform:methanol:water=8:2:0.2).

Example 2(22)

4-(2S-(2-(2-hydroxyethoxy)ethyl)oxycarbonylpyrrolidin-1-ylsulfonyl)-2-methylphenyl 2RS-(4-methylphenyl)butanoic acid ester

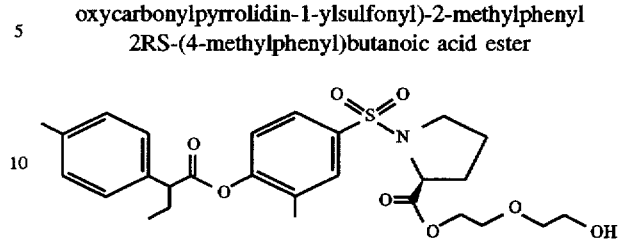

NMR (CDCl₃): δ 7.70 (1H, s), 7.68 (1H, dd, J=7.4 and 2.4 Hz), 7.28 (2H, d, J=8.2 Hz), 7.18 (2H, d, J=8.2 Hz), 7.07 (1H, d, J=8.8 Hz), 4.40–4.20 (3H, m), 3.73–3.37 (8H, m), 3.37–3.16 (1H, m), 2.24–1.63 (6H, m), 2.36 (3H, s), 2.02 (3H, s), 1.70 (1H, s), 1.00 (3H, t, J=7.2 Hz);

TLC: Rf 0.28 (ethyl acetate:hexane=2:1).

Example 2(23)

4-(2S-carboxypyrrolidin-1-ylsulfonyl)phenyl 2RS-(4-nitrophenyl)butanoic acid ester

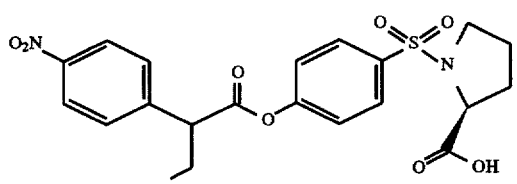

NMR (DMSO-d₆): δ8.25 (2H, d, J=8 Hz), 7.90 (2H, d, J=8 Hz), 7.58 (2H, d, J=8 Hz), 7.19 (2H, d, J=8 Hz), 5.70–4.80 (1H, brs), 4.30 (1H, dd, J=7 Hz, 4 Hz), 3.85 (1H, t, J=7 Hz), 3.60–3.39 (1H, m), 3.39–3.15 (1H, m), 2.45–1.65 (6H, m), 1.01 (3H, t, J=7 Hz);

TLC: Rf 0.34 (acetic acid:methanol:chloroform=1:2:40).

Example 2(24)

4-(2S-carboxypyrrolidin-1-ylsulfonyl)phenyl 2R-(4-nitrophenyl)butanoic acid ester

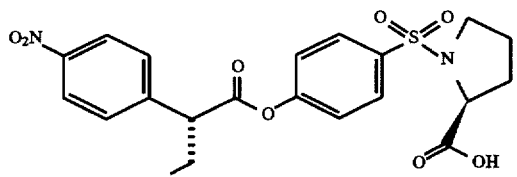

NMR (CDCl₃): δ 8.26 (d, J=8.8 Hz, 2H), 7.90 (d, J=8.8 Hz, 2H), 7.58 (d, J=8.8 Hz, 2H), 7.20 (d, J=8.8 Hz, 2H), 4.30 (dd, J=4.0, 7.8 Hz, 1H), 3.86 (t, J=7.6 Hz, 1H), 3.5–3.4 (m, 1H), 3.4–3.2 (m, 1H), 2.4–1.7 (m, 6H) 1.02 (t, J=7.3 Hz, 3H);

TLC: Rf 0.63 (chloroform:methanol=6:1).

Example 2(25)

4-(2S-carboxypyrrolidin-1-ylsulfonyl)phenyl 2S-(4-nitrophenyl)butanoic acid ester

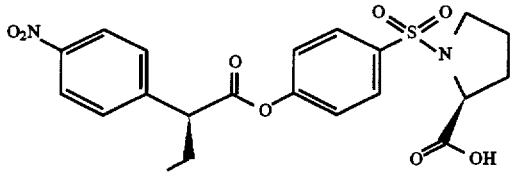

NMR (CDCl₃): δ8.26 (d, J=8.8 Hz, 2H), 7.90 (d, J=8.8 Hz, 2H), 7.58 (d, J=8.8 Hz, 2H), 7.19 (d, J=8.8 Hz, 2H), 4.31 (dd, J=4.0, 7.2 Hz, 1H), 3.86 (t, J=7.7 Hz, 1H), 3.6–3.4 (m, 1H), 3.4–3.2 (m, 1H), 2.4–1.7 (m, 6H), 1.03 (t, J=7.6 Hz, 3H);

TLC: Rf 0.63 (chloroform:methanol=6:1).

Example 2(26)

4-(2S-carboxypyrrolidin-1-ylsulfonyl)phenyl 1-(4-nitrophenyl)cyclobutanecarboxylic acid ester

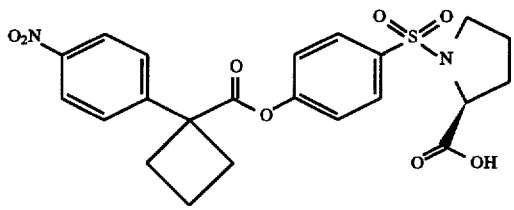

NMR (DMSO-d₆): δ 8.27 (2H, d, J=8 Hz), 7.88 (2H, d, J=8 Hz), 7.56 (2H, d, J=8 Hz), 7.16 (2H, d, J=8 Hz), 6.00–5.10 (1H, brs), 4.29 (1H, dd, J=7 Hz, 4 Hz), 3.55–3.40 (1H, m), 3.34–3.19 (1H, m), 3.15–2.98 (2H, m), 2.80–2.60 (2H, m), 2.38–1.66 (6H, m);

TLC: Rf 0.40 (acetic acid:methanol:chloroform=1:2:40).

Example 2(27)

4-(2S-carboxypyrrolidin-1-ylsulfonyl)phenyl 2RS-(4-nitrophenyl)butanoic acid ester

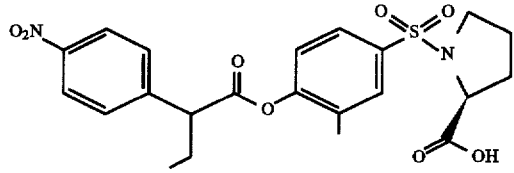

NMR (DMSO-d₆): δ 8.27 (2H, d, J=8.8 Hz),7.74 (2H, d, J=8.8 Hz), 7.79–7.66 (2H, m), 7.23 (1H, d, J=8.4 Hz), 4.20 (1H, t, J=7.6 Hz), 4.12–4.06 (1H, m), 3.40–3.07 (2H, m), 2.35–1.40 (6H, m), 2.00 (3H, s), 0.92 (3H, t, J=7.2 Hz);

TLC: Rf 0.19 (acetic acid:methanol:chloroform=1:2:40).

Example 2(28)

4-(2R-carboxypyrrolidin-1-ylsulfonyl)phenyl 2RS-(4-nitrophenyl)butanoic acid ester

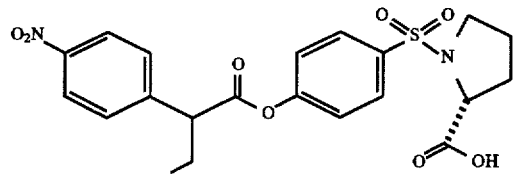

NMR (DMSO-d₆): δ 13.5–11.6 (1H, brs), 8.27 (2H, d, J=8.8 Hz), 7.88 (2H, d, J=8.8 Hz), 7.73 (2H, d, J=8.8 Hz), 7.32 (2H, d, J=8.8 Hz), 4.16 (1H, t, J=7.2 Hz), 4.16–4.06 (1H, m), 3.5–3.0 (2H, m), 2.35–1.45 (6H, m), 0.92 (3H, t, J=7.2 Hz);

TLC: Rf 0.43 (acetic acid:methanol:chloroform=1:2:40).

Example 2(29)

4-(2R-carboxypyrrolidin-1-ylsulfonyl)phenyl 1-(4-nitrophenyl)cyclobutanecarboxylic acid ester

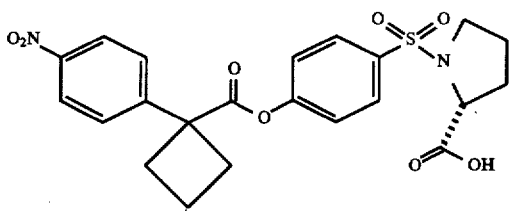

NMR (DMSO-d₆): δ 12.9–12.6 (1H, brs), 8.28 (2H, d, J=8.8 Hz), 7.87 (2H, d, J=8.8 Hz), 7.71 (2H, d, J=8.8 Hz), 7.31 (2H, d, J=8.8 Hz), 4.16–4.04 (1H, m), 3.43–3.10 (2H, m), 3.10–2.90 (2H, m), 2.75–2.55 (2H, q-like), 2.28–1.46 (6H, m);

TLC: Rf 0.46 (acetic acid:methanol:chloroform=1:2:40).

Example 2(30)

4-(2S-carboxypyrrolidin-1-ylsulfonyl)phenyl 2RS-phenylbutanoic acid ester

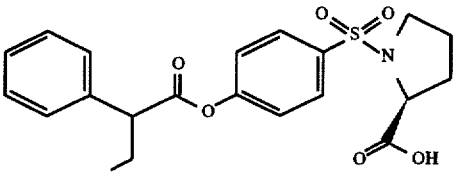

NMR (CDCl₃): δ 7.93–7.83 (2H, m), 7.50–7.14 (5H, m), 7.23–7.14 (2H, m), 7.14–6.70 (1H, brs), 4.26 (1H, dd, J=10 Hz, 5 Hz), 3.71 (1H, t, J=7 Hz), 3.56–3.43 (1H, m), 3.33–3.17 (1H, m), 2.35–1.65 (6H, m), 0.98 (3H, t, J=7 Hz);

TLC: Rf 0.67 (acetic acid:methanol:chloroform=1:3:30).

Example 2(31)

4-(2RS-carboxyindolin-1-ylsulfonyl)phenyl 2RS-(4-(pyrrolidin-1-yl)phenyl)butanoic acid ester.hydrochloride

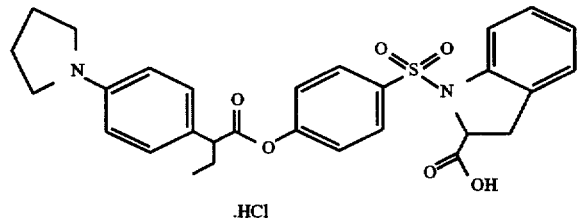

NMR (CDCl$_3$): δ 7.73 (2H, d, J=8.6 Hz), 7.58 (1H, d, J=8.2 Hz), 7.17 (2H, d, J=8.6 Hz), 7.12–6.94 (5H, m), 6.53 (2H, d, J=8.8 Hz), 4.73 (1H, dd, J=8.9 Hz and 6.8 Hz), 3.54 (1H, t, J=7.8 Hz), 3.35–3.21 (4H, m), 3.17 (2H, d, J=6.8 Hz), 2.25–1.70 (2H, m), 2.05–1.94 (4H, m), 0.95 (3H, t, J=7.2 Hz);

TLC: Rf 0.46 (acetic acid:methanol:chloroform=1:2:40).

Example 2(32)

4-(2-carboxyindol-1-ylsulfonyl)phenyl 2RS-(4-(pyrrolidin-1-yl)phenyl)butanoic acid ester.hydrochloride

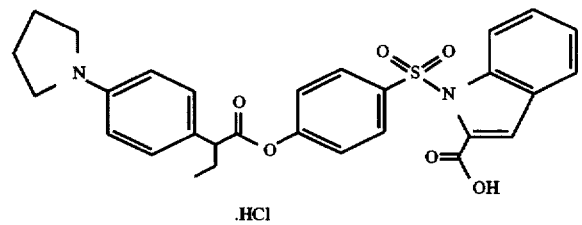

NMR (DMSO-d$_6$): δ 8.08 (2H, d, J=8.8 Hz), 8.01 (1H, d, J=8.4 Hz), 7.68 (1H, d, J=8.0 Hz), 7.46 (1H, m), 7.40–7.16 (2H, m), 7.24 (2H, d, J=8.8 Hz), 7.20 (2H, d, J=8.6 Hz), 6.85–6.60 (2H, m), 3.69 (1H, t, J=7.4 Hz), 3.40–3.15 (4H, m), 2.20–1.84 (5H, m), 1.84–1.60 (1H, m), 0.86 (3H, t, J=7.4 Hz);

TLC: Rf 0.20 (chloroform:methanol:water=9:1:0.1).

Example 2(33)

4-(2S-carboxyindolin-1-ylsulfonyl)phenyl 2RS-(4-(pyrrolidin-1-yl)phenyl)butanoic acid ester

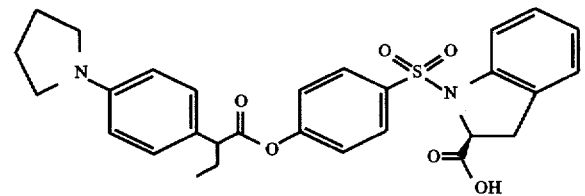

NMR (CDCl$_3$): δ 7.72 (2H, d, J=8.6 Hz), 7.57 (1H, d, J=7.8 Hz), 7.17 (2H, d, J=8.6 Hz), 7.28–6.88 (5H, m), 6.53 (2H, d, J=8.6 Hz), 4.72 (1H, dd, J=5.8 Hz and 9.1 Hz), 3.54 (1H, t, J=7.8 Hz), 3.35–3.22 (4H, m), 3.22–3.08 (2H, m), 2.25–1.70 (2H, m), 2.05–1.95 (4H, m), 0.95 (3H, t, J=7.2 Hz);

TLC: Rf 0.46 (acetic acid:methanol:chloroform=1:2:40).

Example 2(34)

4-(2S-carboxyperhydroindol-1-ylsulfonyl)phenyl 2RS-(4-(pyrrolidin-1-yl)phenyl)butanoic acid ester.hydrochloride

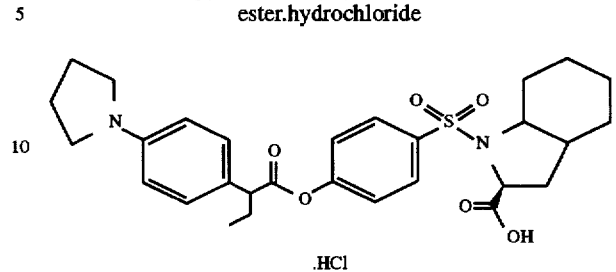

NMR (CDCl$_3$): δ 7.89 (2H, d, J=8.8 Hz), 7.71 (2H, d, J=8.6 Hz), 7.51 (2H, d, J=8.6 Hz), 7.17 (2H, d, J=8.8 Hz), 4.20 (1H, t, J=8.6 Hz), 4.0–3.5 (6H, m), 2.5–2.2 (4H, m), 2.4–1.0 (13H, m), 0.99 (3H, t, J=7.4 Hz);

TLC: Rf 0.60 (chloroform:methanol:acetic acid=40:2:1).

Example 2(35)

4-(2RS-carboxyindolin-1-ylsulfonyl)-2-methylphenyl 2RS-(4-(pyrrolidin-1-yl)phenyl)butanoic acid ester.hydrochloride

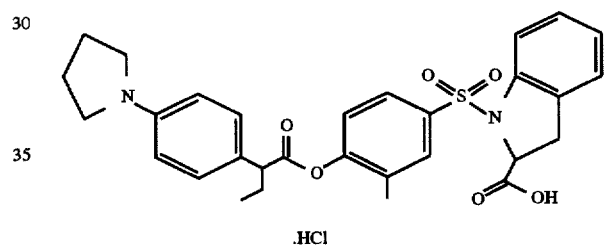

NMR (DMSO-d$_6$): δ 7.79 (1H, d-like), 7.67 (1H, dd, J=2.2 and 8.4 Hz), 7.35–6.95 (7H, m), 6.71–6.67 (2H, m), 4.97 (1H, dd, J=4.4 and 10.7 Hz), 3.71 (1H, t, J=7.6 Hz), 3.35–2.96 (6H, m), 2.14–1.68 (2H, m), 2.00–1.94 (4H, m), 1.91 (3H, s), 0.87 (3H, t, J=7.2 Hz);

TLC: Rf 0.45 (chloroform methanol:water=8:2:0.2).

Example 2(36)

4-(2RS-(N-carboxymethylcarbamoyl)indolin-1-ylsulfonyl)phenyl 2RS-(4-(pyrrolidin-1-yl)phenyl) butanoic acid ester

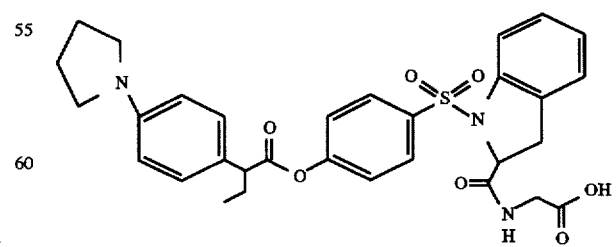

NMR (CDCl$_3$): δ 7.70 (1H, d, J=7.8 Hz), 7.58 (2H, d, J=8.8 Hz), 7.28–7.02 (8H, m), 6.66 (2H, d, J=8.8 Hz), 4.64

(1H, dd, J=10.4, 2.8 Hz), 4.02 (2H, d, J=3.0 Hz), 3.56 (1H, t, J=7.6 Hz), 3.37–3.05 (5H, m), 2.81 (1H, dd, J=16.0, 10.4 Hz), 2.35–1.74 (6H, m), 0.95 (3H, t, J=7.6 Hz);

TLC: Rf 0.33 (chloroform:methanol:acetic acid=40:2:1).

Example 2(37)

4-(2RS-carboxyindolin-1-ylsulfonyl)phenyl 2S-(4-(pyrrolidin-1-yl)phenyl)butanoic acid ester

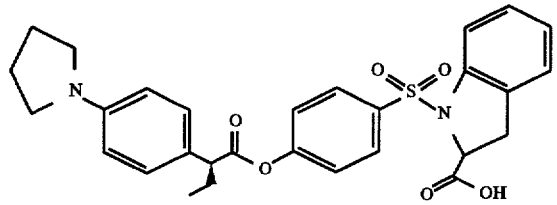

NMR (CDCl₃): δ 7.72 (2H, d, J=8 Hz), 7.59 (1H, d, J=8 Hz), 7.27–7.03 (7H, m), 6.54 (2H, d, J=8 Hz), 6.08 (1H, br), 4.77–4.69 (1H, m), 3.55 (1H, t, J=8 Hz), 3.31–3.24 (4H, m), 3.19–3.15 (2H, m), 2.20–1.76 (2H, m), 2.03–1.96 (4H, m), 0.95 (3H, t, J=8 Hz);

TLC: Rf 0.45 (chloroform:methanol:water=8:2:0.2).

Example 2(38)

4-(2RS-carboxy-3,3-dimethylindolin-1-ylsulfonyl)phenyl 2RS-(4-(pyrrolidin-1-yl)phenyl)butanoic acid ester

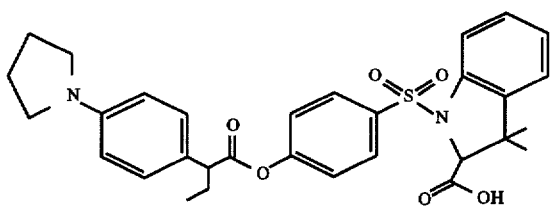

NMR (CDCl₃): δ 7.83 (2H, d, J=8.5 Hz), 7.55 (1H, d, J=8.0 Hz), 7.25–6.93 (3H, m), 7.17 (2H, d, J=8.5 Hz), 7.09 (2H, d, J=8.5 Hz), 6.53 (2H, d, J=8.5 Hz), 4.36 (1H, s), 3.54 (1H, t, J=8.0 Hz), 3.35–3.10 (4H, m), 2.05–1.90 (4H, m), 2.25–1.70 (2H, m), 1.31 (3H, s), 1.04 (3H, s), 0.94 (3H, t, J=7.5 Hz);

TLC: Rf 0.48 (chloroform:methanol:acetic acid=40:2:1).

Example 2(39)

4-(2RS-carboxyindolin-1-ylsulfonyl)-2-methoxyphenyl 2RS-(4-(pyrrolidin-1-yl)phenyl)butanoic acid ester

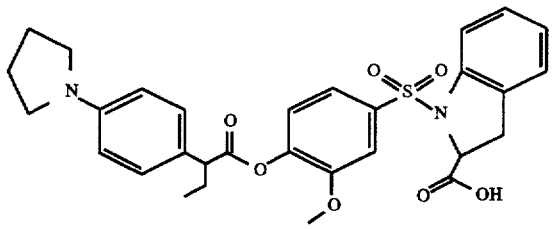

NMR (CDCl₃): δ 7.7–7.6 (m, 1H), 7.5–6.9 (m, 8H), 6.5–6.4 (m, 2H), 4.8–4.6 (m, 1H), 3.8–3.5 (m, 4H), 3.4–3.0 (m, 6H), 2.2–1.7 (m, 6H), 1.1–0.9 (m, 3H);

TLC: Rf 0.65 (chloroform:methanol=3:1).

Example 2(40)

4-(2RS-(N-2-carboxyethylcarbamoyl)indolin-1-ylsulfonyl)-2-methylphenyl 2RS-(4-(pyrrolidin-1-yl)phenyl)butanoic acid ester

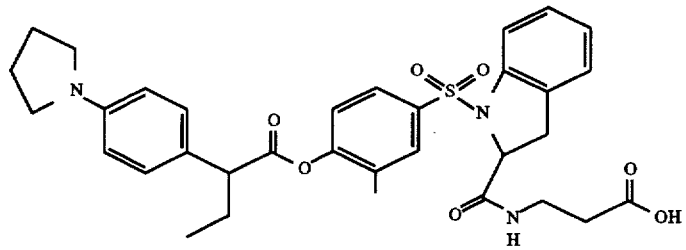

NMR (CDCl₃): δ 7.8–6.8 (m, 11H), 4.7–4.5 (m, 1H), 3.8–3.5 (m, 7H), 3.3–3.1 (m, 1H), 3.0–2.8 (m, 1H), 2.7–2.5 (m, 2H), 2.3–2.1 (m, 4H), 2.1–1.8 (m, 5H), 0.97 (t, J=7.2 Hz, 3H);

TLC: Rf 0.76 (methanol:chloroform=1:3).

Example 2(41)

4-(2RS-(N-2-hydroxyethylcarbamoyl)indolin-1-ylsulfonyl)-2-methylphenyl 2RS-(4-(pyrrolidin-1-yl)phenyl)butanoic acid ester

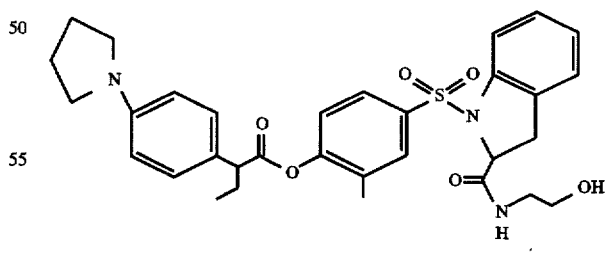

NMR (CDCl₃): δ 7.72 (1H, d, J=8.0 Hz), 7.45–6.92 (9H, m), 6.51 (2H, d, J=8.6 Hz), 4.57 (1H, dd, J=2.8, 10.6 Hz), 3.77–3.52 (5H, m), 3.39–3.17 (5H, m), 2.88 (1H, dd, J=10.6, 16.8 Hz), 2.23–1.78 (6H, m), 1.92 (3H, s), 0.96 (3H, t, J=7.4 Hz);

TLC: Rf 0.43 (chloroform:methanol:acetic acid=25:5:1).

Example 2(42)

4-(2-carboxy-5,6-dimethoxyindol-1-ylsulfonyl)-2-methylphenyl 2RS-(4-(pyrrolidin-1-yl)phenyl) butanoic acid ester

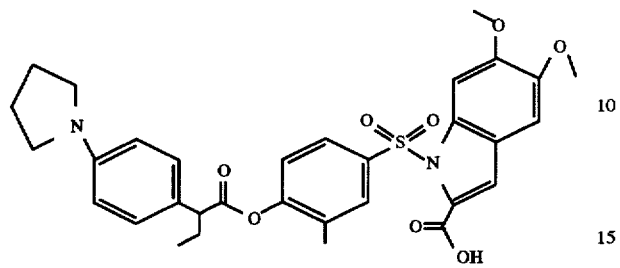

NMR (CDCl₃): δ 7.78–7.62 (3H, m), 7.35 (1H, s), 7.18 (2H, d, J=9 Hz), 7.00 (1H, d, J=8 Hz), 6.95 (1H, s), 6.52 (2H, d, J=9 Hz), 4.00 (3H, s), 3.91 (3H, s), 3.70–3.10 (1H, brs), 3.57 (1H, t, J=7 Hz), 3.35–3.18 (4H, m), 2.25–1.75 (9H, m), 0.96 (3H, t, J=7 Hz).

TLC: Rf 0.19 (ethyl acetate:hexane:acetic acid=5:10:0.5).

Example 2(43)

4-(2RS-(2-aminoethyl)oxycarbonylindolin-1-ylsulfonyl)-2-methylphenyl 2RS-(4-(pyrrolidin-1-yl)phenyl)butanoic acid ester.2hydrochloride

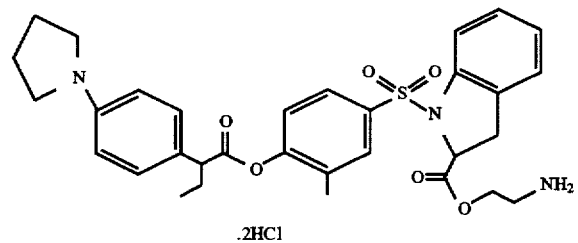

NMR (DMSO-d₆): δ 8.30 (2H, brs), 7.76 (1H, s), 7.66 (1H, d, J=8.0 Hz), 7.37 (1H, d, J=8.0 Hz), 7.23–7.00 (6H, m), 6.70 (2H, d, J=8.0 Hz), 5.08 (1H, dd, J=6.2, 9.4 Hz), 4.37–4.32 (2H, m), 3.69 (1H, t, J=7.2 Hz), 3.35–3.07 (8H, m), 2.14–1.69 (9H, m), 0.89 (3H, t, J=7.2 Hz);

TLC: Rf 0.46 (chloroform:methanol:acetic acid=25:5:1).

Example 2(44)

4-(2-carboxyindol)-2-methylphenyl 2RS-(4-(pyrrolidin-1-yl)phenyl)butanoic acid ester

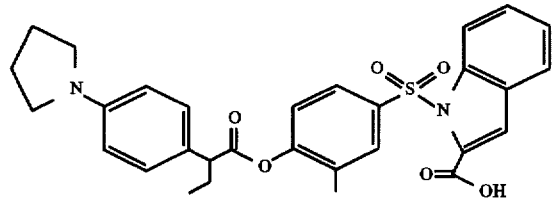

NMR (CDCl₃): δ 8.13 (1H, d, J=9 Hz), 7.90–7.78 (2H, m), 7.60 (1H, d, J=9 Hz), 7.46 (1H, td, J=8.1 Hz), 7.39 (1H, s), 7.35–7.25 (1H, m), 7.21 (2H, d, J=9 Hz), 6.75–6.50 (2H, m), 3.59 (1H, t, J=7 Hz), 3.38–3.23 (4H, m), 3.23–2.90 (1H, brs), 2.25–1.75 (6H, m), 0.96 (3H, t, J=7 Hz);

TLC: Rf 0.20 (ethyl acetate:hexane:acetic acid=5:10:0.5).

Example 2(45)

4-(2RS-carboxy-5,6-dimethoxyindolin-1-ylsulfonyl)-2-methylphenyl 2RS-(4-(pyrrolidin-1-yl)phenyl) butanoic acid ester

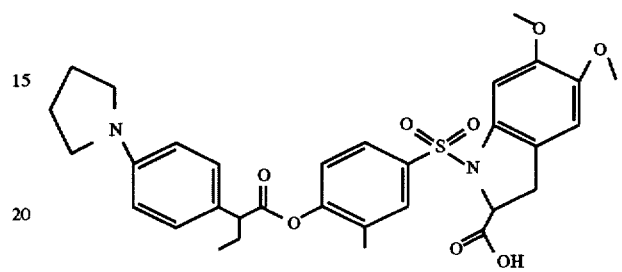

NMR (CDCl₃+CD₃OD): δ 7.6–7.4 (m, 2H), 7.26 (s, 1H), 7.19 (d, J=8.7 Hz, 2H), 6.96 (dd, J=1.2, 8.4 Hz, 1H), 6.58 (s, 1H), 6.54 (d, J=8.7 Hz, 2H), 4.7–4.6 (m, 1H), 3.91 (s, 3H), 3.79 (s, 3H), 3.58 (t, J=7.7 Hz, 1H), 3.4–3.2 (m, 4H), 3.1–2.9 (m, 2H), 2.3–1.8 (m, 6H), 1.94 (s, 3H), 0.96 (t, J=7.4 Hz, 3H);

TLC: Rf 0.45 (chloroform:methanol=4:1).

Example 2(46)

4-(2-carboxy-5-hydroxyindol-1-ylsulfonyl)-2-methylphenyl 2RS-(4-(pyrrolidin-1-yl)phenyl) butanoic acid ester

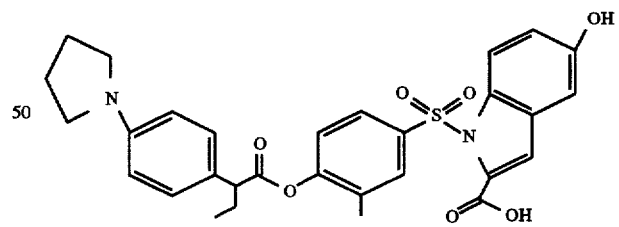

NMR (CD₃OD): δ 7.85–7.63 (3H, m), 7.03 (2H, d, J=8 Hz), 6.93 (1H, d, J=8 Hz), 6.87–6.70 (3H, m), 6.53 (2H, d, J=8 Hz), 3.56 (1H, t, J=7 Hz), 3.30–3.10 (4H, m), 2.20–1.90 (5H, m), 1.90–1.65 (1H, m), 1.84 (3H, s), 0.91 (3H, t, J=7 Hz);

TLC: Rf 0.23 (ethyl acetate:hexane:acetic acid= 10:10:0.5).

Example 2(47)

4-(2RS-(2-(2-hydroxyethoxy)ethyl)
oxycarbonylindolin-1-ylsulfonyl)-2-methylphenyl
2RS-(4-(pyrrolidin-1-yl)phenyl)butanoic acid
ester.hydrochloride

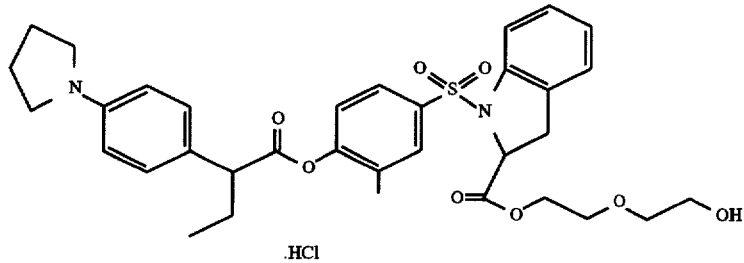

NMR (CDCl$_3$): δ 7.61–7.51 (3H, m), 7.23–7.10 (3H, m), 7.10–6.95 (3H, m), 6.51 (2H, d, J=8.0 Hz), 4.75 (1H, dd, J=5.6, 10.2 Hz), 4.38–4.33 (2H, m), 3.75–3.51 (7H, m), 3.30–3.22 (5H, m), 3.09 (1H, dd, J=5.6, 16.6 Hz), 2.23–178 (6H, m), 1.96 (3H, s), 0.96 (3H, t, J=7.4 Hz);

TLC: Rf 0.65 (chloroform:methanol=15:1).

Example 2(48)

4-(2RS-hydroxymethylindolin-1-ylsulfonyl)-
methylphenyl 2RS-(4-(pyrrolidin-1-yl)phenyl)
butanoic acid ester.hydrochloride

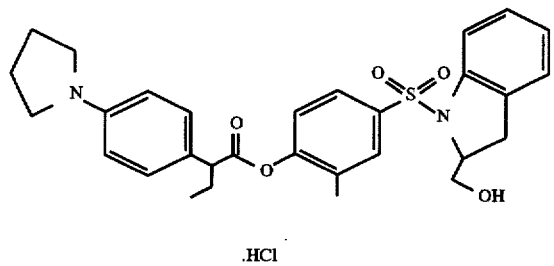

NMR (DMSO-d$_6$): δ 7.60 (1H, s-like), 7.51–7.40 (2H, m), 7.22–6.97 (6H, m), 6.51 (2H, d, J=8 Hz), 4.40–4.24 (1H, m), 3.68–3.37 (3H, m), 3.65 (1H, t, J=7 Hz), 3.23–3.17 (4H, m), 2.87–2.69 (2H, m), 2.19–1.62 (each 1H, m), 1.99–1.93 (4H, m), 1.86 (3H, s), 0.87 (3H, t, J=7 Hz);

TLC: Rf 0.29 (hexane:ethyl acetate=2:1).

Example 2(49)

4-(2RS-carboxy-5-hydroxyindolin-1-ylsulfonyl)-2-
methylphenyl 2RS-(4-(pyrrolidin-1-yl)phenyl)
butanoic acid ester

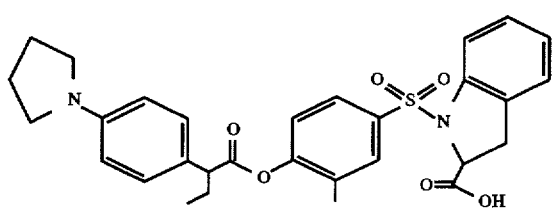

NMR (CDCl$_3$+3 drops of CD$_3$OD): δ 7.5–7.4 (m, 3H), 7.2–7.1 (m, 3H), 7.0–6.9 (m, 1H), 6.5–6.4 (m, 3H), 4.7–4.6 (m, 1H), 3.58 (t, J=7.8 Hz, 1H), 3.4–3.2 (m, 4H), 3.1–2.9 (m, 2H), 2.2–1.8 (m, 6H), 1.94 (s, 3H), 0.97 (t, J=7.2 Hz, 3H);

TLC: Rf 0.2 (chloroform:methanol=6:1).

Example 2(50)

4-(2RS-(2-(piperazin-1-yl)ethyl)oxycarbonylindolin-
1-ylsulfonyl)-2-methylphenyl 2RS-(4-(pyrrolidin-1-
yl)phenyl)butanoic acid ester.3hydrochloride

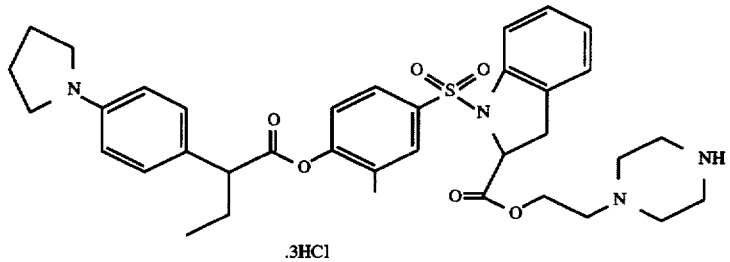

NMR (CD$_3$OD): δ 7.72–7.64 (3H, m), 7.57–7.49 (4H, m), 7.26–7.00 (4H, m), 5.12 (1H, dd, J=6.0, 8.8 Hz), 4.63–4.59 (2H, m), 3.90 (1H, t, J=8.0 Hz), 3.77–3.59 (14H, m), 3.23–3.20 (2H, m), 2.32–1.83 (6H, m), 1.96 (3H, s), 0.97 (3H, t, J=7.4 Hz);

TLC: Rf 0.41 (chloroform:methanol:acetic acid=25:5:1).

Example 2(51)

4-(2RS-(N-hydroxycarbamoyl)indolin-1-ylsulfonyl)phenyl 2RS-(4-(pyrrolidin-1-yl)phenyl)butanoic acid ester.hydrochloride

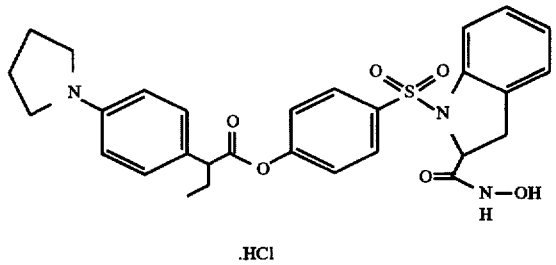

NMR (CD$_3$OD): δ 7.75 (2H, d, J=8.6 Hz), 7.60 (1H, d, J=8.0 Hz), 7.58–7.48 (4H, m), 7.21 (1H, dd, J=6.5 Hz, 1.5 Hz), 7.12 (2H, d, J=8.6 Hz), 7.09–7.01 (2H, m), 4.68 (1H, dd, J=9.0 Hz, 5.0 Hz), 3.87 (1H, t, J=7.0 Hz), 3.77–3.70 (4H, m), 3.03–2.98 (2H, m), 2.28–2.23 (4H, m), 2.20–2.13 (0.5H, m), 1.97–1.81 (1.5H, m), 0.90 (3H, t, J=7.0 Hz);

TLC: Rf 0.49 (hexane:ethyl acetate:acetic acid=8:8:1).

Example 2(52)

4-(2RS-carboxyindolin-1-ylsulfonyl)phenyl 2RS-(4-methoxyphenyl)butanoic acid ester

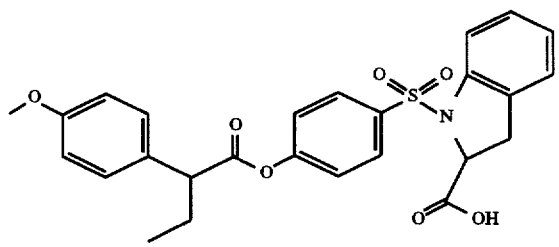

NMR (CDCl$_3$): δ 7.74 (2H, d, J=8.8 Hz), 7.58 (1H, d, J=8.0 Hz), 7.29–7.02 (7H, m), 6.87 (2H, d, J=8.8 Hz), 4.90 (1H, brs), 4.73 (1H, dd, J=9.2, 5.8 Hz), 3.80 (3H, s), 3.60 (1H, t, J=7.8 Hz), 3.20–3.15 (2H, m), 2.23–2.05 (1H, m), 1.94–1.76 (1H, m), 0.951 (3H, t, J=7.6 Hz);

TLC: Rf 0.36 (chloroform:methanol:acetic acid=40:2:1).

Example 2(53)

4-(2RS-carboxyindolin-1-ylsulfonyl)-2-methylphenyl 2RS-(4-methoxyphenyl)butanoic acid ester

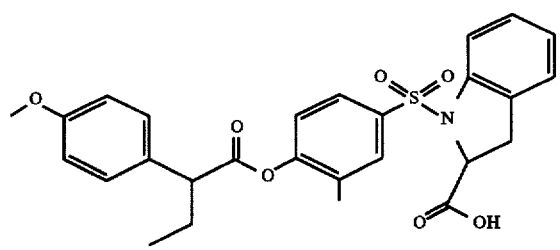

NMR (DMSO-d$_6$): δ 7.82 (1H, d-like), 7.72 (1H, d-like), 7.38 (2H, d, J=8.6 Hz), 7.32 (1H, d, J=7.8 Hz), 7.23–7.10 (3H, m), 7.03–6.96 (3H, m), 4.73 (1H, dd, J=5.2 and 9.3 Hz), 3.88 (1H, t, J=7.6 Hz), 3.82 (3H, s), 3.14–3.05 (2H, m), 2.25–2.10 and 1.96–1.79(each 1H, m), 0.96 (3H, t, J=7.2 Hz);

TLC: Rf 0.41 (chloroform:methanol:water=8:2:0.2).

Example 2(54)

4-(2-carboxy-5,6-dimethoxyindol-1-ylsulfonyl)-2-methylphenyl 2RS-(4-methoxyphenyl)butanoic acid ester

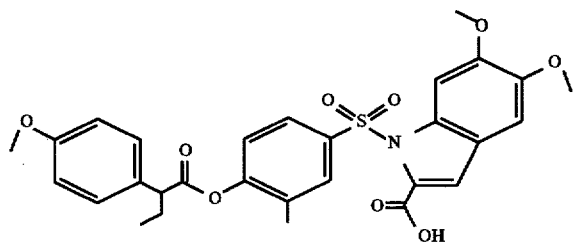

NMR (CDCl$_3$): δ 7.79–7.64 (3H, m), 7.36 (1H, s), 7.23 (2H, d, J=9 Hz), 7.01 (1H, d, J=9 Hz), 6.96 (1H, s), 6.88 (2H, d, J=9 Hz), 4.00 (3H, s), 3.91 (3H, s), 3.80 (3H, s), 3.64 (1H, t, J=7 Hz), 2.27–2.03 (1H, m), 2.00–1.80 (1H, m), 1.96 (3H, s), 0.96 (3H, t, J=7 Hz);

TLC: Rf 0.10 (ethyl acetate:hexane:acetic acid=5:10:0.5).

Example 2(55)

4-(2-carboxyindol-1-ylsulfonyl)-2-methylphenyl 2RS-(4-methoxyphenyl)butanoic acid ester

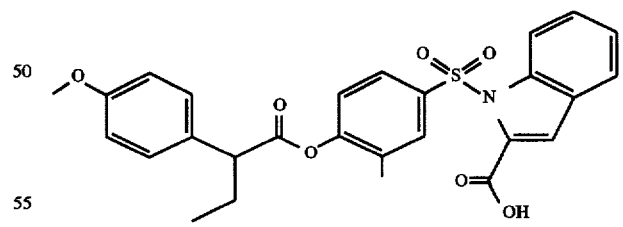

NMR (CDCl$_3$): δ 8.14 (1H, d, J=9 Hz), 7.90–7.78 (2H, m), 7.60 (1H, d, J=9 Hz), 7.52–7.40 (1H, m), 7.38 (1H, s), 7.35–7.20 (3H, m), 7.03 (1H, d, J=9 Hz), 6.87 (2H, d, J=9 Hz), 3.79 (3H, s), 3.64 (1H, t, J=7 Hz), 2.28–2.05 (1H, m), 2.00–1.79 (1H, m), 1.96 (3H, s), 0.96 (3H, t, J=7 Hz);

TLC: Rf 0.26 (ethyl acetate:hexane:acetic acid=5:10:0.5).

Example 2(56)

4-(2-carboxy-5-hydroxyindol-1-ylsulfonyl)-2-methylphenyl 2RS-(4-methoxyphenyl)butanoic acid ester

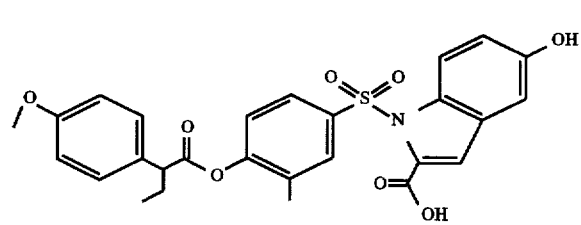

NMR (CDCl$_3$): δ 7.94 (1H, d, J=9 Hz), 7.80–7.69 (2H, m), 7.26 (2H, d, J=9 Hz), 7.17 (1H, s), 6.99 (1H, d, J=9 Hz), 6.96 (1H, dd, J=9,2 Hz), 6.87 (2H, d, J=9 Hz), 6.87 (1H, d, J=2 Hz), 3.80–3.40 (1H, brs), 3.79 (3H, s), 3.64 (1H, t, J=7 Hz), 2.26–2.05 (1H, m), 2.00–1.75 (1H, m), 1.93 (3H, s), 0.95 (3H, t, J=7 Hz);

TLC: Rf 0.16 (ethyl acetate:hexane:acetic acid= 10:10:0.5).

Example 2(57)

4-(2RS-hydroxymethylindolin-1-ylsulfonyl)-2-methylphenyl 2RS-(4-methoxyphenyl)butanoic acid ester

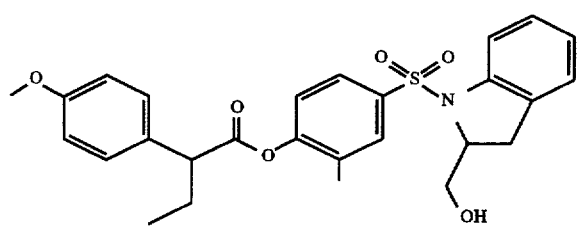

NMR (DMSO-d$_6$): δ 7.61 (1H, s-like), 7.50–7.40 (2H, m), 7.28 (2H, d, J=8 Hz), 7.21–6.96 (4H, m), 6.92 (2H, d, J=8 Hz), 5.02 (1H, t-like), 4.32 (1H, m), 3.78 (1H, t, J=7 Hz), 3.74 (3H, s), 3.67–3.57 and 3.47–3.37 (each 1H, m), 2.83–2.70 (2H, m), 2.10–1.95 and 1.86–1.65 (each 1H, m), 1.85 (3H, s), 0.88 (3H, t, J=7 Hz);

TLC: Rf 0.21 (hexane:ethyl acetate=2:1).

Example 2(58)

4-(2RS-(2-aminoethyl)oxycarbonylindolin-1-ylsulfonyl)-2-methylphenyl 2RS-(4-methoxyphenyl)butanoic acid ester.hydrochloride

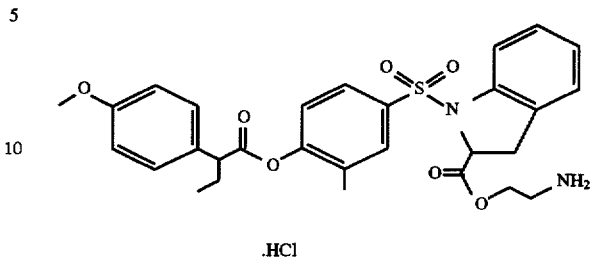

NMR (DMSO-d$_6$): δ 8.25 (3H, brs), 7.78–7.65 (2H, m), 7.39–7.00 (5H, m), 7.28 (2H, d, J=8.8 Hz), 6.91 (2H, d, J=8.8 Hz), 5.08 (1H, dd, J=5.8, 10.0 Hz) 4.34 (2H, t, J=5.2 Hz), 3.83–3.74 (1H, m), 3.74 (3H, s), 3.30–3.09 (4H, m), 2.17–1.75 (2H, m), 1.90 (3H, s), 0.89 (3H, t, J=7.2 Hz);

TLC: Rf 0.53 (chloroform:methanol:acetic acid=25:5:1).

Example 2(59)

4-(2RS-(2-(piperazin-4-yl)ethyl)oxycarbonylindolin-1-ylsulfonyl)-2-methylphenyl 2RS-(4-methoxyphenyl)butanoic acid ester.2hydrochloride

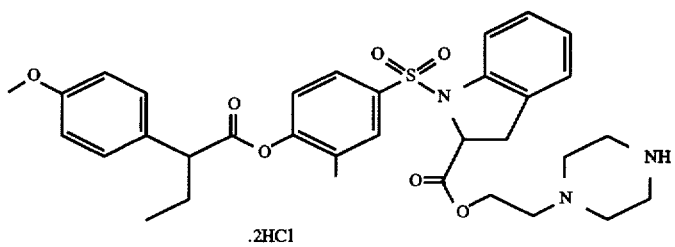

NMR (CD$_3$OD): δ 7.68–7.63 (2H, m), 7.51 (1H, d, J=7.8 Hz), 7.27 (2H, d, J=8.4 Hz), 7.22–7.02 (4H, m), 6.90 (2H, d, J=8.4 Hz), 5.10 (1H, t, J=7.2 Hz), 4.60 (2H, brs), 3.78 (3H, s), 3.75–3.19 (13H, m), 2.23–1.78 (2H, m), 1.89 (3H, s), 0.95 (3H, t, J=7.4 Hz);

TLC: Rf 0.16 (chloroform:methanol=10:1).

Example 2(60)

4-(2RS-(2-(2-hydroxyethoxy)ethyl)
oxycarbonylindolin-1-ylsulfonyl)-2-methylphenyl
2RS-(4-methoxyphenyl)butanoic acid ester

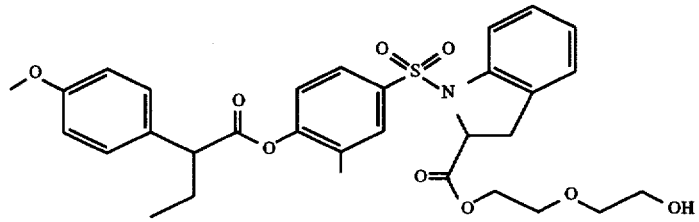

NMR (CDCl₃): δ 7.62–7.51 (3H, m), 7.26 (2H, d, J=8.4 Hz), 7.28–6.96 (4H, m), 6.87 (2H, d, J=8.4 Hz), 4.76 (1H, dd, J=5.4,10.6 Hz), 4.38–4.34 (2H, m), 3.80 (3H, s), 3.75–3.55 (7H, m), 3.31–3.04 (2H, m), 2.26–1.80 (2H, m), 1.93 (3H, s), 0.97 (3H, t, J=7.4 Hz);

TLC: Rf 0.11 (hexane:ethyl acetate=1:1).

Example 2(61)

4-(2RS-carboxyindolin-1-ylsulfonyl)phenyl 2RS-(3-methoxyphenyl)butanoic acid ester

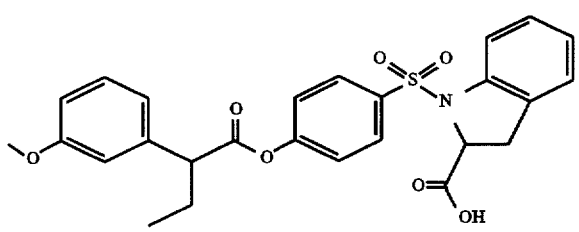

NMR (CDCl₃): δ 7.75 (2H, d, J=8.8 Hz), 7.57 (1H, d, J=7.8 Hz), 7.30–6.79 (9H, m), 4.73 (1H, t, J=8.0 Hz), 3.80 (3H, s), 3.62 (1H, t, J=7.8 Hz), 3.20–3.17 (2H, m), 2.28–2.05 (1H, m), 1.99–1.77 (1H, m), 0.96 (3H, t, J=7.4 Hz);

TLC: Rf 0.66 (chloroform:methanol:acetic acid=40:2:1).

Example 2(62)

4-(2RS-carboxyindolin-1-ylsulfonyl)phenyl 2RS-(2-methoxyphenyl)butanoic acid ester

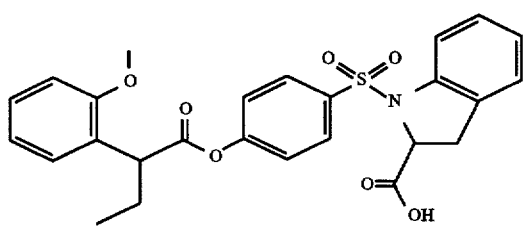

NMR (CDCl₃): δ 7.75 (2H, d, J=8.8 Hz), 7.58 (1H, d, J=8.0 Hz), 7.25 (2H, d, J=8.8 Hz), 7.31–6.87 (7H, m), 4.74 (1H, t, J=8.0 Hz), 4.04 (1 H, t, J=7.2 Hz), 3.84 (3H, s), 3.18 (2H, brd, J=7.2 Hz), 2.22–2.05 (1H, m), 1.96–1.74 (1H, m), 0.95 (3H, t, J=7.6 Hz);

TLC: Rf 0.48 (chloroform:methanol:acetic acid=40:2:1).

Example 2(63)

4-(2RS-carboxyindolin-1-ylsulfonyl)-2-methylphenyl 2RS-(2-methoxyphenyl)butanoic acid ester NMR (DMSO-d₆): δ 13.19 (1H, br), 7.79 (1H, d, J=2.0 Hz), 7.68 (1H, dd, J=2.0 and 8.5 Hz), 7.36–6.92 (9H, m), 4.96 (1H, dd, J=4.2 and 10.9 Hz), 4.08 (1H, t, J=7.6 Hz), 3.80 (3H, s), 3.39–2.96 (2H, m), 2.19–1.69 (2H, m), 1.95 (3H, s), 0.87 (3H, t, J=7.2 Hz);

TLC: Rf 0.39 (chloroform:methanol:water=8:2:0.2).

Example 2(64)

4-(2RS-carboxyindolin-1-ylsulfonyl)phenyl 2RS-(3,4-dimethoxyphenyl)butanoic acid ester

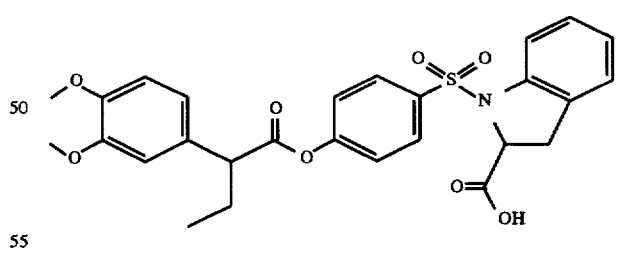

NMR (CDCl₃): δ 7.76 (2H, d, J=8.8 Hz), 7.57 (1H, d, J=8.0 Hz), 7.25–7.02 (5H, m), 6.86–6.85 (3H, m), 4.73 (1H, t, J=8.0 Hz), 3.87 (6H, s), 3.59 (1H, t, J=7.8 Hz), 3.21–3.17 (2H, brd), 2.24–2.05 (1H, m), 1.97–1.76 (1H, m), 0.97 (3H, t, J=7.6 Hz);

TLC: Rf 0.50 (chloroform:methanol:acetic acid=40:2:1).

Example 2(65)

4-(2RS-carboxyindolin-1-ylsulfonyl)-2-methylphenyl 2RS-(3,4-dimethoxyphenyl)butanoic acid ester

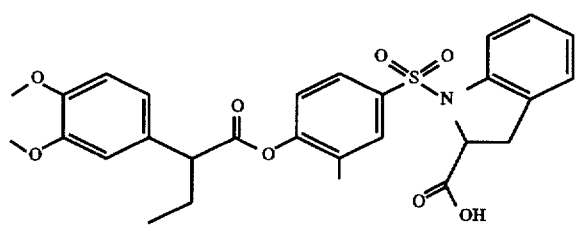

NMR (DMSO-d$_6$): δ 13.14 (1H, br), 7.80 (1H, s), 7.68 (1H, d-like), 7.35–7.11 (4H, m), 7.02–6.86 (4H, m), 4.97 (1H, dd, J=4.2 and 10.5 Hz), 3.79 (1H, t, J=7.4 Hz), 3.74 (6H, s), 3.39–2.97 (2H, m), 2.16–1.98 and 1.95–1.72 (each 1H, m), 1.91 (3H, s), 0.89 (3H, t, J=7.2 Hz);

TLC: Rf 0.39 (chloroform:methanol:water=8:2:0.2).

Example 2(66)

4-(2RS-carboxyindolin-1-ylsulfonyl)phenyl 2RS-(4-methylphenyl)butanoic acid ester

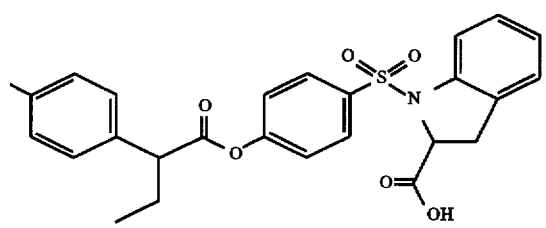

NMR (CDCl$_3$): δ 7.74 (2H, d, J=8.8 Hz), 7.58 (1H, d, J=8.0 Hz), 7.24–7.02 (9H, m), 4.74 (1H, t, J=8.6 Hz), 3.62 (1H, t, J=7.8 Hz), 3.18 (2H, brd), 2.34 (3H, s), 2.27–2.05 (1H, m), 1.97–1.75 (1H, m), 0.96 (3H, t, J=7.4 Hz);

TLC: Rf 0.43 (chloroform:methanol:acetic acid=40:2:1).

Example 2(67)

4-(2RS-carboxyindolin-1-ylsulfonyl)-2-methylphenyl 2RS-(4-methylphenyl)butanoic acid ester

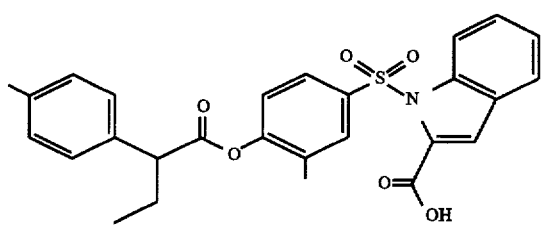

NMR (DMSO-d$_6$): δ 13.08 (1H, br), 7.73 (1H, d, J=2.0 Hz),7.61(1H, dd, J=2.0 and 8.6 Hz), 7.28–6.87 (9H, m), 4.90 (1H, dd, J=4.0 and 10.8 Hz), 3.75 (1H, t, J=7.6 Hz), 3.32–2.90 (2H, m), 2.22 (3H, s), 2.13–1.91 and 1.86–1.64 (each 1H, m), 1.82 (3H, s), 0.80 (3H, t, J=7.2 Hz);

TLC: Rf 0.43 (chloroform:methanol:water=8:2:0.2).

Example 2(68)

4-(2-carboxy-5,6-dimethoxyindol-1-ylsulfonyl)-2-methylphenyl 2RS-(4-methylphenyl)butanoic acid ester

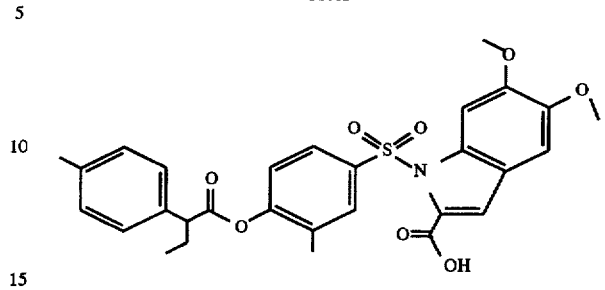

NMR (CDCl$_3$): δ 7.78–7.64 (3H, m), 7.35 (1H, s), 7.23 (2H, d, J=9 Hz), 7.15 (2H, d, J=9 Hz), 7.00 (1H, d, J=9 Hz), 6.95 (1H, s), 4.00 (3H, s), 3.91 (3H, s), 3.85–3.30 (1H, br), 3.65 (1H, t, J=7 Hz), 2.33 (3H, s), 2.30–2.10 (1H, m), 2.00–1.80 (1H, m), 1.96 (3H, s), 0.96 (3H, t, J=7 Hz);

TLC: Rf 0.23 (ethyl acetate:hexane:acetic acid=5:10:0.5).

Example 2(69)

4-(2-carboxyindol-1-ylsulfonyl)-2-methylphenyl 2RS-(4-methylphenyl)butanoic acid ester

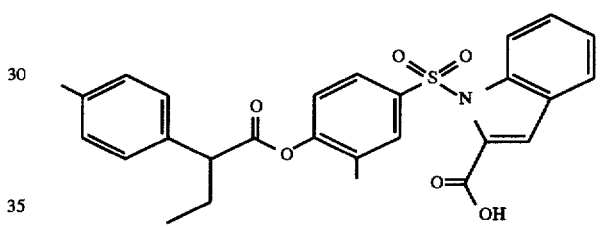

NMR (CDCl$_3$): δ 8.14 (1H, d, J=9 Hz), 7.90–7.78 (2H, m), 7.60 (1H, d, J=9 Hz), 7.52–7.41 (1H, m), 7.39 (1H, s), 7.35–7.10 (5H, m), 7.03 (1H, d, J=9 Hz), 4.00–3.60 (1H, br), 3.66 (1H, t, J=7 Hz), 2.33 (3H, s), 2.30–2.07 (1H, m), 2.00–1.75 (1H, m), 1.97 (3H, s), 0.96 (3H, t, J=7 Hz);

TLC: Rf 0.28 (ethyl acetate:hexane:acetic acid=5:10:0.5).

Example 2(70)

4-(2-carboxy-5-hydroxyindol-1-ylsulfonyl)-2-methylphenyl 2RS-(4-methylphenyl)butanoic acid ester

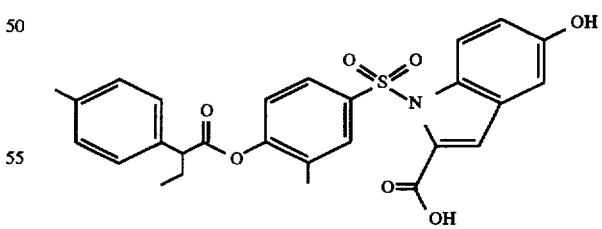

NMR (CDCl$_3$): δ 7.95 (1H, d, J=9 Hz), 7.81–7.69 (2H, m), 7.22 (2H, d, J=8 Hz), 7.20 (1H, s), 7.15 (2H, d, J=8 Hz), 7.00 (1H, d, J=8 Hz), 6.97 (1H, dd, J=9.2 Hz), 6.89 (1H, d, J=2 Hz), 3.80–3.30 (1H, br), 3.66 (1H, t, J=7 Hz), 2.33 (3H, s), 2.28–2.10 (1H, m), 2.00–1.80 (1H, m), 1.94 (3H, s), 0.96 (3H, t, J=7 Hz);

TLC: Rf 0.24 (ethyl acetate:hexane:acetic acid= 10:10:0.5).

Example 2(71)

4-(2RS-(2-aminoethyl)oxycarbonylindolin-1-ylsulfonyl)-2-methylphenyl 2RS-(4-methylphenyl)butanoic acid ester.hydrochloride

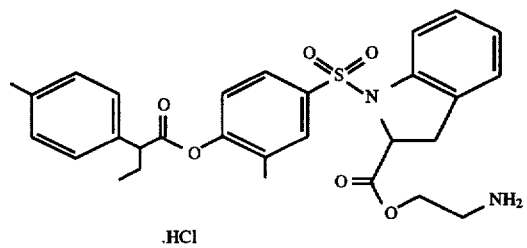

NMR (CDCl$_3$+CD$_3$OD): δ 7.8–7.5 (m, 4H), 7.3–7.0 (m, 7H), 5.0–4.8 (m, 1H), 4.6–4.4 (m, 2H), 3.67 (t, J=9.2 Hz, 1H), 3.4–3.3 (m, 2H), 3.3–3.2 (m, 2H), 2.34 (s, 3H), 2.3–1.8 (m, 2H), 1.95 (s, 3H), 0.97 (t, J=7.0 Hz, 3H);

TLC: Rf 0.5 (chloroform:methanol=4:1).

Example 2(72)

4-(2RS-hydroxymethylindolin-1-ylsulfonyl)-2-methylphenyl 2RS-(4-methylphenyl)butanoic acid ester

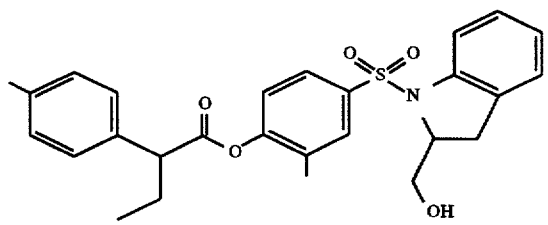

NMR (DMSO-d$_6$): δ 7.61 (1H, s-like), 7.51–7.40 (2H, m), 7.27–6.96 (8H, m), 5.04 (1H, t-like), 4.34 (1H, m), 3.81 (1H, t, J=7 Hz), 3.67–3.57 and 3.48–3.39 (each 1H, m), 2.83–2.68 (2H, m), 2.29 (3H, s), 2.20–1.97 and 1.88–1.67 (each 1H, m), 1.86 (3H, s), 0.87 (3H, t, J=7 Hz);

TLC: Rf 0.30 (hexane:ethyl acetate=2:1).

Example 2(73)

4-(2RS-(2-(2-hydroxyethoxy)ethyl)oxycarbonylindolin-1-ylsulfonyl)-2-methylphenyl 2RS-(4-methylphenyl)butanoic acid ester

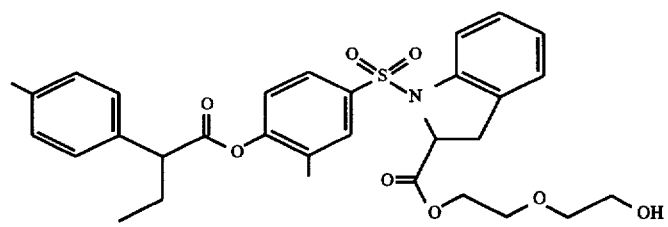

NMR (CDCl$_3$): δ 7.7–7.5 (m, 3H), 7.3–6.9 (m, 8H), 4.9–4.7 (m, 1H), 4.4–4.3 (m, 2H), 3.8–3.5 (m, 7H), 3.4–3.0 (m, 2H), 2.34 (s, 3H), 2.4–1.8 (m, 2H), 1.93 (s, 3H), 0.97 (t, J=7.2 Hz, 3H);

TLC: Rf 0.25 (hexane:ethyl acetate=1:1).

Example 2(74)

4-(2RS-(2-(piperazin-4-yl)ethyl)oxycarbonylindolin-1-ylsulfonyl)-2-methylphenyl 2RS-(4-methylphenyl)butanoic acid ester.hydrochloride

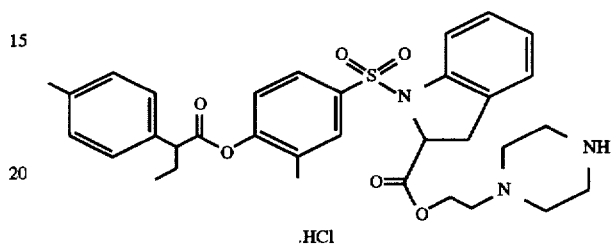

NMR (CDCl$_3$): δ 7.7–7.5 (m, 3H), 7.5–7.4 (m, 1H), 7.3–6.9 (m, 7H), 5.2–5.0 (m, 1H), 4.7–4.5 (m, 2H), 4.0–3.5 (m, 11H), 3.4–3.0 (m, 2H), 2.30 (s, 3), 2.4–2.0 (m, 1H), 1.88 (s, 3H), 2.0–1.8 (m, 1H), 0.93 (t, J=7.2 Hz, 3H);

TLC: Rf 0.3 (chloroform:methanol=2:1).

Example 2(75)

4-(2RS-carboxyindolin-1-ylsulfonyl)-2-methylphenyl 2RS-(4-hydroxyphenyl)butanoic acid ester

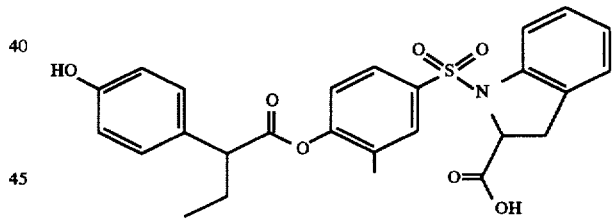

NMR (CDCl$_3$): δ 7.7–7.5 (3H,m), 7.3–7.1 (3H, m), 7.1–6.9 (3H, m), 6.80 (2H, d, J=8.4 Hz), 4.8–4.7 (1H, m), 3.7–3.3 (1H, m), 3.3–3.1 (2H, m), 2.3–2.0 (1H, m), 2.0–1.8 (1H,m), 1.91 (3H, s), 0.96 (3H, t, J=7.4 Hz);

TLC: Rf 0.42 (chloroform:methanol:water=8:2:0.2).

181

Example 2(76)

4-(2RS-carboxyindolin-1-ylsulfonyl)phenyl 2RS-(4-aminophenyl)butanoic acid ester

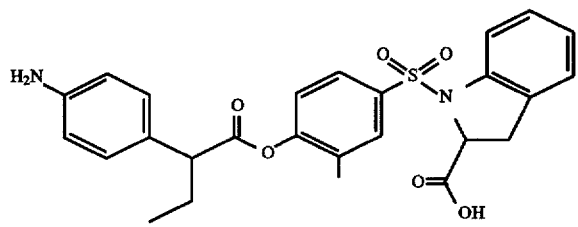

NMR (DMSO-d$_6$): δ 7.83 (2H, d, J=8.4 Hz), 7.30 (1H, d, J=8.2 Hz), 7.12 (2H, d, J=8.4 Hz), 6.97 (2H, d, J=8.4 Hz), 7.17–6.90 (3H, m), 6.53 (2H, d, J=8.4 Hz), 4.80–4.73 (1H, m), 3.54 (1H, t, J=7.6 Hz), 3.25–2.93 (2H, m), 2.09–1.90 (1H, m), 1.78–1.60 (1H, m), 0.86 (3H, t, J=7.2 Hz);

TLC: Rf 0.20 (chloroform:methanol:acetic acid=40:2:1).

Example 2(77)

4-(4S-carboxyperhydrothiazol-3-ylsulfonyl)phenyl 2RS-(4-(pyrrolidin-1-yl)phenyl)butanoic acid ester.hydrochloride

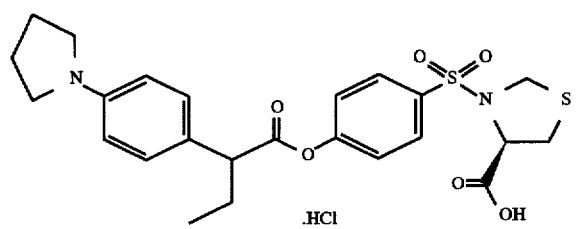

NMR (CDCl$_3$): δ 7.85 (2H, d, J=8.8 Hz), 7.21 (2H, d, J=8.8 Hz), 7.17 (2H, d, J=8.8 Hz), 6.57 (2H, d, J=8.8 Hz), 4.83 (1H, dd, J=7.0 and 3.4 Hz), 4.67 (1H, d, J=9.0 Hz), 4.40 (1H, d, J=9.0 Hz), 3.59 (1H, t, J=7.6 Hz), 3.40–3.18 (5H, m), 3.01 (1H, dd, J=11.4 and 7.0 Hz), 2.30–2.05 and 2.05–1.75 (each 1H, m), 2.10–1.95 (4H, m), 0.98 (3H, t, J=7.6 Hz);

TLC: Rf 0.36 (acetic acid:methanol:chloroform=1:2:40).

Example 2(78)

4-(4-carboxypiperidin-1-ylsulfonyl)phenyl 2RS-(4-(pyrrolidin-1-yl)phenyl)butanoic acid ester.hydrochloride

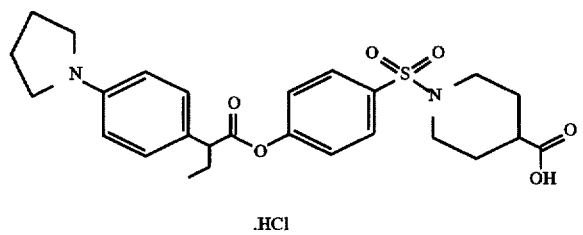

NMR (CDCl$_3$): δ 7.71 (2H, d, J=8.8 Hz), 7.21 (2H, d, J=8.8 Hz), 7.17 (2H, d, J=8.8 Hz), 6.55 (2H, d, J=8.8 Hz), 3.72–3.54 (2H, m), 3.59 (1H, t, J=7.6 Hz), 3.36–3.20 (4H, m), 2.45 (2H, t-like) 2.38–1.70 (7H, m), 2.08–1.94 (4H, m), 0.98 (3H, t, J=7.4 Hz);

TLC: Rf 0.34 (acetic acid:methanol:chloroform=1:2:40).

182

Example 2(79)

4-(2RS-carboxypiperidin-1-ylsulfonyl)phenyl 2RS-(4-(pyrrolidin-1-yl)phenyl)butanoic acid ester.hydrochloride

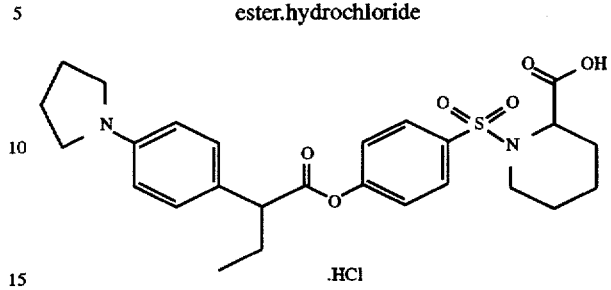

NMR (CDCl$_3$): δ 7.75 (2H, d, J=8.8 Hz), 7.21 (2H, d, J=8.8 Hz), 7.08 (2H, d, J=8.8 Hz), 6.55 (2H, d, J=8.8 Hz), 4.8–4.7 (1H, m), 3.8–3.7 (1H, m), 3.58 (1H, t, J=7.5 Hz), 3.4–3.1 (5H, m), 2.3–1.2 (12H, m), 0.97 (3H, t, J=7.4 Hz);

TLC: Rf 0.48 (acetic acid:methanol:chloroform=1:2:50).

Example 2(80)

4-(3RS-carboxypiperidin-1-ylsulfonyl)phenyl 2RS-(4-(pyrrolidin-1-yl)phenyl)butanoic acid ester.hydrochloride

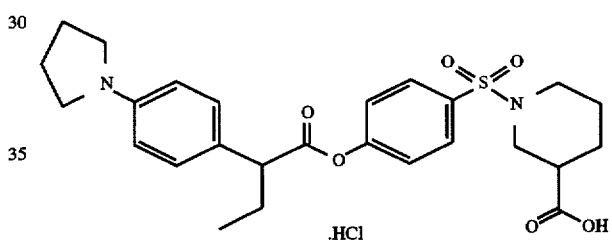

NMR (CDCl$_3$): δ 7.75 (2H, d, J=8.4 Hz), 7.7–7.3 (4H, m), 7.19 (2H, d, J=8.4 Hz), 4.0–3.4 (8H, m), 2.7–2.5 (2H, m), 2.5–2.1 (5H, m), 2.1–1.3 (5H, m), 1.00 (3H, t, J=7.4 Hz);

TLC: Rf 0.32 (acetic acid:methanol:chloroform=1:2:100).

Example 2(81)

4-(4S-carboxyperhydrothiazol-3-ylsulfonyl)-2-methylphenyl 2RS-(4-(pyrrolidin-1-yl)phenyl) butanoic acid ester

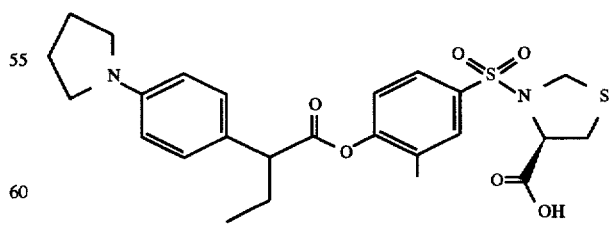

NMR (CDCl$_3$+CD$_3$OD): δ 7.69 (1H, s), 7.66 (1H, d, J=8.0 Hz), 7.21 (2H, d, J=8.6 Hz), 7.07 (1H, d, J=8.0 Hz), 6.55 (2H, d, J=8.6 Hz), 4.71 (1H, dd, J=7.2, 3.2 Hz), 4.63 (1H, d, J=9.8 Hz), 4.45 (1H, d, J=9.8 Hz), 3.61 (1H, t, J=7.7

Hz), 3.4–3.2 (5H, m), 2.84 (1H, dd, J=11.2, 7.2 Hz), 2.3–2.1 (1H, m), 2.1–1.8 (4H, br), 2.02 (3H, s), 0.98 (3H, d, J=7.3 Hz);

TLC: Rf 0.55 (chloroform:methanol:acetic acid=25:5:1).

Example 2(82)

4-(2RS-carboxymorpholin-1-ylsulfonyl)-2-methylphenyl 2RS-(4-(pyrrolidin-1-yl)phenyl)butanoic acid ester

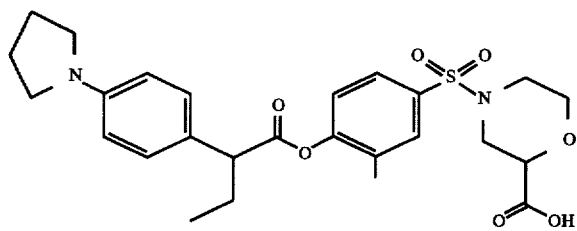

NMR (CD$_3$OD): δ 7.65–7.54 (2H, m), 7.20 (2H, d, J=8 Hz), 7.15 (1H, d, J=8 Hz), 6.58 (2H, d, J=8 Hz), 4.03–3.80 (3H, m), 3.71–3.38 (3H, m), 3.37–3.15 (4H, m), 2.50–1.78 (11H, m), 0.97 (3H, t, J=7 Hz);

TLC: Rf 0.25 (methanol:chloroform=3:17).

Example 2(83)

4-(1S-oxo-4S-carboxyperhydrothiazol-3-ylsulfonyl)-2-methylphenyl 2RS-(4-(pyrrolidin-1-yl)phenyl)butanoic acid ester.hydrochloride

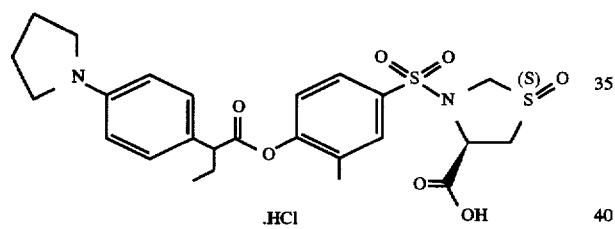

NMR (CD$_3$O): δ 7.90–7.75 (2H, m), 7.61 (4H, s), 7.18 (1H, d, J=8.5 Hz), 5.25 (1H, dd, J=8.5, 2.0 Hz), 5.19 (1H, d, J=12.0 Hz), 4.13 (1H, d, J=12.0 Hz), 3.98 (1H, t, J=7.5 Hz), 3.85–3.70 (4H, m), 3.41 (1H, dd, J=14.5, 2.0 Hz), 3.03 (1H, dd, J=14.5, 8.5 Hz), 2.35–2.20 (4H, m), 2.40–1.80 (2H, m), 2.04 (3H, s), 1.00 (3H, t, J=7.5 Hz);

TLC: Rf 0.18 (chloroform:methanol:acetic acid= 40:10:1).

Example 2(84)

4-(4S-carboxy-1,1-dioxoperhydrothiazol-3-ylsulfonyl)-2-methylphenyl 2RS-(4-(pyrrolidin-1-yl)phenyl)butanoic acid ester.hydrochloride

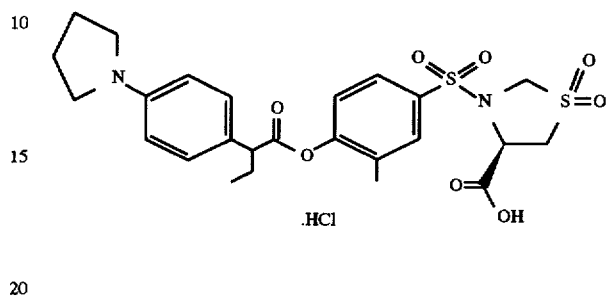

NMR (CDCl$_3$): δ 7.75–7.65 (2H, m), 7.48 (4H, s), 7.10 (1H, d, J=8.5 Hz), 5.06 (1H, dd, J=8.5, 4.0 Hz), 4.68 (1H, d, J=11.0 Hz), 4.26 (1H, d, J=11.0 Hz), 3.78 (1H, t, J=7.5 Hz), 3.70–3.55 (4H, m), 3.55–3.35 (2H, m), 2.40–2.25 (4H, m), 2.40–1.80 (2H, m), 2.07 (3H, s), 1.01 (3H, t, J=7.5 Hz);

TLC: Rf 0.14 (chloroform:methanol:acetic acid= 40:10:1).

Example 2(85)

4-(4-(2-hydroxyethyl)piperazin-1-ylsulfonyl)-2-methylphenyl 2RS-(4-(pyrrolidin-1-yl)phenyl)butanoic acid ester.2hydrochloride

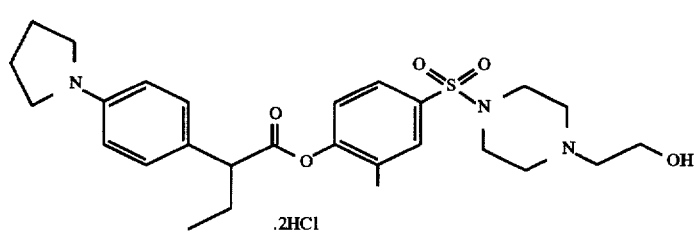

NMR (CD$_3$OD): δ 7.75–7.47 (6H, m), 7.23 (1H, d, J=8.8 Hz), 4.03–3.79 (5H, m), 3.79–3.57 (6H, m), 3.40–3.14 (4H, m), 2.77 (2H, t-like, J=13.8 Hz), 2.38–2.15 (5H, m), 2.06 (3H, s), 2.15–1.84 (1H, m), 1.00 (3H, t, J=7.4 Hz);

TLC: Rf 0.21 (hexane:ethyl acetate=1:1).

Example 2(86)

4-(4-carboxymethylpiperazin-1-ylsulfonyl)-2-methylphenyl 2RS-(4-(pyrrolidin-1-yl)phenyl) butanoic acid ester.2hydrochloride

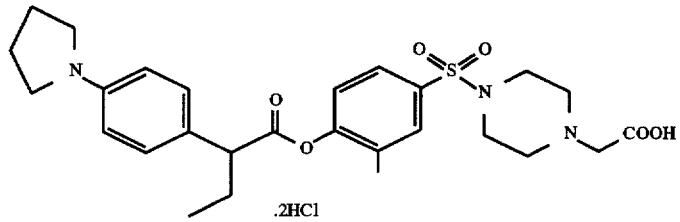

NMR (CD₃OD): δ 7.79–7.53 (6H, m), 7.24 (1H, d, J=8.0 Hz), 4.14 (2H, s), 4.00 (1H, t, J=7.8 Hz), 3.87–3.70 (4H, m), 3.52 (8H, brs), 2.44–2.15 (5H, m), 2.07 (3H, s), 2.15–1.82 (1H, m), 1.00 (3H, t, J=7.2 Hz);

TLC: Rf 0.63 (chloroform:methanol acetic acid=15:2:1).

Example 2(87)

4-(4S-carboxyperhydrothiazol-3-ylsulfonyl)phenyl 2RS-(4-nitrophenyl)butanoic acid ester

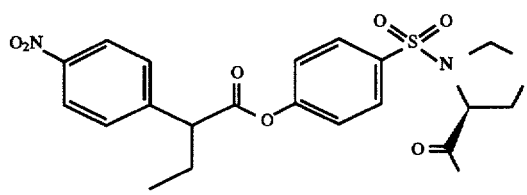

NMR (CDCl₃): δ 8.27 (2H, d, J=8.8 Hz), 7.94 (2H, d, J=8.8 Hz), 7.68 (2H, d, J=8.8 Hz), 7.26 (2H, d, J=8.8 Hz), 4.86 (1H, dd, J=3.6 and 7.4 Hz), 4.73 (1H, d, J=8.0 Hz), 4.41 (1H, d, J=8.0 Hz), 4.03 (1H, t, J=7.6 Hz), 3.17 (1H, dd, J=11.5 and 3.6 Hz), 2.93 (1H, dd, J=11.5 and 7.4 Hz), 2.40–2.15 and 2.10–1.85 (each 1H, m), 1.00 (3H, t, J=7.2 Hz);

TLC: Rf 0.38 (acetic acid:methanol:chloroform=1:2:40).

Example 2(88)

4-(N-carboxymethyl-N-2-methoxyethylsulfamoyl) phenyl 2RS-(4-(pyrrolidin-1-yl)phenyl)butanoic acid ester.trifluoroacetate

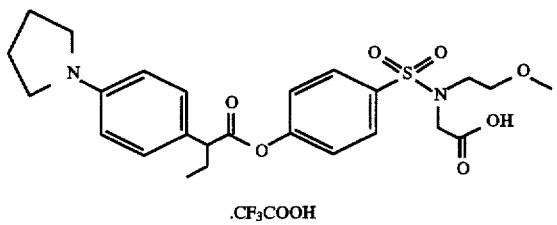

NMR (CD₃OD): δ 7.85 (2H, d, J=8.6 Hz), 7.41 (2H, d, J=8.6 Hz), 7.17 (2H, d, J=8.6 Hz), 7.11 (2H, d, J=8.6 Hz), 4.10 (2H, s), 3.77 (1H, t, J=6.0 Hz), 3.46 (8H, m), 3.20 (3H, s), 2.20 (1H, m), 2.15 (4H, m), 1.90 (1H, m), 0.97 (3H, t, J=7.0 Hz);

TLC: Rf 0.32 (chloroform:methanol:water=9:1:0.1).

Example 2(89)

4-(N-1RS,2-dicarboxyethylsulfamoyl)phenyl 2RS-(4-(pyrrolidin-1-yl)phenyl)butanoic acid ester.trifluoroacetate

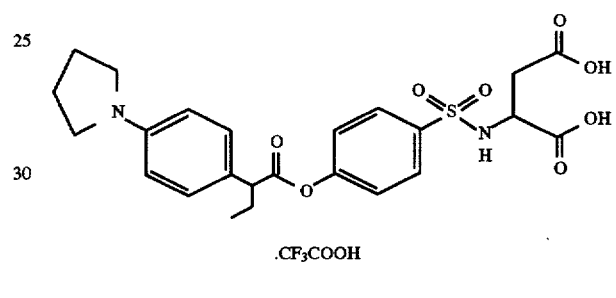

NMR (CD₃OD): δ 7.87 (2H, d, J=8.6 Hz), 7.36 (2H, brd, J=8.6 Hz), 7.14 (2H, d, J=8.6 Hz), 7.00 (2H, brd, J=8.6 Hz), 4.21 (1H, t, J=6.0 Hz), 3.74 (1H, m), 3.48 (4H, m), 2.72 (2H, d, J=6.2 Hz), 2.18 (1H, m), 2.13 (4H, m), 1.87 (1H, m), 0.97 (3H, t, J=7.4 Hz);

TLC: Rf 0.26 (chloroform:methanol:water=9:1:0.1).

Example 2(90)

4-(N-(1-carboxycyclopropane)sulfamoyl)phenyl 2RS-(4-(pyrrolidin-1-yl)phenyl)butanoic acid ester.hydrochloride

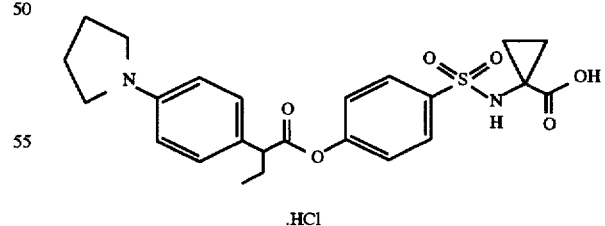

NMR (CDCl₃): δ 7.81 (2H, d, J=8.8 Hz), 7.15 (2H, d, J=8.8 Hz), 7.05 (2H, d, J=8.8 Hz), 6.55 (2H, d, J=8.8 Hz), 5.66 (1H, s), 3.58 (1H, t, J=7.6 Hz), 3.36–3.18 (4H, t-like), 2.30–2.00 and 2.00–1.75 (each 1H, m), 2.06–1.96 (4H, m), 1.56–1.35 (4H, m), 0.97 (3H, t, J=7.4 Hz);

TLC: Rf 0.38 (acetic acid:methanol:chloroform=1:2:40).

Example 2(91)

4-(N-1RS-carboxy-2-phenylethylsulfamoyl)phenyl 2RS-(4-(pyrrolidin-1-yl)phenyl)butanoic acid ester.hydrochloride

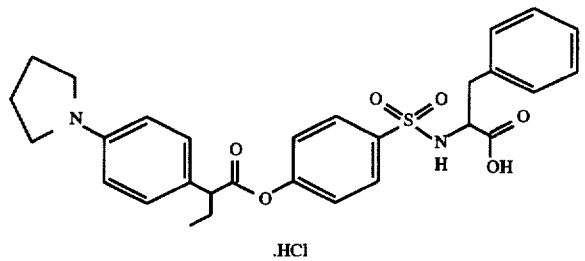

NMR (DMSO-d$_6$): δ 8.38 (1H, d, J=10 Hz), 7.55 (2H, d, J=9 Hz), 7.30–7.00 (9H, m), 6.76 (2H, d, J=9 Hz), 3.95–3.79 (1H, m), 3.71 (1H, t, J=7 Hz), 3.40–3.20 (4H, m), 2.94 (1H, dd, J=15 Hz, 5 Hz), 2.70 (1H, dd, J=15 Hz, 8 Hz), 2.20–1.90 (5H, m), 1.90–1.65 (1H, m), 0.90 (3H, t, J=7 Hz);

TLC Rf 0.19 (ethyl acetate:hexane:acetic acid=5:5:0.1).

Example 2(92)

4-(N-1S-carboxy-2-methylpropylsulfamoyl)phenyl 2RS-(4-(pyrrolidin-1-yl)phenyl)butanoic acid ester.hydrochloride

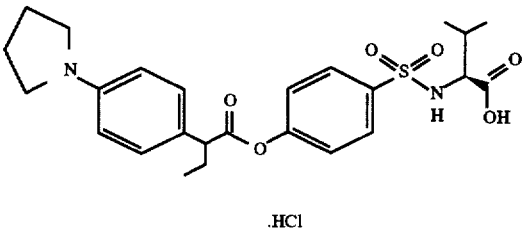

NMR (DMSO-d$_6$): δ 8.05 (1H, d, J=9 Hz), 7.78 (2H, d, J=8 Hz), 7.25 (2H, d, J=8 Hz), 7.17 (2H, d, J=8 Hz), 6.86–6.70 (2H, m), 3.73 (1H, t, J=7Hz), 3.50 (1H, dd, J=9 Hz, 6 Hz), 3.38–3.20 (4H, m), 2.20–1.68 (7H, m), 0.88 (3H, t, J=7 Hz), 0.80 (3H, d, J=7 Hz), 0.76 (3H, d, J=7 Hz);

TLC: Rf 0.34 (ethyl acetate).

Example 2(93)

4-(N-(1S-carboxy-2-carboxymethylthioethyl)sulfamoyl)phenyl 2RS-(4-(pyrrolidin-1-yl)phenyl)butanoic acid ester.hydrochloride

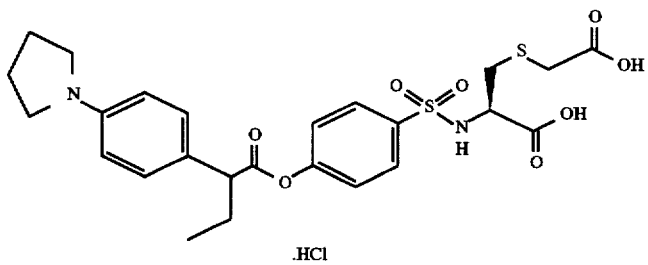

NMR (CD$_3$OD): δ 7.89 (2H, d, J=8.8 Hz), 7.63 (2H, d, J=15.0 Hz), 7.62 (2H, d, J=15.0 Hz), 7.18 (2H, d, J=8.8 Hz), 4.08 (1H, dd, J=5.9, 7.5 Hz), 3.91 (1H, t, J=7.5 Hz), 3.82–3.70 (4H, m), 3.19 (2H, s), 3.00 (1H, dd, J=5.9, 14.0 Hz), 2.84 (1H, dd, J=7.5, 14.0 Hz), 2.40–2.12 (5H, m), 2.02–1.80 (1H, m), 0.98 (3H, t, J=7.0 Hz);

TLC: Rf 0.20 (chloroform:methanol:water=7:3:0.3).

Example 2(94)

4-(N-1RS-carboxy-1-(thiophen-2-yl)methylsulfamoyl)phenyl 2RS-(4-(pyrrolidin-1-yl)phenyl)butanoic acid ester.hydrochloride

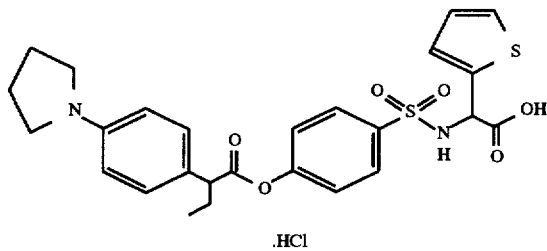

NMR (DMSO-d$_6$): δ 8.88 (1H, d, J=9.0 Hz), 7.77 (2H, d, J=8.8 Hz), 7.40 (1H, dd, J=1.2, 5.0 Hz), 7.24 (2H, d, J=8.4 Hz), 7.14 (2H, d, J=8.8 Hz), 7.00–6.91 (1H, m), 6.88 (1H, dd, J=3.7, 5.0 Hz), 6.85–6.72 (2H, m), 5.16 (1H, d, J=9.0 Hz), 3.71 (1H, t, J=7.2 Hz), 3.40–3.20 (4H, m), 2.20–1.90 (5H, m), 1.88–1.70 (1H, m), 0.89 (3H, t, J=7.2 Hz);

TLC: Rf 0.27 (chloroform:methanol:water=4:1:0.1).

Example 2(95)

4-(N-1RS-carboxy-1-(furan-2-yl)methylsulfamoyl)phenyl 2RS-(4-(pyrrolidin-1-yl)phenyl)butanoic acid ester.hydrochloride

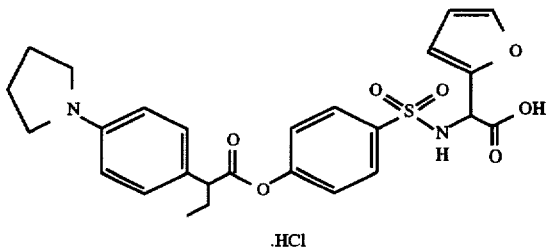

NMR (DMSO-d$_6$): δ 8.78 (1H, d, J=9.0 Hz), 7.75 (2H, d, J=8.6 Hz), 7.46 (1H, m), 7.24 (2H, d, J=8.2 Hz), 7.12 (2H, d, J=8.6 Hz), 6.90–6.70 (2H, m), 6.31–6.24 (1H, m), 6.19

(1H, d, J=2.8 Hz), 5.02 (1H, d, J=9.0 Hz), 3.71 (1H, t, J=7.6 Hz), 3.40–3.20 (4H, m), 2.20–1.86 (5H, m), 1.86–1.68 (1H, m), 0.89 (3H, t, J=7.4 Hz);

TLC: Rf 0.27 (chloroform:methanol:water=4:1:0.1).

Example 2(96)

4-(N-carboxymethyl-N-2-methoxyethylsulfamoyl)-2-methylphenyl 2RS-(4-(pyrrolidin-1-yl)phenyl) butanoic acid ester

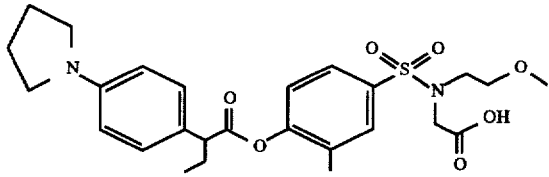

NMR (CDCl₃): δ 7.64 (1H, d, J=2.0 Hz), 7.61 (1H, dd, J=8.0, 2.0 Hz), 7.21 (2H, d, J=8.5 Hz), 7.04 (1H, d, J=8.0 Hz), 6.55 (2H, d, J=8.5 Hz), 4.08 (2H, s), 3.61 (1H, t, J=7.5 Hz), 3.55 (2H, t, J=4.5 Hz), 3.40 (2H, t, J=4.5 Hz), 3.35–3.20 (4H, m), 3.29 (3H, s), 2.30–1.70 (2H, m), 2.05–1.95 (4H, m), 2.01 (3H, s), 0.99 (3H, t, J=7.5 Hz);

TLC: Rf 0.47 (chloroform:methanol:acetic acid=40:2:1).

Example 2(97)

4-(N-propyl-N-carboxymethylsulfamoyl)-2-methylphenyl 2RS-(4-(pyrrolidin-1-yl)phenyl) butanoic acid ester

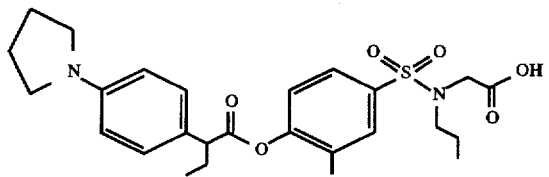

NMR (CDCl₃): δ 7.70–7.55 (2H, m), 7.23 (2H, d, J=8 Hz), 7.01 (1H, d, J=8 Hz), 6.55 (2H, d, J=8 Hz), 4.20–3.80 (1H, br), 3.98 (2H, s), 3.60 (1H, t, J=7 Hz), 3.35–3.07 (6H, m), 2.28–1.75 (9H, m), 1.60–1.38 (2H, m), 0.98 (3H, t, J=7 Hz), 0.90 (3H, t, J=7 Hz);

TLC: Rf 0.23 (chloroform:methanol=19:1).

Example 2(98)

4-(N-1S-carboxy-5-aminopentylsulfamoyl)-2-methylphenyl 2RS-(4-(pyrrolidin-1-yl)phenyl) butanoic acid ester.2hydrochloride

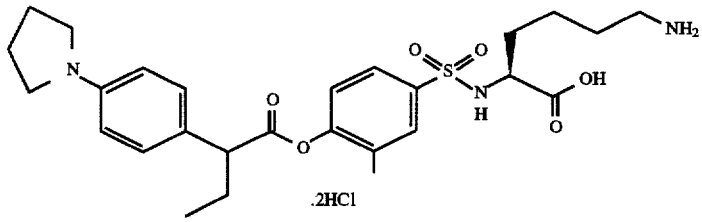

NMR (CD₃OD): δ 7.80–7.47 (6H, m), 7.10 (1H, d, J=8 Hz), 3.95 (1H, t, J=7 Hz), 3.90–3.68 (5H, m), 2.95–2.80 (2H, m), 2.35–2.20 (5H, m), 2.10–1.85 (1H, m), 1.99 (3H, s), 1.85–1.30 (6H, m), 0.98 (3H, t, J=7 Hz);

TLC: Rf 0.22 (chloroform:methanol:water=8:2:0.1).

Example 2(99)

4-(N-carboxymethylsulfamoyl)phenyl 2-(4-methoxyphenyl)-2-ethylbutanoic acid ester

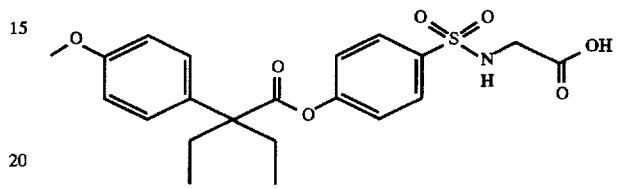

NMR (CDCl₃): δ 7.80 (2H, d, J=8.8 Hz), 7.25 (2H, d, J=8.8 Hz), 7.04 (2H, d, J=8.6 Hz), 6.90 (2H, d, J=8.8 Hz), 3.80 (3H, s), 3.73 (2H, brs), 2.25–2.00 (4H, m), 0.82 (6H, t, J=7.4 Hz);

TLC: Rf 0.10 (hexane:ethyl acetate=2:1).

Example 2(100)

4-(N-2-methoxyethyl-N-carboxymethylsulfamoyl) phenyl 1-(4-nitrophenyl)cyclobutanecarboxylic acid ester

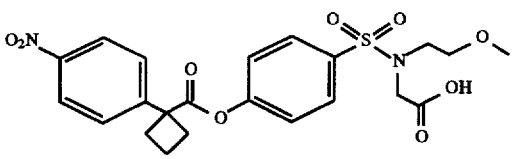

NMR (CDCl₃): δ 8.25 (2H, d, J=9.0 Hz), 7.82 (2H, d, J=9.0 Hz), 7.55 (2H, d, J=9.0 Hz), 7.11 (2H, d, J=9.0 Hz), 4.13 (2H, s), 3.53 (2H, t, J=5.0 Hz), 3.41 (2H, t, J=5.0 Hz), 3.27 (3H, s), 3.06 (2H, m), 2.67 (2H, m), 2.26 (1H, m), 2.04 (1H, m);

TLC: Rf 0.29 (chloroform:methanol:water=9:1:0.1).

Example 2(101)

4-(N-1RS,2-dicarboxyethylsulfamoyl)phenyl 1-(4-nitrophenyl)cyclobutanecarboxylic acid ester

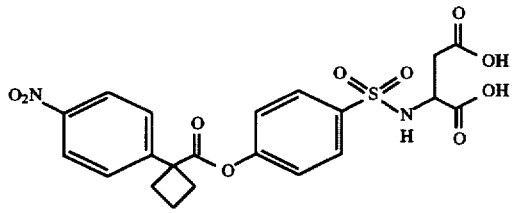

NMR (CD₃OD): δ 8.27 (2H, d, J=8.8 Hz), 7.87 (2H, d, J=8.8 Hz), 7.65 (2H, d, J=8.8 Hz), 7.15 (2H, d, J=8.8 Hz), 4.21 (1H, t, J=5.8 Hz), 3.05 (2H, m), 2.71 (4H, m), 2.25 (1H, m), 2.04 (1H, m);

TLC: Rf 0.17 (chloroform:methanol:water=8:2:0.2).

Example 2(102)

4-(N-carboxymethylsulfamoyl)phenyl 2RS-phenylbutanoic acid ester

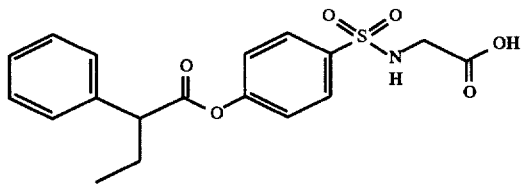

NMR (DMSO-d₆): δ 8.04 (1H, brs), 7.82 (2H, d, J=8 Hz), 7.45–7.25 (5H, m), 7.21 (2H, d, J=8 Hz), 3.86 (1H, t, J=7 Hz), 3.56 (2H, s), 2.10 and 1.85(each 1H, m), 0.91 (3H, t, J=7 Hz);

TLC: Rf 0.32 (acetic acid:methanol:chloroform=1:3:30).

Example 2(103)

4-(N-propyl-N-carboxymethylsulfamoyl)phenyl 2RS-phenylbutanoic acid ester

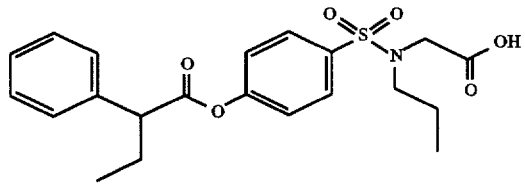

NMR (DMSO-d₆): δ 12.65 (1H, brs), 8.04 (1H, brs), 7.84 (2H, d, J=8 Hz), 7.45–7.25 (5H, m), 7.21 (2H, d, J=8 Hz), 3.92 (2H, s), 3.85 (1H, t, J=7 Hz), 3.10 (2H, t), 2.10 and 1.86 (each 1H, m), 1.44 (2H, m), 0.92 (3H, t, J=7 Hz), 0.77 (3H, t, J=7 Hz);

TLC: Rf 0.54 (acetic acid:methanol:chloroform=1:3:30).

Example 2(104)

4-(N-benzyl-N-carboxymethylsulfamoyl)phenyl 2RS-phenylbutanoic acid ester

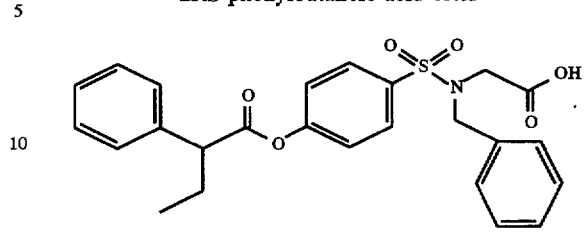

NMR (CDCl₃): δ 7.90–7.79 (2H, m), 7.43–7.08 (12H, m), 6.34 (1H, br), 4.46 (2H, s), 3.90 (2H, s), 3.70 (1H, t, J=7 Hz), 2.22 (1H, ddq, J=14 Hz, 7 Hz, 7 Hz), 1.92 (1H, ddq, J=14 Hz, 7 Hz, 7 Hz), 0.98 (3H, t, J=7 Hz);

TLC: Rf 0.42 (dichloromethane:methanol=9:1).

Example 2(105)

4-(N-2-phenylethyl-N-carboxymethylsulfamoyl) phenyl 2RS-phenylbutanoic acid ester

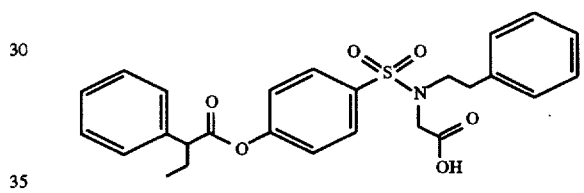

NMR (CDCl₃): δ 7.77 (2H, d, J=8 Hz), 7.40–7.04 (12H, m), 5.89 (1H, br), 3.95 (2H, s), 3.69 (1H, t, J=7 Hz), 3.53–3.40 (2H, m), 2.91–2.80 (2H, m), 2.2 (1H, ddq, J=14 Hz, 7 Hz, 7 Hz), 1.90 (1H, ddq, J=14 Hz, 7 Hz, 7 hz), 0.97 (3H, t, J=7 Hz);

TLC: Rf 0.41 (dichloromethane:methanol=9:1).

Example 2(106)

4-(N-phenyl-N-carboxymethylsulfamoyl)phenyl 2RS-phenylbutanoic acid ester

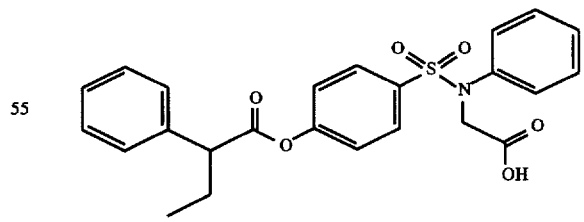

NMR (CDCl₃): δ 7.63 (2H, d, J=8 Hz), 7.45–7.04 (12H, m), 6.20 (1H, br), 4.40 (2H, s), 3.70 (1H, t, J=7 Hz), 2.23 (1H, ddq, J=1 4 Hz, 7 Hz, 7 hz), 1.91 (1H, ddq, J=14 Hz, 7 Hz, 7 Hz), 0.99 (3H, t, J=7 Hz);

TLC: Rf 0.41 (dichloromethane:methanol=9:1).

Example 2(107)

4-(N,N-bis(2-hydroxyethyl)sulfamoyl)-2-methyl 2RS-(4-(pyrrolidin-1-yl)phenyl)butanoic acid ester.hydrochloride

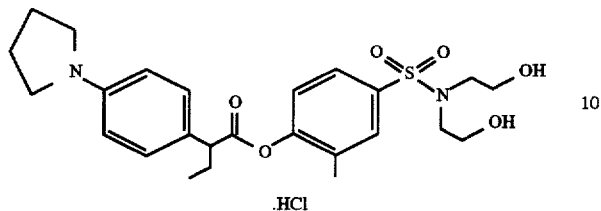

NMR (CD$_3$OD): δ 7.78–7.50 (6H, m), 7.15 (1H, d, J=8 Hz), 3.96 (1H, t, J=7 Hz), 3.95–3.80 (8H, m), 3.35–3.18 (4H, m), 2.40–2.15 (5H, m), 2.10–1.80 (1H, m), 2.02 (3H, s), 0.99 (3H, t, J=7 Hz);

TLC: Rf 0.23 (hexane:ethyl acetate=1:1).

Example 2(108)

4-(N,N-bis(2-(2-hydroxyethoxy)ethyl)sulfamoyl)-2-methylphenyl 2RS-(4-(pyrrolidin-1-yl)phenyl) butanoic acid ester

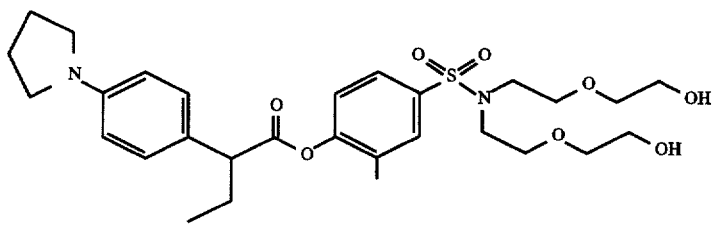

NMR (CDCl$_3$): δ 7.70–7.55 (2H, m), 7.23 (2H, d, J=9 Hz), 7.06 (1H, d, J=8 Hz), 6.55 (2H, d, J=9 Hz), 3.75–3.45 (13H, m), 3.43–3.23 (8H, m), 3.05 (2H, brs), 2.30–1.73 (9H, m), 0.98 (3H, t, J=7 Hz);

TLC: Rf 0.33 (ethyl acetate).

Example 2(109)

4-(N-(3RS-carboxy-1,4-benzodioxan-5-yl)sulfamoyl)phenyl 2RS-(4-(pyrrolidin-1-yl)phenyl) butanoic acid ester.hydrochloride

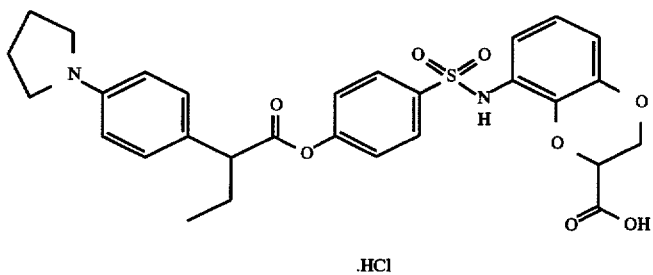

NMR (DMSO-d$_6$): δ 9.67 (1H, s), 7.80 (2H, d, J=9 Hz), 7.20 (2H, d, J=9 Hz), 7.13 (2H, d, J=9 Hz), 6.84–6.57 (5H, m), 4.78 (1H, t, J=3 Hz), 4.28 (1H, dd, J=11 Hz, 3 Hz), 4.13–4.00 (1H, m), 3.68 (1H, t, J=7 Hz), 3.35–3.18 (4H, m), 2.15–1.88 (5H, m), 1.88–1.60 (1H, m), 0.88 (3H, t, J=7 Hz);

TLC: Rf 0.18 (chloroform:methanol:acetic acid=40:2:1).

Example 2(110)

4-(N-2RS-hydroxy-4R-hydroxy-5R-hydroxy-6R-hydroxymethylperhydropyran-3R-ylsulfamoyl)-2-methylphenyl 2RS-(4-(pyrrolidin-1-yl)phenyl) butanoic acid ester

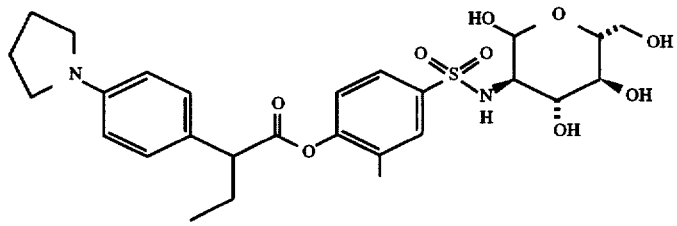

NMR (DMSO-d$_6$+3 drop of CD$_3$OD): δ 7.80–7.60 (2H, m), 7.20 (2H, d, J=8.5 Hz), 7.05 (1H, d, J=8.5 Hz), 6.60 (2H, d, J=8.5 Hz), 4.78 (1H, d, J=3.5 Hz), 3.70 (1H, t, J=7.5 Hz), 3.65–3.35 (4H, m), 3.30–3.15 (4H, m), 3.03 (1H, t, J=9.0 Hz), 2.90 (1H, dd, J=10.5, 3.5 Hz), 2.20–1.60 (2H, m), 2.00–1.90 (4H, m), 1.94 (3H, s), 0.91 (3H, t, J=7.5 Hz);

TLC: Rf 0.55 (chloroform:methanol:water=40:10:1).

Example 2(111)

4-(N-3-carboxyadamantan-1-ylsulfamoyl)phenyl 2RS-(4-(pyrrolidin-1-yl)phenyl)butanoic acid ester

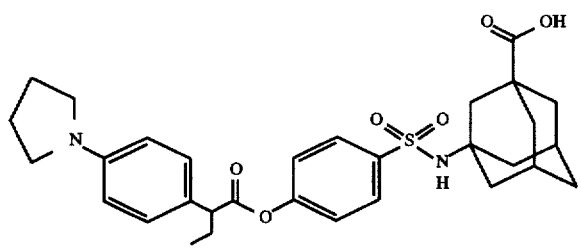

NMR (CDCl$_3$): δ 7.85 (2H, d, J=8.8 Hz), 7.22 (2H, d, J=8.8 Hz), 7.12 (2H, d, J=8.8 Hz), 6.54 (2H, d, J=8.8 Hz), 4.60 (1H, s), 3.59 (1H, t, J=7.4 Hz), 3.40–3.15 (4H, m), 2.30–1.40 (20H, m), 0.98 (3H, t, J=7.6 Hz);

TLC: Rf 0.60 (chloroform:methanol:acetic acid=40:2:1).

Example 2(112)

4-(N-(1S,4R,3R-carboxybicyclo[2.2.1]heptan-2S-yl)sulfamoyl)phenyl 2RS-(4-(pyrrolidin-1-yl)phenyl) butanoic acid ester

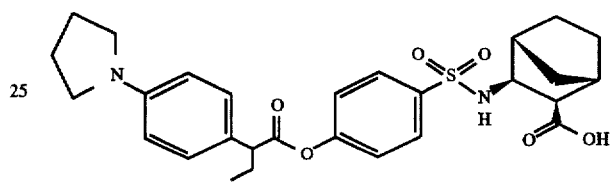

NMR (CDCl$_3$): δ 7.83 (2H, d, J=8.6 Hz), 7.21 (2H, d, J=8.6 Hz), 7.11 (2H, d, J=8.6 Hz), 6.55 (2H, d, J=8.6 Hz), 7.6–7.4 (1H, br), 3.58 (1H, t, J=7.6 Hz), 3.58 (1H, t, J=8.0 Hz), 3.40–3.20 (4H, m), 2.64 (1H, d, J=8.0 Hz), 2.42 (1H, s), 2.30–1.70 (4H, m), 2.10–1.90 (4H, m), 1.50–1.30 (2H, m), 1.30–0.90 (3H, m), 0.97 (3H, t, J=7.3 Hz);

TLC: Rf 0.33 (chloroform:methanol:acetic acid=40:2:1).

Example 2(113)

4-(N-3S-carboxycyclohexane-1R-ylsulfamoyl)phenyl 2RS-(4-(pyrrolidin-1-yl)phenyl)butanoic acid ester.hydrochloride

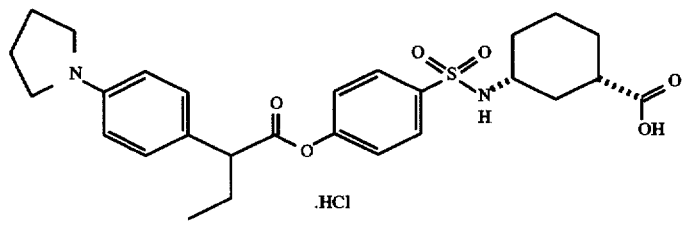

NMR (DMSO-d$_6$): δ 7.90–7.70 (3H, m), 7.30–7.10 (4H, m), 6.70 (2H, d, J=9 Hz), 3.71 (1H, t, J=7 Hz), 3.35–3.15 (4H, m), 3.09–2.86 (1H, m), 2.27–1.45 (11H, m), 1.33–0.95 (4H, m), 0.89 (3H, t, J=7 Hz);

TLC: Rf 0.36 (ethyl acetate:hexane:acetic acid=5:5:0.1).

Example 2(114)

4-(N-2RS-carboxycyclohexane-1RS-ylsulfamoyl) phenyl 2RS-(4-(pyrrolidin-1-yl)phenyl)butanoic acid ester

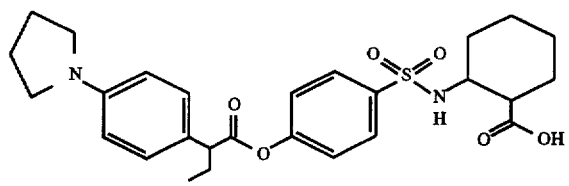

NMR (CDCl$_3$): δ 7.84 (2H, d, J=8.8 Hz), 7.23–7.08 (4H, m), 6.55 (2H, d, J=8.6 Hz), 5.70 (1H, brs), 3.59 (1H, t, J=8.0 Hz), 3.45 (1H, brs), 3.32–3.26 (4H, m), 2.65 (1H, brs), 2.25–1.20 (14H, m), 0.98 (3H, t, J=7.0 Hz);

TLC: Rf 0.22 (hexane:ethyl acetate=1:1).

Example 2(115)

4-(2S-carboxypyrrolidin-1-ylsulfonyl)phenyl 2RS-(2H-1,4-benzoxazin-3-on-6-yl)butanoic acid ester

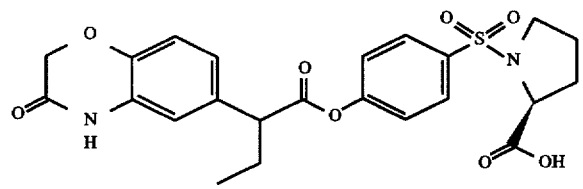

NMR (DMSO-d$_6$): δ 10.73 (1H, s), 7.88 (2H, d, J=8.6 Hz), 7.26 (2H, d, J=8.6 Hz), 6.95 (3H, s), 4.57 (2H, s), 4.13–4.00 (1H, m), 3.79 (1H, t, J=7.6 Hz), 3.40–3.08 (2H, m), 2.20–1.40 (6H, m), 0.91 (3H, t, J=7.2 Hz);

TLC: Rf 0.35 (acetic acid:methanol:chloroform=1:2:40).

Example 2(116)

4-(2R-carboxypyrrolidin-1-ylsulfonyl)phenyl 2RS-(2H-1,4-benzoxazin-3-on-6-yl)butanoic acid ester

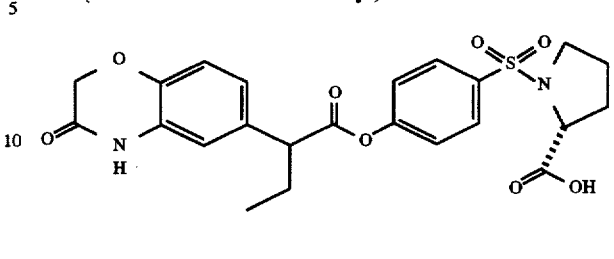

NMR (DMSO-d$_6$): δ 13.4–12.2 (1H, br), 10.72 (1H, s), 7.88 (2H, d, J=8.6 Hz), 7.29 (2H, d, J=8.6 Hz), 6.95 (3H, s), 4.57 (2H, s), 4.16–4.08 (1H, m), 3.80 (1H, t, J=7.6 Hz), 3.50–3.05 (2H, m), 2.05–1.45 (6H, m), 0.91 (3H, t, J=7.2 Hz);

TLC: Rf 0.36 (acetic acid:methanol:chloroform=1:2:40).

Example 2(117)

4-(2S-carboxypyrrolidin-1-ylsulfonyl)phenyl 2RS-(2-methylbenzimidazol-5-yl)butanoic acid ester.hydrochloride

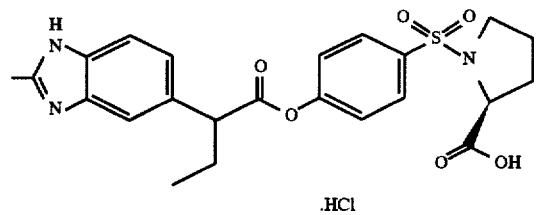

NMR (CD$_3$OD): δ 7.90–7.61 (5H, m), 7.23 (2H, d, J=9 Hz), 4.23–4.17 (1H, m), 4.06 (1H, t, J=8 Hz), 3.51–3.40 (1H, m), 3.31–3.20 (2H, m), 2.87 (3H, s), 2.38–2.24 (1H, m), 2.06–1.86 (3H, m), 1.76–1.64 (1H, m), 1.01 (3H, t, J=7 Hz);

TLC: Rf 0.21 (chloroform:methanol:water=8:2:0.2).

Example 2(118)

4-(N-2-(N'-carboxymethylcarbamoyl) phenylsulfamoyl)phenyl 2-(naphthalen-1-yl)acetic acid ester

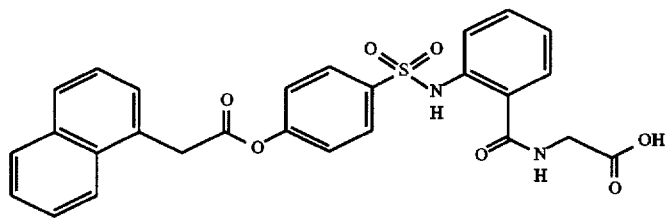

NMR (DMSO-$d_6$): δ 12.74 (1H, br), 11.58 (1H, br), 9.20 (1H, t, J=5 Hz), 8.08–7.70 (6H, m), 7.63–7.42 (6H, m), 7.29 (2H, d, J=9 Hz), 7.17–7.10 (1H, m), 4.46 (2H, s), 3.89 (2H, d, J=6 Hz);

TLC: Rf 0.28 (acetic acid:methanol:chloroform=1:2:40).

Example 2(119)

4-(N-2-(N'-carboxymethylcarbamoyl)phenylsulfamoyl)phenyl 2-(naphthalen-2-yl)acetic acid ester

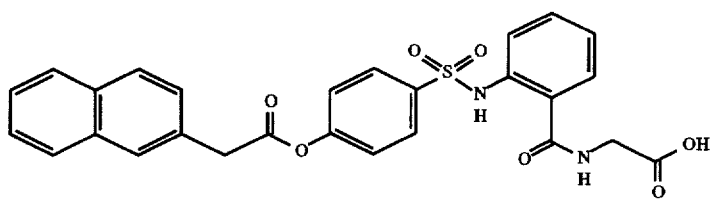

NMR (DMSO-$d_6$): δ 12.67 (1H, br), 11.63 (1H, br), 9.24 (1H, t-like), 7.93–7.71 (7H, m), 7.54–7.43 (5H, m), 7.36–7.29 (2H, m), 7.18–7.10 (1H, m), 4.15 (2H, s), 3.90 (2H, d, J=6 Hz);

TLC: Rf 0.31 (acetic acid:methanol:chloroform=1:2:40).

Example 2(120)

4-(N-2-(N'-carboxymethylcarbamoyl)phenylsulfamoyl)phenyl 2RS-(1,3-benzodioxol-5-yl)butanoic acid ester

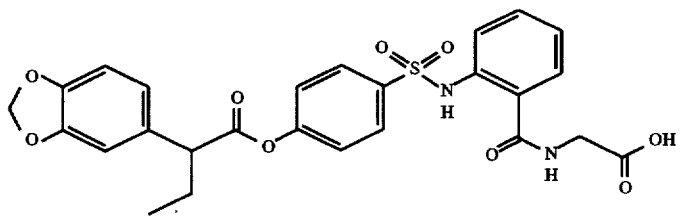

NMR (DMSO-$d_6$): δ 12.73 (1H, br), 11.62 (1H, br), 9.22 (1H, t, J=6 Hz), 7.82–7.71 (3H, m), 7.53–7.42 (2H, m), 7.26–7.10 (3H, m), 6.94–6.79 (3H, m), 6.01 (2H, s), 3.89 (2H, d, J=5 Hz), 3.75 (1H, t, J=8 Hz), 2.16–1.95 and 1.86–1.64 (each 1H, m), 0.86 (3H, t, J=7 Hz);

TLC: Rf 0.68 (acetic acid:methanol:chloroform=1:3:30).

Example 2(121)

4-(N-2-(N'-carboxymethylcarbamoyl)phenylsulfamoyl)phenyl 2RS-(thiophen-2-yl)butanoic acid ester

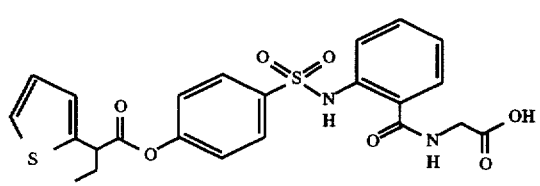

NMR (DMSO-$d_6$): δ 9.4–9.2 (1H, br), 7.9–7.7 (3H, m), 7.6–7.4 (3H, m), 7.3–7.0 (5H, m), 4.19 (1H, t, J=7 Hz), 3.90 (2H, d, J=5 Hz), 2.2–2.0 (1H, m), 2.0–1.8 (1H, m), 0.92 (3H, t, J=7 Hz);

TLC: Rf 0.18 (acetic acid:methanol:chloroform=1:2:40).

Example 2(122)

4-(N-2-(N'-carboxymethylcarbamoyl)phenylsulfamoyl)phenyl 2-(1,3-benzodioxol-5-yl)-2-ethylbutanoic acid ester

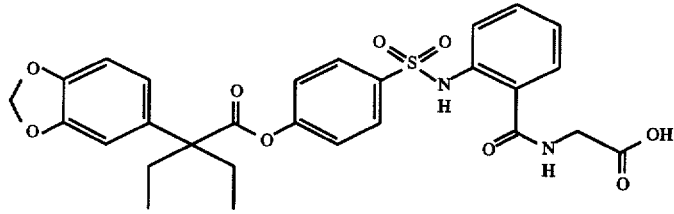

NMR (DMSO-$d_6$): δ 12.62 (1H, br), 11.66 (1H, br), 9.24 (1H, t-like), 7.82–7.71 (3H, m), 7.52–7.42 (2H, m), 7.31–7.10 (3H, m), 6.91–6.76 (3H, m), 6.01 (2H, s), 3.89 (2H, d, J=5 Hz), 2.09–1.96 (4H, m), 0.75 (6H, t, J=8 Hz);

TLC: Rf 0.39 (acetic acid:methanol:chloroform=1:2:40).

Example 2(123)

4-(N-2-(N'-carboxymethylcarbamoyl)phenylsulfamoyl)phenyl 2RS-(thiophen-2-yl)-3-methylbutanoic acid ester

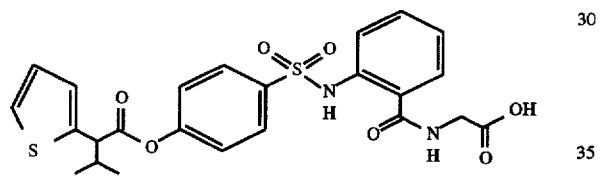

NMR (DMSO-$d_6$): δ 12.64 (1H, br), 11.70 (1H, br), 9.24 (1H, t-like), 7.82 (2H, d, J=8 Hz), 7.74 (1H, d, J=8 Hz), 7.54–7.43 (3H, m), 7.26–7.00 (5H, m), 3.95 (1H, d, J=7 Hz), 3.90 (2H, d, J=6 Hz), 2.36–2.18 (1H, m), 1.07 and 0.83 (each 3H, each d, J=7 Hz);

TLC: Rf 0.24 (acetic acid:methanol:chloroform=1:2:40).

Example 2(124)

4-(N-2-(N'-carboxymethylcarbamoyl)phenylsulfamoyl)phenyl 2RS-(cyclohexane-1-yl)butanoic acid ester

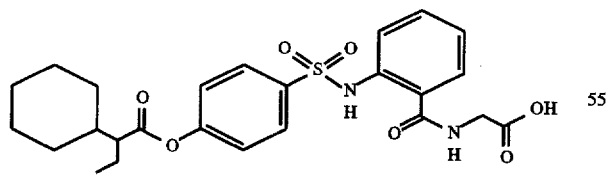

NMR (DMSO-$d_6$): δ 12.72 (1H, br), 11.64 (1H, br), 9.27 (1H, br), 7.83 (2H, d, J=10 Hz), 7.75 (1H, d, J=10 Hz), 7.51 (1H, t, J=10 Hz), 7.48 (1H, t, J=8 Hz), 7.27 (2H, d, J=12 Hz), 7.15 (1H, t, J=10 Hz), 3.90 (2H, d, J=3 Hz), 2.35–2.30 (1H, m), 1.78 (1H, d-like), 1.71–1.55 (7H, m), 1.25–0.98 (5H, m), 0.92 (3H, t, J=7 Hz);

TLC: Rf 0.30 (acetic acid:methanol:chloroform=1:2:20).

Example 2(125)

4-(N-2-(N'-carboxymethylcarbamoyl)phenylsulfamoyl)phenyl 2RS-(pyridin-3-yl)butanoic acid ester NMR (DMSO-$d_6$): δ 12.00 (2H, br), 9.36 (1H, br), 8.68–8.46 (2H, br), 7.85–7.78 (4H, m), 7.50–7.10 (6H, m), 4.04–3.75 (3H, br), 2.27–2.02 and 1.96–1.74 (each 1H, m), 0.90 (3H, br);

TLC: Rf 0.37 (acetic acid:methanol:chloroform=1:3:30).

Example 2(126)

4-(N-2-(N'-carboxymethylcarbamoyl)
phenylsulfamoyl)phenyl 2RS-(2H-1,4-benzoxazin-
3-on-6yl)butanoic acid ester

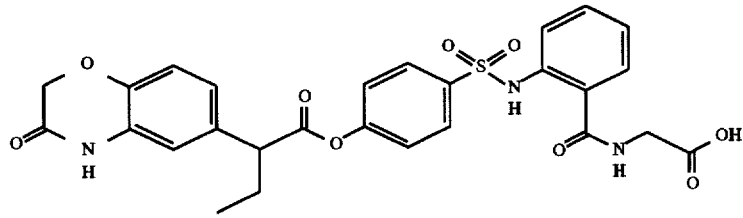

NMR (DMSO-d$_6$): δ 10.69 (1H, s), 9.53 (1H, t-like), 8.29 (1H, s), 7.83–7.73 (3H, m), 7.49–7.39 (2H, m), 7.20–6.91 (6H, m), 4.55 (2H, s), 3.90–3.86 (2H, d-like), 3.73 (1H, t, J=7 Hz), 2.14–1.98 and 1.80–1.66 (each 1H, m), 0.88 (3H, t, J=7 Hz);

TLC: Rf 0.38 (acetic acid:methanol:chloroform=1:3:30).

Example 2(127)

4-(N-2-(N'-carboxymethylcarbamoyl)
phenylsulfamoyl)phenyl 2RS-(2-(N-
methoxycarbonylamino)thiazol-4-yl)butanoic acid
ester

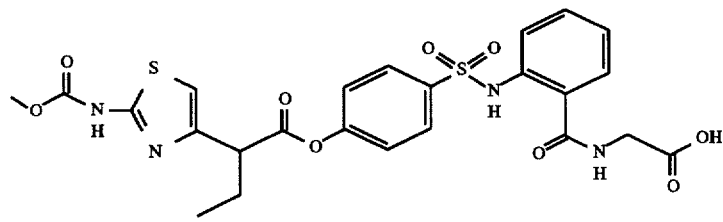

NMR (DMSO-d$_6$): δ 12.30 (1H, br), 11.81 (2H, br), 9.24 (1H, t-like), 7.81 (2H, d, J=7 Hz), 7.74 (1H, d, J=8 Hz), 7.51–7.45 (2H, m), 7.25–7.10 (3H, m), 7.07 (1H, s), 3.90 (1H, t, J=7 Hz), 3.89 (2H, d, J=4 Hz), 3.73 (3H, s), 2.12–1.81 (2H, m), 0.90 (3H, t, J=7 Hz);

TLC: Rf 0.28 (chloroform:methanol:water=8:2:0.2).

Example 2(128)

4-(N-2-(N'-carboxymethylcarbamoyl)
phenylsulfamoyl)phenyl 2RS-(2-
methylbenzimidazol-5-yl)butanoic acid
ester.hydrochloride

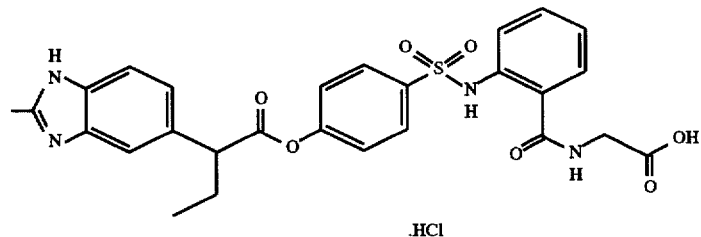

NMR (CD$_3$OD): δ 7.75–7.68 (4H, m), 7.63–7.57 (3H, m), 7.46–7.37 (1H, m), 7.16–7.07 (3H, m), 4.00 (1H, t, J=8 Hz), 3.94 (2H, s), 2.85 (3H, s), 2.34–2.15 and 2.06–1.88 (each 1H, m), 0.97 (3H, t, J=7 Hz);

TLC: Rf 0.26 (chloroform:methanol:water=8:2:0.2).

Example 2(129)

4-(N-2-(N'-carboxymethylcarbamoyl)
phenylsulfamoyl)phenyl 2RS-(1H-1-methyl-2-
pyridon-3-yl)butanoic acid ester

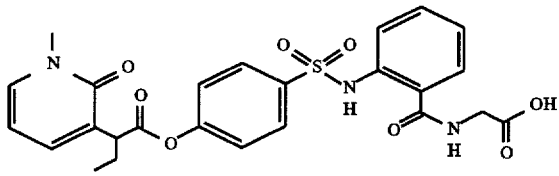

NMR (DMSO-$d_6$): δ 12.59 (1H, br), 11.65 (1H, br), 9.23 (1H, t-like), 7.82–7.63 (4H, m), 7.49–7.40 (3H, m), 7.25–7.09 (3H, m), 6.23 (1H, t, J=7 Hz), 3.90 (2H, d, J=6 Hz), 3.72 (1H, t, J=7 Hz), 3.45 (3H, s), 2.04–1.70 (2H, m), 0.88 (3H, t, J=7 Hz);

TLC: Rf 0.27 (chloroform:methanol:water=8:2:0.2).

Example 2(130)

4-(N-2-(N'-carboxymethylcarbamoyl)
phenylsulfamoyl)phenyl 2RS-phenylbutanoic acid
ester

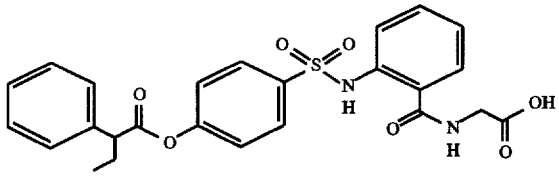

NMR (CDCl$_3$): δ 7.67 (3H, m), 7.50–7.20 (7H, m), 7.08 (1H, t, J=8 Hz), 6.97 (2H, d, J=8 Hz), 6.60 (1H, s), 5.69 (2H, brs), 4.00 (2H, m), 3.66 (1H, t, J=7 Hz), 2.16 (1H, m), 1.86 (1H, m), 0.94 (3H, t, J=7 Hz);

TLC: Rf 0.23 (chloroform:methanol=5:1).

Example 2(131)

4-(N-2-(N'-carboxymethylcarbamoyl)
phenylsulfamoyl)phenyl 2-phenyl-2-ethylbutanoic
acid ester

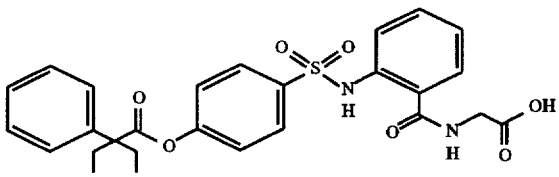

NMR (DMSO-$d_6$): δ 12.63 (1H, br), 11.67 (1H, br), 9.22 (1H, t-like), 7.82–7.70 (3H, m), 7.51–7.07 (10H, m), 3.89 (2H, d, J=6 Hz), 2.09 (4H, m), 0.76 (6H, m);

TLC: Rf 0.58 (acetic acid:methanol:chloroform=1:3:30).

Example 2(132)

4-(N-2-(N'-carboxymethylcarbamoyl)
phenylsulfamoyl)phenyl 2RS-phenylpropanoic acid
ester NMR ($d_6$-DMSO): δ 12.73 (1H, br), 11.59 (1H, br), 9.25–9.19 (1H, t-like), 7.82–7.70 (3H, m), 7.50–7.10 (10H, m), 4.10 (1H, q, J=7 Hz), 3.89 (2H, d, J=5 Hz), 1.49 (3H, d, J=7 Hz);

TLC: Rf 0.32 (acetic acid:methanol:chloroform=1:2:40).

Example 2(133)

4-(N-2-(N'-carboxymethylcarbamoyl)
phenylsulfamoyl)phenyl 2R-phenylbutanoic acid
ester NMR (CDCl$_3$): δ 10.22 (1H, s), 7.71–7.65 (3H, m), 7.49–7.26 (6H, m), 7.15–7.10 (2H, m), 6.99–6.95 (2H, m), 6.49 (1H, br), 6.36 (1H, br), 4.01 (2H, d, J=5 Hz), 3.65 (1H, t, J=7 Hz), 2.24–2.11 and 1.95–1.81 (each 1H, m), 0.95 (3H, t, J=7 Hz);

TLC: Rf 0.36 (acetic acid:methanol:chloroform=1:2:40).

Example 2(134)

4-(N-2-(N'-carboxymethylcarbamoyl)
phenylsulfamoyl)phenyl 2S-phenylbutanoic acid
ester NMR (CDCl$_3$): δ 10.29 (1H, s), 7.70–7.65 (3H, m), 7.45–7.26 (6H, m), 7.13–7.05 (2H, m), 7.00–6.96 (2H, m), 6.60 (1H, br), 4.01 (2H, d, J=5 Hz), 3.66 (1H, t, J=8 Hz), 2.24–2.10 and 1.95–1.81 (each 1H, m), 0.95 (3H, t, J=7 Hz);

TLC: Rf 0.36 (acetic acid:methanol:chloroform=1:2:40).

Example 2(135)

4-(N-2-(N'-carboxymethylcarbamoyl)
phenylsulfamoyl)phenyl 2-phenyl-2-
methylpropanoic acid ester

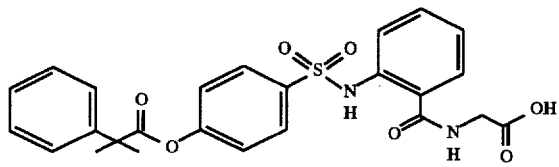

NMR (DMSO-d$_6$): δ 12.67 (1H, br), 11.65 (1H, br), 9.22 (1H, t-like), 7.82–7.71 (3H, m), 7.52–7.09 (10H, m), 3.89 (2H, d, J=6 Hz), 1.63 (6H, s);

TLC: Rf 0.34 (acetic acid:methanol:chloroform=1:3:30).

Example 2(136)

4-(N-2-(N'-carboxymethylcarbamoyl)
phenylsulfamoyl)phenyl 1-
phenylcyclohexanecarboxylic acid ester

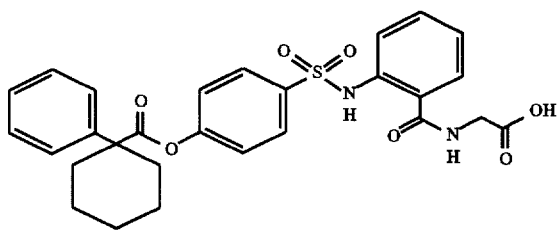

NMR (DMSO-d$_6$): δ 12.72 (1H, br), 11.61 (1H, br), 9.24 (1H, t-like), 7.81–7.70 (3H, m), 7.48–7.25 (7H, m), 7.14–7.10 (3H, m), 3.88 (2H, d, J=6 Hz), 2.56–2.41 (2H, m), 1.85–1.23 (8H, m);

TLC: Rf 0.48 (acetic acid:methanol:chloroform=1:3:30).

Example 2(137)

4-(N-2-(N'-carboxymethylcarbamoyl)
phenylsulfamoyl)phenyl 1-
phenylcyclopropanecarboxylic acid ester

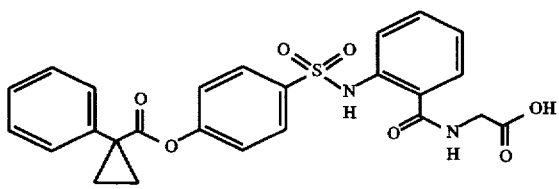

NMR (DMSO-d$_6$): δ 9.3–9.1 (1H, brt), 7.8–7.6 (3H, m), 7.5–7.0 (10H, m), 3.88 (2H, d, J=5 Hz), 1.68 (2H, dd, J=6,4 Hz), 1.39 (2H, dd, J=6,4 Hz);

TLC: Rf 0.20 (acetic acid:methanol:chloroform=1:2:40).

Example 2(138)

4-(N-2-(N'-carboxymethylcarbamoyl)
phenylsulfamoyl)phenyl 1-
phenylcyclopentanecarboxylic acid ester

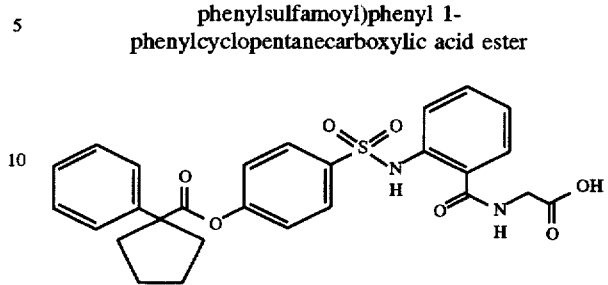

NMR (DMSO-d$_6$): δ 9.3–9.1 (1H, brt), 7.8–7.7 (3H, m), 7.5–7.2 (7H, m), 7.2–7.0 (3H, m), 3.87 (2H, d, J=5 Hz), 2.7–2.5 (2H, m), 2.1–1.9 (2H, m), 1.9–1.6 (4H, m);

TLC: Rf 0.21 (acetic acid:methanol:chloroform=1:2:40).

Example 2(139)

4-(N-2-(N'-carboxymethylcarbamoyl)
phenylsulfamoyl)phenyl 1-
phenylcyclobutanecarboxylic acid ester

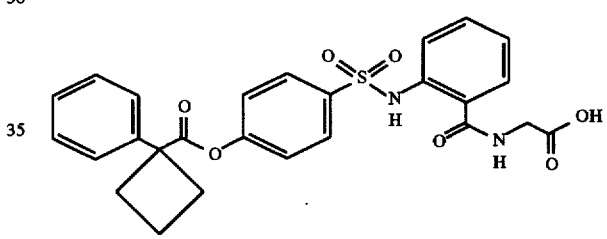

NMR (DMSO-d$_6$): δ 9.3–9.1 (1H, brt), 7.8–7.6 (3H, m), 7.5–7.2 (7H, m), 7.2–7.1 (3H, m), 3.88 (2H, d, J=5 Hz), 3.0–2.8 (2H, m), 2.6–2.4 (2H, m), 2.1–1.8 (2H, m);

TLC: Rf 0.19 (acetic acid:methanol:chloroform=1:2:40).

Example 2(140)

4-(N-2-(N'-carboxymethylcarbamoyl)
phenylsulfamoyl)phenyl 2-phenylacetic acid ester

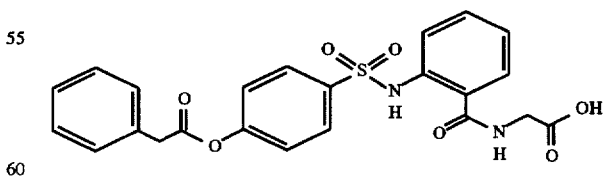

NMR (DMSO-d$_6$): δ 10.01–9.76 (1H, br), 7.82–7.76 (4H, m), 7.41–7.22 (9H, m), 7.03–6.90 (1H, m), 3.96 (2H, s), 3.86 (2H, m);

TLC: Rf 0.66 (acetic acid:methanol:chloroform=1:3:30).

Example 2(141)

4-(N-2-(N'-carboxymethylcarbamoyl)phenylsulfamoyl)phenyl 2RS-chloro-2-phenylacetic acid ester

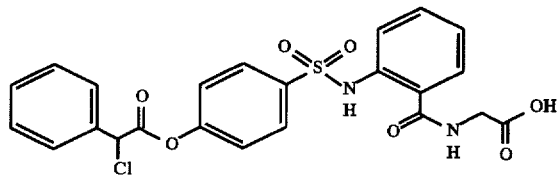

NMR (DMSO-d$_6$): δ 9.2–9.1 (1H, brt), 7.82 (2H, d, J=8 Hz), 7.71 (1H, d, J=8 Hz), 7.6–7.4 (7H, m), 7.29 (2H, d, J=8 Hz), 7.2–7.1 (1H, m), 6.26 (1H, s), 3.88 (2H, d, J=5 Hz);

TLC: Rf 0.18 (acetic acid:methanol:chloroform=1:2:40).

Example 2(142)

4-(N-2-(N'-carboxymethylcarbamoyl)phenylsulfamoyl)phenyl 2RS-chloro-2-phenylbutanoic acid ester

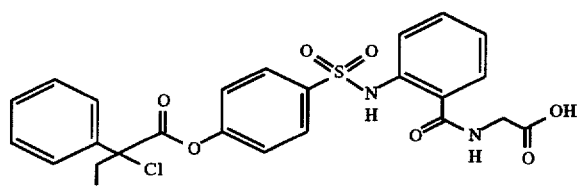

NMR (DMSO-d$_6$): δ 9.3–9.2 (1H, br), 7.93 (2H, d, J=8 Hz), 7.72 (1H, d, J=8 Hz), 7.65–7.55 (2H, m), 7.6–7.4 (5H, m), 7.37 (2H, d, J=8 Hz), 7.2–7.1 (1H, m), 3.88 (2H, d, J=5 Hz), 2.6–2.4 (2H, m), 0.97 (3H, t, J=7 Hz);

TLC: Rf 0.20 (acetic acid:methanol:chloroform=1:2:40).

Example 2(143)

4-(N-2-(N'-carboxymethylcarbamoyl)phenylsulfamoyl)phenyl 2,2-diphenylbutanoic acid ester

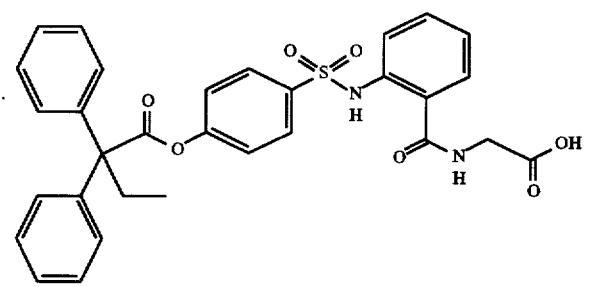

NMR (DMSO-d$_6$): δ 9.51–9.38 (1H, m), 7.86–7.68 (4H, m), 7.51–7.20 (1 1H, m), 7.19–7.01 (4H, m), 3.84 (2H, d, J=6 Hz), 2.53–2.41 (2H, m), 0.79 (3H, t, J=7 Hz);

TLC: Rf 0.44 (acetic acid:methanol:chloroform=1:3:30).

Example 2(144)

4-(N-2-(N'-carboxymethylcarbamoyl)phenylsulfamoyl)phenyl 2RS-methyl-2-phenylbutanoic acid ester

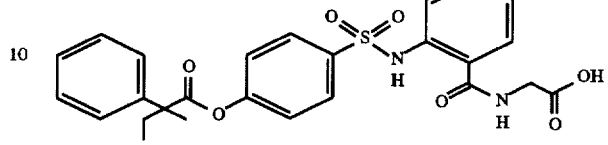

NMR (DMSO-d$_6$): δ 9.3–9.2 (1H, br), 7.88 (2H, d, J=8 Hz), 7.70 (1H, d, J=8 Hz), 7.5–7.1 (10H, m), 3.88 (2H, d, J=5 Hz), 2.2–1.9 (2H, m), 1.57 (3H, s), 0.85 (3H, t, J=7 Hz);

TLC: Rf 0.15 (acetic acid:methanol:chloroform=1:2:40).

Example 2(145)

4-(N-2-(N'-carboxymethylcarbamoyl)phenylsulfamoyl)phenyl 2R-trifluoromethyl-2-phenyl-2-methoxyacetic acid ester

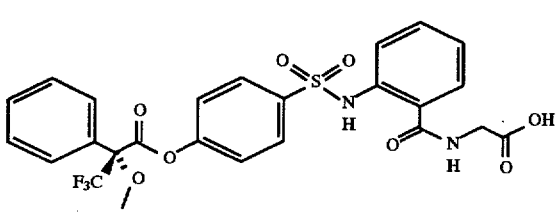

NMR (CD$_3$OD): δ 7.81 (2H, d, J=8.8 Hz), 7.62 (4H, m), 7.48 (4H, m), 7.27 (2H, d, J=8.8 Hz), 7.15 (1H, t, J=7.6 Hz), 3.97 (2H, s), 3.65 (3H, s);

TLC: Rf 0.28 (chloroform:methanol:water=9:1:0.1).

Example 2(146)

4-(N-2-(N'-carboxymethylcarbamoyl)phenylsulfamoyl)phenyl 2S-trifluoromethyl-2-phenyl-2-methoxyacetic acid ester

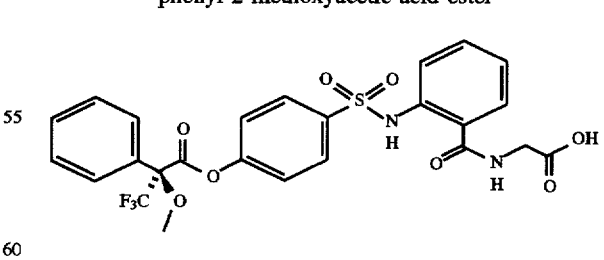

NMR (CD$_3$OD): δ 7.81 (2H, d, J=8.6 Hz), 7.62 (4H, m), 7.47 (4H, m) 7.27 (2H, d, J=8.6 Hz), 7.15 (1H, t, J=7.6 Hz), 3.97 (2H, s), 3.65 (3H, s);

TLC: Rf 0.27 (chloroform:methanol:water=9:1:0.1).

Example 2(147)

4-(N-2-(N'-carboxymethylcarbamoyl)
phenylsulfamoyl)phenyl 2RS-(4-methoxyphenyl)
butanoic acid ester

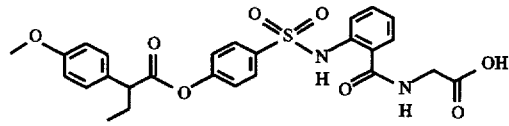

NMR (CDCl$_3$): δ 7.70–7.64 (2H, m), 7.42 (2H, t, J=8 Hz), 7.27–7.06 (4H, m), 6.97 (2H, d, J=9 Hz), 6.88 (2H, d, J=9 Hz), 6.55 (1H, t-like), 4.82 (2H, brs), 3.99 (2H, d, J=5 Hz), 3.79 (3H, s), 3.61 (1H, t, J=8 Hz), 2.12 and 1.85(each 1H, m), 0.94 (3H, t, J=7 Hz);

TLC: Rf 0.50 (acetic acid:methanol:chloroform=1:3:30).

Example 2(148)

4-(N-2-(N'-carboxymethylcarbamoyl)
phenylsulfamoyl)phenyl 2RS-(4-methoxyphenyl)-3-
methylbutanoic acid ester

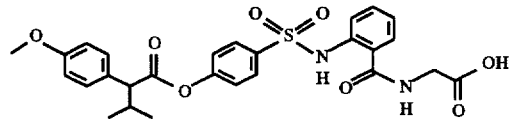

NMR (CDCl$_3$): δ 10.20 (1H, s), 7.73–7.64 (3H, m), 7.48–7.39 (2H, m), 7.33–7.22 (2H, m), 7.12 (1H, t, J=8 Hz), 6.98–6.85 (4H, m), 6.46 (1H, t-like), 5.08 (1H, br), 4.00 (2H, d, J=4 Hz), 3.80 (3H, s), 3.31 (1H, d, J=10 Hz), 2.46–2.27 (1H, m), 1.12 and 0.76 (each 3H, each d, J=7 Hz);

TLC: Rf 0.58 (acetic acid:methanol:chloroform=1:3:30).

Example 2(149)

4-(N-2-(N'-carboxymethylcarbamoyl)
phenylsulfamoyl)phenyl 2-(4-methoxyphenyl)-2-
methylpropanoic acid ester

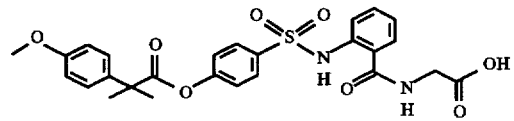

NMR (DMSO-d$_6$): δ 12.66 (1H, br), 11.64 (1H, br), 9.23 (1H, t-like), 7.81–7.70 (3H, m), 7.52–7.10 (7H, m), 6.92 (2H, d, J=9 Hz), 3.89 (2H, d, J=6 Hz), 3.74 (3H, s), 1.60 (6H, s);

TLC: Rf 0.35 (acetic acid:methanol:chloroform=1:3:30).

Example 2(150)

4-(N-2-(N'-carboxymethylcarbamoyl)
phenylsulfamoyl)phenyl 2RS-(4-methoxyphenyl)
propanoic acid ester

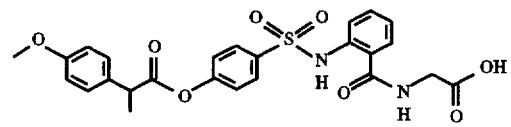

NMR (DMSO-d$_6$): δ 12.67 (1H, br), 11.64 (1H, br), 9.21 (1H, t-like), 7.81–7.70 (3H, m), 7.52–7.41 (2H, m), 7.30–7.09 (5H, m), 6.91 (2H, d, J=8 Hz), 4.00 (1H, q, J=7 Hz), 3.88 (2H, d, J=5 Hz), 3.73 (3H, s), 1.46 (3H, d, J=7 Hz);

TLC: Rf 0.30 (acetic acid:methanol:chloroform=1:3:30).

Example 2(151)

4-(N-2-(N'-carboxymethylcarbamoyl)
phenylsulfamoyl)phenyl 2-(4-methoxyphenyl)-2-
ethylbutanoic acid ester

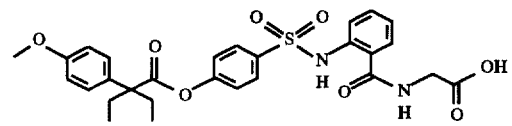

NMR (DMSO-d$_6$): δ 12.68 (1H, br), 11.62 (1H, br), 9.24 (1H, t-like), 7.82–7.71 (3H, m), 7.52–7.46 (2H, m), 7.30–7.09 (5H, m), 6.93 (2H, d, J=9 Hz), 3.89 (2H, d, J=6 Hz), 3.75 (3H, s), 2.10–1.98 (4H, m), 0.75 (6H, t, J=7 Hz);

TLC: Rf 0.34 (acetic acid:methanol:chloroform=1:3:30).

Example 2(152)

4-(N-2-(N'-carboxymethylcarbamoyl)
phenylsulfamoyl)phenyl 1-(4-methoxyphenyl)
cyclohexanecarboxylic acid ester

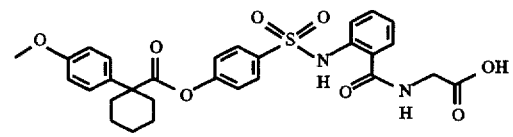

NMR (DMSO-d$_6$): δ 12.71 (1H, br), 11.57 (1H, br), 9.19 (1H, t-like), 7.77–7.66 (3H, m), 7.44–7.30 (4H, m), 7.13–7.04 (3H, m), 6.89 (2H, d, J=8 Hz), 3.85 (2H, d, J=6 Hz), 3.69 (3H, s), 2.47–2.36 (2H, m), 1.77–1.20 (8H, m);

TLC: Rf 0.51 (acetic acid:methanol:chloroform=1:3:30).

Example 2(153)

4-(N-2-(N'-carboxymethylcarbamoyl)
phenylsulfamoyl)phenyl 1-(4-methoxyphenyl)
cyclopentanecarboxylic acid ester

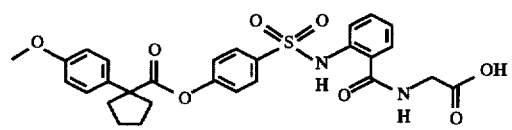

NMR (DMSO-d$_6$): δ 12.69 (1H, br), 11.66 (1H, br), 9.23 (1H, t-like), 7.80–7.71 (3H, m), 7.51–7.29 (4H, m), 7.18–7.07 (3H, m), 6.92 (2H, dd, J=1 and 8 Hz), 3.89 (2H, d, J=5 Hz), 3.74 (3H, s), 2.66–2.53 (2H, m), 2.01–1.87 (2H, m), 1.79–1.67 (4H, m);

TLC: Rf 0.68 (acetic acid:methanol:chloroform=1:3:30).

Example 2(154)

4-(N-2-(N'-carboxymethylcarbamoyl)
phenylsulfamoyl)phenyl 1-(4-methoxyphenyl)
cyclobutanecarboxylic acid ester

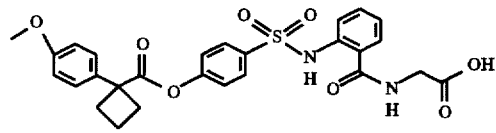

NMR (DMSO-d$_6$): δ 9.2–9.1 (1H, brt), 7.8–7.7 (3H, m), 7.5–7.4 (2H, m), 7.30 (2H, d, J=8 Hz), 7.2–7.0 (3H, m), 6.92 (2H, d, J=8 Hz), 3.87 (2H, d, J=5 Hz), 3.74 (3H, s), 2.9–2.7 (2H, m), 2.6–2.4 (2H, br), 2.1–1.7 (2H, br);

TLC: Rf 0.21 (acetic acid:methanol:chloroform=1:2:40).

Example 2(155)

4-(N-2-(N'-carboxymethylcarbamoyl)
phenylsulfamoyl)phenyl 1-(4-methoxyphenyl)
cyclopropanecarboxylic acid ester

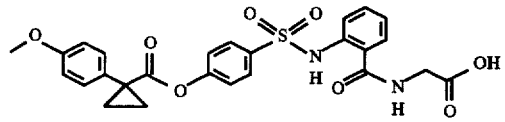

NMR (DMSO-d$_6$): δ 9.53–9.38 (1H, m), 7.79–7.72 (3H, m), 7.51–7.28 (4H, m), 7.26–7.19 (2H, m), 7.16–7.00 (1H, m), 6.89–6.84 (2H, m), 3.88 (2H, d, J=6 Hz), 3.73 (3H, s), 1.70–1.61 (2H, m), 1.38–1.29 (2H, m);

TLC: Rf 0.49 (acetic acid:methanol:chloroform=1:3:30).

Example 2(156)

4-(N-2-(N'-carboxymethylcarbamoyl)
phenylsulfamoyl)phenyl 2-(3,4-dimethoxyphenyl)-
2-ethylbutanoic acid ester

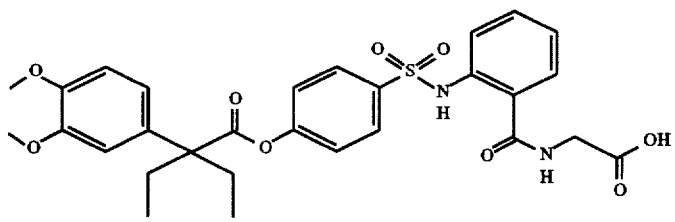

NMR (DMSO-d$_6$): δ 9.52–9.38 (1H, br), 7.83–7.71 (3H, m), 7.53–7.39 (2H, m), 7.19–7.02 (3H, m), 7.00–6.78 (3H, m), 3.89 (2H, d, J=6 Hz), 3.76 (6H, s), 2.06 (4H, q, J=7 Hz), 0.78 (6H, t, J=7 Hz);

TLC: Rf 0.39 (acetic acid:methanol:chloroform=1:3:30).

Example 2(157)

4-(N-2-(N'-carboxymethylcarbamoyl)
phenylsulfamoyl)phenyl 2RS-(3,4-
dimethoxyphenyl)butanoic acid ester

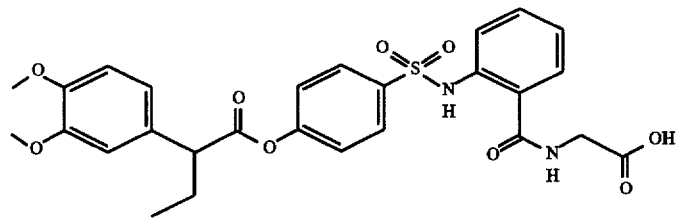

NMR (CDCl$_3$+CD$_3$OD): δ 7.45–7.41 (2H, m), 7.30–7.19 (2H, m), 7.18–7.01 (1H, m), 6.82–6.69 (3H, m), 6.56–6.52 (3H, m), 3.63 (2H, s), 3.53 (6H, s), 3.28 (1H, t, J=7 Hz), 1.98–1.42 (2H, m), 0.63 (3H, t, J=7 Hz);

TLC: Rf 0.64 (acetic acid:methanol:chloroform=1:3:30).

Example 2(158)

4-(N-2-(N'-carboxymethylcarbamoyl)
phenylsulfamoyl)phenyl 2-(3-methoxyphenyl)-2-
ethylbutanoic acid ester

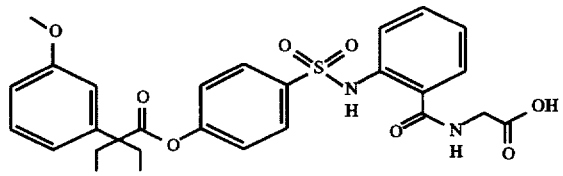

NMR (DMSO-d$_6$): δ 12.71 (1H, br), 11.65 (1H, br), 9.23 (1H, t-like), 7.83–7.71 (3H, m), 7.53–7.42 (2H, m), 7.35–7.10 (4H, m), 6.92–6.84 (3H, m), 3.89 (2H, d, J=6 Hz), 3.75 (3H, s), 2.12–2.01 (4H, m), 0.76 (6H, t, J=7 Hz);

TLC: Rf 0.39 (acetic acid:methanol:chloroform=1:2:40).

Example 2(159)

4-(N-2-(N'-carboxymethylcarbamoyl)
phenylsulfamoyl)phenyl 2RS-(2-methoxyphenyl)
butanoic acid ester

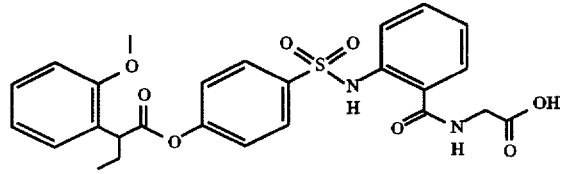

NMR (DMSO-d$_6$): δ 11.58 (1H, s), 9.24–9.18 (1H, m), 7.86–7.64 (3H, m), 7.57–7.44 (2H, m), 7.38–7.09 (5H, m), 7.08–6.91 (3H, m), 4.02–3.98 (1H, m), 3.88 (2H, d, J=6 Hz), 3.77 (3H, s), 2.18–1.84 (2H, m), 0.87 (3H, t, J=7 Hz);

TLC: Rf 0.41 (acetic acid:methanol:chloroform=1:3:30).

Example 2(160)

4-(N-2-(N'-carboxymethylcarbamoyl)
phenylsulfamoyl)phenyl 2-(2-methoxyphenyl)-2-
ethylbutanoic acid ester

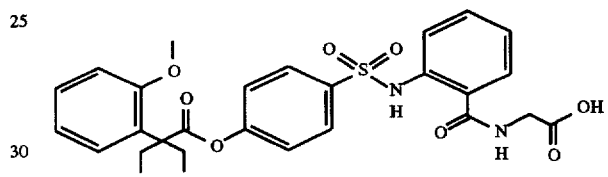

NMR (DMSO-d$_6$): δ 9.28–9.19 (1H, m), 7.82–7.69 (3H, m), 7.48–7.41 (2H, m), 7.28–7.08 (4H, m), 7.00–6.75 (4H, m), 3.89 (2H, d, J=6 Hz), 3.77 (3H, s), 2.18–1.82 (4H, m), 0.86 (6H, t, J=7 Hz);

TLC: Rf 0.39 (acetic acid:methanol:chloroform=1:3:30).

Example 2(161)

4-(N-2-(N'-carboxymethylcarbamoyl)
phenylsulfamoyl)phenyl 2RS-(3-methoxyphenyl)
butanoic acid ester

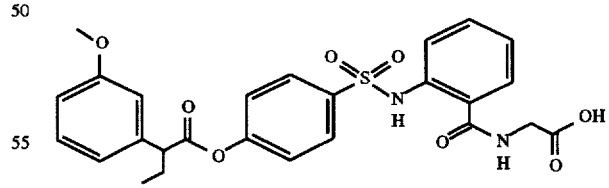

NMR (DMSO-d$_6$): δ 10.79 (1H, br), 7.85–7.79 (3H, m), 7.33–7.25 (2H, m), 7.17–7.06 (3H, m), 6.95–6.85 (3H, m), 6.74 (1H, t, J=7 Hz), 3.85 (2H, d-like), 3.80–3.69 (1H, m), 3.75 (3H, s), 2.15–2.01 and 1.91–1.71 (each 1H, m), 0.89 (3H, t, J=7 Hz);

TLC: Rf 0.47 (acetic acid:methanol:chloroform=1:2:40).

Example 2(162)

4-(N-2-(N'-carboxymethylcarbamoyl)
phenylsulfamoyl)phenyl 1-(2-methoxyphenyl)
cyclobutanecarboxylic acid ester

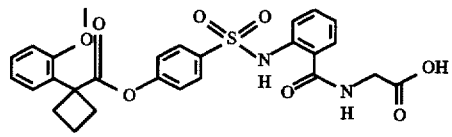

NMR (DMSO-d$_6$): δ 12.9–12.5 (1H, br), 11.7–11.4 (1H, br), 9.20 (1H, t-like), 7.78 (2H, d, J=8.6 Hz), 7.72 (1H, d, J=7.4 Hz), 7.52–7.38 (3H, m), 7.28 (1H, t-like), 7.20–7.08 (3H, m), 7.00 (2H, d, J=7.8 Hz), 3.89 (2H, d, J=5.6 Hz), 3.77 (3H, s), 2.85–2.65 (2H, m), 2.55–2.35 (2H, m) 2.20–2.00 and 2.00–1.80(each 1H, m);

TLC: Rf 0.30 (acetic acid:methanol:chloroform=1:2:40).

Example 2(163)

4-(N-2-(N'-carboxymethylcarbamoyl)
phenylsulfamoyl)-2,6-dimethylphenyl 2RS-(4-methoxyphenyl)butanoic acid ester

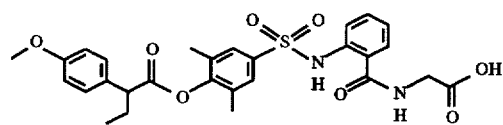

NMR (DMSO-d$_6$): δ 9.8–9.5 (brs, 1H), 7.8–7.7 (m, 1H), 7.5–7.2 (m, 6H), 7.1–6.8 (m, 4H), 4.0–3.7 (m, 3H), 3.74 (s, 3H), 2.2–1.7 (m, 8H), 0.90 (t, J=7.0 Hz, 3H);

TLC: Rf 0.30 (hexane:ethyl acetate=1:1).

Example 2(164)

4-(N-2-(N'-carboxymethylcarbamoyl)
phenylsulfamoyl)-2-isopropylphenyl 2RS-(4-methoxyphenyl)butanoic acid ester

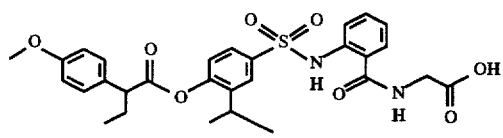

NMR (CDCl$_3$): δ 10.0–9.9 (m, 1H), 7.8–7.7 (m, 1H), 7.6–7.2 (m, 6H), 7.2–7.0 (m, 1H), 7.0–6.8 (m, 3H), 6.5–6.3 (m, 1H), 4.0–3.4 (m, 2H), 3.80 (s, 3H), 3.64 (t, J=7.8 Hz, 1H), 2.7–2.5 (m, 1H), 2.3–2.1 (m, 1H), 2.0–1.8 (m, 1), 0.95 (t, J=7.6 Hz, 3H), 0.83 (dd, J=2.0, 6.9 Hz, 6H);

TLC: Rf 0.49 (chloroform:methanol=3:1).

Example 2(165)

4-(N-2-(N'-carboxymethylcarbamoyl)
phenylsulfamoyl)phenyl 2RS-(4-(2-methylpropyloxy)phenyl)butanoic acid ester

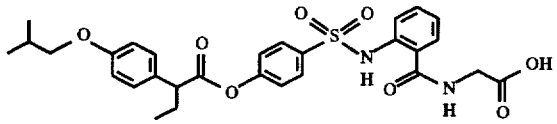

NMR (DMSO-d$_6$): δ 9.25–9.07 (1H, br), 8.02–7.98 (1H, d-like), 7.89–7.80 (2H, d-like), 7.79–7.65 (2H, m), 7.59–7.38 (3H, m), 7.18–7.09 (1H, m), 7.01–6.77 (2H, m), 3.97–3.65 (3H, m), 3.80 (3H, s), 3.97–3.65 (3H, s), 1.19 (6H, d, J=7 Hz);

TLC: Rf 0.37 (acetic acid:methanol:chloroform=1:3:30).

Example 2(166)

4-(N-2-(N'-carboxymethylcarbamoyl)
phenylsulfamoyl)phenyl 2RS-(4-isopropyloxyphenyl)butanoic acid ester

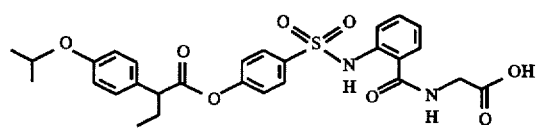

NMR (DMSO-d$_6$): δ 11.58 (1H, s), 9.22–9.13 (1H, m), 7.80–7.63 (4H, m), 7.49–7.40 (2H, m), 7.25–7.06 (5H, m), 6.88–6.84 (2H, m), 4.63–4.48 (1H, m), 3.88 (2H, d, J=6 Hz), 3.72 (1H, t, J=7 Hz), 2.18–1.63 (2H, m), 1.26 (6H, d, J=6 Hz), 0.88 (3H, t, J=7 Hz);

TLC: Rf 0.34 (acetic acid:methanol:chloroform=1:3:30).

Example 2(167)

4-(N-2-(N'-carboxymethylcarbamoyl)
phenylsulfamoyl)phenyl 2RS-(4-propyloxyphenyl)
butanoic acid ester

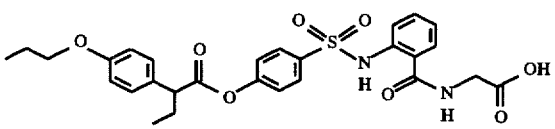

NMR (DMSO-d$_6$): δ 9.38–9.20 (1H, m), 7.81–7.77 (2H, d-like), 7.77–7.70 (2H, m), 7.49–7.31 (2H, m), 7.28–7.03 (5H, m), 6.93–6.89 (2H, d-like), 3.94–3.87 (4H, m), 3.72 (1H, t, J=6 Hz), 2.20–1.98 (1H, m), 1.83–1.62 (3H, m), 0.98 (3H, t, J=7 Hz), 0.88 (3H, t, J=7 Hz);

TLC: Rf 0.35 (acetic acid:methanol:chloroform=1:3:30).

Example 2(168)

4-(N-2-(N'-carboxymethylcarbamoyl)
phenylsulfamoyl)phenyl 2RS-(4-methylphenyl)
pentanoic acid ester

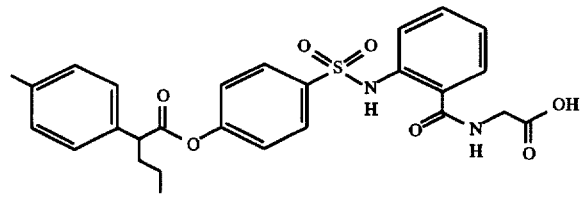

NMR (CDCl$_3$): δ 10.20 (1H, s), 7.68 (1H, d, J=8 Hz), 7.65 (2H, d, J=8 Hz), 7.50-7.35 (2H, m), 7.25-7.05 (5H, m), 6.95 (2H, d, J=8 Hz),6.6-6.5 (1H, br), 4.00 (2H, d, J=5 Hz), 3.72 (1H, t, J=7 Hz), 2.35 (3H, s), 2.2-2.0 (1H, m), 1.9-1.7 (1H, m), 1.4-1.2 (2H, t, J=7 Hz);

TLC: Rf 0.25 (chloroform:methanol:acetic acid=40:2:1).

Example 2(169)

4-(N-2-(N'-carboxymethylcarbamoyl)
phenylsulfamoyl)phenyl 1-(4-methylphenyl)
cyclopentanecarboxylic acid ester

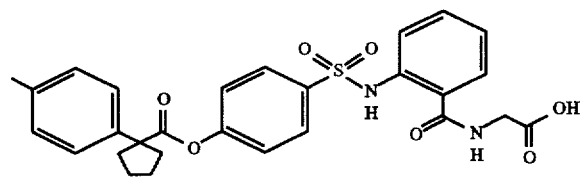

NMR (DMSO-d$_6$): δ 12.70 (1H, br), 11.66 (1H, br), 9.23 (1H, t-like), 7.80-7.70 (3H, m), 7.51-7.41 (2H, m), 7.33-7.29 (2H, m), 7.19-7.09 (5H, m), 3.89 (2H, d, J=6 Hz), 2.65-2.55 (2H, m), 2.29 (3H, s), 2.04-1.90 (2H, m), 1.79-1.65 (4H, m);

TLC: Rf 0.69 (acetic acid:methanol:chloroform=1:3:30).

Example 2(170)

4-(N-2-(N'-carboxymethylcarbamoyl)
phenylsulfamoyl)phenyl 1-(3-methylphenyl)
cyclopentanecarboxylic acid ester

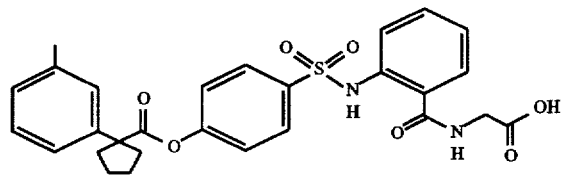

NMR (DMSO-d$_6$): δ 9.22-9.18 (1H, m), 7.80-7.68 (3H, m), 7.49-7.41 (2H, m), 7.29-7.10 (7H, m), 3.89 (2H, d, J=6 Hz), 2.70-2.51 (2H, m), 2.32 (3H, s), 2.04-1.83 (2H, m), 1.74-1.60 (4H, m);

TLC: Rf 0.40 (acetic acid:methanol:chloroform=1:3:30).

Example 2(171)

4-(N-2-(N'-carboxymethylcarbamoyl)
phenylsulfamoyl)phenyl 2RS-(2-methylphenyl)
butanoic acid ester

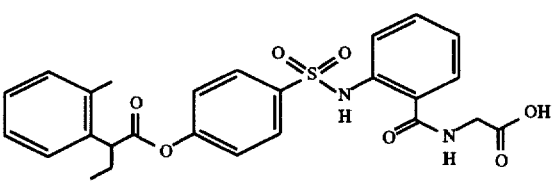

NMR (DMSO-d$_6$): δ 9.4-9.2 (1H, br), 7.8-7.7 (3H, m), 7.5-7.4 (2H, m), 7.3-7.0 (7H, m), 4.06 (1H, t, J=7 Hz), 3.88 (2H, d, J=5 Hz), 2.37 (3H, s), 2.2-2.0 (1H, m), 1.9-1.7 (1H, m), 0.87 (3H, t, J=7 Hz);

TLC: Rf 0.16 (acetic acid:methanol:chloroform=1:2:40).

Example 2(172)

4-(N-2-(N'-carboxymethylcarbamoyl)
phenylsulfamoyl)phenyl 2-(2-methylphenyl)-2-
ethylbutanoic acid ester

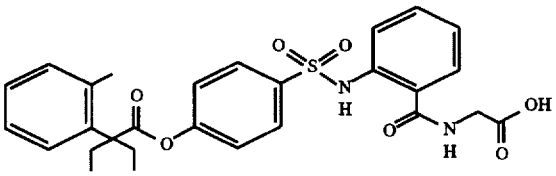

NMR (DMSO-d$_6$): δ 9.5-9.3 (1H, br), 7.9-7.6 (3H, m), 7.6-7.0 (9H, br), 4.0-3.8 (2H, br), 2.27 (3H, s), 2.3-1.9 (4H, br), 0.8-0.6 (6H, br);

TLC: Rf 0.15 (acetic acid:methanol:chloroform=1:2:40).

Example 2(173)

4-(N-2-(N'-carboxymethylcarbamoyl)
phenylsulfamoyl)phenyl 2RS-(4-methylphenyl)
butanoic acid ester

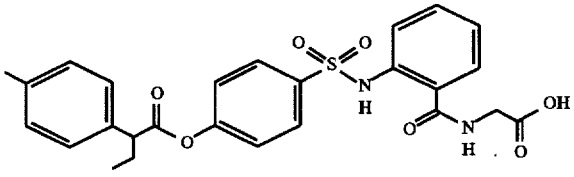

NMR (DMSO-d$_6$): δ 10.61-10.32 (1H, m), 7.85-7.74 (3H, m), 7.36-7.04 (8H, m), 6.90-6.75 (1H, m), 3.92-3.83 (2H, m), 3.77 (1H, t, J=7.6 Hz), 2.29 (3H, s), 2.21-1.96 and 1.89-1.63 (each 1H, m), 0.87 (3H, t, J=7.4 Hz);

TLC: Rf 0.23 (chloroform:methanol:water=8:2:0.2).

Example 2(174)

4-(N-2-(N'-carboxymethylcarbamoyl)
phenylsulfamoyl)phenyl 2RS-(4-nitrophenyl)
butanoic acid ester

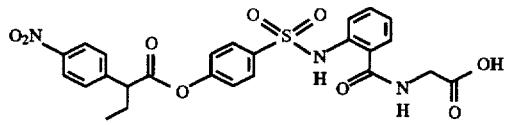

NMR (CDCl$_3$+CD$_3$OD): δ 8.24 (2H, d, J=8 Hz), 7.85–7.55 (6H, m), 7.10 (4H, m), 3.95 (2H, s), 3.87 (1H, t, J=7 Hz), 2.25 and 1.98 (each 1H, m), 0.99 (3H, t, J=7 Hz);

TLC: Rf 0.33 (acetic acid:methanol:chloroform=1:3:30).

Example 2(175)

4-(N-2-(N'-carboxymethylcarbamoyl)
phenylsulfamoyl)phenyl 2-(4-nitrophenyl)-2-
methylpropanoic acid ester

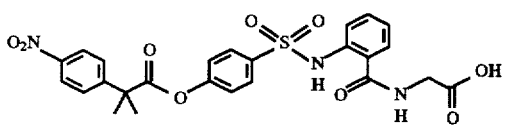

NMR (DMSO-d$_6$): δ 13.50–11.00 (2H, br), 9.30–9.16 (1H, m), 8.23 (2H, d, J=8 Hz), 7.88–7.68 (5H, m), 7.55–7.40 (2H, m), 7.25 (2H, d, J=8 Hz), 7.20–7.09 (1H, m), 3.89 (2H, d, J=6 Hz), 1.68 (6H, s);

TLC: Rf 0.41 (acetic acid:methanol:chloroform=1:3:30).

Example 2(176)

4-(N-2-(N'-carboxymethylcarbamoyl)
phenylsulfamoyl)phenyl 1-(4-nitrophenyl)
cyclopropanecarboxylic acid ester

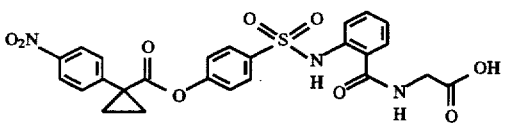

NMR (DMSO-d$_6$): δ 9.2–9.1 (1H, brt), 8.18 (2H, d, J=8 Hz), 7.8–7.6 (5H, m), 7.5–7.4 (2H, m), 7.29 (2H, d, J=8 Hz), 7.2–7.0 (1H, m), 3.90 (2H, d, J=5 Hz), 1.77 (2H, dd, J=6, 4 Hz), 1.48 (2H, dd, J=6, 4 Hz);

TLC: Rf 0.17 (acetic acid:methanol:chloroform=1:2:40).

Example 2(177)

4-(N-2-(N'-carboxymethylcarbamoyl)
phenylsulfamoyl)phenyl 1-(4-nitrophenyl)
cyclopentanecarboxylic acid ester

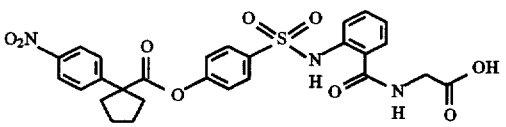

NMR (DMSO-d$_6$): δ 9.2–9.1 (1H, brt), 8.22 (2H, d, J=8 Hz), 7.8–7.6 (5H, m), 7.5–7.4 (2H, m), 7.2–7.1 (3H, m), 3.88 (2H, d, J=5 Hz), 2.8–2.6 (2H, m), 2.2–1.9 (2H, m), 1.9–1.6 (4H, m);

TLC: Rf 0.20 (acetic acid:methanol:chloroform=1:2:40).

Example 2(178)

4-(N-2-(N'-carboxymethylcarbamoyl)
phenylsulfamoyl)phenyl 2-(4-nitrophenyl)-2-
ethylbutanoic acid ester

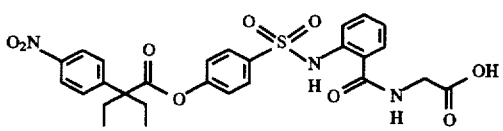

NMR (DMSO-d$_6$): δ 13.40–11.20 (2H, br), 9.35–9.15 (1H, m), 8.24 (2H, d, J=8 Hz), 7.82 (2H, d, J=8 Hz), 7.74 (1H, t, J=8 Hz), 7.67 (2H, d, J=8 Hz), 7.55–7.40 (2H, m), 7.23 (2H, d, J=8 Hz), 7.19–7.08 (1H, m), 3.89 (2H, d, J=6 Hz), 2.25–1.98 (4H, m), 0.76 (6H, t, J=7 Hz);

TLC: Rf 0.28 (acetic acid:methanol:chloroform=1:3:30).

Example 2(179)

4-(N-2-(N'-carboxymethylcarbamoyl)
phenylsulfamoyl)phenyl 1-(4-nitrophenyl)
cyclobutanecarboxylic acid ester

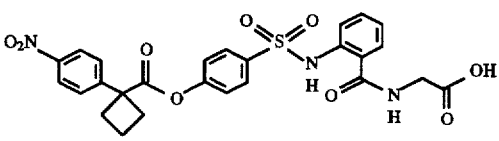

NMR (DMSO-d$_6$): δ 9.2–9.1 (1H, brt), 8.24 (2H, d, J=8 Hz), 7.8–7.6 (5H, m), 7.5–7.4 (2H, m), 7.3–7.1 (3H, m), 3.88 (2H, d, J=5 Hz), 3.0–2.8 (2H, br), 2.7–2.5 (2H, m), 2.2–1.8 (2H, m);

TLC: Rf 0.22 (acetic acid:methanol:chloroform=1:2:40).

Example 2(180)

4-(N-2-(N'-carboxymethylcarbamoyl)
phenylsulfamoyl)-2-methylphenyl 2RS-(4-
nitrophenyl)butanoic acid ester

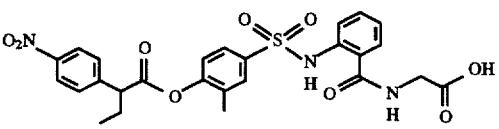

NMR (DMSO-d$_6$): δ 13.00–12.40 (1H, br), 11.80–11.40 (1H, br), 9.19 (1H, t, J=5 Hz), 8.24 (2H, d, J=8 Hz), 7.80–7.55 (5H, m), 7.55–7.40 (2H, m), 7.23–7.06 (2H, m), 4.15 (1H, t, J=7 Hz), 3.88 (2H, d, J=5 Hz), 2.19 (1H, ddq, J=14 Hz, 7 Hz, 7 Hz), 2.05–1.75 (4H, m), 0.88 (3H, t, J=7 Hz);

TLC: Rf 0.20 (acetic acid:methanol:chloroform=1:2:20).

Example 2(181)

4-(N-2-(N'-carboxymethylcarbamoyl)
phenylsulfamoyl)-2-methylphenyl 1-(4-nitrophenyl)
cyclobutanecarboxylic acid ester

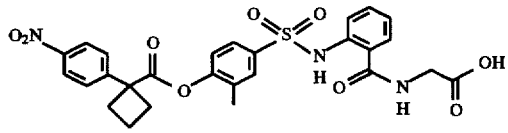

NMR (DMSO-d$_6$): δ 12.80–11.00 (2H, br), 9.20 (1H, t, J=5 Hz), 8.24 (2H, d, J=8 Hz), 7.80–7.55 (5H, m), 7.55–7.37 (2H, m), 7.25–7.05 (2H, m), 3.86 (2H, d, J=5 Hz), 3.04–2.85 (2H, m), 2.74–2.54 (2H, m), 2.23–1.78 (5H, m);

TLC: Rf 0.20 (acetic acid:methanol:chloroform=1:2:40).

Example 2(182)

4-(N-2-(N'-carboxymethylcarbamoyl)
phenylsulfamoyl)-3-methylphenyl 1-(4-nitrophenyl)
cyclobutanecarboxylic acid ester

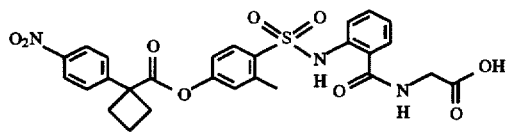

NMR (DMSO-d$_6$): δ 13.30–12.30 (1H, br), 12.00–11.56 (1H, br), 9.34–9.16 (1H, m), 8.26 (2H, d, J=8 Hz), 7.85–7.65 (4H, m), 7.50–7.35 (2H, m), 7.22 (1H, d, J=8 Hz), 7.18–7.05 (1H, m), 6.85 (1H, s), 3.97 (2H, d, J=5 Hz), 3.22–3.03 (2H, m), 2.78–2.58 (2H, m), 2.28 (3H, s), 2.28–2.08 (1H, m), 2.05–1.80 (1H, m);

TLC: Rf 0.43 (acetic acid:methanol:chloroform=1:3:30).

Example 2(183)

4-(N-2-(N'-carboxymethylcarbamoyl)
phenylsulfamoyl)-2,3-dimethylphenyl 1-(4-nitrophenyl)cyclobutanecarboxylic acid ester

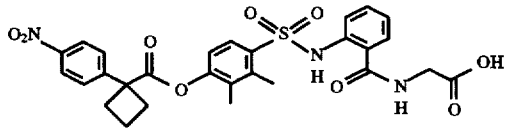

NMR (DMSO-d$_6$): δ 13.10–12.40 (1H, br), 12.00–11.70 (1H, br), 9.35–9.22 (1H, m), 8.27 (2H, d, J=8 Hz), 7.88–7.73 (3H, m), 7.65 (1H, d, J=8 Hz), 7.51–7.39 (2H, m), 7.20 (1H, d, J=8 Hz), 7.15–7.06 (1H, m), 4.08–3.95 (2H, m), 3.18–2.99 (1H, m), 2.99–2.78 (1H, m), 2.66–2.47 (1H, m), 2.33–2.05 (1H, m), 2.18 (3H, s), 2.05–1.82 (1H, m), 1.35 (3H, s);

TLC: Rf 0.43 (acetic acid:methanol:chloroform=1:3:30).

Example 2(184)

7-(N-2-(N'-carboxymethylcarbamoyl)
phenylsulfamoyl)-2,3-dihydroinden-4-yl 1-(4-nitrophenyl)cyclobutanecarboxylic acid ester

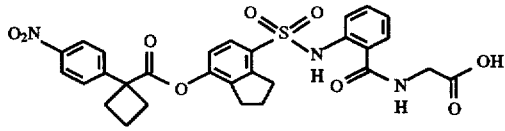

NMR (DMSO-d$_6$): δ 13.10–12.30 (1H, br), 12.00–11.46 (1H, br), 9.22 (1H, t, J=5 Hz), 8.25 (2H, d, J=8 Hz), 7.80–7.60 (4H, m), 7.50–7.34 (2H, m), 7.18–7.02 (2H, m), 3.90 (2H, d, J=5 Hz), 3.14–2.78 (4H, m), 2.74–2.33 (4H, m), 2.20–1.78 (4H, m);

TLC: Rf 0.20 (acetic acid:methanol:chloroform=1:2:60).

Example 2(185)

4-(N-2-(N'-carboxymethylcarbamoyl)
phenylsulfamoyl)phenyl 2RS-(4-(pyrrolidin-1-yl)
phenyl)butanoic acid ester.hydrochloride

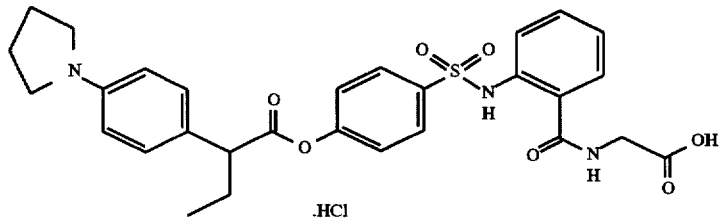

NMR (d$_6$-DMSO): δ 11.60 (1H, s), 9.23 (1H, t, J=6 Hz), 7.85–7.70 (3H, m), 7.55–7.40 (2H, m), 7.27–7.08 (5H, m), 6.80–6.55 (2H, m), 3.88 (2H, d, J=6 Hz), 3.68 (1H, t, J=7 Hz), 3.38–3.19 (4H, m), 2.20–1.86 (5H, m), 1.86–1.62 (1H, m), 0.86 (3H, t, J=7 Hz);

TLC: Rf 0.44 (chloroform:methanol:acetic acid=30:2:1).

Example 2(186)

4-(N-2-(N'-carboxymethylcarbamoyl)
phenylsulfamoyl)-2-methylphenyl 2RS-(4-
(pyrrolidin-1-yl)phenyl)butanoic acid
ester.hydrochloride

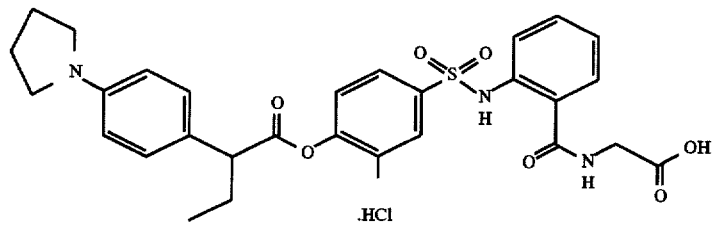

NMR (DMSO-$d_6$): δ 11.56 (1H, s), 9.23 (1H, t, J=5 Hz), 7.83–7.55 (3H, m), 7.55–7.40 (2H, m), 7.30–7.05 (4H, m), 6.84–6.60 (2H, m), 3.88 (2H, d, J=5 Hz), 3.70 (1H, t, J=7 Hz), 3.40–3.13 (4H, m), 2.20–1.65 (9H, m), 0.86 (3H, t, J=7 Hz);

TLC: Rf 0.45 (acetic acid:methanol:chloroform=1:3:30).

Example 2(187)

4-(N-2-(N'-carboxymethylcarbamoyl)
phenylsulfamoyl)-3-methylphenyl 2RS-(4-
(pyrrolidin-1-yl)phenyl)butanoic acid
ester.hydrochloride

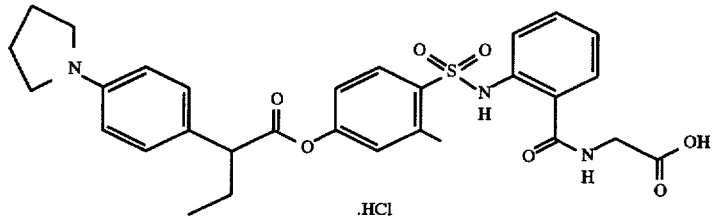

NMR (DMSO-$d_6$): δ 12.20 (1H, s), 9.28 (1H, t, J=5 Hz), 7.85 (2H, d, J=8 Hz), 7.50–7.35 (2H, m), 7.30–7.18 (3H, m), 7.18–7.03 (1H, m), 6.80 (1H, s), 6.73 (2H, d, J=8 Hz), 4.00 (2H, d, J=5 Hz), 3.93–3.75 (1H, m), 3.38–3.20 (4H, m), 2.28 (3H, s), 2.20–2.00 (1H, m), 2.03–1.92 (4H, m), 1.92–1.65 (1H, m), 0.88 (3H, t, J=7 Hz);

TLC: Rf 0.41 (acetic acid:methanol:chloroform=1:3:30).

Example 2(188)

4-(N-2-(N'-carboxymethylcarbamoyl)
phenylsulfamoyl)-2,3-dimethylphenyl 2RS-(4-
(pyrrolidin-1-yl)phenyl)butanoic acid
ester.hydrochloride

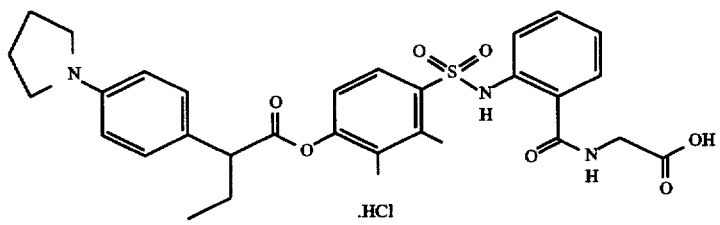

NMR (DMSO-d$_6$): δ 12.09 (1H, s),9.35–9.18 (1H, m),
7.92–7.77 (1H, m), 7.77–7.63 (1H, m), 7.46–7.38 (2H, m),
7.30–7.17 (3H, m), 7.17–7.03 (1H, m), 6.86–6.60 (2H, m),
4.02 (2H, d, J=5 Hz), 3.93–3.80 (1H, m), 3.40–3.15 (4H, m),
2.19 (3H, s), 2.05–1.90 (4H, m), 1.90–1.50 (1H, m), 1.45
(3H, s), 1.30–0.98 (1H, m), 0.88 (3H, t, J=7 Hz);

TLC: Rf 0.40 (acetic acid:methanol:chloroform=1:3:30).

7.19 (2H, d, J=8 Hz), 7.15–7.04 (1H, m), 6.98 (1H, d, J=8
Hz), 6.68 (2H, d, J=8 Hz), 3.89 (2H, d, J=5 Hz), 3.66 (1H,
t, J=5 Hz), 3.35–3.15 (4H, m), 3.15–3.00 (2H, m), 2.55–2.40
(2H, m), 2.18–1.85 (7H, m), 1.85–1.60 (1H, m), 0.86 (3H,
t, J=7 Hz);

TLC: Rf 0.34 (acetic acid:methanol:chloroform=1:3:30).

Example 2(189)

4-(N-2-(N'-carboxymethylcarbamoyl)
phenylsulfamoyl)phenyl 1-(4-(pyrrolidin-1-yl)
phenyl)cyclobutanecarboxylic acid ester

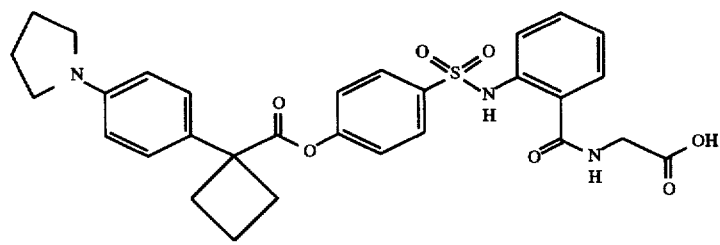

NMR (CD$_3$OD): δ 7.75–7.50 (4H, m), 7.50–7.25 (3H, m),
7.20–6.90 (5H, m), 3.92 (2H, s), 3.46 (4H, brs), 2.90 (2H,
m), 2.56 (2H, m), 2.25–1.85 (6H, m);

TLC: Rf 0.36 (acetic acid:methanol:chloroform=1:3:30).

Example 2(190)

7-(N-2-(N'-carboxymethylcarbamoyl)
phenylsulfamoyl)-2,3-dihydroinden-4-yl 2RS-(4-
(pyrrolidin-1-yl)phenyl)butanoic acid
ester.hydrochloride

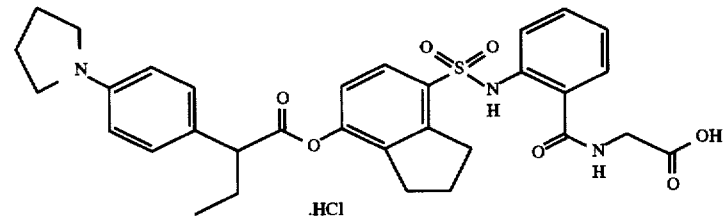

NMR (DMSO-d$_6$): δ 11.69 (1H, s), 9.24 (1H, J=5 Hz),
7.75 (1H, d, J=Hz), 7.69 (1H, d, J=8 Hz), 7.50–7.38 (2H, m),

Example 2(191)

4-(N-2-(N'-carboxymethylcarbamoyl)
phenylsulfamoyl)-2,6-dimethylphenyl 2RS-(4-
(pyrrolidin-1-yl)phenyl)butanoic acid
ester.hydrochloride

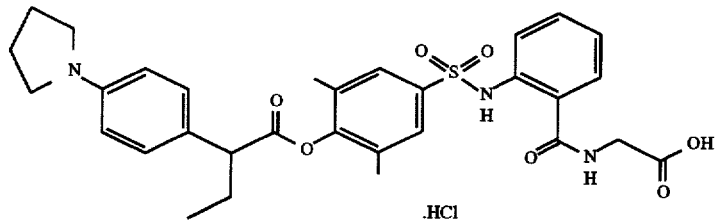

NMR (DMSO-$d_6$): δ 11.49 (s, 1H), 9.3–9.2 (m, 1H), 7.8–7.1 (m, 10H), 6.8–6.6 (m, 1H), 4.0–3.7 (m, 3H), 3.4–3.1 (m, 4H), 2.2–1.7 (m, 12H), 0.89 (t, J=7.0 Hz, 3H);

TLC: Rf 0.60 (chloroform:methanol=2:1).

Example 2(192)

4-(N-2-(N'-carboxymethylcarbamoyl)
phenylsulfamoyl)-2-isopropylphenyl 2RS-(4-
(pyrrolidin-1-yl)phenyl)butanoic acid
ester.hydrochloride

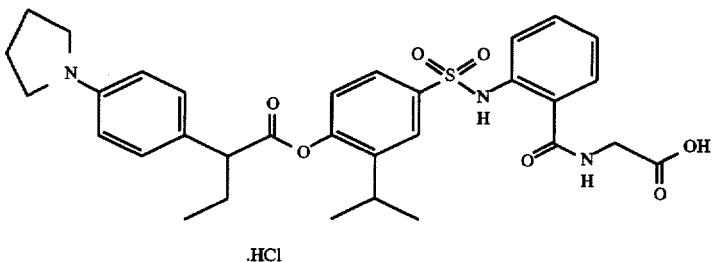

NMR (CDCl$_3$): δ 10.04 (s, 1H), 7.8–7.7 (m, 3H), 7.6–7.5 (m, 7H), 7.2–7.1 (m, 1H), 6.9–6.8 (m, 1H), 6.4–6.3 (m, 1H), 4.0–3.6 (m, 7H), 2.8–2.7 (m, 1H), 2.4–2.2 (m, 5H), 2.0–1.8 (m, 1H), 0.98 (t, J=7.0 Hz, 3H), 0.91 (d, J=7.0 Hz, 6H);

TLC: Rf 0.61 (chloroform:methanol=2:1).

Example 2(193)

4-(N-2-(N'-carboxymethylcarbamoyl)
phenylsulfamoyl)phenyl 2RS-(4-(piperidin-1-yl)
phenyl)butanoic acid ester.trifluoroacetate

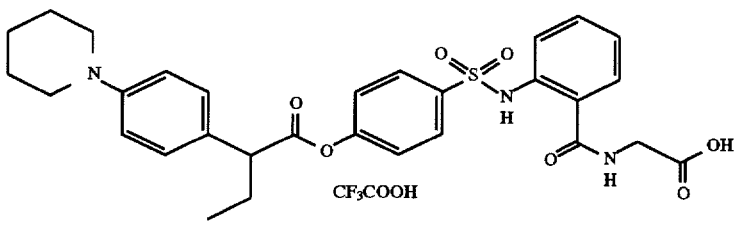

NMR ($d_6$-DMSO): δ 12.60–11.50 (1H, br), 9.43–9.23 (1H, br), 7.83–7.68 (3H, m), 7.52–7.35 (2H, m), 7.30–7.02 (5H, m), 6.88 (2H, d, J=8 Hz), 3.88 (2H, d, J=7 Hz), 3.66 (1H, t, J=8 Hz), 3.20–3.05 (4H, m), 2.15–1.91 (1H, m), 1.85–1.43 (7H, m), 0.93 (3H, t, J=7 Hz);

TLC: Rf 0.28 (chloroform:methanol:acetic acid=30:3:1).

Example 2(194)

4-(N-2-(N'-carboxymethylcarbamoyl)
phenylsulfamoyl)phenyl 2RS-(4-(perhydroazepin-1-
yl)phenyl)butanoic acid ester.trifluoroacetate

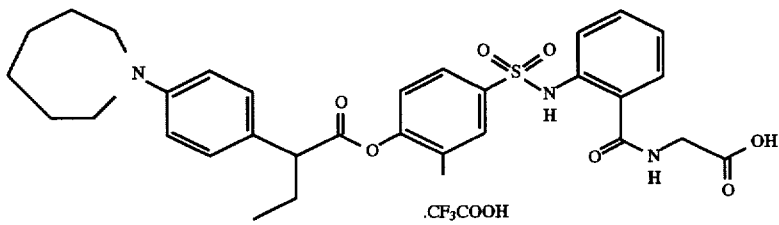

NMR (DMSO-d$_6$): δ 11.57 (1H, s), 9.19 (1H, t, J=7 Hz), 7.85–7.65 (3H, m), 7.55–7.40 (2H, m), 7.30–7.05 (5H, m), 6.64 (2H, d, J=8 Hz), 3.88 (2H, d, J=7 Hz), 3.60 (1H, t, J=8 Hz), 3.48–3.28 (4H, m), 2.10–1.93 (1H, m), 1.88–1.55 (5H, m), 1.55–1.30 (4H, m), 0.86 (3H, t, J=7 Hz);

TLC: Rf 0.35 (acetic acid:methanol:chloroform=1:3:30).

Example 2(195)

4-(N-2-(N'-carboxymethylcarbamoyl)
phenylsulfamoyl)phenyl 2-(4-aminophenyl)-2-
ethylbutanoic acid ester

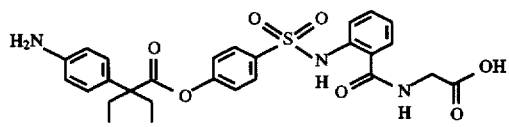

NMR (DMSO-d$_6$): δ 11.58 (1H, br), 9.22 (1H, t, J=5 Hz), 7.80–7.70 (3H, m), 7.53–7.42 (2H, m), 7.18–7.14 (3H, m), 6.98 (2H, d, J=8 Hz), 6.56 (2H, d, J=8 Hz), 3.89 (2H, d, J=6 Hz), 2.09–1.88 (4H, m), 0.74 (6H, t, J=7 Hz); TLC: Rf 0.40 (acetic acid:methanol:chloroform=1:3:30).

Example 2(196)

4-(N-2-(N'-carboxymethylcarbamoyl)
phenylsulfamoyl)phenyl 2RS-(4-aminophenyl)
butanoic acid ester.hydrochloride

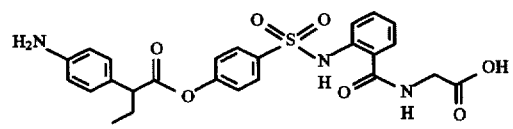

NMR (DMSO-d$_6$): δ 10.65 (1H, br), 7.83–7.76 (3H, m), 7.31–6.96 (6H, m), 6.80–6.73 (1H, m), 6.53 (2H, d, J=8.6 Hz), 3.86 (2H, d-like), 3.55 (1H, t, J=7.4 Hz), 2.12–1.90 and 1.83–1.62 (each 1H, m), 0.87 (3H, t, J=7.0 Hz);

TLC: Rf 0.16 (chloroform:methanol:water=8:2:0.2).

Example 2(197)

4-(N-2-(N'-carboxymethylcarbamoyl)
phenylsulfamoyl)phenyl 2RS-(4-(N,N-
dimethylamino)phenyl)butanoic acid
ester.hydrochloride

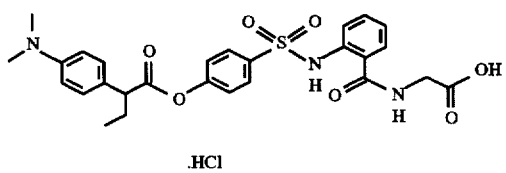

NMR (DMSO-d$_6$): δ 11.62 (1H, s), 9.25 (1H, t, J=6 Hz), 7.80 (2H, d, J=9 Hz), 7.76 (1H, d, J=8 Hz), 7.50–7.44 (5H, m), 7.27–7.14 (4H, m), 3.89 (2H, d, J=6 Hz), 3.86 (1H, t, J=8 Hz), 3.04 (6H, s), 2.17–2.03 and 1.91–1.71 (each 1H, m), 0.88 (3H, t, J=7 Hz);

TLC: Rf 0.48 (acetic acid:methanol:chloroform=1:3:30).

Example 2(198)

4-(N-2-(N'-carboxymethylcarbamoyl)
phenylsulfamoyl)phenyl 1-(4-(N,N-dimethylamino)
phenyl)cyclobutanecarboxylic acid
ester.hydrochloride

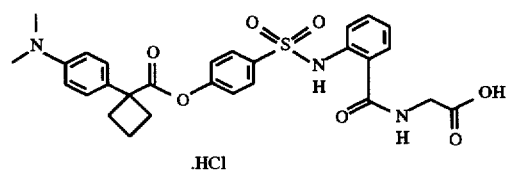

NMR (DMSO-d$_6$): δ 8 11.62 (1H, s), 9.24 (1H, t-like), 7.79 (2H, d, J=8.8 Hz), 7.74 (1H, d, J=8.0 Hz), 7.81–7.70 (9H, m), 3.89 (2H, d, J=5.0 Hz), 3.02 (6H, s), 2.93–2.80 (2H, m), 2.59–2.39 (2H, m), 2.09–1.81 (2H, m);

TLC: Rf 0.26 (chloroform:methanol:water=8:2:0.2).

233

Example 2(199)

4-(N-2-(N'-carboxymethylcarbamoyl)phenylsulfamoyl)phenyl 2RS-(4-(N,N-diethylaminomethyl)phenyl)butanoic acid ester.hydrochloride

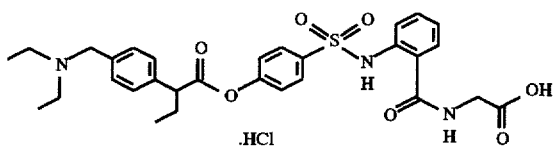

NMR (DMSO-$d_6$): δ 13.00–11.00 (2H, br), 9.35–9.18 (1H, m), 7.90–7.71 (3H, m), 7.68–7.56 (2H, m), 7.56–7.38 (4H, m), 7.30–7.08 (3H, m), 4.24 (2H, s), 3.99–3.79 (2H, m), 3.71–3.65 (1H, m), 3.10–2.90 (4H, m), 2.11 (1H, ddq, J=14 Hz, 7 Hz, 7 Hz), 1.82 (1H, ddq, J=14 Hz, 7 Hz, 7 Hz), 1.23 (6H, t, J=7 Hz), 0.88 (3H, t, J=7 Hz);

TLC: Rf 0.18 (acetic acid:methanol:chloroform=1:2:20).

234

Example 2(200)

4-(N-2-(N'-carboxymethylcarbamoyl)phenylsulfamoyl)phenyl 2RS-(4-hydroxyphenyl)butanoic acid ester

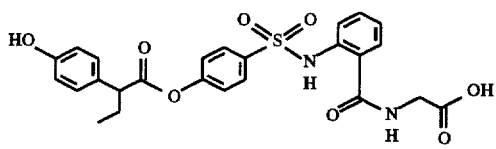

NMR (DMSO-$d_6$): δ 12.90–11.20 (2H, br), 9.39 (1H, br), 9.22 (1H, t-like), 7.79 (2H, d, J=8.8 Hz), 7.73 (1H, d, J=7.8 Hz), 7.53–7.42 (2H, m), 7.19–7.12 (5H, m), 6.74 (2H, d, J=8.6 Hz), 3.89 (2H, d, J=5.6 Hz), 3.68 (1H, t, J=7.6 Hz), 2.11–1.93 and 1.84–1.62 (each 1H, m), 0.86 (3H, t, J=7.2 Hz);

TLC: Rf 0.12 (chloroform:methanol:water=8:2:0.2).

Example 2(201)

4-(N-2-(N'-carboxymethylcarbamoyl)phenylsulfamoyl)phenyl 2RS-(4-cyanophenyl)butanoic acid ester

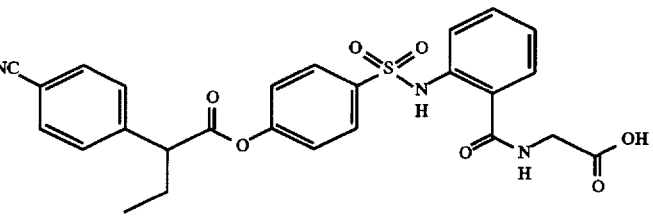

NMR (DMSO-$d_6$): δ 10.72–10.41 (1H, m), 7.88–7.69 (5H, m), 7.59 (2H, d, J=8.2 Hz), 7.29 (2H, d, J=8.2 Hz), 7.22–7.06 (3H, m), 6.78 (1H, t, J=8.2 Hz), 4.01 (1H, t, J=7.4 Hz), 3.91–3.77 (2H, m), 2.24–2.01 and 1.95–1.70 (each 1H, m), 0.88 (3H, t, J=7.4 Hz);

TLC: Rf 0.24 (chloroform:methanol:water=8:2:0.2).

Example 2(202)

4-(N-2-(N'-carboxymethylcarbamoyl)
phenylsulfamoyl)phenyl 2RS-(4-carboxyphenyl)
butanoic acid ester

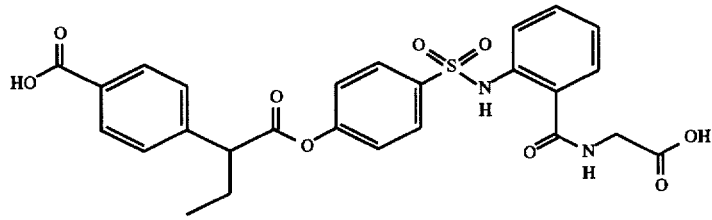

NMR (DMSO-d$_6$): δ 11.36 (1H, s), 10.45 (1H, s), 9.16 (1H, t-like), 7.90 (2H, d, J=8 Hz), 7.71 (1H, d, J=8 Hz), 7.60–7.38 (7H, m), 7.18–7.03 (1H, m), 6.81 (2H, d, J=8 Hz), 3.89 (2H, d, J=6 Hz), 3.40 (1H, t, J=7 Hz), 2.04–1.58 (2H, m), 0.83 (3H, t, J=7 Hz);

TLC: Rf 0.53 (acetic acid:methanol:chloroform=1:5:15).

Example 2(203)

4-(N-2-(N'-carboxymethylcarbamoyl)
phenylsulfamoyl)phenyl 2RS-(4-
trifluoromethylphenyl)butanoic acid ester

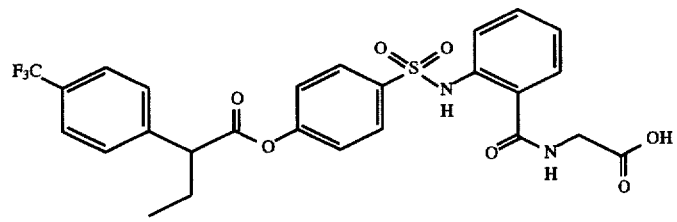

NMR (DMSO-d$_6$): δ 10.75–10.45 (1H, m), 7.87–7.56 (7H, m), 7.35–7.07 (4H, m), 6.87–6.72 (1H, m), 4.02 (1H, t, J=7.7 Hz), 3.93–3.82 (2H, m), 2.25–2.02 and 1.95–1.71 (each 1H, m), 0.89 (3H, t, J=7.0 Hz);

TLC: Rf 0.23 (chloroform:methanol:water=8:2:0.2).

Example 2(204)

4-(N-2-(N'-carboxymethylcarbamoyl)
phenylsulfamoyl)phenyl 2RS-(4-amidinophenyl)
butanoic acid ester.trifluoroacetate

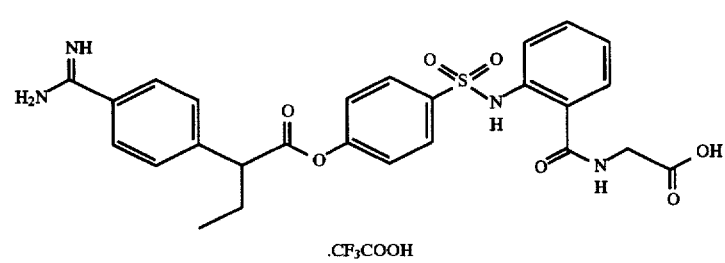

NMR (DMSO-d$_6$): δ 10.42–10.20 (1H, m), 9.95–9.44 (2H, m), 9.44–8.90 (2H, m), 7.86–7.66 (4H, m), 7.66–7.30 (4H, m), 7.30–7.04 (3H, m), 6.88–6.75 (1H, m), 4.01 (1H, t, J=7 Hz), 3.90–3.79 (2H, m), 2.26–2.03 (1H, m), 1.95–1.74 (1H, m), 0.96–0.76 (3H, m);

TLC: Rf 0.40 (acetic acid:methanol:chloroform=1:2:10).

Example 2(205)
4-(N-2-(N'-carboxymethylcarbamoyl)
phenylsulfamoyl)phenyl 2RS-(4-(imidazolin-2-yl)
phenyl)butanoic acid ester.trifluoroacetate

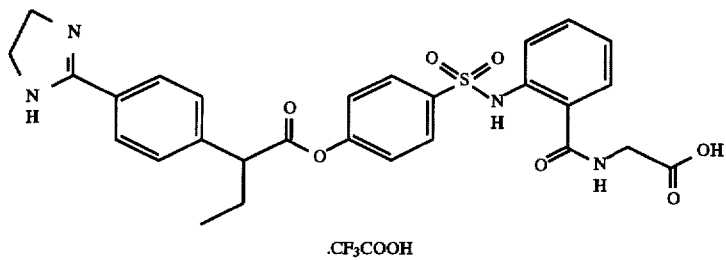

NMR (DMSO-d₆): δ 10.60–10.34 (1H, m), 7.95 (2H, d, J=8 Hz), 7.82–7.71 (3H, m), 7.64 (2H, d, J=8 Hz), 7.34 (1H, d, J=8 Hz), 7.26–7.00 (4H, m), 6.80 (1H, t, J=8 Hz), 4.60–3.93 (7H, m), 2.15 (1H, ddq, J=14 Hz, 7 Hz, 7 Hz), 1.94–1.71 (1H, m), 0.87 (3H, t, J=7 Hz);

TLC: Rf 0.2 (acetic acid:methanol:chloroform=1:2:10).

Example 2(206)
4-(N-2-(N'-carboxymethylcarbamoyl)
phenylsulfamoyl)phenyl 1-(4-chlorophenyl)
cyclobutanecarboxylic acid ester

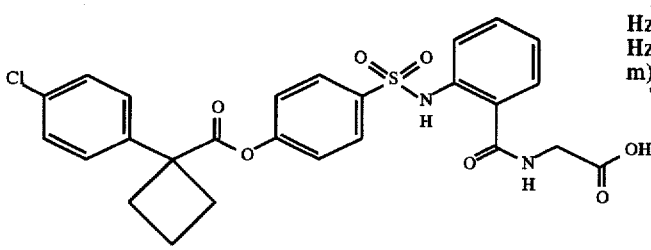

NMR (DMSO-d₆): δ 9.3–9.1 (1H, brt), 7.8–7.6 (3H, m), 7.5–7.3 (6H, m), 7.2–7.0 (3H, m), 3.88 (2H, d, J=5 Hz), 3.0–2.8 (2H, m), 2.6–2.4 (2H, m), 2.2–1.8 (2H, m);

TLC: Rf 0.22 (acetic acid:methanol:chloroform=1:2:40).

Example 2(207)

4-(N-2-(N'-carboxymethylcarbamoyl)
phenylsulfamoyl)phenyl 2RS-(2-chlorophenyl)
butanoic acid ester

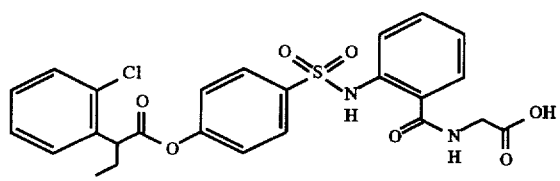

NMR (DMSO-d₆): δ 9.4–9.2 (1H, br), 7.8–7.7 (3H, m), 7.5–7.3 (6H, m), 7.3–7.0 (3H, m), 4.24 (1H, t, J=7 Hz), 3.88 (2H, d, J=5 Hz), 2.2–2.0 (1H, m), 2.0–1.8 (1H, m), 0.87 (3H, t, J=7 Hz);

TLC: Rf 0.16 (acetic acid:methanol:chloroform=1:2:40).

Example 2(208)
4-(N-2-(N'-carboxymethylcarbamoyl)
phenylsulfamoyl)phenyl 2-(2-chlorophenyl)-2-
ethylbutanoic acid ester

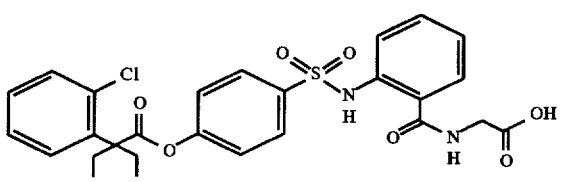

NMR (DMSO-d₆): δ 9.5–9.3 (1H, br), 7.82 (2H, d, J=8 Hz), 7.72 (1H, d, J=8 Hz), 7.6–7.3 (6H, m), 7.23 (2H, d, J=8 Hz), 7.09 (1H, t, J=8 Hz), 3.90 (2H, d, J=5 Hz), 2.4–2.1 (2H, m), 2.2–1.9 (2H, m), 0.70 (6H, t, J=7 Hz);

TLC: Rf 0.12 (acetic acid:methanol:chloroform=1:2:40).

Example 2(209)

4-(N-2-(N'-carboxymethylcarbamoyl)
phenylsulfamoyl)phenyl 1-(2-chlorophenyl)
cyclobutanecarboxylic acid ester

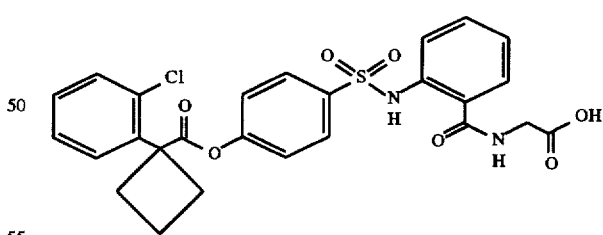

NMR (CDCl₃+CD₃OD): δ 7.72 (2H, d, J=8.5 Hz), 7.68–7.05 (8H, m), 7.02 (2H, d, J=8.5 Hz), 3.99 (2H, s), 3.01–2.82 (2H, m), 2.75–2.50 (2H, m), 2.41–2.15 (1H, m), 2.10–1.80 (1H, m);

TLC: Rf 0.30 (acetic acid:methanol:chloroform=1:2:40).

Example 2(210)
4-(N-2-(N'-carboxymethylcarbamoyl)
phenylsulfamoyl)phenyl 2RS-(4-chlorophenyl)
butanoic acid ester

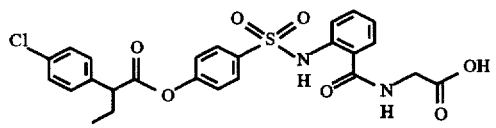

NMR (DMSO-$d_6$): δ 10.47–10.18 (1H, m), 7.86–7.74 (3H, m), 7.51–7.08 (8H, m), 6.93–6.81 (1H, m), 3.95–3.82 (3H, m), 2.20–1.96 and 1.90–1.66 (each 1H, m), 0.87 (3H, t, J=7.4 Hz);

TLC: Rf 0.26 (chloroform:methanol:water=8:2:0.2).

Example 2(211)
4-(N-2-(N'-carboxymethylcarbamoyl)
phenylsulfamoyl)phenyl 2RS-(3-nitro-4-
hydroxyphenyl)butanoic acid ester

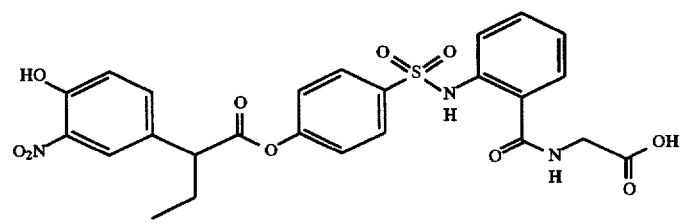

NMR (DMSO-$d_6$): δ 9.36 (1H, t-like), 7.90–7.72 (4H, m), 7.58–7.40 (3H, m), 7.24–7.07 (4H, m), 3.90 (2H, d, J=6 Hz), 2.20–1.97 and 1.89–1.69 (each 1H, m), 0.88 (3H, t, J=7 Hz);

TLC: Rf 0.21 (acetic acid:methanol:chloroform=1:2:40).

Example 2(212)
4-(N-2-(N'-carboxymethylcarbamoyl)
phenylsulfamoyl)phenyl 2RS-(2-chloro-5-
nitrophenyl)butanoic acid ester

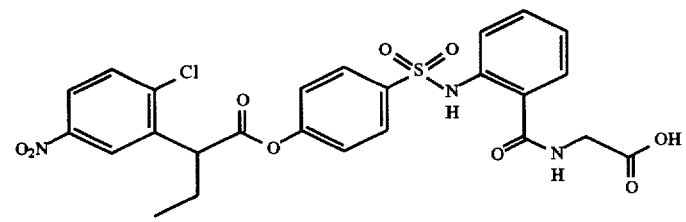

NMR (DMSO-$d_6$): δ 12.10 (2H, br), 9.26 (1H, t-like), 8.32 (1H, t, J=3 Hz), 8.20 (1H, dd, J=3 and 9 Hz), 7.85–7.79 (3H, m), 7.73 (1H, d, J=8 Hz), 7.52–7.41 (2H, m), 7.27 (2H, d, J=9 Hz), 7.15–7.08 (1H, m), 4.43 (1H, t, J=6 Hz), 3.89 (2H, d, J=6 Hz), 2.32–2.18 and 2.09–1.91 (each 1H, m), 0.90 (3H, t, J=7 Hz);

TLC: Rf 0.51 (acetic acid:methanol:chloroform=1:3:30).

Example 2(213)

4-(N-2-(N'-carboxymethylcarbamoyl)phenylsulfamoyl)phenyl 1-(2-chloro-5-nitrophenyl)cyclobutanecarboxylic acid ester

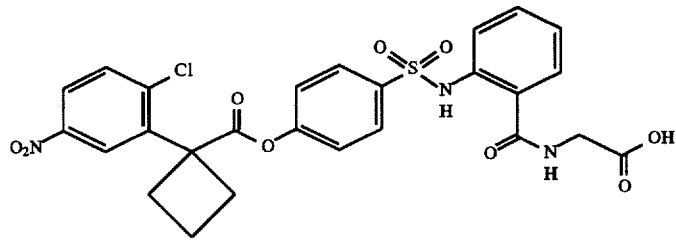

NMR (CDCl$_3$+CD$_3$OD): δ 8.32 (1H, d, J=2.5 Hz), 8.14 (1H, dd, J=2.5, 8.5 Hz), 7.76 (2H, d, J=8.5 Hz), 7.62 (2H, t, J=8.5 Hz), 7.53 (1H, d, J=8.5 Hz), 7.43 (1H, d, J=8.5 Hz), 7.12 (1H, d, J=8.5 Hz), 7.06 (2H, d, J=8.5 Hz), 3.99 (2H, brs), 3.10–2.90 (2H, m), 2.80–2.59 (2H, m), 2.52–2.20 (1H, m), 2.15–1.90 (1H, m);

TLC: Rf 0.23 (acetic acid:methanol:chloroform=1:2:40).

4.08 (1H, t, J=7.4 Hz), 3.84 (2H, d-like), 2.22–2.04 and 1.98–1.76 (each 1H, m), 0.89 (3H, t, J=7.2 Hz);

TLC: Rf 0.30 (chloroform:methanol:water=8:2:0.2).

Example 2(214)

4-(N-2-(N'-carboxymethylcarbamoyl)phenylsulfamoyl)phenyl 1-(3-nitro-4-chlorophenyl)cyclobutanecarboxylic acid ester

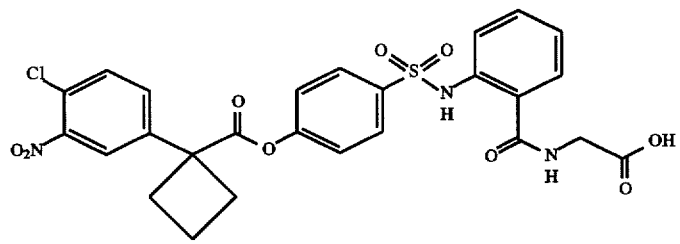

NMR (DMSO-d$_6$): δ 12.73 (1H, brs), 11.60 (1H, brs), 9.17 (1H, t, J=7 Hz), 8.04 (1H, s), 7.90–7.65 (4H, m), 7.55–7.40 (2H, m), 7.35–7.05 (4H, m), 3.90 (2H, d, J=7 Hz), 2.90 (2H, m), 2.60 (2H, m), 2.25–1.80 (2H, m);

TLC: Rf 0.34 (acetic acid:methanol:chloroform=1:3:30).

Example 2(215)

4-(N-2-(N'-carboxymethylcarbamoyl)phenylsulfamoyl)phenyl 2RS-(3-nitro-4-chlorophenyl)butanoic acid ester

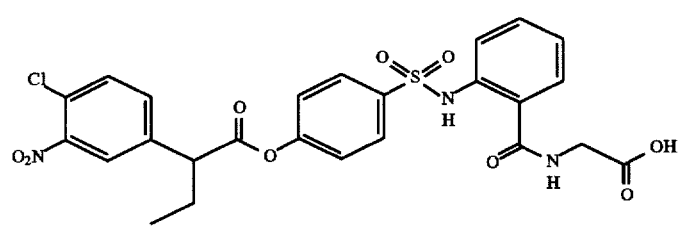

NMR (DMSO-d$_6$): δ 10.79 (1H, br), 8.12 (1H, s), 7.85–7.75 (5H, m), 7.28–7.08 (4H, m), 6.74 (1H, t-like),

Example 2(216)

4-(N-2-(N'-carboxymethylcarbamoyl)
phenylsulfamoyl)phenyl 2RS-(4-ureidophenyl)
butanoic acid ester

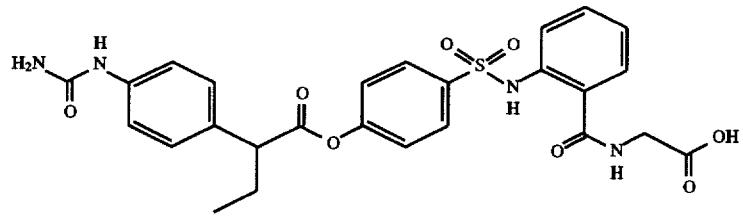

NMR (DMSO-d$_6$): δ 10.5 (1H, br), 8.61 (1H, s), 7.81–7.70 (3H, m), 7.41–7.05 (10H, m), 6.80 (1H, t, J=7.6 Hz), 5.85 (2H, s), 3.84 (2H, s), 3.70 (1H, t, J=7 Hz), 2.30 (2H, s), 2.60–1.95 and 1.90–1.65 (each 1H, m), 0.88 (3H, t, J=7.0 Hz);

TLC: Rf 0.22 (acetic acid:methanol:chloroform=1:3:30).

3.89 (2H, d, J=5 Hz), 3.81 (1H, t, J=6 Hz), 2.19–1.98 and 1.88–1.67 (each 1H, m), 1.47 (3H, d, J=8 Hz), 0.97 (3H, t, J=8 Hz);

TLC: Rf 0.11 (chloroform:methanol:water=8:2:0.2).

Example 2(217)

4-(N-2-(N'-carboxymethylcarbamoyl)
phenylsulfamoyl)phenyl 1-(4-ureidophenyl)
cyclobutanecarboxylic acid ester

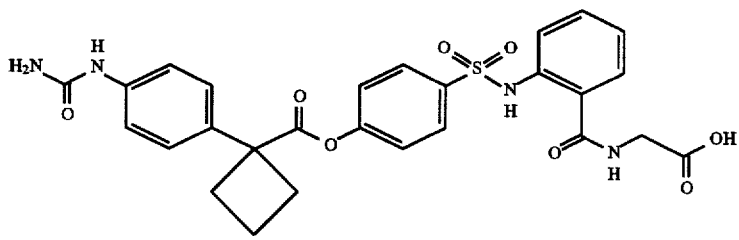

NMR (DMSO-d$_6$): δ 10.0 (1H, brs), 8.50 (1H, s), 7.67 (4H, d, J=8.8 Hz), 7.32—7.09 (2H, m), 7.30 (2H, d, J=8.6 Hz), 7.11 (2H, d, J=8.8 Hz), 6.96 (2H, d, J=8.6 Hz), 6.76 (1H, t, J=6.8 Hz), 5.74 (2H, s), 3.75–3.73 (2H, m), 2.80–2.63 (2H, m), 2.53–2.26 (2H, m), 2.23–2.00 (2H, m);

TLC: Rf 0.10 (chloroform:methanol:acetic acid=40:2:1).

Example 2(218)

4-(N-2-(N'-carboxymethylcarbamoyl)
phenylsulfamoyl)phenyl 2RS-(4-(N-(2S-
aminopropionyl)amino)phenyl)butanoic acid
ester.hydrochloride

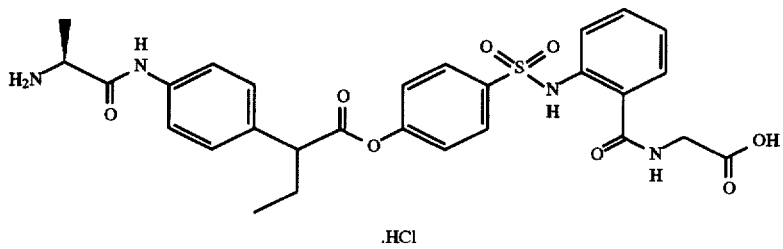

NMR (DMSO-d$_6$): δ 10.92 (1H, s), 9.47–9.32 (1H, m), 7.85–7.73 (3H, m), 7.66 (2H, d, J=9 Hz), 7.54–7.42 (2H, m), 7.34 (2H, d, J=9 Hz), 7.27–7.04 (4H, m), 4.16–3.99 (1H, m),

Example 2(219)

4-(N-2-(N'-carboxymethylcarbamoyl)phenylsulfamoyl)phenyl 2RS-(4-(N-(2S-amino-3-methylbutylyl)amino)phenyl)butanoic acid ester.hydrochloride

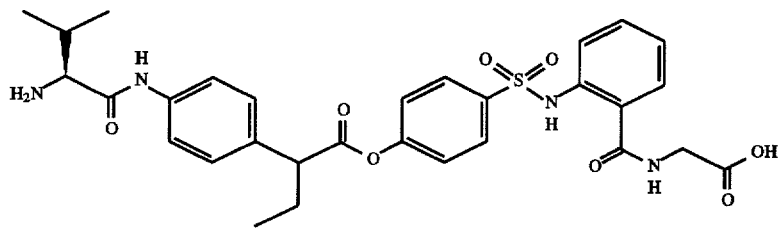

NMR (DMSO-d$_6$): δ 10.96–10.85 (1H, m), 9.45–9.30 (1H, m), 7.85–7.72 (2H, m), 7.66 (2H, d, J=8.4 Hz), 7.54–7.42 (2H, m), 7.34 (2H, d, J=8.4 Hz), 7.27–7.06 (4H, m), 3.90 (2H, d, J=6.0 Hz), 3.81 (1H, t, J=7.8 Hz), 2.33–1.98 and 1.92–1.66 (each 1H, m), 1.01 (6H, d, J=7.2 Hz), 0.87 (3H, t, J=7.4 Hz);

TLC: Rf 0.19 (chloroform:methanol:water=8:2:0:2).

Example 2(220)

4-(N-2-(N'-carboxymethylcarbamoyl)phenylsulfamoyl)phenyl 2RS-(4-(N-(pyrrolidin-2S-ylcarbonyl)amino)phenyl)butanoic acid ester.hydrochloride

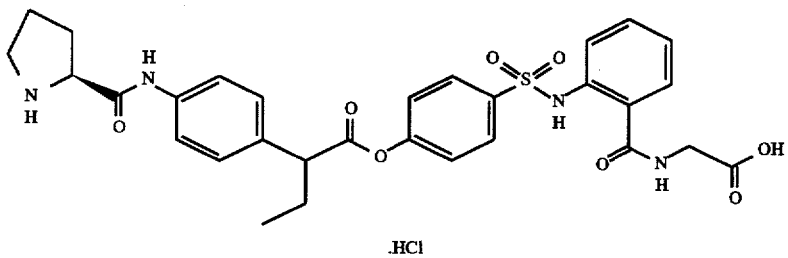

NMR (DMSO-d$_6$): δ 10.62–10.52 (1H, m), 9.95–9.70 (1H, m), 7.86–7.70 (3H, m), 7.62 (2H, d, J=8.8 Hz), 7.48–7.27 (4H, m), 7.13 (2H, m), 7.13 (2H, d, J=8.8 Hz), 7.04–6.93 (1H, m), 4.34–4.20 (1H, m), 3.95–3.85 (2H, m), 3.81 (1H, t, J=7.1 Hz), 3.33–3.16 (2H, m), 2.45–2.21 (1H, m), 2.21–1.68 (5H, m), 0.77 (3H, t, J=7.1 Hz);

TLC: Rf 0.09 (chloroform:methanol:water=8:2:0.2).

Example 2(221)

4-(N-2-(N'-carboxymethylcarbamoyl)phenylsulfamoyl)phenyl 2RS-(3,4,5-trimethoxyphenyl)butanoic acid ester

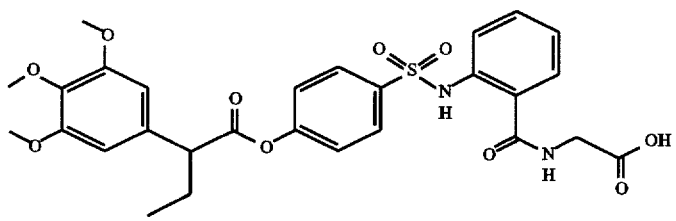

NMR (DMSO-d$_6$): δ 12.71 (1H, br), 11.69 (1H, br), 9.22 (1H, t-like), 7.80 (2H, d, J=8 Hz), 7.73 (1H, d, J=8 Hz), 7.53–7.41 (2H, m), 7.25–7.09 (3H, m), 6.63 (2H, s), 3.89 (2H, d, J=5 Hz), 3.77 (6H, s), 3.65 (3H, s), 3.63 (1H, t, J=7 Hz), 2.19–1.97 and 1.88–1.67 (each 1H, m), 0.90 (3H, t, J=7 Hz);

TLC: Rf 0.57 (acetic acid:methanol:chloroform=1:3:30).

Example 2(222)

4-(N-2-(N'-carboxymethylcarbamoyl)
phenylsulfamoyl)phenyl 2RS-(2,4,6-
trimethylphenyl)butanoic acid ester

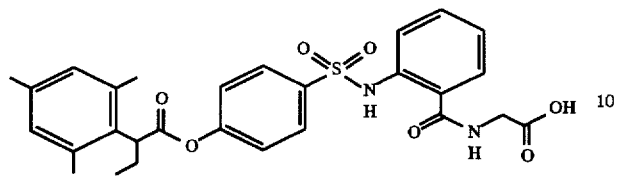

NMR (CD$_3$OD): δ 7.80–6.80 (12H, m), 4.21 (1H, dd, J=8.0 and 6.0 Hz), 3.93 (2H, s), 2.30–2.20 (each 3H, s), 1.90–1.60 (2H, m), 0.90 (3H, t, J=7.2 Hz);

TLC: Rf 0.46 (acetic acid:methanol:chloroform=1:3:30).

Example 2(223)

4-(N-2-(N'-carboxymethylcarbamoyl)
phenylsulfamoyl)phenyl 2RS-(3-nitro-4-
methoxyphenyl)butanoic acid ester

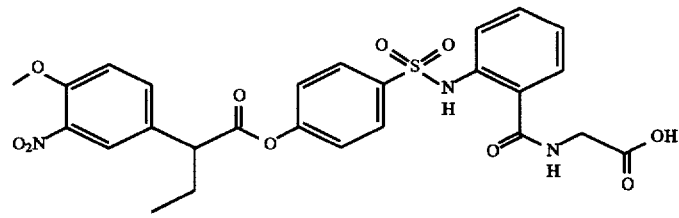

NMR (DMSO-d$_6$): δ 12.72 (1H, br), 11.60 (1H, br), 9.18 (1H, t-like), 7.89–7.59 (5H, m), 7.53–7.46 (2H, m), 7.36 (1H, d, J=9 Hz), 7.24 (2H, d, J=9 Hz), 7.13 (1H, t, J=8 Hz), 3.95 (1H, t, J=8 Hz), 3.92 (3H, s), 3.89 (2H, d, J=6 Hz), 2.23–2.02 and 1.94–1.72 (each 1H, m), 0.88 (3H, t, J=7 Hz);

TLC: Rf 0.51 (acetic acid:methanol:chloroform=1:3:30).

Example 2(224)

4-(N-2-(N'-carboxymethylcarbamoyl)
phenylsulfamoyl)phenyl 2RS-(3-nitro-4-
aminophenyl)butanoic acid ester.hydrochloride

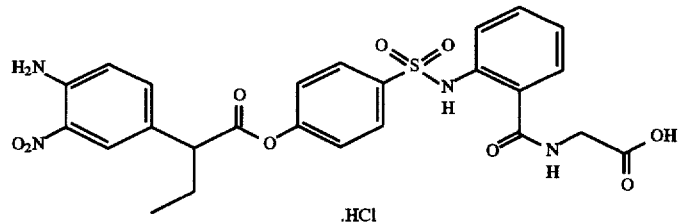

NMR (DMSO-d$_6$): δ 12.14 (2H, br), 9.36 (1H, t-like), 7.95 (1H, d, J=2.0 Hz), 7.79 (2H, d, J=8.8 Hz), 7.76 (1H, d, J=6.6 Hz), 7.51–7.38 (5H, m), 7.21 (2H, m), 7.15–7.02 (2H, m), 3.89 (2H, d, J=5.6 Hz), 3.80 (1H, t, J=7.6 Hz), 2.13–1.99 and 1.84–1.69 (each 1H, m), 0.88 (3H, t, J=7.6 Hz);

TLC: Rf 0.18 (chloroform:methanol:water=8:2:0.2).

Example 2(225)

4-(N-2-(N'-carboxymethylcarbamoyl)
phenylsulfamoyl)phenyl 2RS-(4-(N-acetylamino)
phenyl)butanoic acid ester

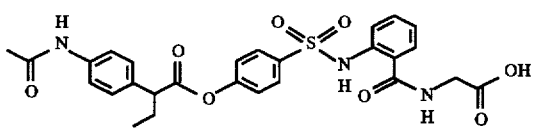

NMR (DMSO-d$_6$): δ 12.76 (1H, br), 11.58 (1H, s), 9.94 (1H, s), 9.20 (1H, t, J=6 Hz), 7.81–7.70 (3H, m), 7.58–7.46 (4H, m), 7.29–7.10 (5H, m), 3.89 (2H, d, J=6 Hz), 3.76 (1H, t, J=7 Hz), 2.14–1.99 and 1.83–1.69 (each 1H, m), 2.03 (3H, s), 0.87 (3H, t, J=7 Hz);

TLC: Rf 0.20 (chloroform:methanol:water=8:2:0.2).

Example 2(226)

4-(N-2-(N'-carboxymethylcarbamoyl)
phenylsulfamoyl)phenyl 2RS-(4-(N-methyl-N-
acetylamino)phenyl)butanoic acid ester

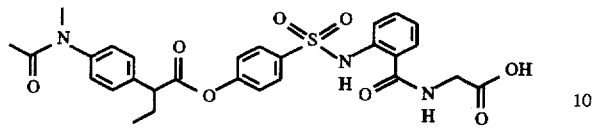

NMR (DMSO-$d_6$): δ 11.59 (1H, s), 9.19 (1H, t, J=5 Hz),
7.80 (2H, d, J=9 Hz), 7.73 (1H, d, J=8 Hz), 7.53–7.41 (4H,
m), 7.34–7.10 (5H, m), 3.89 (2H, d, J=6 Hz), 3.69 (1H, t, J=7
Hz), 3.16 (3H, s), 2.18–2.01 and 1.92–1.71 (each 1H, m),
1.78 (3H, s), 0.90 (3H, t, J=7 Hz);

TLC: Rf 0.27 (chloroform:methanol:water=8:2:0.2).

Example 2(227)

4-(N-2-(N'-carboxymethylcarbamoyl)
phenylsulfamoyl)phenyl 2RS-(4-(morpholin-4-
ylmethyl)phenyl)butanoic acid ester.trifluoroacetate

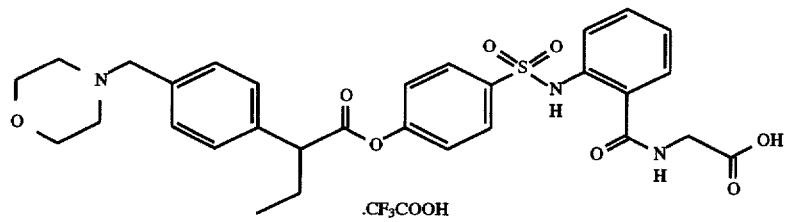

NMR (DMSO-$d_6$): δ 12.00–11.20 (2H, br), 9.28–9.15
(1H, m), 7.88–7.68 (3H, m), 7.56–7.27 (6H, m), 7.27–7.08
(3H, m), 3.95–3.79 (4H, m), 3.68–3.59 (5H, m), 2.90–2.60
(4H, m), 2.20–1.95 (1H, m), 1.95–1.65 (1H, m), 0.95–0.80
(3H, m);

TLC: Rf 0.47 (acetic acid:methanol:chloroform=1:2:20).

Example 2(228)

4-(N-2-(N'-carboxymethylcarbamoyl)
phenylsulfamoyl)phenyl 2RS-(4-(4-benzylpiperazin-
1-yl)phenyl)butanoic acid ester

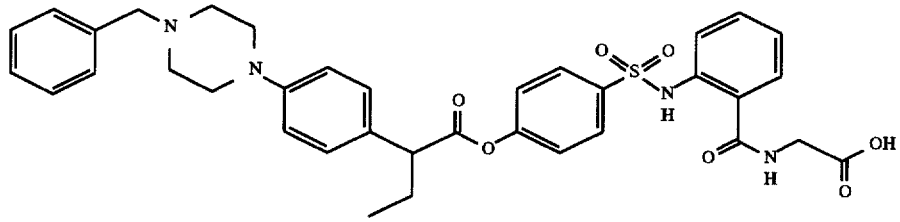

NMR (CDCl$_3$+CD$_3$OD): δ 9.21 (1H, d-like), 7.95–7.86
(4H, m), 7.78–7.71 (1H, m), 7.65–7.58 (2H, m), 7.54–7.46
(6H, m), 7.40–7.32 (2H, m), 7.21–7.10 (2H, m), 3.91 (2H,
d, J=7 Hz), 3.50–3.06 (11H, m), 1.68–1.45 (2H, m), 0.78
(3H, t, J=7 Hz);

TLC: Rf 0.65 (acetic acid:methanol:chloroform=1:3:30).

Example 2(229)

4-(N-2-(N'-carboxymethylcarbamoyl)phenylsulfamoyl)phenyl 2RS-(4-(pyrrolidin-1-ylmethyl)phenyl)butanoic acid ester

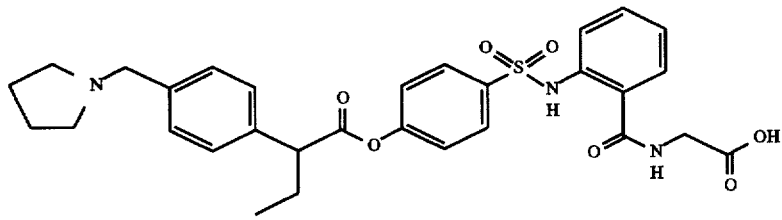

NMR (DMSO-d$_6$): δ 9.65 (1H, brs), 7.77 (2H, d, J=8 Hz), 7.73 (1H, d, J=8 Hz), 7.45–7.30 (6H, m), 7.14 (2H, d, J=8 Hz), 6.99 (1H, d, J=8 Hz), 4.03–3.93 (2H, m), 3.93–3.80 (3H, m), 2.88 (4H, brs), 2.09 (1H, ddq, J=14 Hz, 7 Hz, 7 Hz), 1.88–1.73 (5H, m), 0.88 (3H, t, J=7 Hz);

TLC: Rf 0.10 (acetic acid:methanol:chloroform=1:2:20).

Example 2(230)

4-(N-2-(N'-carboxymethylcarbamoyl)phenylsulfamoyl)phenyl 2-(thiophen-2-yl)-2-ethylbutanoic acid ester

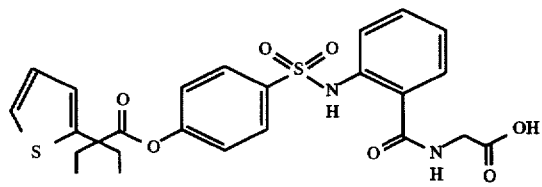

NMR (DMSO-d$_6$): δ 9.5–9.3 (1H, brs), 7.9–7.7 (3H, m), 7.5–7.4 (3H, m), 7.3–7.0 (5H, m), 3.87 (2H, d, J=5 Hz), 2.3–1.9 (4H, m), 0.82 (6H, t, J=7 Hz);

TLC: Rf 0.19 (acetic acid:methanol:chloroform=1:2:40).

Example 2(231)

4-((1R-oxo-4S-carboxyperhydrothiazol-3-yl)sulfonyl)-2-methylphenyl 2RS-(4-(pyrrolidin-1-yl)phenyl)butanoic acid ester

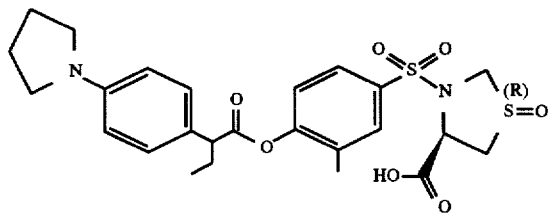

NMR (DMSO-d$_6$): δ 7.85–7.70 (2H, m), 7.18 (2H, d, J=8.5 Hz), 7.09 (1H, d, J=8.5 Hz), 6.53 (2H, d, J=8.5 Hz), 4.85–4.65 (2H, m), 4.30 (1H, d, J=12.5 Hz), 3.69 (1H, t, J=7.5 Hz), 3.35–3.05 (6H, m), 2.20–1.60 (2H, m), 1.99 (3H, s), 2.00–1.85 (4H, m), 0.90 (3H, t, J=7.5 Hz);

TLC: Rf 0.36 (chloroform:methanol:acetic acid=25:5:1).

Example 2(232)

4-((2S-carboxypyrrolidin-1-yl)sulfonyl)-2-methylphenyl 2S-(4-(pyrrolidin-1-yl)phenyl)butanoic acid ester.hydrochloride

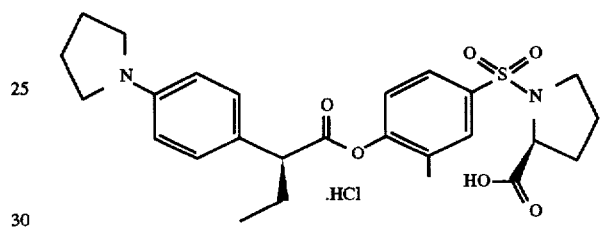

NMR (CD$_3$OD): δ 7.89–7.69 (2H, m), 7.54 and 7.41 (each 2H, d, J=8 Hz), 7.15 (1H, d, J=8 Hz), 4.28–4.16 (1H, m), 3.90 (1H, t, J=7 Hz), 3.69–3.64 (4H, m), 3.51–3.40 and 3.31–3.21 (each 1H, m), 2.28–2.21 (5H, m), 2.02 (3H, s), 2.01–1.89 (4H, m), 1.80–1.65 (1H, m), 0.99 (3H, t, J=7 Hz);

TLC: Rf 0.17 (chloroform:methanol:water=9:1:0.1).

Example 2(233)

4-((2R-carboxypyrrolidin-1-yl)sulfonyl)-2-methylphenyl 2S-(4-(pyrrolidin-1-yl)phenyl)butanoic acid ester.hydrochloride

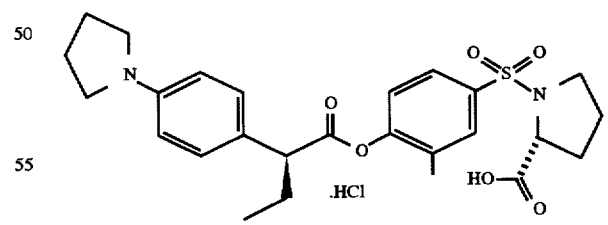

NMR (CD$_3$OD): δ 7.81–7.68 (2H, m), 7.56 and 7.45 (each 2H, d, J=8 Hz), 7.15 (1H, d, J=8 Hz), 4.28–4.16 (1H, m), 3.91 (1H, t, J=7 Hz), 3.71–3.64 (4H, m), 3.50–3.40 and 3.33–3.22 (each 1H, m), 2.31–2.22 (5H, m), 2.03 (3H, s), 2.02–1.84 (4H, m), 1.80–1.64 (1H, m), 1.00 (3H, t, J=7 Hz);

TLC: Rf 0.18 (chloroform:methanol:water=9:1:0.1).

Example 2(234)

4-((2S-carboxypyrrolidin-1-yl)sulfonyl)-2-methylphenyl 2R-(4-(pyrrolidin-1-yl)phenyl) butanoic acid ester.hydrochloride

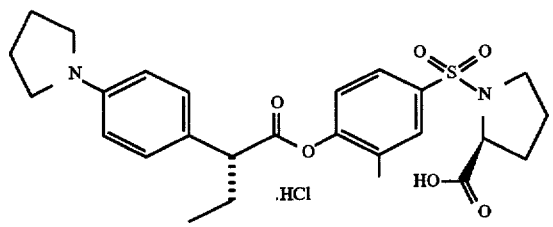

NMR (CD₃OD): δ 7.80–7.68 (2H, m), 7.50 and 7.31 (each 2H, d, J=8 Hz), 7.14 (1H, d, J=8 Hz), 4.22–4.16 (1H, m), 3.87 (1H, t, J=7 Hz), 3.68–3.56 (4H, m), 3.50–3.42 and 3.35–3.20 (each 1H, m), 2.32–2.18 (5H, m), 2.02 (3H, s), 2.01–1.83 (4H, m), 1.79–1.65 (1H, m), 0.99 (3H, t, J=7 Hz);

TLC: Rf 0.17 (chloroform:methanol:water=9:1:0.1).

Example 2(235)

4-((2R-carboxypyrrolidin-1-yl)sulfonyl)-2-methylphenyl 2R-(4-(pyrrolidin-1-yl)phenyl) butanoic acid ester.hydrochloride

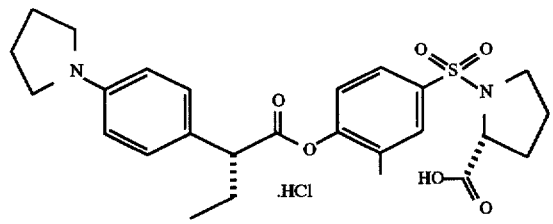

NMR (CD₃OD): δ 7.77–7.68 (2H, m), 7.57 and 7.48 (each 2H, d, J=8 Hz), 7.15 (1H, d, J=8 Hz), 4.22–4.17 (1H, m), 3.93 (1H, t, J=7 Hz), 3.74–3.66 (4H, m), 3.52–3.42 and 3.35–3.21 (each 1H, m), 2.28–2.22 (5H, m), 2.02 (3H, s), 2.01–1.87 (4H, m), 1.80–1.64 (1H, m), 0.99 (3H, t, J=7 Hz);

TLC: Rf 0.18 (chloroform:methanol:water=9:1:0.1).

Example 2(236)

4-((2S-aminomethylpyrrolidin-1-yl)sulfonyl)-2-methylphenyl 2RS-(4-(pyrrolidin-1-yl)phenyl) butanoic acid ester.2hydrochloride

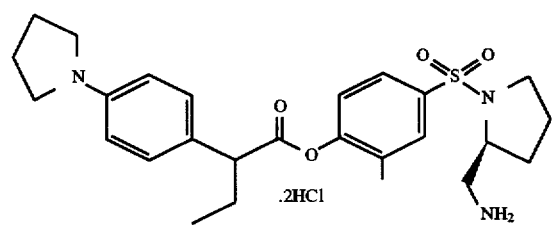

NMR (CD₃OD): δ 7.85–7.70 (2H, m), 7.64 (4H, s), 7.22 (1H, d, J=8.0 Hz), 3.98 (1H, t, J=8.0 Hz), 4.00–3.80 (1H, m), 3.85–3.70 (4H, m), 3.55–3.20 (2H, m), 3.15–2.95 (2H, m), 2.40–1.80 (2H, m), 2.35–2.25 (4H, m), 2.06 (3H, s), 2.00–1.40 (4H, m), 1.00 (3H, t, J=7.5 Hz);

TLC: Rf 0.29 (chloroform:methanol:water=4:1:0.1).

Example 2(237)

4-((4-aminopiperidin-1-yl)sulfonyl)-2-methylphenyl 2RS-(4-(pyrrolidin-1-yl)phenyl)butanoic acid ester.2hydrochloride

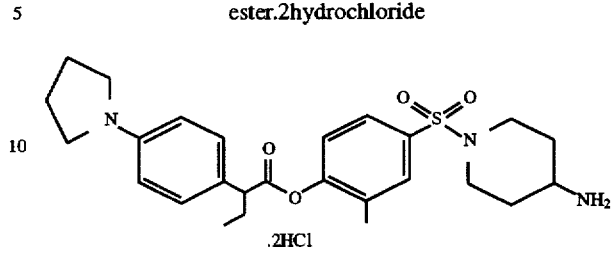

NMR (DMSO-d₆): δ 8.14 (2H, brs), 7.63 (1H, s), 7.60 (1H, d, J=8.4 Hz), 7.21 (2H, d, J=8.4 Hz), 7.20 (1H, d, J=8.4 Hz), 6.64 (2H, d, J=8.4 Hz), 3.8–3.5 (4H, br), 3.3–3.2 (5H, br), 3.2–3.0 (1H, br), 2.5–2.3 (2H, m), 2.2–2.0 (1H, m), 2.0–1.9 (4H, br), 1.98 (3H, s), 1.9–1.7 (1H, m), 1.7–1.5 (2H, m), 0.90 (3H, t, J=7.2 Hz);

TLC: Rf 0.20 (chloroform:methanol=9:1).

Example 2(238)

4-((2S-carboxyazetidin-1-yl)sulfonyl)-2-methylphenyl 2RS-(4-(pyrrolidin-1-yl)phenyl) butanoic acid ester

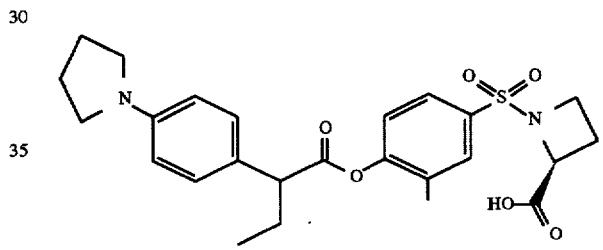

NMR (CD₃OD): δ 7.72 (1H, s), 7.71 (1H, d, J=8.0 Hz), 7.22 (2H, d, J=8.8 Hz), 7.17 (1H, d, J=8.0 Hz), 6.58 (2H, d, J=8.8 Hz), 4.30 (1H, t, J=8.5 Hz), 3.8–3.6 (3H, m), 3.4–3.2 (4H, m), 2.4–2.1 (3H, m), 2.1–2.0 (4H, brs), 2.0–1.8 (1H, m), 2.04 (3H, s), 1.00 (3H, t, J=7.4 Hz);

TLC: Rf 0.59 (chloroform:methanol:acetic acid=25:5:1).

Example 2(239)

4-((2RS-carboxypiperidin-1-yl)sulfonyl)-2-methylphenyl 2RS-(4-(pyrrolidin-1-yl)phenyl) butanoic acid ester

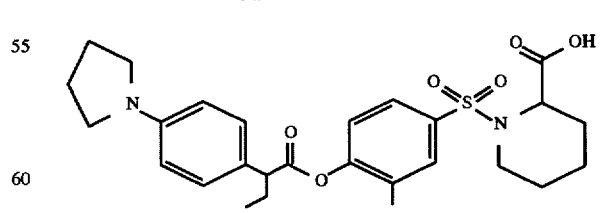

NMR (CDCl₃): δ 7.65 (1H, s), 7.63 (1H, d, J=8.2 Hz), 7.21 (2H, d, J=8.6 Hz), 6.99 (1H, d, J=8.2 Hz), 6.53 (2H, d, J=8.6 Hz), 4.7–4.6 (1H, brs), 4.7–4.1 (1H, br), 3.59 (1H, t, J=7.7 Hz), 3.5–3.2 (6H, brs), 2.3–2.1 (1H, m), 2.1–1.9 (4H, brs), 2.0–1.8 (1H, m), 1.98 (3H, s), 1.6–1.2 (6H, br), 0.96 (3H, t, J=7.4 Hz);

TLC: Rf 0.12 (chloroform:methanol=9:1).

Example 2(240)

4-((2-oxo-5S-carboxypyrrolidin-1-yl)sulfonyl)-2-methylphenyl 2R-(4-(pyrrolidin-1-yl)phenyl) butanoic acid ester.hydrochloride

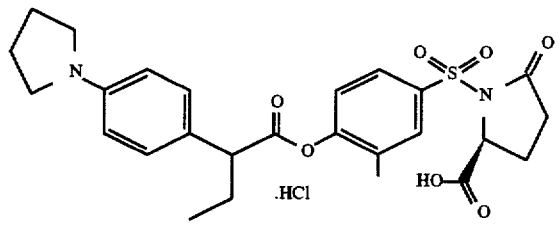

NMR (CD$_3$OD): δ 7.96–7.82 (2H, m), 7.57 (2H, d, J=8.5 Hz), 7.42 (2H, d, J=8.5 Hz), 7.13 (1H, d, J=8.0 Hz), 4.90–4.80 (1H, m), 3.92 (1H, t, J=7.5 Hz), 3.74–3.60 (4H, m), 2.65–1.80 (10H, m), 2.02 (3H, s), 0.99 (3H, t, J=7.5 Hz);

TLC: Rf 0.35 (chloroform:methanol:acetic acid=4:1:0.1).

Example 2(241)

4-((2S-carboxypyrrolidin-1-yl)sulfonyl)-2-methylphenyl 2RS-(3-(pyrrolidin-1-yl)phenyl) butanoic acid ester

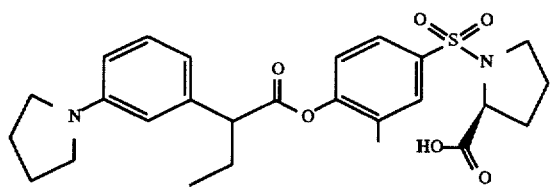

NMR (CDCl$_3$): δ 7.70–7.64 (2H, m), 7.20 (1H, t, J=7.8 Hz), 7.09 (1H, d, J=7.8 Hz), 6.66 (1H, d, J=7.8 Hz), 6.53–6.47 (2H, m), 4.3–4.2 (1H, m), 3.8–3.4 (2H, m), 3.4–3.2 (5H, m), 2.3–1.7 (13H, m), 1.01 (3H, t, J=7.4 Hz);

TLC: Rf 0.58 (chloroform:methanol:acetic acid=9:1:0.2).

Example 2(242)

4-((2S-carboxy-4R-methoxypyrrolidin-1-yl)sulfonyl)-2-methylphenyl 2RS-(4-(pyrrolidin-1-yl)phenyl) butanoic acid ester.hydrochloride

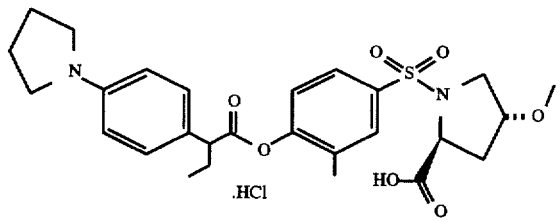

NMR (DMSO-d$_6$): δ 7.73 (1H, s), 7.66 (1H, d, J=8.6 Hz), 7.26 (2H, d, J=8.8 Hz), 7.15 (1H, d, J=8.6 Hz), 6.78 (2H, d, J=8.8 Hz), 5.00 (1H, brs), 4.02 (1H, t, J=7 Hz), 3.82 (1H, m), 3.76 (1H, t, J=7 Hz), 3.41 (2H, m), 3.31 (4H, m), 2.83 (3H, s), 2.15 (2H, m), 2.00 (4H, m), 1.98 (3H, s), 1.95 (2H, m), 0.92 (3H, t, J=7.4 Hz);

TLC: Rf 0.34 (chloroform:methanol:water=4:1:0.1).

Example 2(243)

4-((2R-carboxy-4R-methoxypyrrolidin-1-yl) sulfonyl)-2-methylphenyl 2RS-(4-(pyrrolidin-1-yl) phenyl)butanoic acid ester.hydrochloride

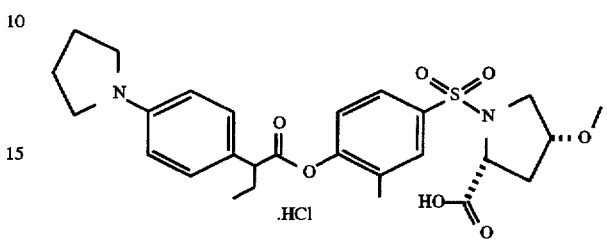

NMR (DMSO-d$_6$): δ 7.77 (1H, d, J=2.4 Hz), 7.70 (1H, dd, J=8.4 Hz, 2.4 Hz), 7.26 (2H, d, J=8.2 Hz), 7.16 (1H, d, J=8.4 Hz), 6.75 (2H, d, J=8.2 Hz), 4.80 (1H, brs), 4.31 (1H, dd, J=9.2 Hz, 3.2 Hz), 3.76 (2H, m), 3.33 (6H, m), 3.12 (3H, s), 2.12 (2H, m), 2.02 (4H, m), 1.98 (3H, s), 1.80 (2H, m), 0.91 (3H, t, J=7.2 Hz);

TLC: Rf 0.47 (chloroform:methanol:water=4:1:0.1).

Example 2(244)

4-((2S-carboxypyrrolidin-1-yl)sulfonyl)-2-methylphenyl 2RS-(2-methyl-4-(pyrrolidin-1-yl) phenyl)butanoic acid ester.hydrochloride

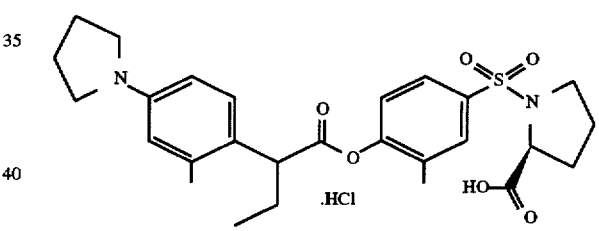

NMR (CD$_3$OD): δ 7.76–7.66 (2H, m), 7.60–7.40 (3H, m), 7.15 (1H, d, J=8.0 Hz), 4.30–4.10 (2H, m), 3.85–3.70 (4H, m), 3.55–3.15 (2H, m), 2.57 (3H, s), 2.40–2.15 (5H, m), 2.00 (3H, s), 2.10–1.60 (5H, m), 1.01 (3H, t, J=7.5 Hz);

TLC: Rf 0.33 (chloroform:methanol:acetic acid=4:1:0.1).

Example 2(245)

4-((2S-carboxy-4R-hydroxypyrrolidin-1-yl)sulfonyl)-2-methylphenyl 2RS-(4-(pyrrolidin-1-yl)phenyl) butanoic acid ester.hydrochloride

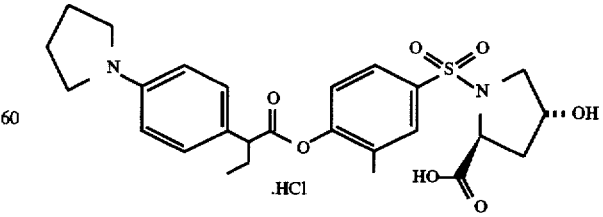

NMR (CD$_3$OD): δ 7.72 (1H, s), 7.70 (1H, m), 7.20 (2H, d, J=8.6 Hz), 7.09 (1H, d, J=8.0 Hz), 6.58 (2H, d, J=8.6 Hz), 4.32 (1H, m), 4.21 (1H, m), 3.73–3.42 (2H, m), 3.38–3.16 (5H, m), 2.35–1.68 (11H, m), 0.98 (3H, t, J=7.0 Hz);

TLC: Rf 0.55 (chloroform:methanol:acetic acid=15:2:1).

Example 2(246)

4-(N-methoxy-N-carboxymethylaminosulfonyl)-2-methylphenyl 2RS-(4-(pyrrolidin-1-yl)phenyl) butanoic acid ester.hydrochloride

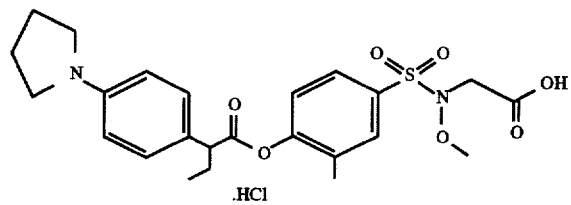

NMR (CDCl₃): δ 7.66 (1H, s), 7.63 (1H, d, J=8.0 Hz), 7.22 (2H, d, J=8.8 Hz), 7.08 (1H, d, J=8.0 Hz), 6.54 (2H, d, J=8.8 Hz), 5.3–4.6 (1H, br), 3.81 (3H, s), 3.70 (2H, s), 3.69 (1H, t, J=7.8 Hz), 3.3–3.2 (4H, brs), 2.2–2.0 (1H, m), 2.1–1.9 (4H, brs), 2.01 (3H, s), 2.0–1.8 (1H, m), 0.97 (3H, t, J=7.4 Hz);

TLC:Rf 0.44 (hexane:ethyl acetate=2:1).

Example 2(247)

4-((2S-carboxypyrrolidin-1-yl)sulfonyl)-2-methylphenyl 2RS-(2-methoxy-4-(pyrrolidin-1-yl)phenyl)butanoic acid ester.hydrochloride

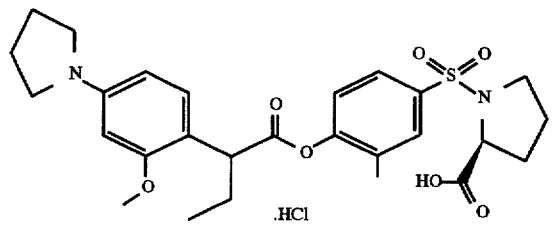

NMR (DMSO-d₆): δ 7.74 (1H, s), 7.68 (1H, d, J=8.5 Hz), 7.24–7.06 (2H, m), 6.50–6.30 (2H, m), 4.18–4.06 (1H, m), 4.00 (1H, t, J=7.0 Hz), 3.83 (3H, s), 3.40–3.05 (6H, m), 2.20–1.45 (10H, m), 2.05 (3H, s), 0.89 (3H, t, J=7.5 Hz);

TLC: Rf 0.40 (chloroform:methanol:acetic acid=4:1:0.1).

Example 2(248)

4-((2S-carboxyaziridin-1-yl)sulfonyl)-2-methylphenyl 2RS-(4-(pyrrolidin-1-yl)phenyl) butanoic acid ester

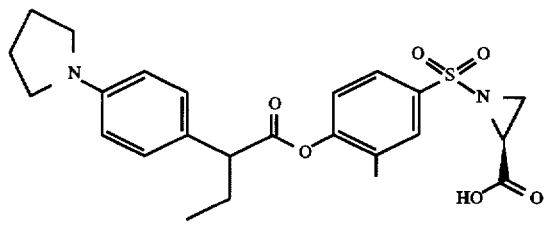

NMR (CDCl₃+CD₃OD): δ 7.74 (1H, s), 7.70 (1H, d, J=8.4 Hz), 7.20 (2H, d, J=8.4 Hz), 7.08 (1H, d, J=8.4 Hz), 6.54 (2H, d, J=8.4 Hz), 3.61 (1H, t, J=7.5 Hz), 3.3–3.2 (4H, brs), 2.6–2.3(3H, brs), 2.3–2.1 (1H, m), 2.1–1.9 (4H, brs), 2.0–1.8 (1H, m), 1.99(3H, s), 0.97 (3H, t, J=7.4 Hz);

TLC: Rf 0.28 (chloroform:methanol=4:1).

Example 2(249)

4-(N,N-bis(2-aminoethyl)aminosulfonyl)-2-methylphenyl 2RS-(4-(pyrrolidin-1-yl)phenyl) butanoic acid ester.3 hydrochloride

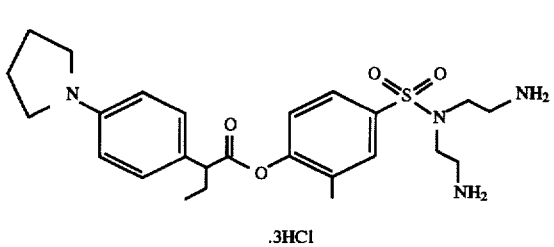

NMR (DMSO-d₆): δ 8.25 (4H, m), 7.80 (1H, d, J=1.0 Hz), 7.71 (1H, dd, J=8.6 Hz, 1.0 Hz), 7.26 (3H, m), 6.82 (2H, m), 3.78 (1H, t, J=7.8 Hz), 3.35 (8H, m), 3.04 (4H, m), 2.13 (1H, m), 2.02 (3H, s), 1.98 (4H, m), 1.85 (1H, m), 0.92 (3H, t, J=7.2 Hz);

TLC: Rf 0.31 (chloroform:methanol:water=6:4:1).

Example 2(250)

4-(N-carboxymethyl-N-(2-(N',N'-dimethylamino) ethyl)aminosulfonyl)-2-methylphenyl 2RS-(4-(pyrrolidin-1-yl)phenyl)butanoic acid ester trifluoroacetate

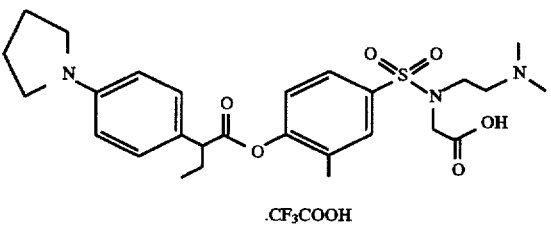

NMR (CDCl₃): δ 7.61–7.55 (2H, m), 7.21 (2H, d, J=8.7 Hz), 7.07 (1H, d, J=8.2 Hz), 6.54 (2H, d, J=8.7 Hz), 3.80 (2H, s), 3.60 (1H, t, J=7.8 Hz), 3.5514 3.10 (8H, m), 2.83 (6H, s), 2.30–1.70 (9H, m), 0.98 (3H, t, J=7.4 Hz);

TLC: Rf 0.43 (chloroform:methanol:water=8:2:0.2).

Example 2(251)

4-((2S-carboxypyrrolidin-1-yl)sulfonyl)-2-ethylphenyl 2RS-(4-(pyrrolidin-1-yl)phenyl) butanoic acid ester

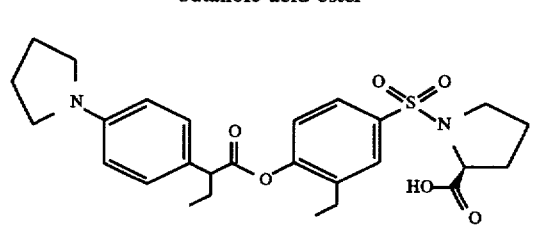

NMR (CDCl₃): δ 7.8–7.6 (m, 2H), 7.36 (d, J=8.4 Hz, 2H), 7.07 (d, J=8.4 Hz, 1H), 7.02 (d, J=8.4 Hz, 2H), 4.3–4.2 (m,

1H), 3.70 (t, J=7.2 Hz, 1H), 3.6–3.4 (m, 5H), 3.3–3.1 (m, 1H), 2.37 (q, J=7.6 Hz, 2H), 2.3–1.6 (m, 10H), 1.03 (t, J=7.6 Hz, 3H), 0.99 (t, J=7.6 Hz, 3H);

TLC: Rf 0.33 (chloroform:methanol:acetic acid=50:2:1).

Example 2(252)

4-(N-carboxymethyl-N-benzyloxyaminosulfonyl)-2-methylphenyl 2RS-(4-(pyrrolidin-1-yl)phenyl) butanoic acid ester.hydrochloride

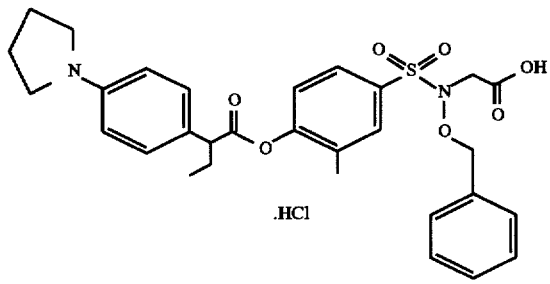

NMR (DMSO-d$_6$): δ 7.70 (1H, s), 7.68 (1H, d, J=8.6 Hz), 7.32 (5H, s), 7.20 (2H, d, J=8.2 Hz), 7.16 (1H, d, J=8.6 Hz), 6.52 (2H, d, J=8.2 Hz), 5.25 (2H, s), 3.8–3.4 (2H, m), 3.5–3.4 (2H, brs), 3.3–3.1 (4H, brs), 2.2–2.0 (1H, m), 2.0–1.8 (4H, brs), 1.9–1.7 (1H, m), 1.93(3H, s), 0.89 (3H, t, J=7.2 Hz);

TLC: Rf 0.29 (chloroform:methanol=9:1).

Example 2(253)

4-(N-(4-carboxybutyl)aminosulfonyl)-2-methylphenyl 2RS-(4-(pyrrolidin-1-yl)phenyl) butanoic acid ester.hydrochloride

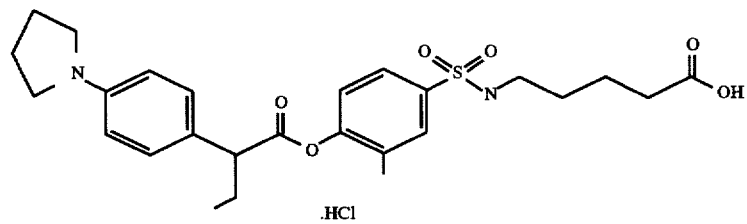

NMR (DMSOd$_6$+2 drops of D2O): δ 7.66 (1H, s-like), 7.63 (1H, dd, J=2 and 8 Hz), 7.24 (2H, d, J=8 Hz), 7.14 (2H, d, J=8 Hz), 6.69 (2H, d, J=8 Hz), 3.74 (1H, t, J=7 Hz), 3.31–3.25 (4H, m), 2.71 (2H, t, J=7 Hz), 2.18–1.72 (2H, m), 2.15 (2H, t, J=7 Hz), 2.01–1.94 (4H, m), 1.96 (3H, s), 1.53–1.34 (4H, m), 0.91 (3H, t, J=7 Hz);

TLC: Rf 0.38 (chloroform:methanol:water=9:1:0.1).

Example 2(254)

4-(N-(1,1-dimethyl-i-carboxymethyl) aminosulfonyl)-2-methylphenyl 2RS-(4-(pyrrolidin-1-yl)phenyl)butanoic acid ester

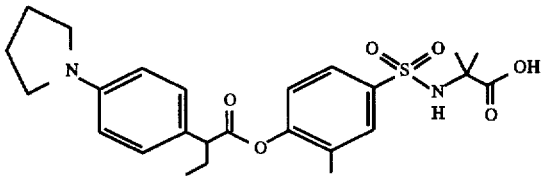

NMR (DMSO-d$_6$): δ 7.68 (1H, s-like), 7.64 (1H, dd, J=2 and 8 Hz), 7.39 (1H, br), 7.18 (2H, d, J=8 Hz), 7.07 (1H, d, J=8 Hz), 6.53 (2H, d, J=8 Hz), 3.69 (1H, t, J=7 Hz), 3.24–3.18 (4H, m), 2.20–1.65 (2H, m), 1.98–1.91 (4H, m), 1.93 (3H, s), 1.18 (6H, s), 0.90 (3H, t, J=7 Hz);

TLC: Rf 0.19 (chloroform:methanol:water=9:1:0.1).

Example 2(255)

4-(N-methyl-N-hydroxyaminosulfonyl)-2-methylphenyl 2RS-(4-(pyrrolidin-1-yl)phenyl) butanoic acid ester

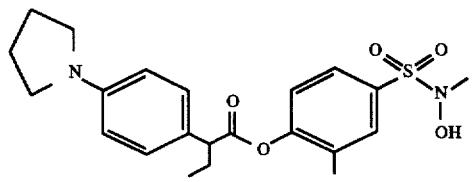

NMR (CDCl$_3$): δ 7.71 (1H, s), 7.69 (1H, d, J=8.6 Hz), 7.23 (2H, d, J=8.8 Hz), 7.13 (1H, d, J=8.6 Hz), 6.55 (2H, d, J=8.8 Hz), 6.54 (1H, s), 3.63 (1H, t, J=7.7 Hz), 3.3–3.2 (4H, brs), 2.81 (3H, s), 2.3–2.1 (1H, m), 2.1–1.9 (4H, brs), 2.06 (3H, s), 2.0–1.8 (1H, m), 0.99 (3H, t, J=7.3 Hz);

TLC: Rf 0.43 (hexane:ethyl acetate=2:1).

Example 2(256)

4-((2S-carboxypyrrolidin-1-yl)sulfonyl)-2-methylphenyl 2RS-(2-methyl-4-nitrophenyl)butanoic acid ester

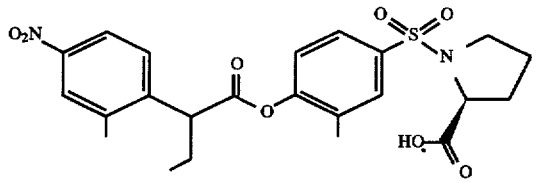

NMR (CDCl₃): δ 8.15–8.05 (2H, m), 7.75–7.65 (2H, m), 7.56 (1H, d, J=8.0 Hz), 7.09 (1H, d, J=9.0 Hz), 4.25 (1H, dd, J=3.5, 7.0 Hz), 4.13 (1H, t, J=7.5 Hz), 3.60–3.40 (1H, m), 3.30–3.10 (1H, m), 2.59 (3H, s), 2.45–1.60 (6H, m), 1.99 (3H, s), 1.02 (3H, t, J=7.5 Hz);

TLC: Rf 0.24 (chloroform:methanol:water=9:1:0.1).

Example 2(257)

4-(N-carboxymethylaminosulfonyl)-2-methylphenyl 2RS-(4-(pyrrolidin-1-yl)phenyl)butanoic acid ester

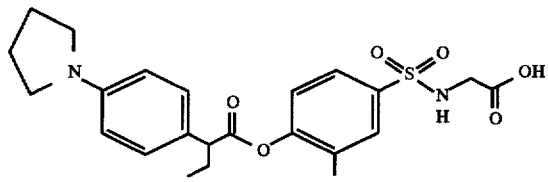

NMR (CDCl₃): δ 7.70–7.58 (2H, m), 7.25 (2H, d, J=8 Hz), 7.01 (1H, d, J=8 Hz), 6.65 (2H, d, J=8 Hz), 5.43–5.23 (1H, br), 5.18–4.80 (1H, br), 3.75 (2H, brs), 3.63 (1H, t, J=7 Hz), 3.40–3.20 (4H, m), 2.28–1.80 (9H, m), 0.98 (3H, t, J=7 Hz);

TLC: Rf 0.1 1 (chloroform:methanol:acetic acid=40:2:1).

Example 2(258)

4-(N-(1,1-dimethyl-i -carboxymethyl)-N-propylaminosulfonyl)-2-methylphenyl 2RS-(4-(pyrrolidin-1-yl)phenyl)butanoic acid ester

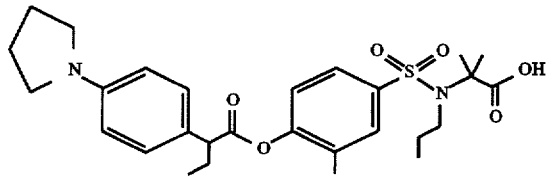

NMR (DMSO-d₆+2 drops of D2O): δ 7.80 (1H, s-like), 7.78 (1H, dd, J=2 and 8 Hz), 7.18 (2H, d, J=8 Hz), 7.11 (1H, d, J=8 Hz), 6.54 (2H, d, J=8 Hz, 3.70 (1H, t, J=7 Hz), 3.25–3.17 (4H, m), 3.12–3.04 (2H, m), 2.20–1.70 (2H, m), 1.99–1.92 (4H, m), 1.95 (3H, s), 1.57–1.42 (2H, m), 1.45 (6H, s), 0.91 (3H, t, J=7 Hz), 0.71 (3H, t, J=7 Hz);

TLC: Rf 0.57 (chloroform:methanol:water=9:1:0.1).

Example 2(259)

4-((2S-carboxy-4S-aminopyrrolidin-1-yl)sulfonyl)-2-methylphenyl 2RS-(4-(pyrrolidin-1-yl)phenyl)butanoic acid ester 2hydrochloride

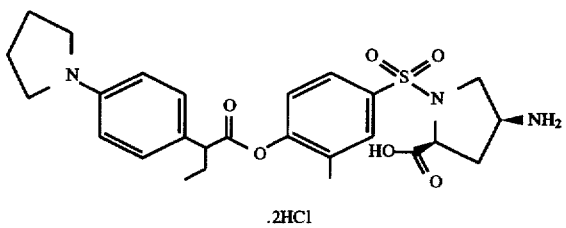

NMR (CD₃OD): δ 7.83–7.68 (2H, m), 7.63 (4H, s-like), 7.22 (1H, d, J=8.2 Hz), 4.21 (1H, dd, J=9.2 and 3.4 Hz), 3.98 (1H, t, J=7.8 Hz), 3.90–3.43 (7H, m), 2.70–1.84 (8H, m), 2.06 (3H, s), 1.00 (3H, t, J=7.4 Hz);

TLC: Rf 0.46 (ethyl acetate:acetic acid:water=6:2:1).

Example 2(260)

4-((2S-carboxy-4R-aminopyrrolidin-1-yl)sulfonyl)-2-methylphenyl 2RS-(4-(pyrrolidin-1-yl)phenyl)butanoic acid ester.2hydrochloride

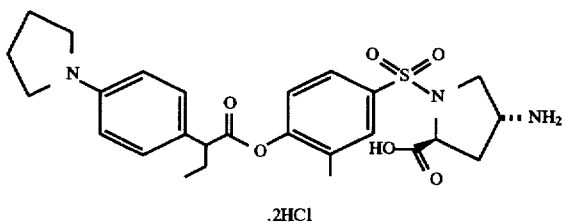

NMR (CD₃OD): δ 7.84–7.68 (2H, m), 7.63 (4H, s-like), 7.18 (1H, d, J=8.0 Hz), 4.55 (1H, dd, J=8.4 and 4.2 Hz), 4.07–3.90 (2H, m), 3.90–3.63 (5H, m), 3.47–3.26 (1H, m), 2.53–1.82 (8H, m), 2.05 (3H, s), 1.00 (3H, t, J=7.4 Hz);

TLC: Rf 0.42 (ethyl acetate:acetic acid:water=6:2:1).

Example 2(261)

4-(N-carboxymethyl-N-(2-(morpholin-4-yl)ethyl) aminosulfonyl)-2-methylphenyl 2RS-(4-(pyrrolidin-1-yl)phenyl)butanoic acid ester.hydrochloride

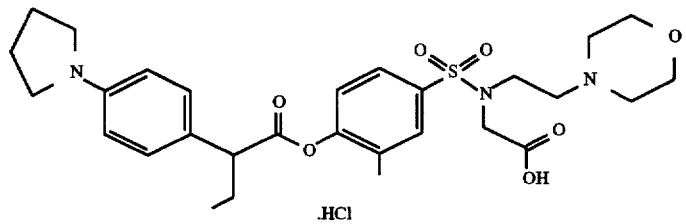

NMR (CDCl$_3$): δ 7.66–7.52 (2H, m), 7.21 (2H, d, J=8.5 Hz), 7.09 (1H, d, J=8.5 Hz), 6.55 (2H, d, J=8.5 Hz), 3.95–3.80 (4H, m), 3.75 (2H, s), 3.61 (1H, t, J=7.5 Hz), 3.45–3.20 (6H, m), 3.10–2.70 (6H, m), 2.30–1.75 (6H, m), 2.04 (3H, s), 0.99 (3H, t, J=7.5 Hz);

TLC: Rf 0.24 (chloroform:methanol:water=9:1:0.1).

Example 2(262)

4-((2S-carboxy-4S-acetylaminopyrrolidin-1-yl) sulfonyl)-2-methylphenyl 2RS-(4-(pyrrolidin-1-yl) phenyl)butanoic acid ester.hydrochloride

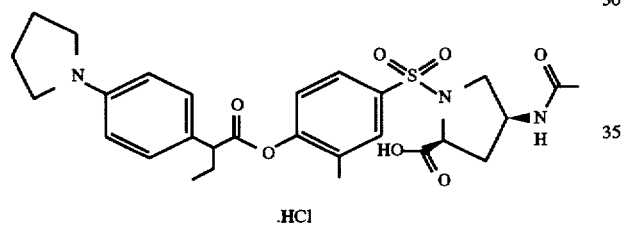

NMR (DMSO-d$_6$): δ 8.02 (1H, d, J=7.8 Hz), 7.74 (1H, d, J=2.2 Hz), 6.69 (1H, dd, J=8.4 Hz, 2.2 Hz), 7.17 (2H, d, J=8.6 Hz), 7.17 (1H, d, J=8.4 Hz), 6.54 (2H, d, J=8.6 Hz), 4.13 (1H, t, J=7.8 Hz), 3.82 (1H, m), 3.70 (1H, t, J=8.4 Hz), 3.50 (1H, m), 3.22 (4H, m), 3.06 (1H, m), 2.31 (1H, m), 2.07 (1H, m), 1.99 (3H, s), 1.96 (4H, m), 1.82 (2H, m), 1.75 (3H, s), 0.91 (3H, t, J=7.4 Hz);

TLC: Rf 0.18 (chloroform:methanol:water=4:1:0.1).

Example 2(263)

4-((2S-carboxypyrrolidin-1-yl)sulfonyl)-2-methylphenyl 2RS-(4-(pyrrolidin-1-yl)phenyl)-2-butanoic acid ester

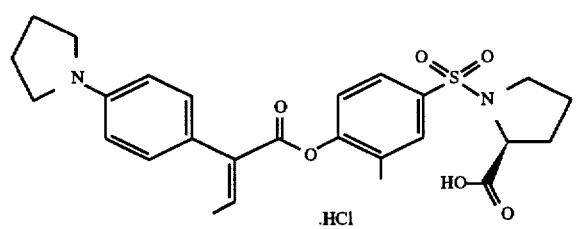

NMR (CDCl$_3$): δ 7.80–7.65 (2H, m), 7.32 (1H, q, J=7 Hz), 7.23 (1H, d, J=8 Hz), 7.13 (2H, d, J=8 Hz), 6.59 (2H, d, J=8 Hz), 4.30–4.20 (1H, m), 4.10–3.60 (1H, b), 3.60–3.45 (1H, m), 3.40–3.20 (5H, m), 2.30–1.65 (8H, m), 2.25 (3H, s), 1.88 (3H, d, J=7 Hz);

TLC: Rf 0.28 (chloroform:methanol:acetic acid=4:2:0.1).

Example 2(264)

4-((2S-carboxy-4R-acetylaminopyrrolidin-1-yl) sulfonyl)-2-methylphenyl 2RS-(4-(pyrrolidin-1-yl) phenyl)butanoic acid ester.hydrochloride

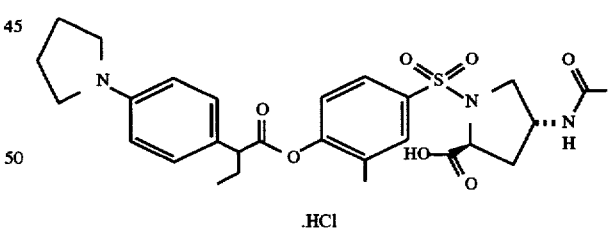

NMR (DMSO-d$_6$): δ 7.78 (1H, d, J=5 Hz), 7.68 (1H, s), 7.64 (1H, d, J=8.0 Hz), 7.19 (2H, d, J=8.6 Hz), 7.16 (1H, d, J=8.0 Hz), 6.56 (2H, d, J=8.6 Hz), 4.28 (1H, t, J=7.8 Hz), 4.12 (1 H. m), 3.75 (1H, m), 3.48 (1 H. m), 3.23 (4H, m), 3.06 (1H, m), 2.12 (1H, m), 2.03 (2H, m), 1.99 (3H, s), 1.96 (4H, m), 1.80 (1H, m), 1.54 (3H, s), 0.91 (3H, t, J=7.2 Hz);

TLC: Rf 0.1 9 (chloroform:methanol:water=4:1:0.1).

Example 2(265)

4-((2RS-carboxy-5-nitroindolin-1-yl)sulfonyl)-2-methylphenyl 2RS-(4-(pyrrolidin-1-yl)phenyl) butanoic acid ester

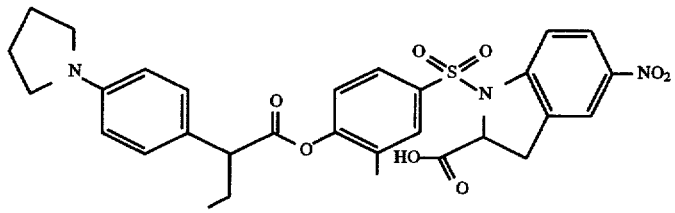

NMR (CDCl₃): δ 8.33 (1H, d, J=2 Hz), 7.89 (1H, dd, J=8, 2 Hz), 7.67 (1H, s), 7.62 (1H, d, J=8 Hz), 7.20 (1H, d, J=8 Hz), 7.18 (2H, d, J=8 Hz), 7.02 (1H, d, J=8 Hz), 6.55 (2H, d, J=8 Hz), 4.85 (1H, dd, J=10, 5 Hz), 4.60–4.25 (1H, br), 3.59 (1H, t, J=7 Hz), 3.40–3.15 (6H, m), 2.25–1.75 (9H, m), 0.95 (3H, t, J=7 Hz);

TLC: Rf 0.30 (chloroform:methanol:acetic acid=4:2:0.1).

Example 2(266)

4-((2S-carboxypyrrolidin-1-yl)sulfonyl)-2-methylphenyl 2RS-(2-methoxy-4-nitrophenyl) butanoic acid ester

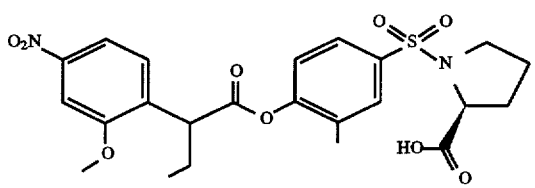

NMR (CDCl₃): δ 7.88 (1H, dd, J=2.0, 8.5 Hz), 7.78 (1H, d, J=2.0 Hz), 7.75–7.65 (2H, m), 7.49 (1H, d, J=8.5 Hz), 7.12 (1H, d, J=9.0 Hz), 4.30–4.15 (2H, m), 3.98 (3H, s), 3.60–3.40 (1H, m), 3.30–3.1 0 (1H, m), 2.40–1.60 (6H, m), 2.08 (3H, s), 1.00 (3H, t, J=7.5 Hz);

TLC: Rf 0.38 (chloroform:methanol:acetic acid=4:2:0.1).

Example 2(267)

4-((2S-carboxy-4S-methylaminopyrrolidin-1-yl)sulfonyl)-2-methylphenyl 2RS-(4-(pyrrolidin-1-yl) phenyl)butanoic acid ester.2hydrochloride

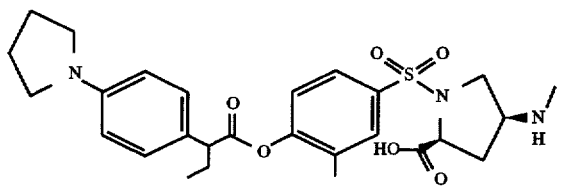

NMR (CD₃OD): δ 7.77 (1H, s), 7.75 (1H, d, J=8.0 Hz), 7.37 (2H, d, J=8.6 Hz), 7.19 (1H, d, J=8.0 Hz), 6.98 (2H, d, J=8.6 Hz), 4.18 (1H, m), 3.69 (3H, m), 3.59 (1H, m), 3.46 (4H, m), 2.72 (3H, s), 2.57 (1H, m), 2.21 (2H, m), 2.13 (4H, m), 2.02 (3H, s), 1.93 (1H, m), 0.98 (3H, t, J=7.4 Hz);

TLC: Rf 0.28 (chloroform:methanol:water=4:1:0.1).

Example 2(268)

4-((2S-carboxy-4S-(N,N-dimethylamino)pyrrolidin-1-yl)sulfonyl)-2-methylphenyl 2RS-(4-(pyrrolidin-1-yl)phenyl)butanoic acid ester.2hydrochloride

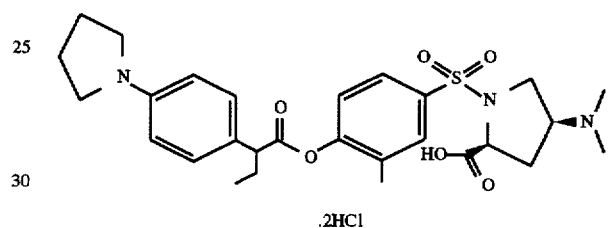

NMR (CD₃OD): δ 7.81 (1H, s), 7.78 (1H, d, J=8.2 Hz), 7.62 (4H, s), 7.21 (1H, d, J=8.2 Hz), 4.25 (1H, t, J=7 Hz), 3.98 (1H, t, J=7 Hz), 3.77 (4H, m), 3.65 (3H, m), 2.90 (6H, s), 2.80 (1H, m), 2.29 (4H, m), 2.24 (2H, m), 2.06 (3H, s), 1.99 (1H, m), 1.00 (3H, t, J=7.4 Hz);

TLC: Rf 0.42 (chloroform:methanol:water=6:4:1).

Example 2(269)

4-(N-hydroxyaminosulfonyl)-2-methylphenyl 2RS-(4-(pyrrolidin-1-yl)phenyl)butanoic acid ester.hydrochloride

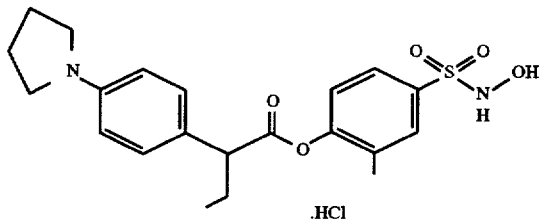

NMR (CDCl₃): δ 7.73 (1H, s), 7.68 (1H, d, J=8.6 Hz), 7.23 (2H, d, J=8.0 Hz), 7.2–7.0 (2H, br), 7.04 (1H, d, J=8.6 Hz), 6.63 (2H, d, J=8.0 Hz), 3.63 (1H, t, J=7.7 Hz), 3.4–3.2 (4H, brs), 2.3–2.1 (1H, m), 2.1–1.9 (4H, brs), 2.00 (3H, s), 2.0–1.8 (1H, m), 0.97 (3H, t, J=7.3 Hz);

TLC: Rf 0.25 (hexane:ethyl acetate=2:1).

Example 2(270)

4-((2S,6S-di methylpiperazin-4-yl)sulfonyl)-2-methylphenyl 2RS-(4-(pyrrolidin-1-yl)phenyl)butanoic acid ester.2methanesulfonic acid salt

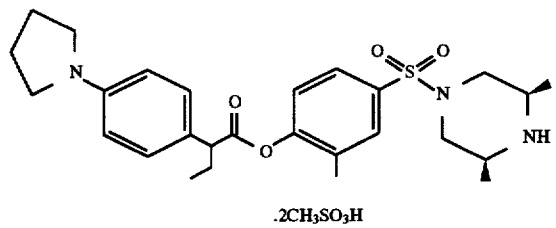

NMR (CDCl₃): δ 7.76–7.62 (6H, m), 7.23 (1H, d, J=8.5 Hz), 4.01 (1H, t, J=7.5 Hz), 4.00–3.75 (6H, m), 3.55–3.30 (2H, m), 2.68 (6H, s), 2.45–1.80 (8H, m), 2.07 (3H, s), 1.31 (6H, d, J=6.5 Hz), 1.00 (3H, t, J=7.5 Hz);

TLC: Rf 0.66 (chloroform:methanol:water=4:1:0.1).

Example 2(271)

4-((2RS-methylpiperazin-4-yl)sulfonyl)-2-methylphenyl 2RS-(4-(pyrrolidin-1-yl)phenyl)butanoic acid ester.2methanesulfonic acid salt

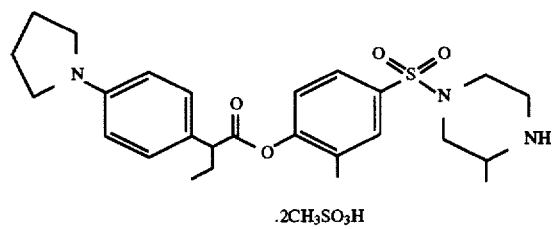

NMR (CDCl₃): δ 7.76–7.60 (6H, m), 7.23 (1H, d, J=8.0 Hz), 4.01 (1H, t, J=7.5 Hz), 3.90–3.72 (6H, m), 3.55–3.35 (2H, m), 3.32–3.13 (1H, m), 2.82–2.62 (1H, m), 2.67 (6H, s), 2.49 (1H, dd, J=13.0, 10.0 Hz), 2.40–1.80 (6H, m), 2.07 (3H, s), 1.32 (3H, d, J=6.5 Hz), 1.00 (3H, t, J=7.5 Hz);

TLC: Rf 0.45 (chloroform:methanol:water=9:1:0.1).

Example 2(272)

4-((2S-carboxy-4R-(N,N-dimethylamino)pyrrolidin-1-yl)sulfonyl)-2-methylphenyl 2RS-(4-(pyrrolidin-1-yl)phenyl)butanoic acid ester.2hydrochloride

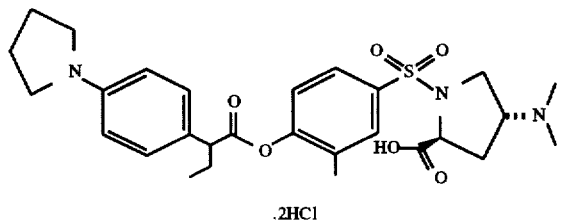

NMR (DMSO-d₆): δ 11.38 (1H, m), 7.77 (1H, s), 7.72 (1H, d, J=8.2 Hz), 7.19 (3H, m), 6.63 (2H, d, J=8.6 Hz), 4.38 (1H, m), 4.01 (1H, m), 3.82 (1H, m), 3.73 (1H, t, J=7.4 Hz), 3.49 (1H, t, J=8.6 Hz), 3.24 (4H, m), 2.70 (6H, s), 2.36 (2H, m), 2.11 (1H, m), 1.99 (3H, s), 1.97 (4H, m), 1.83 (1H, m), 0.91 (3H, t, J=7.2 Hz);

TLC: Rf 0.44 (chloroform:methanol:water=6:4:1).

Example 2(273)

4-((2S-carboxy-4R-methylaminopyrrolidin-1-yl)sulfonyl)-2-methylphenyl 2RS-(4-(pyrrolidin-1-yl)phenyl)butanoic acid ester.2hydrochloride

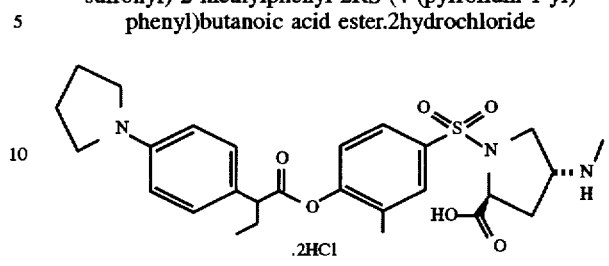

NMR (CD₃OD): δ 7.76 (1H, s), 7.73 (1H, d, J=8.0 Hz), 7.25 (2H, d, J=8.4 Hz), 7.13 (1H, d, J=8.0 Hz), 6.71 (2H, d, J=8.4 Hz), 4.53 (1H, m), 3.97 (1H, m), 3.86 (1H, m), 3.70 (1H, t, J=8 Hz), 3.41 (1H, m), 3.35 (4H, m), 2.70 (3H, s), 2.49 (1H, m), 2.31 (1H, m), 2.17 (1H, m), 2.06 (4H, m), 2.00 (3H, s), 1.92 (1H, m), 0.98 (3H, t, J=7.2 Hz);

TLC: Rf 0.46 (chloroform:methanol:water=6:4:1).

Example 2(274)

4-(piperazin-4-ylsulfonyl)-2-ethylphenyl 2S-(4-(pyrrolidin-1-yl)phenyl)butanoic acid ester.2hydrochloride

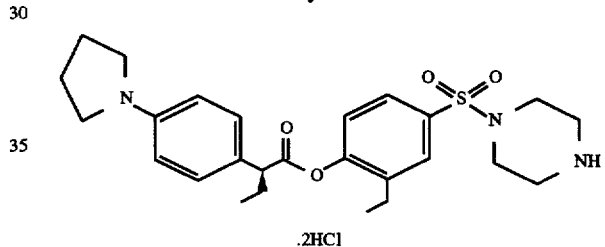

NMR (CD₃OD): δ 7.75–7.50 (6H, m), 7.25 (1H, d, J=9.0 Hz), 3.97 (1H, t, J=7.5 Hz), 3.85–3.70 (4H, m), 3.35–3.15 (8H, m), 2.50–1.80 (8H, m), 1.00 (6H, t, J=7.5 Hz);

TLC: Rf 0.46 (chloroform:methanol:water=9:1:0.1).

Example 2(275)

4-(piperazin-4-ylsulfonyl)-2-ethylphenyl 2R-(4-(pyrrolidin-1-yl)phenyl)butanoic acid ester.2hydrochloride

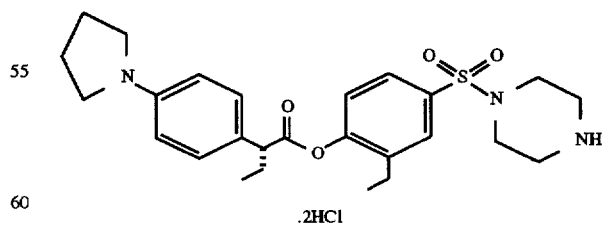

NMR (CD₃OD): δ87.75–7.58 (6H, m), 7.25 (1H, d, J=9.0 Hz), 3.98 (1H, t, J=7.5 Hz), 3.90–3.70 (4H, m), 3.40–3.20 (8H, m), 2.50–1.80 (8H, m), 1.00 (6H, t, J=7.5 Hz);

TLC: Rf 0.46 (chloroform methanol:water=9:1:0.1).

Example 2(276)

4-(piperazin-4-ylsulfonyl)-2-methylphenyl 2S-(4-(pyrrolidin-1-yl)phenyl)butanoic acid ester.2hydrochloride

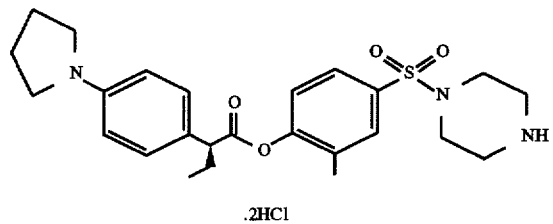

NMR (CD₃OD): δ 7.71 (6H, m), 7.22 (1H, d, J=8.0 Hz), 4.00 (1H, t, J=8 Hz), 3.81 (4H, m), 3.31 (8H, s), 2.33 (4H, m), 2.24 (1H, m), 2.07 (3H, s), 1.98 (1H, m), 1.01 (3H, t, J=7.4 Hz);

TLC: Rf 0.66 (chloroform:methanol:water=4:1:0.1).

Example 2(277)

4-(piperazin-4-ylsulfonyl)-2-methylphenyl 2R-(4-(pyrrolidin-1-yl)phenyl)butanoic acid ester.2hydrochloride

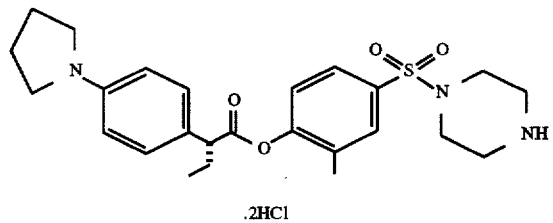

NMR (CD₃OD): δ 7.70 (6H, m), 7.22 (1H, d, J=8.0 Hz), 4.00 (1H, t, J=8 Hz), 3.81 (4H, m), 3.30 (8H, s), 2.32 (4H, m), 2.24 (1H, m), 2.06 (3H, s), 1.99 (1H, m), 1.00 (3H, t, J=7.4 Hz);

TLC: Rf 0.66 (chloroform:methanol:water=4:1:0.1).

Example 2(278)

4-((2S-carboxymethylpyrrolidin-1-yl)sulfonyl)-2-methylphenyl 2RS-(4-(pyrrolidin-1-yl)phenyl)butanoic acid ester

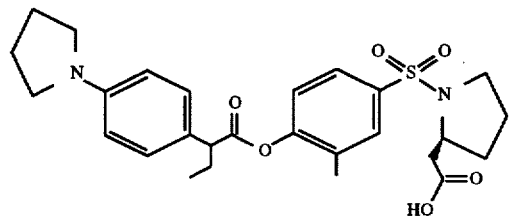

NMR (CDCl₃): δ 7.70–7.58 (2H, m), 7.23 (2H, d, J=8 Hz), 7.09 (1H, d, J=8 Hz), 6.55 (2H, d, J=8 Hz), 4.00–3.84 (1H, m), 3.62 (1H, t, J=7 Hz), 3.50–3.35 (1H, m), 3.35–3.20 (4H, m), 3.18–3.03 (2H, m), 2.54 (1H, dd, J=15, 10 Hz), 2.30–1.40 (13H, m), 0.98 (3H, t, J=7 Hz);

TLC: Rf 0.39 (hexane:ethyl acetate:acetic acid=50:50:1).

Example 2(279)

4-((2S-carboxy-4-acetylaminopyrrolidin-1-yl)sulfonyl)-2-methylphenyl 2S-(4-(pyrrolidin-1-yl)phenyl)butanoic acid ester.hydrochloride

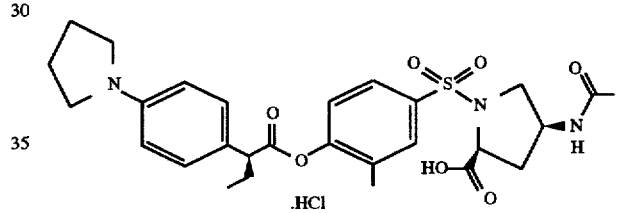

NMR (DMSO-d₆): δ 8.02 (1H, d, J=6 Hz), 7.74 (1H, s), 7.69 (1H, d, J=8.8 Hz), 7.24 (2H, d, J=8.6 Hz), 7.18 (1H, d, J=8.6 Hz), 6.69 (1H, d, J=8.8 Hz), 4.15 (1H, t, J=7 Hz), 3.75 (2H, m), 3.51 (1H, m), 3.28 (4H, m), 3.05 (1H, m), 2.33 (1H, m), 2.12 (1H, m), 1.99 (7H, s-like), 1.83 (2H, m), 1.75 (3H, s), 0.91 (3H, t, J=7.4 Hz);

TLC: Rf 0.67 (chloroform:methanol:water=6:4:1).

Example 2(280)

4-((2-carboxy-5,6-dimethoxyindol-1-yl)sulfonyl)-2-methylphenyl 2S-(4-(pyrrolidin-1-yl)phenyl)butanoic acid ester.hydrochloride

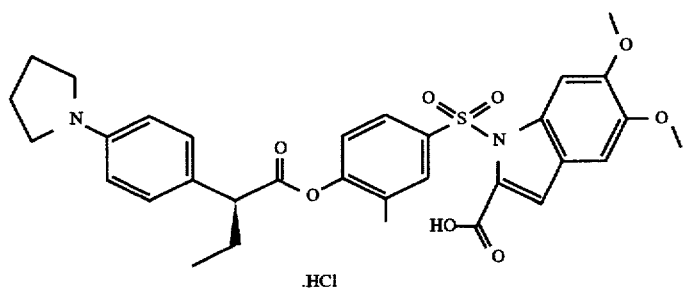

NMR (DMSO-d₆): δ 7.87 (1H, d, J=2.2 Hz), 7.79 (1H, dd, J=8.6 Hz, 2.2 Hz), 7.50 (1H, s), 7.25–7.13 (5H, m), 6.66 (2H, d, J=8.0 Hz), 3.88 (3H, s), 3.78 (3H, s), 3.71 (1H, t, J=7.2 Hz), 3.26 (4H, m), 2.08 (1H, m), 1.97 (4H, m), 1.93 (3H, s), 1.78 (1H, m), 0.88 (3H, t, J=7.6 Hz);

TLC: Rf 0.45 (chloroform:methanol:water=4:1:0.1).

Example 2(281)

4-((2RS-carboxyindolin-1-yl)sulfonyl)-2-methylphenyl 2S-(4-(pyrrolidin-1-yl)phenyl)butanoic acid ester.hydrochloride

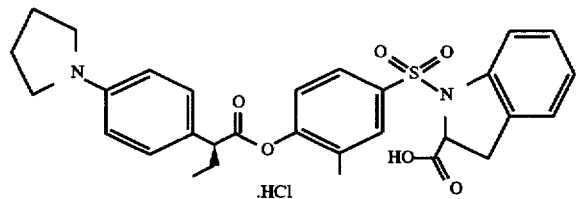

NMR (DMSO -d₆): δ 7.78 (1H, s), 7.67 (1H, dd, J=2 and 8 Hz), 7.35–6.94 (7H, m), 6.80–6.64 (2H, br), 5.00–4.93 (1H, m), 3.70 (1H, t, J=7 Hz), 3.39–2.96 (6H, m), 2.17–1.64 (2H, m), 2.04–1.94 (4H, m), 1.91 (3H, s), 0.87 (3H, t J=7 Hz); TLC: Rf 0.30 (chloroform:methanol:water=4:1:0. 1).

Example 2(282)

4-((2RS -methylpiperazin-4-yl)sulfonyl)-2-methylphenyl 2S-(4-(pyrrolidin-1-yl)phenyl)butanoic acid ester.2methanesulfonic acid salt

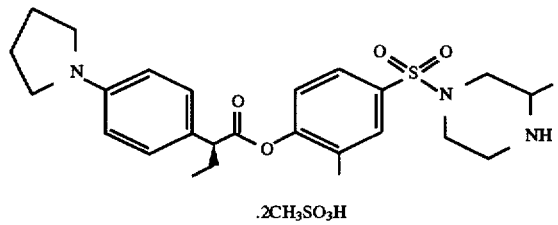

NMR (CD₃OD): δ 7.75–7.60 (6H, m), 7.23 (1H, d, J=8.5 Hz), 4.00 (1H, t, J=7.5 Hz), 3.90–3.70 (6H, m), 3.55–3.35 (2H, m), 3.35–3.10 (1H, m), 2.80–2.65 (1H, m), 2.66 (6H, s), 2.47 (1H, t, J=1 0.0 Hz), 2.06 (3H, s), 1.31 (3H, d, J=6.5 Hz), 1.00 (3H, t, J=7.5 Hz);

TLC: Rf 0.45 (chloroform:methanol:water=9:1:0.1).

Example 2(283)

4-((4-formylpiperazin-1-yl)sulfonyl)-2-methylphenyl 2RS-(4-(pyrrolidin-1-yl)phenyl)butanoic acid ester.hydrochloride

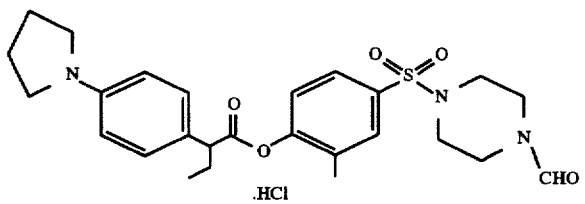

NMR (CD3OD): δ 7.96 (1H, s), 7.73–7.52 (6H, m), 7.19 (1H, d, J=8.4 Hz), 3.97 (1H, t, J=7.6 Hz), 3.88–3.67 (4H, m), 3.67–3.44 (4H, m), 3.12–2.93 (4H, m), 2.43–2.14 (5H, m), 2.12–1.81 (4H ,m), 1.00 (3H, t, J=7.2 Hz);

TLC: Rf 0.38 (hexane:ethyl acetate=1:2).

Example 2(284)

4-((2S-carboxypyrrolidin-1-yl)sulfonyl)-2-methylphenyl 2RS-(4-(pyrrolidin-1-yl)phenyl)butanoic acid ester.sodium salt

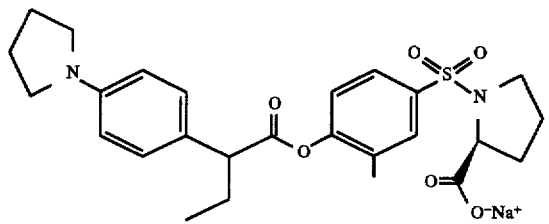

NMR (d₆-DMSO): δ 7.78–7.64 (2H, m), 7.18 (2H, d, J=8.0 Hz), 7.08 (1H, d, J=8.0 Hz), 6.53 (2H, d, J=8.0 Hz), 3.95–3.80 (1H, m), 3.69 (1H, t, J=7.5 Hz), 3.50–3.00 (6H, m), 2.20–1.30 (10H, m), 1.96 (3H, s), 0.91 (3H, t, J=7.5 Hz);

TLC: Rf 0.32 (chloroform:methanol:water=9:1:0.1).

Example 2(285)

4-((2S-carboxypyrrolidin-1-yl)sulfonyl)-2-methylphenyl 2RS-(4-(pyrrolidin-1-yl)phenyl)butanoic acid ester.methanesulfonic acid salt

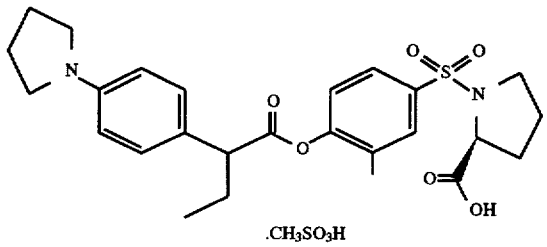

NMR (CDCl₃): δ 7.65 (4H, d, J=8.5 Hz), 7.54 (2H, d, J=8.5 Hz), 7.05 (1H, d, J=8.5 Hz), 4.30–4.15 (1H, m), 4.10–3.50 (4H, m), 3.80 (1H, t, J=7.5 Hz), 3.55– 3.35 (1H, m), 3.30–3.1 0 (1H, m), 2.87 (3H, s), 2.50–1.60 (10H, m), 2.03 (3H, s), 0.99 (3H, t, J=7.5 Hz);

TLC: Rf 0.32 (chloroform:methanol:water=9:1:0.1).

Example 2(286)

4-((piperazin-4-yl)sulfonyl)-2-methylphenyl 2RS-(4-(pyrrolidin-1-yl)phenyl)butanoic acid ester.2methanesulfonic acid salt

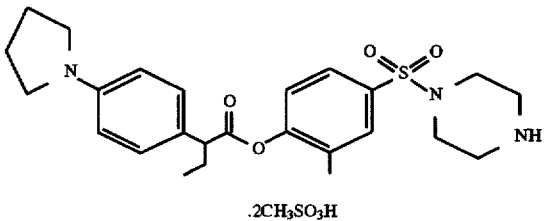

NMR (CD₃OD): δ 7.75–7.60 (6H, m), 7.23 (1H, d, J=8.0 Hz), 4.01 (1H, t, J=7.5 Hz), 3.90–3.70 (4H, m), 3.35–3.20

(8H, m), 2.68 (6H, s), 2.40–1.80 (6H, m), 2.06 (3H, s), 1.00 (3H, t, J=7.5 Hz);

TLC: Rf 0.14 (chloroform:methanol:acetic acid=40:2:1).

Example 2(287)

4-(piperazin-4-ylsulfonyl)-2-methylphenyl 2S-(4-(pyrrolidin-1-yl)phenyl)butanoic acid ester.citric acid salt.ethanol salts

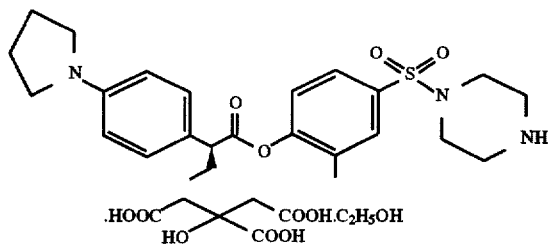

NMR (CD₃OD): δ 7.66 (1H, brs), 7.62 (1H, brd, J=8.0 Hz), 7.20 (2H, d, J=8.5 Hz), 7.18 (1H, d, J=8.0 Hz), 6.58 (2H, d, J=8.5 Hz), 3.67 (1H, t, J=7.5 Hz), 3.60 (2H, q, J=7.0 Hz), 3.40–3.15 (12H, m), 2.76 (4H, dd, J=8.0, 14.0 Hz), 2.30–1.70 (9H, m), 1.17 (3H, t, J=7.0 Hz), 0.97 (3H, t, J=7.5 Hz);

TLC: Rf 0.11 (chloroform:methanol:acetic acid=40:2:1).

Example 2(288)

4-(piperazin-4-ylsulfonyl)-2-methylphenyl 2S-(4-(pyrrolidin-1-yl)phenyl)butanoic acid ester.succinic acid salts

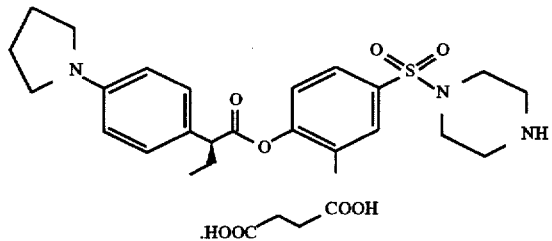

NMR (CD₃OD): δ 7.64 (1H, brs), 7.61 (1H, brd, J=8.0 Hz), 7.19 (2H, d, J=8.5 Hz), 7.17 (1H, d, J=8.0 Hz), 6.57 (2H, d, J=8.5 Hz), 3.64 (1H, t, J=7.5 Hz), 3.40–3.20 (4H, m), 3.12 (8H, s), 2.51 (4H, s), 2.30–1.76 (9H, m), 0.97 (3H, t, J=7.5 Hz);

TLC: Rf 0.11 (chloroform:methanol:acetic acid=40:2:1).

Example 2(289)

4-(piperazin-4-ylsulfonyl)-2-methylphenyl 2S-(4-(pyrrolidin-1-yl)phenyl)butanoic acid ester.L-malic acid salts

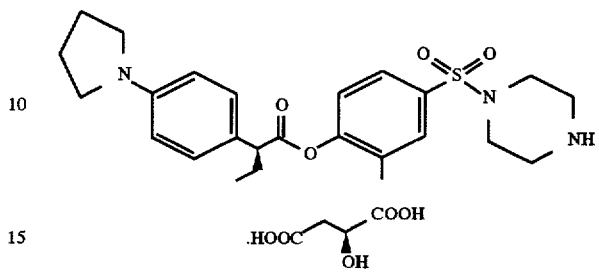

NMR (CD₃OD): δ 7.67 (1H, brs), 7.62 (1H, brd, J=8.0 Hz), 7.22 (2H, d, J=8.5 Hz), 7.19 (1H, d, J=8.0 Hz), 6.58 (2H, d, J=8.5 Hz), 4.28 (1H, dd, J=5.0, 7.5 Hz), 3.68 (1H, t, J=7.5 Hz), 3.40–3.05 (12H, m), 2.78 (1H, dd, J=5.0, 15.0 Hz), 2.52 (1H, dd, J=7.5,15.0 Hz), 2.40–1.72 (9H, m), 0.98 (3H, t, J=7.5 Hz);

TLC: Rf 0.11 (chloroform:methanol:acetic acid=40:2:1).

Example 2(290)

4-(piperazin-4-ylsulfonyl)-2-methylphenyl 2S-(4-(pyrrolidin-1-yl)phenyl)butanoic acid ester.fumaric acid salt

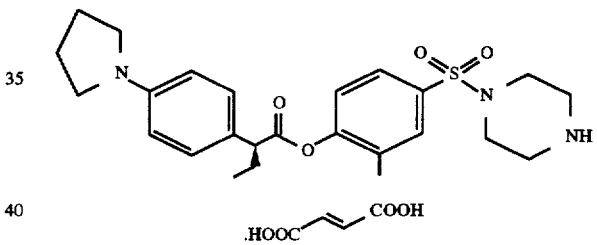

NMR (CD₃OD): δ 7.68 (1H, brs), 7.63 (1H, brd, J=8.0 Hz), 7.21 (2H, d, J=8.5 Hz), 7.19 (1H, d, J=8.0 Hz), 6.82 (2H, s), 6.59 (2H, d, J=8.5 Hz), 3.65 (1H, t, J=7.5 Hz), 3.40–3.10 (12H, m), 2.30–1.70 (9H, m), 0.98 (3H, t, J=7.5 Hz);

TLC: Rf 0.11 (chloroform:methanol:acetic acid=40:2:1).

Example 2(291)

4-(piperazin-4-ylsulfonyl)-2-methylphenyl 2S-(4-(pyrrolidin-1-yl)phenyl)butanoic acid ester.oxalic acid salt

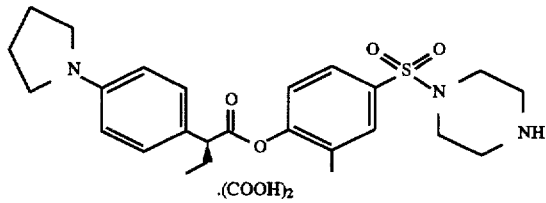

NMR (CD₃OD): δ 7.68 (1H, s), 7.63 (1H, brd, J=8.0 Hz), 7.20 (2H, d, J=8.5 Hz), 7.19 (1H, d, J=8.0 Hz), 6.60 (2H, d, J=8.5 Hz), 3.66 (1H, t, J=7.5 Hz), 3.45–3.10 (12H, m), 2.30–1.75 (9H, m), 0.98 (3H, t, J=7.5 Hz);

TLC: Rf 0.11 (chloroform:methanol:acetic acid=40:2:1).

Example 2(292)

4-(piperazin-4-ylsulfonyl)-2-methylphenyl 2S-(4-(pyrrolidin-1-yl)phenyl)butanoic acid ester.lactic acid salt

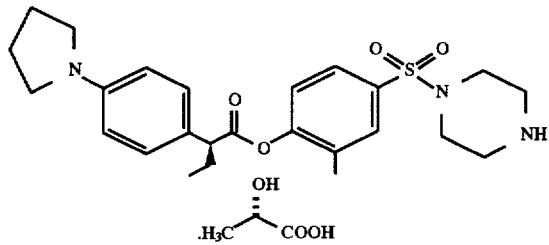

NMR (CD₃OD): δ 7.65 (1H, s), 7.61 (1H, brd, J=8.0 Hz), 7.20 (2H, d, J=8.5 Hz), 7.17 (1H, d, J=8.0 Hz), 6.57 (2H, d, J=8.5 Hz), 4.04 (1H, q, J=7.0 Hz), 3.65 (1H, t, J=7.5 Hz), 3.40–3.20 (4H, m), 3.14 (8H, s), 2.15 (3H, s), 2.20–1.75 (6H, m), 1.31 (3H, d, J=7.0 Hz), 0.97 (3H, t, J=7.5 Hz);

TLC: Rf 0.1 1 (chloroform:methanol:acetic acid=40:2:1).

Example 2(293)

4-(piperazin-4-ylsulfonyl)-2-methylphenyl 2S-(4-(pyrrolidin-1-yl)phenyl)butanoic acid ester.L-tartaric acid salt

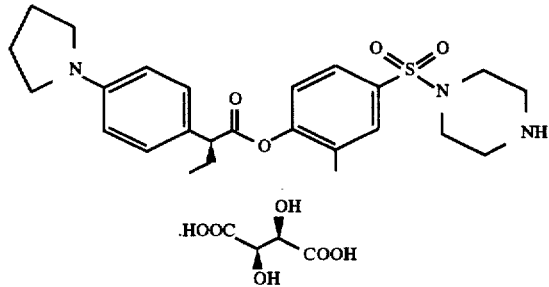

NMR (CD₃OD): δ 7.68 (1H, s), 7.64 (1H, brd, J=8.0 Hz), 7.21 (2H, d, J=8.5 Hz), 7.18 (1H, d, J=8.0 Hz), 6.59 (2H, d, J=8.5 Hz), 4.43 (2H, s), 3.68 (1H, t, J=7.5 Hz), 3.45–3.10 (12H, m), 2.40–1.78 (9H, m), 0.98 (3H, t, J=7.5Hz);

TLC: Rf 0.11 (chloroform:methanol:acetic acid=40:2:1).

Example 2(294)

4-(piperazin-4-ylsulfonyl)-2-methylphenyl 2S-(4-(pyrrolidin-1-yl)phenyl)butanoic acid ester.2(p-toluenesulfonic acid) salt

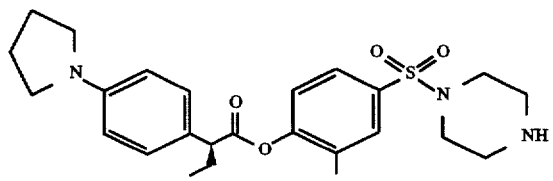

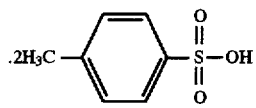

NMR (CD₃OD): δ 7.68 (6H, d, J=8.0 Hz), 7.63 (4H, d, J=9.0 Hz), 7.22 (5H, d, J=8.0 Hz), 3.99 (1H, t, J=7.4 Hz), 3.83–3.65 (4H, m), 3.30 (8H, m), 2.36 (6H, s), 2.36–2.20 (5H, m), 2.04 (3H, s), 1.95 (1H, m), 0.99 (3H, t, J=7.4 Hz

TLC: Rf 0.11 (chloroform:methanol:acetic acid=40:2:1).

Example 2(295)

4-(piperazin-4-ylsulfonyl)-2-methylphenyl 2S-(4-(pyrrolidin-1-yl)phenyl)butanoic acid ester.phosphoric acid salt

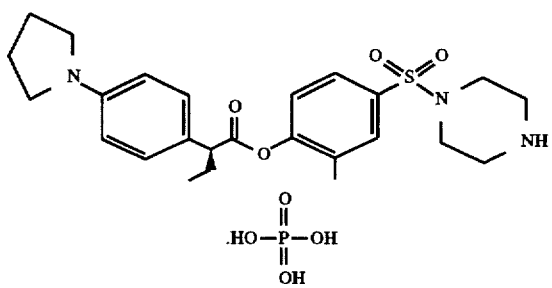

NMR (CD₃OD): δ 8.00–7.40 (3H, m), 7.67 (1H, brs), 7.62 (1H, brd, J=8.8 Hz), 7.25 (1H, d, J=8.8 Hz), 7.21 (2H, d, J=8.8 Hz), 6.56 (2H, d, J=8.8 Hz), 3.75 (1H, t, J=7.4 Hz), 3.23 (4H, brs), 2.94 (8H, brs), 2.01 (3H, s), 2.20–1.80 (6H, m), 0.93 (3H, t, J=7.4 Hz);

TLC: Rf 0.11 (chloroform:methanol:acetic acid=40:2:1).

Example 2(296)

4-(piperazin-4-ylsulfonyl)-2-methylphenyl 2S-(4-(pyrrolidin-1-yl)phenyl)butanoic acid ester.maleic acid salt

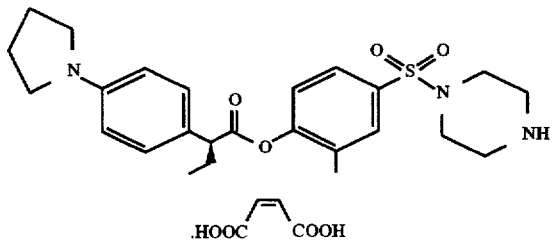

NMR (CD₃OD): δ 7.67 (1H, s), 7.62 (1H, brd, J=8.0 Hz), 7.20 (2H, d, J=8.5 Hz), 7.19 (1H, d, J=8.0 Hz), 6.58 (2H, d, J=8.5 Hz), 6.23 (2H, s), 3.65 (1H, t, J=7.5 Hz), 3.40–3.05 (12H, m), 2.30–1.78 (6H, m), 1.98 (3H, s), 0.97 (3H,t, J=7.5 Hz);

TLC: Rf 0.11 (chloroform:methanol:acetic acid=40:2:1).

Example 3

4-(2S-hydroxysulfonyloxymethylpyrrolidin-1-ylsulfonyl)-2-methylphenyl 2RS-(4-methylphenyl)butanoic acid ester

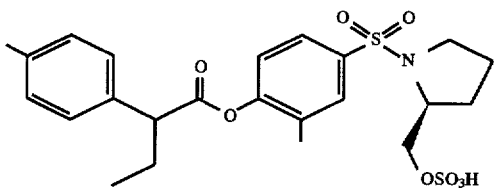

To a solution of the compound prepared in example 2(19) (690 mg) in pyridine (10 ml) was added sulfur trioxide pyridine complex (766 mg) and the reaction mixture was stirred for 30 min at room temperature. The reaction mixture was concentrated, and the residue was purified by column chromatography on silica gel (chloroform:methanol=10:1) to give the title compound (700 mg) having the following physical data.

NMR (DMSO-d$_6$): δ 7.74 (1H, d, J=2.0 Hz), 7.67 (1H, dd, J=8.5, 2.0 Hz), 7.30 (2H, d, J=8.5 Hz), 7.20 (2H, d, J=8.5 Hz), 7.18 (1H, d, J=8.5 Hz), 3.94–3.78 (2H, m), 3.76–3.60 (1H, m), 3.58 (1H, t, J=7.0 Hz), 3.3–3.2 (1H, m), 3.12–2.94 (1H, m), 2.31 (3H, s), 2.25–2.00 and 1.95–1.70 (each 1H, m), 1.97 (3H, s), 1.90–1.60 (2H, m), 1.60–1.30 (2H, m), 0.91 (3H, t, J=7.5 Hz);

TLC:Rf 0.39 (water:methanol:chloroform=1:10:40).

Example 3(1)

4-(2S-hydroxysulfonyloxymethylpyrrolidin-1-ylsulfonyl)-2-methylphenyl 2RS-(4-(pyrrolidin-1-yl)phenyl)butanoic acid ester

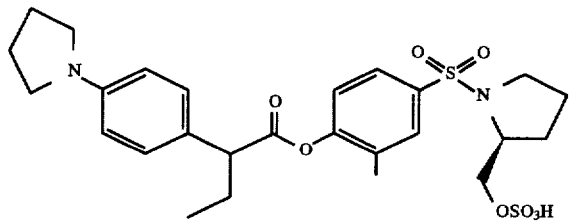

By the same procedure as example 3, the title compound having the following physical data was given by using the compound prepared in example 2(10).

NMR (DMSO-d$_6$): δ 7.74 (1H, s), 7.67 (1H, d, J=8.5 Hz), 7.25–7.10 (3H, m), 6.55 (2H, d, J=8.0 Hz), 3.91 (1H, d, J=8.5 Hz), 3.80–3.50 (3H, m), 3.40–3.20 (1H, m), 3.35–3.20 (4H, m), 3.15–2.90 (1H, m), 2.20–1.60 (2H, m), 1.98 (3H, s), 2.05–1.90 (4H, m), 1.90–1.60 (2H, m), 1.60–1.30 (2H, m), 0.91 (3H, t, J=7.5 Hz);

TLC: Rf 0.38 (water:methanol:chloroform=1:10:40).

FORMULATION EXAMPLES

Formulation Example 1

The following components were admixed in conventional manner and punched out to obtain 100 tablets each containing 50 mg of active ingredient.

| | |
|---|---|
| 4-(piperazin-4-ylsulfonyl)-2-methylphenyl 2S-(4-(pyrrolidin-1-yl)phenyl) butanoic acid ester.2hydrochloride | 5.0 g |
| Carboxymethylcellulose calcium (disintegrating agent) | 0.2 g |
| Magnesium stearate (lubricating agent) | 0.1 g |
| Microcrystalline cellulose | 4.7 g |

Formulation example 2

The following components were admixed in conventional manner. The solution was sterilized in conventional manner, placed 5 ml portion into ampoules and freeze-dried to obtain 100 ampoules each containing 20 mg of the active ingredient.

| | |
|---|---|
| 4-(piperazin-4-ylsulfonyl)-2-methylphenyl 2S-(4-(pyrrolidin-1-yl)phenyl) butanoic acid ester.2hydrochloride | 2.0 g |
| mannitol | 20 g |
| Distilled water | 1000 ml |

We claim:

1. A sulfonamide derivative of the formula (I)

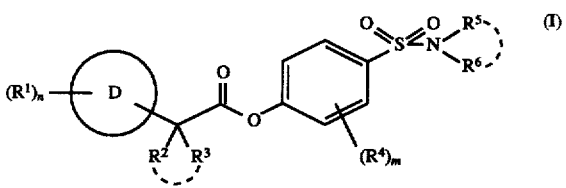

wherein R$^1$ is C1–8 alkyl, C1–8 alkoxy, hydroxy, keto, nitro, halogen atom, trihalomethyl, cyano, amidino, —COOR$^7$ (in which R$^7$ is hydrogen atom or C1–8 alkyl), or

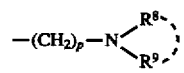

(in which p is an integer from 0 to 4, and

R$^8$ and R$^9$ each, independently, is hydrogen atom, C1–4 alkyl, C2–5 acyl, —COOR$^{10}$ (in which R$^{10}$ is hydrogen atom or C1–8 alkyl), —CONR$^{11}$R$^{12}$ (in which R$^{11}$ and R$^{12}$ each, independently, is hydrogen atom or C1–4 alkyl),

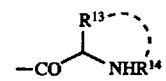

(in which

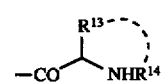

is an α-amino acid residue), or

R$^8$ and R$^9$ taken together with the nitrogen atom to which they are attached represent an aliphatic heterocyclic ring which is unsubstituted or substituted by C1–4 alkyl or phenyl C1–4 alkyl);

n is an integer from 0 to 5;

is a carbocyclic ring;

is

in which $R^2$ and $R^3$ each, independently, is hydrogen atom, C1-4 alkyl, C1-4 alkoxy, halogen atom, trihalomethyl or phenyl, or $R^2$ and $R^3$, taken together, represent C1-4 alkylidene, or

is

in which $R^2$ and $R^3$, taken together with the carbon atom to which they are attached represent C3-7 cycloalkyl;

$R^4$ is C1-4 alkyl or C1-4 alkoxy or two of $R^4$, attached to the benzene nucleus at ortho positions relative to each other, taken together, represent C3-5 alkylene;

m is an integer from 0 to 4; and

is

in which $R^5$ and $R^6$ each, independently, is
1) hydrogen atom,
2) hydroxy,
3) C1-8 alkyl,
4) C1-8 alkoxy
5) phenyl C1-4 alkoxy,
6) amidino,
7) —M—$R^{16}$ (in which M is single bond or C1-8 alkylene, and $R^{16}$ is i) —$NR^{17}R^{18}$ (in which $R^{17}$ and $R^{18}$ each, independently, is hydrogen atom or C1-4 alkyl), ii) —$CONR^{19}R^{20}$ (in which $R^{19}$ and $R^{20}$ each, independently, is hydrogen atom or C1-4 alkyl), iii)

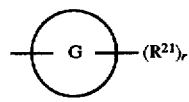

(in which

is a carbocyclic ring, r is an integer from 0 to 5, and $R^{21}$ is C1-4 alkyl, C1-4 alkoxy, nitro, amidino, —$COOR^{22}$ (in which $R^{22}$ is hydrogen atom, C1-8 alkyl, phenyl or phenyl C1-4 alkyl), —$SO_3H$, —$CONR^{23}$—E—$R^{24}$ (in which $R^{23}$ is hydrogen atom or C1-4 alkyl, E is 1-4 alkylene and alkylene and $R^{24}$ is —$COOR^{25}$ (in which $R^{25}$ is hydrogen atom, C1-8 alkyl, phenyl or phenyl C1-4 alkyl) or tetrazole ring), tetrazole ring or morpholino ring), iv) heterocyclic ring, unsubstituted or substituted by 1 to 4 substituents selected from C1-4 alkyl, C1-4 alkoxy, hydroxy, phenyl C1-4 alkyl, —$COOR^{26}$ (in which $R^{26}$ is hydrogen atom, C1-8 alkyl, phenyl or phenyl C1-4 alkyl), hydroxy C1-4 alkyl or C2-4 alkoxyalkyl), 8) C1-8 alkyl substituted by one or two of —$OR^{27}$ (in which $R^{27}$ is hydrogen atom, C1-4 alkyl, C2-4 alkoxyalkyl or C2-4 alkyl substituted by —$OR^{28}$ (in which $R^{28}$ is hydrogen atom or C2-4 alkoxyalkyl)), 9) —J—$COOR^{29}$ (in which $R^29$ is hydrogen atom, C1-8 alkyl, phenyl or phenyl C1-4 alkyl, and J is a single bond, —$(CH_2)_s$— or

(in which s is an integer from 2 to 6, and $R^{30}$ and $R^{31}$ each, independently, is
i) hydrogen atom,
ii) C1-8 alkyl,
iii) —$COOR^{32}$ (in which $R^{32}$ is hydrogen atom, C1-8 alkyl, phenyl or phenyl C1-4 alkyl),
iv) carbocyclic or heterocyclic ring, unsubstituted or substituted by one or more substituents selected from C1-4 alkyl, C1-4 alkoxyalkyl, amino, nitro, hydroxy, halogen atom, nitrile, guanidino and amidino, or
v) C1-8 alkyl substituted by one or more substituents selected from hydroxy, —$COOR^{33}$ (in which $R^{33}$ is hydrogen atom, C1-8 alkyl, phenyl or phenyl C1-4 alkyl), —$NR^{34}R^{35}$ (in which $R^{34}$ and $R^{35}$ each, independently, is hydrogen atom or C1-4 alkyl), carbocyclic or heterocyclic ring, unsubstituted or substituted by one or more substituents selected from C1-4 alkyl, C1-4 alkoxyalkyl, amino, nitro, hydroxy, halogen atom, nitrile, guanidino and amidino, with the proviso that a carbon atom of C1-8 alkyl may be replaced by a sulfur atom), or

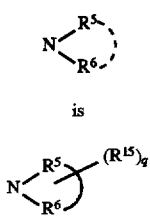

is

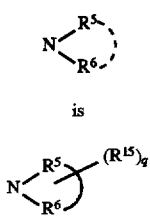

in which R⁵ and R⁶, taken together with the nitrogen atom to which they are attached represent a heterocyclic ring, q is an integer from 0 to 4, and
$R^{15}$ is
1) hydroxy,
2) keto,
3) protected keto,
4) C1–4 alkyl,
5) C1–4 alkoxy,
6) phenyl,
7) phenoxy,
8) phenyl C1–4 alkyl,
9) phenyl C1–4 alkoxy,
10) nitro,
11) —COOR³⁶ (in which R³⁶ is hydrogen atom, C1–8 alkyl, C1–4 alkyl substituted by —CONR³⁷R³⁸ (in which R³⁷ and R³⁸ each, independently, is hydrogen atom or C1–4 alkyl), C1–4 alkyl substituted by —NR³⁹R⁴⁰ (in which R³⁹ and R⁴⁰ each, independently, is hydrogen atom or C1–4 alkyl), C1–4 alkyl substituted by —OR⁴¹ (in which R⁴¹ is C2–4 alkyl substituted by —OR⁴² (in which R⁴² is hydrogen atom or C2–4 alkoxyalkyl)) or C1–4 alkyl substituted by piperadino ring),
12) —NR⁴³R⁴⁴ (in which R⁴³ and R⁴⁴ each, independently, is hydrogen atom, C1–4 alkyl or C2–5 acyl),
13) —CONR⁴⁵R⁴⁶ (in which R⁴⁵ and R⁴⁶ each, independently, is hydrogen atom, hydroxy, C1–4 alkyl, phenyl C1–4 alkyloxy or C1–4 alkyl substituted by hydroxy or —COOR⁴⁷ (in which R⁴⁷ is hydrogen atom or C1–8 alkyl),),
14) C1–4 alkyl substituted by one or more substituents selected from hydroxy, —COOR⁴⁸ (in which R⁴⁸ is hydrogen atom or C1–8 alkyl), —NR⁴⁹R⁵⁰ (in which R⁴⁹ and R⁵⁰ each, independently, is hydrogen atom or C1–4 alkyl), —OSO₃H or 5- or 6-membered heterocyclic ring containing one or two nitrogen atoms,
15) 5- or 6-membered heterocyclic ring containing one or two nitrogen atoms,
16) halogen atom,
17) —CHO, or
18) —NR⁵¹—COOR⁵² (in which R⁵¹ and R⁵² each, independently, is hydrogen atom or C1–8 alkyl);
or a non-toxic salt, acid addition salt or solvate thereof.

2. A compound according to claim 1, wherein

is 3–15 membered mono- or poly-cyclic aromatic hydrocarbon ring or aliphatic hydrocarbon ring.

3. A compound according to claim 1, wherein

in which all symbols are as claim 1 defined.

4. A compound according to claim 1, wherein

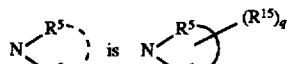

in which all symbols are as claim 1 defined.

5. A compound according to claim 1, wherein R¹ is C1–8 alkyl, C1–8 alkoxy, hydroxy, keto, nitro, halogen atom, trihalomethyl, cyano, amidino, —COOR⁷ (in which R⁷ is as claim 1 defined), or

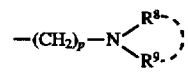

(in which p is as claim 1 defined, and
R⁸ and R⁹ each, independently, is hydrogen atom, C1–4 alkyl, C2–5 acyl, —COOR¹⁰ (in which R¹⁰ is as claim 1 defined), —CONR¹¹R¹² (in which R¹¹ and R¹² are as claim 1 defined),

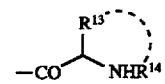

(in which

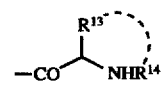

is as claim 1 defined).

6. A compound according to claim 1, wherein R¹ is

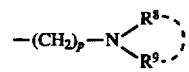

in which R⁸ and R⁹ taken together with the nitrogen atom to which they are attached represent an aliphatic heterocyclic ring which is unsubstituted or substituted by C1–4 alkyl or phenyl C1–4 alkyl.

7. A compound according to claim 1, which is
4-(2S-1-butyloxycarbonylpyrrolidin-1-ylsulfonyl)-2-methylphenyl 2RS-(4-(pyrrolidin-1-yl)phenyl)butanoic acid ester,
4-(2S-hydroxymethylpyrrolidin-1-ylsulfonyl)phenyl 2RS-(4-(pyrrolidin-1-yl)phenyl)butanoic acid ester,
4-(2-oxopyrrolidin-1-ylsulfonyl)phenyl 2RS-(4-(pyrrolidin-1-yl)phenyl)butanoic acid ester,
4-(pyrrolidin-1-ylsulfonyl)-2-methylphenyl 2RS-(4-(pyrrolidin-1-yl)phenyl)butanoic acid ester,
4-(2S-(pyrrolidin-1-ylmethyl)pyrrolidin-1-ylsulfonyl)-2-methylphenyl 2RS-(4-(pyrrolidin-1-yl)phenyl)butanoic acid ester,
4-(pyrrolidin-1-ylsulfonyl)phenyl 2RS-phenylbutanoic acid ester, 4-(indolin-1-ylsulfonyl)phenyl 2RS-(4-(pyrrolidin-1-yl) phenyl)butanoic acid ester, 4-(2-(ethoxycarbonyl)indolin-1-ylsulfonyl)2-methylphenyl 2RS-(4-(pyrrolidin-1-yl)phenyl)butanoic acid ester, 4-(2-(ethoxycarbonyl)indolin-1-ylsulfonyl)phenyl 2RS-(4-(pyrrolidin-1-yl)phenyl)butanoic acid ester, 4-(2RS-(N,N-dimethylaminocarbonylmethoxycarbonyl) indolin-1-ylsulfonyl)-2-methylphenyl 2RS-(4-(pyrrolidin-1-yl)phenyl)butanoic acid ester, 4-(2RS-(N-benzyloxycarbamoyl)indolin-1-ylsulfonyl) phenyl 2RS-(4-(pyrrolidin-1-yl)phenyl)butanoic acid ester, 4-(6-nitroindolin-1-ylsulfonyl)-2-methylphenyl 2RS-(4-(pyrrolidin-1-yl)phenyl)butanoic acid ester, 4-(6-aminoindolin-1-ylsulfonyl)-2-methylphenyl 2RS-(4-(pyrrolidin-1-yl)phenyl)butanoic acid ester, 4-(7-nitroindolin-1-ylsulfonyl)-2-methylphenyl 2RS-(4-(pyrrolidin-1-yl)phenyl)butanoic acid ester, 4-(7-aminoindolin-1-ylsulfonyl)-2-methylphenyl 2RS-(4-(pyrrolidin-1-yl)phenyl)butanoic acid ester, 4-(benzimidazol-1-ylsulfonyl)-2-methylphenyl 2RS-(4-(pyrrolidin-1-yl)phenyl)butanoic acid ester, 4-(morpholin-4-ylsulfonyl)phenyl 2RS-(4-(pyrrolidin-1-yl) phenyl)butanoic acid ester, 4-(6-aza-7-oxo-bicyclo[3.2.1]octan-6-ylsulfonyl)phenyl 2RS-(4-(pyrrolidin-1-yl)phenyl)butanoic acid ester, 4-(4-benzylpiperazin-1-ylsulfonyl)phenyl 2RS-(4-(pyrrolidin-1-yl)phenyl)butanoic acid ester, 4-(4-(2-hydroxyethyl)piperidin-1-ylsulfonyl)phenyl 2RS-(4-(pyrrolidin-1-yl)phenyl)butanoic acid ester, 4-(2RS-hydroxymethylpiperidin-1-ylsulfonyl)phenyl 2RS-(4-(pyrrolidin-1-yl)phenyl)butanoic acid ester, 4-(4-(N,N-dimethylamino)piperidin-1-ylsulfonyl)phenyl 2RS-(4-(pyrrolidin-1-yl)phenyl)butanoic acid ester, 4-(4-(pyrimidin-2-yl)piperazin-1-ylsulfonyl)phenyl 2RS-(4-(pyrrolidin-1-yl)phenyl)butanoic acid ester, 4-(1,4-dioxa-8-azaspiro[4.5]decan-8-ylsulfonyl)phenyl 2RS-(4-(pyrrolidin-1-yl)phenyl)butanoic acid ester, 4-(3-azabicyclo[3.2.2]nonan-3-ylsulfonyl)phenyl 2RS-(4-(pyrrolidin-1-yl)phenyl)butanoic acid ester, 4-(1,3,3-trimethyl-6-azabicyclo[3.2.1]octan-6-ylsulfonyl) phenyl 2RS-(4-(pyrrolidin-1-yl)phenyl)butanoic acid ester, 4-(2-oxopiperidin-1-ylsulfonyl)phenyl 2RS-(4-(pyrrolidin-1-yl)phenyl)butanoic acid ester, 4-(2-oxo-4S-benzyltetrahydroxazol-3-ylsulfonyl)phenyl 2RS-(4-(pyrrolidin-1-yl)phenyl)butanoic acid ester, 4-(2-oxo-4S-isopropylperhydroxazol-3-ylsulfonyl)phenyl 2RS-(4-(pyrrolidin-1-yl)phenyl)butanoic acid ester, 4-(2-oxo-4S-methyl-5S-phenylperhydroxazol-3-ylsulfonyl) phenyl 2RS-(4-(pyrrolidin-1-yl)phenyl)butanoic acid ester, 4-(1RS-oxo-4S-methoxycarbonylperhydrothiazol-3-ylsulfonyl)phenyl 2RS-(4-(pyrrolidin-1-yl)phenyl) butanoic acid ester, 4-(morpholin-4-ylsulfonyl)-2-methylphenyl 2RS-(4-(pyrrolidin-1-yl)phenyl)butanoic acid ester, 4-(imidazol-1-ylsulfonyl)-2-methylphenyl 2RS-(4-(pyrrolidin-1-yl)phenyl)butanoic acid ester, 4-(piperazin-4-ylsulfonyl)-2-methylphenyl 2RS-(4-(pyrrolidin-1-yl)phenyl)butanoic acid ester, 4-(morpholin-4-ylsulfonyl)phenyl 2RS-(4-nitrophenyl) butanoic acid ester, 4-(morpholin-4-ylsulfonyl)phenyl 1-(4-nitrophenyl) cyclobutanecarboxylic acid ester, 4-(6-aza-7-oxobicyclo[3.2.1]octan-6-ylsulfonyl)phenyl 2-(4-methoxyphenyl)-2-ethylbutanoic acid ester, 4-(morpholin-4-ylsulfonyl)-2-methylphenyl 2RS-(4-methylphenyl)butanoic acid ester, 4-(imidazol-1-ylsulfonyl)phenyl 2RS-phenylbutanoic acid ester, 4-(morpholin-4-ylsulfonyl)phenyl 2RS-phenylbutanoic acid ester, 4-(N-1RS-(ethoxycarbonyl)-2-(morpholin-4-yl) ethylsulfamoyl)phenyl 2RS-(4-(pyrrolidin-1-yl)phenyl) butanoic acid ester, 4-(N-1RS-(ethoxycarbonyl)-2-(morpholin-4-yl) ethylsulfamoyl)phenyl 2RS-(4-nitrophenyl)butanoic acid ester, 4-(N-1RS-(ethoxycarbonyl)-2-(morpholin-4-yl) ethylsulfamoyl)phenyl 1-(4-nitrophenyl) cyclobutanecarboxylic acid ester, 4-(N-1RS-(ethoxycarbonyl)-2-(morpholin-4-yl) ethylsulfamoyl)phenyl 2RS-phenyl-2-methoxyacetic acid ester, 4-(N-benzyloxycarbonylsulfamoyl)phenyl 2RS-(4-(pyrrolidin-1-yl)phenyl)butanoic acid ester, 4-(N-1RS-phenyl-2RS-methylbutylsulfamoyl)phenyl 2RS-(4-(pyrrolidin-1-yl)phenyl)butanoic acid ester, 4-sulfamoylphenyl 2RS-(4-(pyrrolidin-1-yl)phenyl) butanoic acid ester, 4-(N-2-methoxyethylsulfamoyl)phenyl 2RS-(4-(pyrrolidin-1-yl)phenyl)butanoic acid ester, 4-(N-2-methoxyethyl-N-benzylsulfamoyl)phenyl 2RS-(4-(pyrrolidin-1-yl)phenyl)butanoic acid ester, 4-(N-t-butyloxysulfamoyl)phenyl 2RS-(4-(pyrrolidin-1-yl) phenyl)butanoic acid ester, 4-(N-4-hydroxybutylsulfamoyl)phenyl 2RS-(4-(pyrrolidin-1-yl)phenyl)butanoic acid ester, 4-(N-1RS-hydroxymethyl-2-methylpropylsulfamoyl)phenyl 2RS-(4-(pyrrolidin-1-yl)phenyl)butanoic acid ester, 4-(N-2RS,3-dihydroxypropylsulfamoyl)phenyl 2RS-(4-(pyrrolidin-1-yl)phenyl)butanoic acid ester, 4-(N-benzyloxysulfamoyl)phenyl 2RS-(4-(pyrrolidin-1-yl) phenyl)butanoic acid ester, 4-(N-(N',N'-dimethylamino)sulfamoyl)phenyl 2RS-(4-(pyrrolidin-1-yl)phenyl)butanoic acid ester, 4-(N-(N'-methylamino)sulfamoyl)phenyl 2RS-(4-(pyrrolidin-1-yl)phenyl)butanoic acid ester, 4-(N-(carbamoylmethyl)sulfamoyl)phenyl 2RS-(4-(pyrrolidin-1-yl)phenyl)butanoic acid ester, 4-(N-t-butylsulfamoyl)phenyl 2RS-(4-(pyrrolidin-1-yl) phenyl)butanoic acid ester, 4-(N-adamantan-1-ylsulfamoyl)phenyl 2RS-(4-(pyrrolidin-1-yl)phenyl)butanoic acid ester, 4-guanidinosulfonyl-2-methylphenyl 2RS-(4-(pyrrolidin-1-yl)phenyl)butanoic acid ester, 4-(N-2RS,3-dihydroxypropylsulfamoyl)-2-methylphenyl 2RS-(4-(pyrrolidin-1-yl)phenyl)butanoic acid ester, 4-(N,N-bis(2-(methyloxymethoxy)ethyl)sulfamoyl)-2-methylphenyl 2RS-(4-(pyrrolidin-1-yl)phenyl)butanoic acid ester, 4-(N,N-bis(2-(2-(methoxymethoxy)ethoxy)ethyl) sulfamoyl)-2-methylphenyl 2RS-(4-(pyrrolidin-1-yl) phenyl)butanoic acid ester, 4-(N-methyl-N-methoxysulfamoyl)-2-methylphenyl 2RS-(4-(pyrrolidin-1-yl)phenyl)butanoic acid ester, 4-(N-benzylsulfamoyl)-2-methylphenyl 2RS-(4-(pyrrolidin-1-yl)phenyl)butanoic acid ester, 4-(N-2-(N',N'-dimethylamino)ethylsulfamoyl)phenyl 2RS-(4-nitrophenyl)butanoic acid ester, 4-guanidinosulfonylphenyl 1-(4-nitrophenyl) cyclobutanecarboxylic acid ester, 4-guanidinosulfonylphenyl 2RS-(4-nitrophenyl)butanoic acid ester, 4-(N-2RS,3-dihydroxypropylsulfamoyl)-2-methylphenyl 2RS-(4-methylphenyl)butanoic acid ester, 4-(N-2-methoxyethylsulfamoyl)phenyl 2-(4-methoxyphenyl)-2-ethylbutanoic acid ester, 4-(N-2-(N',N'-dimethylamino)ethylsulfamoyl)phenyl 2-(4-methoxyphenyl)-2-ethylbutanoic acid ester, 4-(guanidinosulfonyl)-2-methylphenyl 2RS-(4-methoxyphenyl)butanoic acid ester, 4-(N,N-diethylsulfamoyl)phenyl 2RS-phenylbutanoic acid ester, 4-(N-benzylsulfamoyl)phenyl 2RS-phenylbutanoic acid ester, 4-(N-methyl-N-benzylsulfamoyl)phenyl 2RS-phenylbutanoic acid ester, 4-(N-2-phenylethylsulfamoyl)phenyl 2RS-phenylbutanoic acid ester, 4-(N-methyl-N-2-phenylethylsulfamoyl)phenyl 2RS-phenylbutanoic acid ester, 4-(N-1RS-(4-methylphenyl)butylsulfamoyl)phenyl 2RS-phenylbutanoic acid ester, 4-(N-2-(pyridin-2-yl)ethylsulfamoyl)phenyl 2RS-(4-(pyrrolidin-1-yl)phenyl)butanoic acid ester, 4-(N-2-(piperidin-1-yl)ethylsulfamoyl)phenyl 2RS-(4-(pyrrolidin-1-yl)phenyl)butanoic acid ester, 4-(N-(tetrazol-5-yl)sulfamoyl)phenyl 2RS-(4-(pyrrolidin-1-yl)phenyl)butanoic acid ester, 4-(N-(morpholin-4-yl)sulfamoyl)phenyl 2RS-(4-(pyrrolidin-1-yl)phenyl)butanoic acid ester, 4-(N-(pyrrolidin-3-yl)sulfamoyl)phenyl 2RS-(4-(pyrrolidin-1-yl)phenyl)butanoic acid ester, 4-(N-(1-benzylpiperidin-4-yl)sulfamoyl)phenyl 2RS-(4-(pyrrolidin-1-yl)phenyl)butanoic acid ester, 4-(N-(pyridin-2-yl)sulfamoyl)phenyl 2RS-(4-(pyrrolidin-1-yl)phenyl)butanoic acid ester, 4-(N-2-(morpholin-4-yl)ethylsulfamoyl)phenyl 2RS-(4-(pyrrolidin-1-yl)phenyl)butanoic acid ester, 4-(N-(pyrazin-2-yl)sulfamoyl)phenyl 2RS-(4-(pyrrolidin-1-yl)phenyl)butanoic acid ester, 4-(N-(imidazol-2-yl)sulfamoyl)phenyl 2RS-(4-(pyrrolidin-1-yl)phenyl)butanoic acid ester, 4-(N-(quinuclidin-3RS-yl)sulfamoyl)phenyl 2RS-(4-(pyrrolidin-1-yl)phenyl)butanoic acid ester, 4-(N-(2,2,6,6-tetramethylpiperidin-4-yl)sulfamoyl)phenyl 2RS-(4-(pyrrolidin-1-yl)phenyl)butanoic acid ester, 4-(N-(quinuclidin-3RS-yl)sulfamoyl)-2-methylphenyl 2RS-(4-(pyrrolidin-1-yl)phenyl)butanoic acid ester, 4-(N-2-(morpholin-4-yl)ethylsulfamoyl)-2-methylphenyl 2RS-(4-(pyrrolidin-1-yl)phenyl)butanoic acid ester, 4-(N-2-(piperazin-4-yl)ethylsulfamoyl)-2-methylphenyl 2RS-(4-(pyrrolidin-1-yl)phenyl)butanoic acid ester, 4-(N-(piperidin-4-yl)sulfamoyl)-2-methylphenyl 2RS-(4-(pyrrolidin-1-yl)phenyl)butanoic acid ester, 4-(N-2-(morpholin-4-yl)ethylsulfamoyl)phenyl 2RS-(4-nitrophenyl)butanoic acid ester, 4-(N-2-(pyridin-2-yl)ethylsulfamoyl)phenyl 1-(4-nitrophenyl)cyclobutanecarboxylic acid ester, 4-(N-2-(piperidin-1-yl)ethylsulfamoyl)phenyl 1-(4-nitrophenyl)cyclobutanecarboxylic acid ester, 4-(N-2-(1-methylpyrrol-2-yl)ethylsulfamoyl)phenyl 1-(4-nitrophenyl)cyclobutanecarboxylic acid ester, 4-(N-(tetrazol-5-ylmethyl)sulfamoyl)phenyl 2RS-(4-nitrophenyl)butanoic acid ester, 4-(N-(tetrazol-5-ylmethyl)sulfamoyl)phenyl 1-(4-nitrophenyl)cyclobutanecarboxylic acid ester, 4-(N-(tetrazol-5-yl)sulfamoyl)phenyl 1-(4-nitrophenyl)cyclobutanecarboxylic acid ester, 4-(N-(tetrazol-5-yl)sulfamoyl)phenyl 2RS-(4-nitrophenyl)butanoic acid ester, 4-(N-(quinuclidin-3RS-yl)sulfamoyl)-2-methylphenyl 2RS-(4-methylphenyl)butanoic acid ester, 4-(N-2R-methoxy-3R-hydroxy-4S-hydroxy-5R-hydroxyperhydropyran-6R-ylmethylsulfamoyl)-2-methylphenyl 2RS-(4-(pyrrolidin-1-yl)phenyl)butanoic acid ester, 4-(N-phenylsulfamoyl)phenyl 2RS-phenylbutanoic acid ester, 4-(N-4-nitrophenylsulfamoyl)phenyl 2RS-phenylbutanoic acid ester, 4-(N-phenylsulfamoyl)phenyl 2RS-(4-aminophenyl)butanoic acid ester, 4-(N-(2-(tetrazol-5-yl)phenyl)sulfamoyl)phenyl 2RS-(4-(pyrrolidin-1-yl)phenyl)butanoic acid ester, 4-(N-4-(morpholin-4-yl)phenylsulfamoyl)phenyl 2RS-(4-(pyrrolidin-1-yl)phenyl)butanoic acid ester, 2-(N-(4-(2RS-(4-(pyrrolidin-1-yl)phenyl)butylyloxy)-3-methylphenyl sulfonyl)amino)phenylsulfonic acid 4-(N-3,5-dimethoxyphenylsulfamoyl)-2-methylphenyl 2RS-(4-(pyrrolidin-1-yl)phenyl)butanoic acid ester, 4-(N-phenylsulfamoyl)-2-methylphenyl 2RS-(4-(pyrrolidin-1-yl)phenyl)butanoic acid ester, 4-(N-2-(N'-(tetrazol-5-ylmethyl)carbamoyl)benzen-1-ylsulfamoyl)phenyl 2RS-(4nitrophenyl)butanoic acid ester, 4-(N-2-(N'-(tetrazol-5-ylmethyl)carbamoyl)benzen-1-ylsulfamoyl)phenyl 1-(4-nitrophenyl)cyclobutanecarboxylic acid ester, 4-(N-(4-amidinophenyl)sulfamoyl)phenyl 2RS-(4-nitrophenyl)butanoic acid ester, 4-(N-(4-amidinophenyl)sulfamoyl)phenyl 1-(4-nitrophenyl)cyclobutanecarboxylic acid ester, 4-(N-2-(tetrazol-5-yl)phenylsulfamoyl)phenyl 1-(4-nitrophenyl)cyclobutanecarboxylic acid ester, 4-(N-4-(morpholin-4-yl)phenylsulfamoyl)phenyl 1-(4-nitrophenyl)cyclobutanecarboxylic acid ester, 4-(N-2-(tetrazol-5-yl)phenylsulfamoyl)phenyl 2RS-(4-nitrophenyl)butanoic acid ester, 4-(N-2-(N'-carboxymethylcarbamoyl)phenylsulfamoyl)phenyl 2RS-(4-(N-t-butyloxycarbonylamino)phenyl)butanoic acid ester, 4-(3,5-dimethoxybenzylaminosulfonyl)-2-methylphenyl 2RS-(4-(pyrrolidin-1-yl)phenyl)butanoic acid ester, 4-((4-t-butoxycarbonylaminopiperidin-1-yl)sulfonyl)-2-methylphenyl 2RS-(4-(pyrrolidin-1-yl)phenyl)butanoic acid ester, 4-(N-methoxy-N-benzylaminosulfonyl)-2-methylphenyl 2RS-(4-(pyrrolidin-1-yl)phenyl)butanoic acid ester, 4-(N-benzyloxy-N-methylaminosulfonyl)-2-methylphenyl 2RS-(4-(pyrrolidin-1-yl)phenyl)butanoic acid ester, 4-(2-(N,N-dimethylamino)ethylaminosulfonyl)-2-methylphenyl 2RS-(4-(pyrrolidin-1-yl)phenyl)butanoic acid ester, 4-(2-(piperidin-1-yl)ethylaminosulfonyl)-2-methylphenyl 2RS-(4-(pyrrolidin-1-yl)phenyl)butanoic acid ester, 4-(3-(morpholin-4-yl)propylaminosulfonyl)-2-methylphenyl 2RS-(4-(pyrrolidin-1-yl)phenyl)butanoic acid ester, 4-(indolin-1-ylsulfonyl)-2-methylphenyl 2RS-(4-(pyrrolidin-1-yl)phenyl)butanoic acid ester, 4-((2-oxo-4R-isopropylperhydroxazol-3-yl)sulfonyl)-2-methylphenyl 2RS-(4-(pyrrolidin-1-yl)phenyl)butanoic acid ester, 4-(N-2-(morpholin-4-yl)ethyl-N-methoxyaminosulfonyl)-2-methylphenyl 2RS-(4-(pyrrolidin-1-yl)phenyl)butanoic acid ester, 4-(5-nitroindolin-1-ylsulfonyl)-2-methylphenyl 2S-(4-(pyrrolidin-1-yl)phenyl)butanoic acid ester, 4-(morpholin-4-ylaminosulfonyl)-2-methylphenyl 2RS-(4-(pyrrolidin-1-yl)phenyl)butanoic acid ester, 4-(6-fluoroindolin-1-ylsulfonyl)-2-methylphenyl 2RS-(4-(pyrrolidin-1-yl)phenyl)butanoic acid ester, 4-(5-(N,N-dimethylamino)indolin-1-ylsulfonyl)-2-methylphenyl 2RS-(4-(pyrrolidin-1-yl)phenyl)butanoic acid ester, 4-(4-methylpiperazin-1-ylsulfonyl)-2-methylphenyl 2RS-(4-(pyrrolidin-1-yl)phenyl)butanoic acid ester, 4-(5-nitroindolin-1-ylsulfonyl)-2-methylphenyl 2R-(4-(pyrrolidin-1-yl)phenyl)butanoic acid ester, 4-(2-(morpholin-4-yl)ethylaminosulfonyl)-2-ethylphenyl 2S-(4-(pyrrolidin-1-yl)phenyl)butanoic acid ester, 4-(2-(morpholin-4-yl)ethylaminosulfonyl)-2-ethylphenyl 2R-(4-(pyrrolidin-1-yl)phenyl)butanoic acid ester, 4-(2-(morpholin-4-yl)ethylaminosulfonyl)-2-methylphenyl 2R(4-(pyrrolidin-1-yl)phenyl)butanoic acid ester, 4-(2-(morpholin-4-yl)ethylaminosulfonyl)-2-methylphenyl 2S-(4-(pyrrolidin-1-yl)phenyl)butanoic acid ester, 4-(4-methyl-1,4-perhydrodiazepin-1-ylsulfonyl)-2-methylphenyl 2RS-(4-(pyrrolidin-1-yl)phenyl)butanoic acid ester, 4-(2RS-ethoxycarbonylindolin-1-ylsulfonyl)-2-methylphenyl 2S-(4-(pyrrolidin-1-yl)phenyl)butanoic acid ester, 4-(quinuclidin-3RS-ylaminosulfonyl)-2-methylphenyl 2S-(4-(pyrrolidin-1-yl)phenyl)butanoic acid ester, 4-(2-(morpholin-4-yl)ethylaminosulfonyl)-2-methylphenyl 2RS-(4-(pyrrolidin-1-yl)phenyl)butanoic acid ester, 4-(3,5-dimethoxyphenylaminosulfonyl)-2-methylphenyl 2RS-(4-(pyrrolidin-1-yl)phenyl)butanoic acid ester, 4-(2S-carboxypyrrolidin-1-ylsulfonyl)-2-methylphenyl 2RS-(4-(pyrrolidin-1-yl)phenyl)butanoic acid ester, 4-(2S-carboxypyrrolidin-1-ylsulfonyl)phenyl 2RS-(4-(pyrrolidin-1-yl)phenyl)butanoic acid ester, 4-(2R-carboxypyrrolidin-1-ylsulfonyl)phenyl 2RS-(4-(pyrrolidin-1-yl)phenyl)butanoic acid ester, 4-(2S-carboxy-4R-hydroxypyrrolidin-1-ylsulfonyl)phenyl 2RS-(4-(pyrrolidin-1-yl)phenyl)butanoic acid ester, 4-(2S-carboxy-4R-benzyloxypyrrolidin-1-ylsulfonyl) phenyl 2RS-(4-(pyrrolidin-1-yl)phenyl)butanoic acid ester, 4-(2S-carboxy-4S-aminopyrrolidin-1-ylsulfonyl)phenyl 2RS-(4-(pyrrolidin-1-yl)phenyl)butanoic acid ester, 4-(2S-carboxy-4R-aminopyrrolidin-1-ylsulfonyl)phenyl 2RS-(4-(pyrrolidin-1-yl)phenyl)butanoic acid ester, 4-(2S-(N-carboxymethylcarbamoyl)pyrrolidin-1-ylsulfonyl)phenyl 2RS-(4-(pyrrolidin-1-yl)phenyl) butanoic acid ester, 4-(2S-(2-aminoethoxycarbonyl)pyrrolidin-1-ylsulfonyl)-2-methylphenyl 2RS-(4-(pyrrolidin-1-yl)phenyl)butanoic acid ester, 4-(2S-(2-(2-hydroxyethoxy)ethoxycarbonyl)pyrrolidin-1-ylsulfonyl)-2-methylphenyl 2RS-(4-(pyrrolidin-1-yl) phenyl)butanoic acid ester, 4-(2S-hydroxymethylpyrrolidin-1-ylsulfonyl)-2-methylphenyl 2RS-(4-(pyrrolidin-1-yl)phenyl)butanoic acid ester, 4-(2S-(2-(piperazin-4-yl)ethyl)oxycarbonylpyrrolidin-1-ylsulfonyl)-2-methylphenyl 2RS-(4-(pyrrolidin-1-yl) phenyl)butanoic acid ester, 4-(2S-carboxypyrrolidin-1-ylsulfonyl)phenyl 2-(2-methoxyphenyl)-2-ethylbutanoic acid ester, 4-(2S-carboxypyrrolidin-1-ylsulfonyl)-2-methylphenyl 2RS-(2-methoxyphenyl)butanoic acid ester, 4-(2S-carboxypyrrolidin-1-ylsulfonyl)-2-methylphenyl 2RS-(4-methoxyphenyl)butanoic acid ester, 4-(2S-(2-(piperazin-1-yl)ethyl)oxycarbonylpyrrolidin-1-ylsulfonyl)-2-methylphenyl 2RS-(4-methoxyphenyl) butanoic acid ester, 4-(2S-(2-(2-hydroxyethoxy)ethoxycarbonyl)pyrrolidin-1-ylsulfonyl)-2-methylphenyl 2RS-(4-methoxyphenyl) butanoic acid ester, 4-(2S-(2-aminoethyl)oxycarbonylpyrrolidin-1-ylsulfonyl)-2-methylphenyl 2RS-(4-methoxyphenyl)butanoic acid ester, 4-(2S-carboxypyrrolidin-1-ylsulfonyl)-2-methylphenyl 2RS-(4-methylphenyl)butanoic acid ester, 4-(2S-hydroxymethylpyrrolidin-1-ylsulfonyl)-2-methylphenyl 2RS-(4-methylphenyl)butanoic acid ester, 4-(2S-(2-aminoethyl)oxycarbonylpyrrolidin-1-ylsulfonyl)-2-methylphenyl 2RS-(4-methylphenyl)butanoic acid ester, 4-(2S-(2-(piperazin-4-yl)ethyl)oxycarbonylpyrrolidin-1-ylsulfonyl)-2-methylphenyl 2RS-(4-methylphenyl) butanoic acid ester, 4-(2S-(2-(2-hydroxyethoxy)ethyl)oxycarbonylpyrrolidin-1-ylsulfonyl)-2-methylphenyl 2RS-(4-methylphenyl) butanoic acid ester, 4-(2S-carboxypyrrolidin-1-ylsulfonyl)phenyl 2RS-(4-nitrophenyl)butanoic acid ester, 4-(2S-carboxypyrrolidin-1-ylsulfonyl)phenyl 2R-(4-nitrophenyl)butanoic acid ester, 4-(2S-carboxypyrrolidin-1-ylsulfonyl)phenyl 2S-(4-nitrophenyl)butanoic acid ester, 4-(2S-carboxypyrrolidin-1-ylsulfonyl)phenyl 1-(4-nitrophenyl)cyclobutanecarboxylic acid ester, 4-(2S-carboxypyrrolidin-1-ylsulfonyl)phenyl 2RS-(4-nitrophenyl)butanoic acid ester, 4-(2R-carboxypyrrolidin-1-ylsulfonyl)phenyl 2RS-(4-nitrophenyl)butanoic acid ester, 4-(2R-carboxypyrrolidin-1-ylsulfonyl)phenyl 1-(4-nitrophenyl)cyclobutanecarboxylic acid ester, 4-(2S-carboxypyrrolidin-1-ylsulfonyl)phenyl 2RS-phenylbutanoic acid ester, 4-(2RS-carboxyindolin-1-ylsulfonyl)phenyl 2RS-(4-(pyrrolidin-1-yl)phenyl)butanoic acid ester, 4-(2-carboxyindol-1-ylsulfonyl)phenyl 2RS-(4-(pyrrolidin-1-yl)phenyl)butanoic acid ester, 4-(2S-carboxyindolin-1-ylsulfonyl)phenyl 2RS-(4-(pyrrolidin-1-yl)phenyl)butanoic acid ester, 4-(2S-carboxyperhydroindol-1-ylsulfonyl)phenyl 2RS-(4-(pyrrolidin-1-yl)phenyl)butanoic acid ester, 4-(2RS-carboxyindolin-1-ylsulfonyl)-2-methylphenyl 2RS-(4-(pyrrolidin-1-yl)phenyl)butanoic acid ester, 4-(2RS-(N-carboxymethylcarbamoyl)indolin-1-ylsulfonyl) phenyl 2RS-(4-(pyrrolidin-1-yl)phenyl)butanoic acid ester, 4-(2RS-carboxyindolin-1-ylsulfonyl)phenyl 2S-(4-(pyrrolidin-1-yl)phenyl)butanoic acid ester, 4-(2RS-carboxy-3,3-dimethylindolin-1-ylsulfonyl)phenyl 2RS-(4-(pyrrolidin-1-yl)phenyl)butanoic acid ester, 4-(2RS-carboxyindolin-1-ylsulfonyl)-2-methoxyphenyl 2RS-(4-(pyrrolidin-1-yl)phenyl)butanoic acid ester, 4-(2RS-(N-2-carboxyethylcarbamoyl)indolin-1-ylsulfonyl)-2-methylphenyl 2RS-(4-(pyrrolidin-1-yl)phenyl)butanoic acid ester, 4-(2RS-(N-2-hydroxyethylcarbamoyl)indolin-1-ylsulfonyl) -2-methylphenyl 2RS-(4-(pyrrolidin-1-yl)phenyl) butanoic acid ester, 4-(2-carboxy-5,6-dimethoxyindol-1-ylsulfonyl)-2-methylphenyl 2RS-(4-(pyrrolidin-1-yl)phenyl)butanoic acid ester, 4-(2RS-(2-aminoethyl)oxycarbonylindolin-1-ylsulfonyl)-2-methylphenyl 2RS-(4-(pyrrolidin-1-yl)phenyl)butanoic acid ester, 4-(2-carboxyindol-1-ylsulfonyl)-2-methylphenyl 2RS-(4-(pyrrolidin-1-yl)phenyl)butanoic acid ester, 4-(2RS-carboxy-5,6-dimethoxyindolin-1-ylsulfonyl)-2-methylphenyl 2RS-(4-(pyrrolidin-1-yl)phenyl)butanoic acid ester, 4-(2-carboxy-5-hydroxyindol-1-ylsulfonyl)-2-methylphenyl 2RS-(4-(pyrrolidin-1-yl)phenyl)butanoic acid ester, 4-(2RS-(2-(2-hydroxyethoxy)ethyl)oxycarbonylindolin-1-ylsulfonyl)-2-methylphenyl 2RS-(4-(pyrrolidin-1-yl)phenyl)butanoic acid ester, 4-(2RS-hydroxymethylindolin-1-ylsulfonyl)-methylphenyl 2RS-(4-(pyrrolidin-1-yl)phenyl)butanoic acid ester, 4-(2RS-carboxy-5-hydroxyindolin-1-ylsulfonyl)-2-methylphenyl 2RS-(4-(pyrrolidin-1-yl)phenyl)butanoic acid ester, 4-(2RS-(2-(piperazin-1-yl)ethyl)oxycarbonylindolin-1-ylsulfonyl)-2-methylphenyl 2RS-(4-(pyrrolidin-1-yl)phenyl)butanoic acid ester, 4-(2RS-(N-hydroxycarbamoyl)indolin-1-ylsulfonyl)phenyl 2RS-(4-(pyrrolidin-1-yl)phenyl)butanoic acid ester, 4-(2RS-carboxyindolin-1-ylsulfonyl)phenyl 2RS-(4-methoxyphenyl)butanoic acid ester, 4-(2RS-carboxyindolin-1-ylsulfonyl)-2-methylphenyl 2RS-(4-methoxyphenyl)butanoic acid ester, 4-(2-carboxy-5,6-dimethoxyindol-1-ylsulfonyl)-2-methylphenyl 2RS-(4-methoxyphenyl)butanoic acid ester, 4-(2-carboxyindol-1-ylsulfonyl)-2-methylphenyl 2RS-(4-methoxyphenyl)butanoic acid ester, 4-(2-carboxy-5-hydroxyindol-1-ylsulfonyl)-2-methylphenyl 2RS-(4-methoxyphenyl)butanoic acid ester, 4-(2RS-hydroxymethylindolin-1-ylsulfonyl)-2-methylphenyl 2RS-(4-methoxyphenyl)butanoic acid ester, 4-(2RS-(2-aminoethyl)oxycarbonylindolin-1-ylsulfonyl)-2-methylphenyl 2RS-(4-methoxyphenyl)butanoic acid ester, 4-(2RS-(2-(piperazin-4-yl)ethyl)oxycarbonylindolin-1-ylsulfonyl)-2-methylphenyl 2RS-(4-methoxyphenyl)butanoic acid ester, 4-(2RS-(2-(2-hydroxyethoxy)ethyl)oxycarbonylindolin-1-ylsulfonyl)-2-methylphenyl 2RS-(4-methoxyphenyl)butanoic acid ester, 4-(2RS-carboxyindolin-1-ylsulfonyl)phenyl 2RS-(3-methoxyphenyl)butanoic acid ester, 4-(2RS-carboxyindolin-1-ylsulfonyl)phenyl 2RS-(2-methoxyphenyl)butanoic acid ester, 4-(2RS-carboxyindolin-1-ylsulfonyl)-2-methylphenyl 2RS-(2-methoxyphenyl)butanoic acid ester, 4-(2RS-carboxyindolin-1-ylsulfonyl)phenyl 2RS-(3,4-dimethoxyphenyl)butanoic acid ester, 4-(2RS-carboxyindolin-1-ylsulfonyl)-2-methylphenyl 2RS-(3,4-dimethoxyphenyl)butanoic acid ester, 4-(2RS-carboxyindolin-1-ylsulfonyl)phenyl 2RS-(4-methylphenyl)butanoic acid ester, 4-(2RS-carboxyindolin-1-ylsulfonyl)-2-methylphenyl 2RS-(4-methylphenyl)butanoic acid ester, 4-(2-carboxy-5,6-dimethoxyindol-1-ylsulfonyl)-2-methylphenyl 2RS-(4-methylphenyl)butanoic acid ester, 4-(2-carboxyindol-1-ylsulfonyl)-2-methylphenyl 2RS-(4-methylphenyl)butanoic acid ester, 4-(2-carboxy-5-hydroxyindol-1-ylsulfonyl)-2-methylphenyl 2RS-(4-methylphenyl)butanoic acid ester, 4-(2RS-(2-aminoethyl)oxycarbonylindolin-1-ylsulfonyl)-2-methylphenyl 2RS-(4-methylphenyl)butanoic acid ester, 4-(2RS-hydroxymethylindolin-1-ylsulfonyl)-2-methylphenyl 2RS-(4-methylphenyl)butanoic acid ester, 4-(2RS-(2-(2-hydroxyethoxy)ethyl)oxycarbonylindolin-1-ylsulfonyl)-2-methylphenyl 2RS-(4-methylphenyl)butanoic acid ester, 4-(2RS-(2-(piperazin-4-yl)ethyl)oxycarbonylindolin-1-ylsulfonyl)-2-methylphenyl 2RS-(4-methylphenyl)butanoic acid ester, 4-(2RS-carboxyindolin-1-ylsulfonyl)-2-methylphenyl 2RS-(4-hydroxyphenyl)butanoic acid ester, 4-(2RS-carboxyindolin-1-ylsulfonyl)phenyl 2RS-(4-aminophenyl)butanoic acid ester, 4-(4S-carboxyperhydrothiazol-3-ylsulfonyl)phenyl 2RS-(4-(pyrrolidin-1-yl)phenyl)butanoic acid ester, 4-(4-carboxypiperidin-1-ylsulfonyl)phenyl 2RS-(4-(pyrrolidin-1-yl)phenyl)butanoic acid ester, 4-(2RS-carboxypiperidin-1-ylsulfonyl)phenyl 2RS-(4-(pyrrolidin-1-yl)phenyl)butanoic acid ester, 4-(3RS-carboxypiperidin-1-ylsulfonyl)phenyl 2RS-(4-(pyrrolidin-1-yl)phenyl)butanoic acid ester, 4-(4S-carboxyperhydrothiazol-3-ylsulfonyl)-2-methylphenyl 2RS-(4-(pyrrolidin-1-yl)phenyl)butanoic acid ester, 4-(2RS-carboxymorpholin-1-ylsulfonyl)-2-methylphenyl 2RS-(4-(pyrrolidin-1-yl)phenyl)butanoic acid ester, 4-(1S-oxo-4S-carboxyperhydrothiazol-3-ylsulfonyl)-2-methylphenyl 2RS-(4-(pyrrolidin-1-yl)phenyl)butanoic acid ester, 4-(4S-carboxy-1,1-dioxoperhydrothiazol-3-ylsulfonyl)-2-methylphenyl 2RS-(4-(pyrrolidin-1-yl)phenyl)butanoic acid ester, 4-(4-(2-hydroxyethyl)piperazin-1-ylsulfonyl)-2-methylphenyl 2RS-(4-(pyrrolidin-1-yl)phenyl)butanoic acid ester, 4-(4-carboxymethylpiperazin-1-ylsulfonyl)-2-methylphenyl 2RS-(4-(pyrrolidin-1-yl)phenyl)butanoic acid ester, 4-(4S-carboxyperhydrothiazol-3-ylsulfonyl)phenyl 2RS-(4-nitrophenyl)butanoic acid ester, 4-(N-carboxymethyl-N-2-methoxyethylsulfamoyl)phenyl 2RS-(4-(pyrrolidin-1-yl)phenyl)butanoic acid ester, 4-(N-1RS,2-dicarboxyethylsulfamoyl)phenyl 2RS-(4-(pyrrolidin-1-yl)phenyl)butanoic acid ester, 4-(N-(1-carboxycyclopropane)sulfamoyl)phenyl 2RS-(4-(pyrrolidin-1-yl)phenyl)butanoic acid ester, 4-(N-1RS-carboxy-2-phenylethylsulfamoyl)phenyl 2RS-(4-(pyrrolidin-1-yl)phenyl)butanoic acid ester, 4-(N-1S-carboxy-2-methylpropylsulfamoyl)phenyl 2RS-(4-(pyrrolidin-1-yl)phenyl)butanoic acid ester, 4-(N-(1S-carboxy-2-carboxymethylthioethyl)sulfamoyl)phenyl 2RS-(4-(pyrrolidin-1-yl)phenyl)butanoic acid ester, 4-(N-1RS-carboxy-1-(thiophen-2-yl)methylsulfamoyl)phenyl 2RS-(4-(pyrrolidin-1-yl)phenyl)butanoic acid ester, 4-(N-1RS-carboxy-1-(furan-2-yl)methylsulfamoyl)phenyl 2RS-(4-(pyrrolidin-1-yl)phenyl)butanoic acid ester, 4-(N-carboxymethyl-N-2-methoxyethylsulfamoyl)-2-methylphenyl 2RS-(4-(pyrrolidin-1-yl)phenyl)butanoic acid ester, 4-(N-propyl-N-carboxymethylsulfamoyl)-2-methylphenyl 2RS-(4-(pyrrolidin-1-yl)phenyl)butanoic acid ester, 4-(N-1S-carboxy-5-aminopentylsulfamoyl)-2-methylphenyl 2RS-(4-(pyrrolidin-1-yl)phenyl)butanoic acid ester, 4-(N-carboxymethylsulfamoyl)phenyl 2-(4-methoxyphenyl)-2-ethylbutanoic acid ester, 4-(N-2-methoxyethyl-N-carboxymethylsulfamoyl)phenyl 1-(4-nitrophenyl)cyclobutanecarboxylic acid ester, 4-(N-1RS,2-dicarboxyethylsulfamoyl)phenyl 1-(4-nitrophenyl)cyclobutanecarboxylic acid ester, 4-(N-carboxymethylsulfamoyl)phenyl 2RS-phenylbutanoic acid ester, 4-(N-propyl-N-carboxymethylsulfamoyl)phenyl 2RS-phenylbutanoic acid ester, 4-(N-benzyl-N-carboxymethylsulfamoyl)phenyl 2RS-phenylbutanoic acid ester, 4-(N-2-phenylethyl-N-carboxymethylsulfamoyl)phenyl 2RS-phenylbutanoic acid ester, 4-(N-phenyl-N-carboxymethylsulfamoyl)phenyl 2RS-phenylbutanoic acid ester, 4-(N,N-bis(2-hydroxyethyl)sulfamoyl)-2-methyl 2RS-(4-(pyrrolidin-1-yl)phenyl)butanoic acid ester, 4-(N,N-bis(2-(2-hydroxyethoxy)ethyl)sulfamoyl)-2-methylphenyl 2RS-(4-(pyrrolidin-1-yl)phenyl)butanoic acid ester, 4-(N-(3RS-carboxy-1,4-benzodioxan-5-yl)sulfamoyl)phenyl 2RS-(4-(pyrrolidin-1-yl)phenyl)butanoic acid ester, 4-(N-2RS-hydroxy-4R-hydroxy-5R-hydroxy-6R-hydroxymethylperhydropyran-3R-ylsulfamoyl)-2-methylphenyl 2RS-(4-(pyrrolidin-1-yl)phenyl)butanoic acid ester, 4-(N-3-carboxyadamanatan-1-ylsulfamoyl)phenyl 2RS-(4-(pyrrolidin-1-yl)phenyl)butanoic acid ester, 4-(N-(1S,4R,3R-carboxybicyclo[2.2.1]heptan-2S-yl)sulfamoyl)phenyl 2RS-(4-(pyrrolidin-1-yl)phenyl)butanoic acid ester, 4-(N-3S-carboxycyclohexane-1R-ylsulfamoyl)phenyl 2RS-(4-(pyrrolidin-1-yl)phenyl)butanoic acid ester, 4-(N-2RS-carboxycyclohexane-1RS-ylsulfamoyl)phenyl 2RS-(4-(pyrrolidin-1-yl)phenyl)butanoic acid ester, 4-(N-2-(N'-carboxymethylcarbamoyl)phenylsulfamoyl) phenyl 2-(naphthalen-1-yl)acetic acid ester, 4-(N-2-(N'-carboxymethylcarbamoyl)phenylsulfamoyl) phenyl 2-(naphthalen-2-yl)acetic acid ester, 4-(N-2-(N'-carboxymethylcarbamoyl)phenylsulfamoyl) phenyl 2RS-(cyclohexane-1-yl)butanoic acid ester, 4-(N-2-(N'-carboxymethylcarbamoyl)phenylsulfamoyl) phenyl 2RS-phenylbutanoic acid ester, 4-(N-2-(N'-carboxymethylcarbamoyl)phenylsulfamoyl) phenyl 2-phenyl-2-ethylbutanoic acid ester, 4-(N-2-(N'-carboxymethylcarbamoyl)phenylsulfamoyl) phenyl 2RS-phenylpropanoic acid ester, 4-(N-2-(N'-carboxymethylcarbamoyl)phenylsulfamoyl) phenyl 2R-phenylbutanoic acid ester, 4-(N-2-(N'-carboxymethylcarbamoyl)phenylsulfamoyl) phenyl 2S-phenylbutanoic acid ester, 4-(N-2-(N'-carboxymethylcarbamoyl)phenylsulfamoyl) phenyl 2-phenyl-2-methylpropanoic acid ester, 4-(N-2-(N'-carboxymethylcarbamoyl)phenylsulfamoyl) phenyl 1-phenylcyclohexanecarboxylic acid ester, 4-(N-2-(N'-carboxymethylcarbamoyl)phenylsulfamoyl) phenyl 1-phenylcyclopropanecarboxylic acid ester, 4-(N-2-(N'-carboxymethylcarbamoyl)phenylsulfamoyl) phenyl 1-phenylcyclopentanecarboxylic acid ester, 4-(N-2-(N'-carboxymethylcarbamoyl)phenylsulfamoyl) phenyl 1-phenylcyclobutanecarboxylic acid ester, 4-(N-2-(N'-carboxymethylcarbamoyl)phenylsulfamoyl) phenyl 2-phenylacetic acid ester, 4-(N-2-(N'-carboxymethylcarbamoyl)phenylsulfamoyl) phenyl 2RS-chloro-2-phenylacetic acid ester, 4-(N-2-(N'-carboxymethylcarbamoyl)phenylsulfamoyl) phenyl 2RS-chloro-2-phenylbutanoic acid ester, 4-(N-2-(N'-carboxymethylcarbamoyl)phenylsulfamoyl) phenyl 2,2-diphenylbutanoic acid ester, 4-(N-2-(N'-carboxymethylcarbamoyl)phenylsulfamoyl) phenyl 2RS-methyl-2-phenylbutanoic acid ester, 4-(N-2-(N'-carboxymethylcarbamoyl)phenylsulfamoyl) phenyl 2R-trifluoromethyl-2-phenyl-2-methoxyacetic acid ester, 4-(N-2-(N'-carboxymethylcarbamoyl)phenylsulfamoyl) phenyl 2S-trifluoromethyl-2-phenyl-2-methoxyacetic acid ester, 4-(N-2-(N'-carboxymethylcarbamoyl)phenylsulfamoyl) phenyl 2RS-4-methoxyphenyl)butanoic acid ester, 4-(N-2-(N'-carboxymethylcarbamoyl)phenylsulfamoyl) phenyl 2RS-(4-methoxyphenyl)-3-methylbutanoic acid ester, 4-(N-2-(N'-carboxymethylcarbamoyl)phenylsulfamoyl) phenyl 2-(4-methoxyphenyl)-2-methylpropanoic acid ester, 4-(N-2-(N'-carboxymethylcarbamoyl)phenylsulfamoyl) phenyl 2RS-(4-methoxyphenyl)propanoic acid ester, 4-(N-2-(N'-carboxymethylcarbamoyl)phenylsulfamoyl) phenyl 2-(4-methoxyphenyl)-2-ethylbutanoic acid ester, 4-(N-2-(N'-carboxymethylcarbamoyl)phenylsulfamoyl) phenyl 1-(4-methoxyphenyl)cyclohexanecarboxylic acid ester, 4-(N-2-(N'-carboxymethylcarbamoyl)phenylsulfamoyl) phenyl 1-(4-methoxyphenyl)cyclopentanecarboxylic acid ester, 4-(N-2-(N'-carboxymethylcarbamoyl)phenylsulfamoyl) phenyl 1-(4-methoxyphenyl)cyclobutanecarboxylic acid ester, 4-(N-2-(N'-carboxymethylcarbamoyl)phenylsulfamoyl) phenyl 1-(4-methoxyphenyl)cyclopropanecarboxylic acid ester, 4-(N-2-(N'-carboxymethylcarbamoyl)phenylsulfamoyl) phenyl 2-(3,4-dimethoxyphenyl)-2-ethylbutanoic acid ester, 4-(N-2-(N'-carboxymethylcarbamoyl)phenylsulfamoyl) phenyl 2RS-(3,4-dimethoxyphenyl)butanoic acid ester, 4-(N-2-(N'-carboxymethylcarbamoyl)phenylsulfamoyl) phenyl 2-(3-methoxyphenyl)-2-ethylbutanoic acid ester, 4-(N-2-(N'-carboxymethylcarbamoyl)phenylsulfamoyl) phenyl 2RS-(2-methoxyphenyl)butanoic acid ester, 4-(N-2-(N'-carboxymethylcarbamoyl)phenylsulfamoyl) phenyl 2-(2-methoxyphenyl)-2-ethylbutanoic acid ester, 4-(N-2-(N'-carboxymethylcarbamoyl)phenylsulfamoyl) phenyl 2RS-(3-methoxyphenyl)butanoic acid ester, 4-(N-2-(N'-carboxymethylcarbamoyl)phenylsulfamoyl) phenyl 1-(2-methoxyphenyl)cyclobutanecarboxylic acid ester, 4-(N-2-(N'-carboxymethylcarbamoyl)phenylsulfamoyl)-2,6-dimethylphenyl 2RS-(4-methoxyphenyl)butanoic acid ester, 4-(N-2-(N'-carboxymethylcarbamoyl)phenylsulfamoyl)-2-isopropylphenyl-2RS-(4-methoxyphenyl)butanoic acid ester, 4-(N-2-(N'-carboxymethylcarbamoyl)phenylsulfamoyl) phenyl 2RS-(4-(2-methylpropyloxy)phenyl)butanoic acid ester, 4-(N-2-(N'-carboxymethylcarbamoyl)phenylsulfamoyl) phenyl 2RS-(4-isopropyloxyphenyl)butanoic acid ester, 4-(N-2-(N'-carboxymethylcarbamoyl)phenylsulfamoyl) phenyl 2RS-(4-propyloxyphenyl)butanoic acid ester, 4-(N-2-(N'-carboxymethylcarbamoyl)phenylsulfamoyl) phenyl 2RS-(4-methylphenyl)pentanoic acid ester, 4-(N-2-(N'-carboxymethylcarbamoyl)phenylsulfamoyl) phenyl 1-(4-methylphenyl)cyclopentanecarboxylic acid ester, 4-(N-2-(N'-carboxymethylcarbamoyl)phenylsulfamoyl) phenyl 1-(3-methylphenyl)cyclopentanecarboxylic acid ester, 4-(N-2-(N'-carboxymethylcarbamoyl)phenylsulfamoyl) phenyl 2RS-(2-methylphenyl)butanoic acid ester, 4-(N-2-(N'-carboxymethylcarbamoyl)phenylsulfamoyl) phenyl 2-(2-methylphenyl)-2-ethylbutanoic acid ester, 4-(N-2-(N'-carboxymethylcarbamoyl)phenylsulfamoyl) phenyl 2RS-(4-methylphenyl)butanoic acid ester, 4-(N-2-(N'-carboxymethylcarbamoyl)phenylsulfamoyl) phenyl 2RS-(4-nitrophenyl)butanoic acid ester, 4-(N-2-(N'-carboxymethylcarbamoyl)phenylsulfamoyl) phenyl 2-(4-nitrophenyl)-2-methylpropanoic acid ester, 4-(N-2-(N'-carboxymethylcarbamoyl)phenylsulfamoyl) phenyl 1-(4-nitrophenyl)cyclopropanecarboxylic acid ester, 4-(N-2-(N'-carboxymethylcarbamoyl)phenylsulfamoyl) phenyl 1-(4-nitrophenyl)cyclopentanecarboxylic acid ester, 4-(N-2-(N'-carboxymethylcarbamoyl)phenylsulfamoyl) phenyl 2-(4-nitrophenyl)-2-ethylbutanoic acid ester, 4-(N-2-(N'-carboxymethylcarbamoyl)phenylsulfamoyl) phenyl 1-(4-nitrophenyl)cyclobutanecarboxylic acid ester, 4-(N-2-(N'-carboxymethylcarbamoyl)phenylsulfamoyl)-2-methylphenyl 2RS-(4-nitrophenyl)butanoic acid ester, 4-(N-2-(N'-carboxymethylcarbamoyl)phenylsulfamoyl)-2-methylphenyl 1-(4-nItrophenyl)cyclobutanecarboxylic acid ester, 4-(N-2-(N'-carboxymethylcarbamoyl)phenylsulfamoyl)-3-methylphenyl 1-(4-nitrophenyl)cyclobutanecarboxylic acid ester, 4-(N-2-(N'-carboxymethylcarbamoyl)phenylsulfamoyl)-2,3-dimethylphenyl 1-(4-nitrophenyl)cyclobutanecarboxylic acid ester, 7-(N-2-(N'-carboxymethylcarbamoyl)phenylsulfamoyl)-2,3-dihydroinden-4-yl 1-(4-nitrophenyl)cyclobutanecarboxylic acid ester, 4-(N-2-(N'-carboxymethylcarbamoyl)phenylsulfamoyl) phenyl 2RS-(4-(pyrrolidin-1-yl)phenyl)butanoic acid ester, 4-(N-2-(N'-carboxymethylcarbamoyl)phenylsulfamoyl)-2-methylphenyl 2RS-(4-(pyrrolidin-1-yl)phenyl)butanoic acid ester, 4-(N-2-(N'-carboxymethylcarbamoyl)phenylsulfamoyl)-3-methylphenyl 2RS-(4-(pyrrolidin-1-yl)phenyl) butanoic acid ester, 4-(N-2-(N'-carboxymethylcarbamoyl)phenylsulfamoyl)-2,3-dimethylphenyl 2RS-(4-(pyrrolidin-1-yl)phenyl) butanoic acid ester, 4-(N-2-(N'-carboxymethylcarbamoyl)phenylsulfamoyl) phenyl 1-(4-(pyrrolidin-1-yl)phenyl) cyclobutanecarboxylic acid ester, 7-(N-2-(N'-carboxymethylcarbamoyl)phenylsulfamoyl)-2,3-dihydroinden-4-yl 2RS-(4-(pyrrolidin-1-yl)phenyl) butanoic acid ester, 4-(N-2-(N'-carboxymethylcarbamoyl)phenylsulfamoyl)-2,6-dimethylphenyl 2RS-(4-(pyrrolidin-1-yl)phenyl) butanoic acid ester, 4-(N-2-(N'-carboxymethylcarbamoyl)phenylsulfamoyl)-2-isopropylphenyl 2RS-(4-(pyrrolidin-1-yl)phenyl) butanoic acid ester, 4-(N-2-(N'-carboxymethylcarbamoyl)phenylsulfamoyl) phenyl 2RS-(4-(piperidin-1-yl)phenyl)butanoic acid ester, 4-(N-2-(N'-carboxymethylcarbamoyl)phenylsulfamoyl) phenyl 2RS-(4-(perhydroazepin-1-yl)phenyl)butanoic acid ester, 4-(N-2-(N'-carboxymethylcarbamoyl)phenylsulfamoyl) phenyl 2-(4-aminophenyl)-2-ethylbutanoic acid ester, 4-(N-2-(N'-carboxymethylcarbamoyl)phenylsulfamoyl) phenyl 2RS-(4-aminophenyl)butanoic acid ester, 4-(N-2-(N'-carboxymethylcarbamoyl)phenylsulfamoyl) phenyl 2RS-(4-(N,N-dimethylamino)phenyl)butanoic acid ester, 4-(N-2-(N'-carboxymethylcarbamoyl)phenylsulfamoyl) phenyl 1-(4-(N,N-dimethylamino)phenyl) cyclobutanecarboxylic acid ester, 4-(N-2-(N'-carboxymethylcarbamoyl)phenylsulfamoyl) phenyl 2RS-(4-(N,N-diethylaminomethyl)phenyl) butanoic acid ester, 4-(N-2-(N'-carboxymethylcarbamoyl)phenylsulfamoyl) phenyl 2RS-(4-hydroxyphenyl)butanoic acid ester, 4-(N-2-(N'-carboxymethylcarbamoyl)phenylsulfamoyl) phenyl 2RS-(4-cyanophenyl)butanoic acid ester, 4-(N-2-(N'-carboxymethylcarbamoyl)phenyl(sulfamoyl) phenyl 2RS-(4-carboxyphenyl)butanoic acid ester, 4-(N-2-(N'-carboxymethylcarbamoyl)phenylsulfamoyl) phenyl 2RS-(4-trifluoromethylphenyl)butanoic acid ester, 4-(N-2-(N'-carboxymethylcarbamoyl)phenylsulfamoyl) phenyl 2RS-(4-amidinophenyl)butanoic acid ester, 4-(N-2-(N'-carboxymethylcarbamoyl)phenylsulfamoyl) phenyl 2RS-(4-(imidazolin-2-yl)phenyl)butanoic acid ester, 4-(N-2-(N'-carboxymethylcarbamoyl)phenylsulfamoyl) phenyl 1-(4-chlorophenyl)cyclobutanecarboxylic acid ester, 4-(N-2-(N'-carboxymethylcarbamoyl)phenylsulfamoyl) phenyl 2RS-(2-chlorophenyl)butanoic acid ester, 4-(N-2-(N'-carboxymethylcarbamoyl)phenylsulfamoyl) phenyl 2-(2-chlorophenyl)-2-ethylbutanoic acid ester, 4-(N-2-(N'-carboxymethylcarbamoyl)phenylsulfamoyl) phenyl 1-(2-chlorophenyl)cyclobutanecarboxylic acid ester, 4-(N-2-(N'-carboxymethylcarbamoyl)phenylsulfamoyl) phenyl 2RS-(4-chlorophenyl)butanoic acid ester, 4-(N-2-(N'-carboxymethylcarbamoyl)phenylsulfamoyl) phenyl 2RS-(3-nitro-4-hydroxyphenyl)butanoic acid ester, 4-(N-2-(N'-carboxymethylcarbamoyl)phenylsulfamoyl) phenyl 2RS-(2-chloro-5-nitrophenyl)butanoic acid ester, 4-(N-2-(N'-carboxymethylcarbamoyl)phenylsulfamoyl) phenyl 1-(2-chloro-5-nitrophenyl)cyclobutanecarboxylic acid ester, 4-(N-2-(N'-carboxymethylcarbamoyl)phenylsulfamoyl) phenyl 1-(3-nitro-4-chlorophenyl)cyclobutanecarboxylic acid ester, 4-(N-2-(N'-carboxymethylcarbamoyl)phenylsulfamoyl) phenyl 2RS-(3-nitro-4-chlorophenyl)butanoic acid ester, 4-(N-2-(N'-carboxymethylcarbamoyl)phenylsulfamoyl) phenyl 2RS-(4-ureidophenyl)butanoic acid ester, 4-(N-2-(N'-carboxymethylcarbamoyl)phenylsulfamoyl) phenyl 1-(4-ureidophenyl)cyclobutanecarboxylic acid ester, 4-(N-2-(N'-carboxymethylcarbamoyl)phenylsulfamoyl) phenyl 2RS-(4-(N-(2S-aminopropionyl)amino)phenyl) butanoic acid ester, 4-(N-2-(N'-carboxymethylcarbamoyl)phenylsulfamoyl) phenyl 2RS-(4-(N-(2S-amino-3-methylbutylyl)amino) phenyl)butanoic acid ester, 4-(N-2-(N'-carboxymethylcarbamoyl)phenylsulfamoyl) phenyl 2RS-(4-(N-(pyrrolidin-2S-ylcarbonyl)amino) phenyl)butanoic acid ester, 4-(N-2-(N'-carboxymethylcarbamoyl)phenylsulfamoyl) phenyl 2RS-(3,4,5-trimethoxyphenyl)butanoic acid ester, 4-(N-2-(N'-carboxymethylcarbamoyl)phenylsulfamoyl) phenyl 2RS-(2,4,6-trimethylphenyl)butanoic acid ester, 4-(N-2-(N'-carboxymethylcarbamoyl)phenylsulfamoyl) phenyl 2RS-(3-nitro-4-methoxyphenyl)butanoic acid ester, 4-(N-2-(N'-carboxymethylcarbamoyl)phenylsulfamoyl) phenyl 2RS-(3-nitro-4-aminophenyl)butanoic acid ester, 4-(N-2-(N'-carboxymethylcarbamoyl)phenylsulfamoyl) phenyl 2RS-(4-(N-acetylamino)phenyl)butanoic acid ester, 4-(N-2-(N'-carboxymethylcarbamoyl)phenylsulfamoyl) phenyl 2RS-(4-(N-methyl-N-acetylamino)phenyl) butanoic acid ester, 4-(N-2-(N'-carboxymethylcarbamoyl)phenylsulfamoyl) phenyl 2RS-(4-(morpholin-4-ylmethyl)phenyl)butanoic acid ester, 4-(N-2-(N'-carboxymethylcarbamoyl)phenylsulfamoyl) phenyl 28S-(4-(4-benzylpiperazin-1-yl)phenyl)butanoic acid ester, 4-(N-2-(N'-carboxymethylcarbamoyl)phenylsulfamoyl) phenyl 2RS-(4-(pyrrolidin-1-ylmethyl)phenyl)butanoic acid ester, 4-((1R-oxo-4S-carboxyperhydrothiazol-3-yl)sulfonyl)-2-methylphenyl 2RS-(4-(pyrrolidin-1-yl)phenyl)butanoic acid ester, 4-((2S-carboxypyrrolidin-1-yl)sulfonyl)-2-methylphenyl 2S-(4-(pyrroildin-1-yl)phenyl)butanoic acid ester, 4-((2R-carboxypyrrolidin-1-yl)sulfonyl)-2-methylphenyl 2S-(4-(pyrrolidin-1-yl)phenyl)butanoic acid ester, 4-((2S-carboxypyrrolidin-1-yl)sulfonyl)-2-methylphenyl 2R-(4-(pyrrolidin-1-yl)phenyl)butanoic acid ester, 4-((2R-carboxypyrrolidin-1-yl)sulfonyl)-2-methylphenyl 2R-(4-(pyrrolidin-1-yl)phenyl)butanoic acid ester, 4-((2S-aminomethylpyrrolidin-yl)sulfonyl)-2-methylphenyl 2RS-(4-(pyrrolidin-1-yl)phenyl)butanoic acid ester, 4-((4-aminopiperidin-1-yl)sulfonyl)-2-methylphenyl 2RS-(4-(pyrrolidin-1-yl)phenyl)butanoic acid ester, 4-((2S-carboxyazetidin-1-yl)sulfonyl)-2-methylphenyl 2RS-(4-(pyrrolidin-1-yl)phenyl)butanoic acid ester, 4-((2RS-carboxypiperidin-1-yl)sulfonyl)-2-methylphenyl 2RS-(4-(pyrrolidin-1-yl)phenyl)butanoic acid ester, 4-((2-oxo-5S-carboxypyrrolidin-1-yl)sulfonyl)-2-methylphenyl 2R-(4-(pyrrolidin-1-yl)phenyl)butanoic acid ester, 4-((2S-carboxypyrrolidin-1-yl)sulfonyl)-2-methylphenyl 2RS-(3-(pyrrolidin-1-yl)phenyl)butanoic acid ester, 4-((2S-carboxy-4R-methoxypyrrolidin-1-yl)sulfonyl)-2-methylphenyl 2RS-(4-(pyrrolidin-1-yl)phenyl)butanoic acid ester, 4-((2R-carboxy-4R- methoxypyrrolidin-1-yl)sulfonyl)-2-methylphenyl 2RS-(4-(pyrrolidin-1-yl)phenyl)butanoic acid ester, 4-((2S-carboxypyrrolidin-yl)sulfonyl)-2-methylphenyl 2RS-(2-methyl-4-(pyrrolidin-1-yl)phenyl)butanoic acid ester, 4-((2S-carboxy-4R-hydroxypyrrolidin-1-yl)sulfonyl)-2-methylphenyl 2RS-(4-(pyrrolidin-1-yl)phenyl)butanoic acid ester, 4-(N-methoxy-N-carboxymethylaminosulfonyl)-2-methylphenyl 2RS-(4-(pyrrolidin-1-yl)phenyl)butanoic acid ester, 4-((2S-carboxypyrrolidin-1-yl)sulfonyl)-2-methylphenyl 2RS-(2-methoxy-4-(pyrrolidin-1-yl)phenyl)butanoic acid ester, 4-((2S-carboxyaziridin-1-yl)sulfonyl)-2-methylphenyl 2RS-(4-(pyrrolidin-1-yl)phenyl)butanoic acid ester, 4-(N,N-bis(2-aminoethyl)aminosulfonyl)-2-methylphenyl 2RS-(4-(pyrrolidin-1-yl)phenyl)butanoic acid ester, 4-(N-carboxymethyl-N-(2-(N',N'-dimethylamino)ethyl) aminosulfonyl)-2-methylphenyl 2RS-(4-(pyrrolidin-1-yl) phenyl)butanoic acid ester, 4-((2S-carboxypyrrolidin-1-yl)sulfonyl)-2-ethylphenyl 2RS-(4-(pyrrolidin-1-yl)phenyl)butanoic acid ester, 4-(N-carboxymethyl-N-benzyloxyaminosulfonyl)-2-methylphenyl 2RS-(4-(pyrrolidin-1-yl)phenyl)butanoic acid ester, 4-(N-(4-carboxybutyl)aminosulfonyl)-2-methylphenyl 2RS-(4-(pyrrolidin-1-yl)phenyl)butanoic acid ester, 4-(N-(1,1-dimethyl-1-carboxymethyl)aminosulfonyl)-2-methylphenyl 2RS-(4-(pyrrolidin-1-yl)phenyl)butanoic acid ester, 4-(N-methyl-N-hydroxyaminosulfonyl)-2-methylphenyl 2RS-(4-(pyrrolidin-1-yl)phenyl)butanoic acid ester, 4-((2S-carboxypyrrolidin-1-yl)sulfonyl)-2-methylphenyl 2RS-(2-methyl-4-nitrophenyl)butanoic acid ester, 4-(N-carboxymethylaminosulfonyl)-2-methylphenyl 2RS-(4-(pyrrolidin-1-yl)phenyl)butanoic acid ester, 4-(N-(1,1-dimethyl-1-carboxymethyl)-N-propylaminosulfonyl)-2-methylphenyl 2RS-(4-(pyrrolidin-1-yl)phenyl)butanoic acid ester, 4-((2S-carboxy-4S-aminopyrrolidin-1-yl)sulfonyl)-2-methylphenyl 2RS-(4-(pyrrolidin-1-yl)phenyl)butanoic acid ester, 4-((2S-carboxy-4R-aminopyrrolidin-1-yl)sulfonyl)-2-methylphenyl 2RS-(4-(pyrrolidin-1-yl)phenyl)butanoic acid ester, 4-(N-carboxymethyl-N-(2-(morpholin-4-yl)ethyl) aminosulfonyl)-2-methylphenyl 2RS-(4-(pyrrolidin-1-yl) phenyl)butanoic acid ester, 4-((2S-carboxy-4S-acetylaminopyrrolidin-1-yl)sulfonyl)-2-methylphenyl 2RS-(4-(pyrrolidin-1-yl)phenyl)butanoic acid ester, 4-((2S-carboxypyrrolidin-1-yl)sulfonyl)-2-methylphenyl 2RS-(4-(pyrrolidin-1-yl)phenyl)-2-butanoic acid ester, 4-((2S-carboxy-4R-acetylaminopyrrolidin-1-yl)sulfonyl)-2-methylphenyl 2RS-(4-(pyrrolidin-1-yl)phenyl)butanoic acid ester, 4-((2RS-carboxy-5-nitroindolin-1-yl)sulfonyl)-2-methylphenyl 2RS-(4-(pyrrolidin-1-yl)phenyl)butanoic acid ester, 4-((2S-carboxypyrrolidin-1-yl)sulfonyl)-2-methylphenyl 2RS-(2-methoxy-4-nitrophenyl)butanoic acid ester, 4-((2S-carboxy-4S-methylaminopyrrolidin-1-yl)sulfonyl)-2-methylphenyl 2RS-(4-(pyrrolidin-1-yl)phenyl)butanoic acid ester, 4-((2S-carboxy-4S-(N,N-dimethylamino)pyrrolidin-1-yl) sulfonyl)-2-methylphenyl 2RS-(4-(pyrrolidin-1-yl) phenyl)butanoic acid ester, 4-(N-hydroxyaminosulfonyl)-2-methylphenyl 2RS-(4-(pyrrolidin-1-yl)phenyl)butanoic acid ester, 4-((2S,6S-dimethylpiperazin-4-yl)sulfonyl)-2-methylphenyl 2RS-(4-(pyrrolidin-1-yl)phenyl)butanoic acid ester, 4-((2RS-methylpiperazin-4-yl)sulfonyl)-2-methylphenyl 2RS-(4-(pyrrolidin-1-yl)phenyl)butanoic acid ester, 4-((2S-carboxy-4R-(N,N-dimethylamino)pyrrolidin-1-yl) sulfonyl)-2-methylphenyl 2RS-(4-(pyrrolidin-1-yl) phenyl)butanoic acid ester, 4-((2S-carboxy-4R-methylaminopyrrolidin-1-yl)sulfonyl)-2-methylphenyl 2RS-(4-(pyrrolidin-1-yl)phenyl)butanoic acid ester, 4-(piperazin-4-ylsulfonyl)-2-ethylphenyl 2S-(4-(pyrrolidin-1-yl)phenyl)butanoic acid ester, 4-(piperazin-4-ylsulfonyl)-2-ethylphenyl 2R-(4-(pyrrolidin-1-yl)phenyl)butanoic acid ester, 4-(piperazin-4-ylsulfonyl)-2-methylphenyl 2S-(4-(pyrrolidin-1-yl)phenyl)butanoic acid ester, 4-(piperazin-4-ylsulfonyl)-2-methylphenyl 2R-(4-(pyrrolidin-1-yl)phenyl)butanoic acid ester, 4-((2S-carboxymethylpyrrolidin-1-yl)sulfonyl)-2-methylphenyl 2RS-(4-(pyrrolidin-1-yl)phenyl)butanoic acid ester, 4-((2S-carboxy-4-acetylaminopyrrolidin-1-yl)sulfonyl)-2-methylphenyl 2S-(4-(pyrrolidin-1-yl)phenyl)butanoic acid ester, 4-((2-carboxy-5,6-dimethoxyindol-1-yl)sulfonyl)-2-methylphenyl 2S-(4-(pyrrolidin-1-yl)phenyl)butanoic acid ester, 4-((2RS-carboxyindolin-1-yl)sulfonyl)-2-methylphenyl 2S-(4-(pyrrolidin-1-yl)phenyl)butanoic acid ester, 4-((2RS-methylpiperazin-4-yl)sulfonyl)-2-methylphenyl 2S-(4-(pyrrolidin-1-yl)phenyl)butanoic acid ester, 4-((4-formylpiperazin-1-yl)sulfonyl)-2-methylphenyl 2RS-(4-(pyrrolidin-1-yl)phenyl)butanoic acid ester, 4-((2S-carboxypyrrolidin-1-yl)sulfonyl)-2-methylphenyl 2RS-(4-(pyrrolidin-1-yl)phenyl)butanoic acid ester, 4-(2S-hydroxysulfonyloxymethylpyrrolidin-1-ylsulfonyl)-2-methylphenyl 2RS-(4-methylphenyl)butanoic acid ester, 4-(2S-hydroxysulfonyloxymethylpyrrolidin-1-ylsulfonyl)-2-methylphenyl 2RS-(4-(pyrrolidin-1-yl)phenyl)butanoic acid ester, or a non-toxic salt, acid addition salt or solvate thereof.

8. A pharmaceutical composition which comprises, as active ingredient, an effective amount of a compound of the formula (I) depicted claim 1, a non-toxic salt thereof, an acid addition salt thereof or a solvate thereof, with a carrier or coating.

9. A method for the prevention and/or the treatment in animals of diseases induced by elastase, which comprises the administration to a patient of an effective amount of a compound of the formula (I) depicted in claim 1 or a non-toxic salt thereof or a non-toxic acid addition salt thereof or solvate.

10. A method for the prevention and/or the treatment in animals of diseases induced by an abnormal enhancement of the degradation of elastin, collagen fiber and/or proteoglycan, resulting from the action of elastase on a mammalian animal, which comprises the administration to a patient of an effective amount of a compound of the formula (I) depicted in claim 1 or a non-toxic salt thereof or a non-toxic acid addition salt thereof or solvate.

11. The method of claim 9 wherein the animal treated is man.

12. The method of claim 10 wherein the animal treated is man.

13. The method of claim 10 wherein the disease is selected from the group consisting of emphysema, rheumatoid arthritis, atherosclerosis, adult respiratory distress syndrome (ARDS), glomerular nephritis, myocardial infarction, idiopathic ulcerative colitis and gingivitis.

* * * * *